United States Patent
Li et al.

(10) Patent No.: US 12,042,509 B2
(45) Date of Patent: Jul. 23, 2024

(54) PREKALLIKREIN-MODULATING COMPOSITIONS AND METHODS OF USE THEREOF

(71) Applicant: ADARx Pharmaceuticals, Inc., San Diego, CA (US)

(72) Inventors: Zhen Li, San Diego, CA (US); Rui Zhu, San Diego, CA (US); Zhiqing (Joel) Zhou, San Diego, CA (US); Kimberly Fultz, San Diego, CA (US); Sean Studer, San Diego, CA (US)

(73) Assignee: ADARx Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 17/937,344

(22) Filed: Sep. 30, 2022

(65) Prior Publication Data
US 2023/0158059 A1    May 25, 2023

Related U.S. Application Data

(60) Provisional application No. 63/287,969, filed on Dec. 9, 2021, provisional application No. 63/283,175, filed on Nov. 24, 2021, provisional application No. 63/270,504, filed on Oct. 21, 2021, provisional application No. 63/252,554, filed on Oct. 5, 2021, provisional application No. 63/251,571, filed on Oct. 1, 2021.

(51) Int. Cl.
*C12N 15/11*   (2006.01)
*A61K 31/712*  (2006.01)
*A61K 31/7125* (2006.01)

(52) U.S. Cl.
CPC ........ *A61K 31/712* (2013.01); *A61K 31/7125* (2013.01); *C12N 2310/14* (2013.01); *C12N 2310/315* (2013.01); *C12N 2310/321* (2013.01); *C12N 2310/322* (2013.01); *C12N 2310/351* (2013.01)

(58) Field of Classification Search
None
See application file for complete search history.

(56) References Cited

U.S. PATENT DOCUMENTS

| | | |
|---|---|---|
| 9,315,811 B2 | 4/2016 | Bhattacharjee et al. |
| 9,670,492 B2 | 6/2017 | Freier et al. |
| 10,100,310 B2 | 10/2018 | Freier et al. |
| 2006/0264603 A1 | 11/2006 | Markland et al. |
| 2007/0253949 A1 | 11/2007 | Golz et al. |
| 2008/0070797 A1 | 3/2008 | Mounts |
| 2008/0113351 A1 | 5/2008 | Naito et al. |
| 2008/0280811 A1 | 11/2008 | Feener et al. |
| 2011/0200611 A1 | 8/2011 | Sexton |
| 2020/0056185 A1 | 2/2020 | Prakash et al. |

FOREIGN PATENT DOCUMENTS

| | | |
|---|---|---|
| WO | WO 2004/045543 A2 | 6/2004 |
| WO | WO 2005/075665 A2 | 8/2005 |
| WO | WO 2006/006948 A2 | 1/2006 |
| WO | WO 2006/091459 A2 | 8/2006 |
| WO | WO 2009/098450 A2 | 8/2009 |
| WO | WO 2011/085103 A2 | 7/2011 |
| WO | WO 2012/170945 A2 | 12/2012 |
| WO | WO 2015/031679 A2 | 3/2015 |
| WO | WO 2015/168532 A2 | 11/2015 |
| WO | WO 2020/238758 A1 | 12/2020 |
| WO | WO 2021/158858 A1 | 8/2021 |

OTHER PUBLICATIONS

Björkqvist et al., Plasma kallikrein: the bradykinin-producing enzyme. Thromb Haemost. Sep. 2013;110(3):399-407. doi: 10.1160/TH13-03-0258. Epub Jul. 11, 2013.
Joseph et al., Factor XII-independent activation of the bradykinin-forming cascade: Implications for the pathogenesis of hereditary angioedema types I and Ii. J Allergy Clin Immunol. Aug. 2013;132(2):470-5. doi: 10.1016/j.jaci.2013.03.026. Epub May 11, 2013.
Kaplan et al., The plasma bradykinin-forming pathways and its interrelationships with complement. Mol Immunol. Aug. 2010;47(13):2161-9. doi: 10.1016/j.molimm.2010.05.010.
Kaplan, Enzymatic pathways in the pathogenesis of hereditary angioedema: The role of C1 inhibitor therapy. J Allergy Clin Immunol. Nov. 2010;126(5):918-25.
Renné et al., Plasma kallikrein: Novel functions for an old protease. Thromb Haemost 2012;107(06):1012-1013.
Riedl, Hereditary Angioedema Therapy: Kallikrein Inhibition and Bradykinin Receptor Antagonism. World Allergy Organization Journal. 2010;3:S34-8. Epub Sep. 15, 2010.
Safdar et al., Regulation of the F11, Klkb1, Cyp4v3 gene cluster in livers of metabolically challenged mice. PLoS One. Sep. 16, 2013;8(9):e74637. doi: 10.1371/journal.pone.0074637.eCollection 2013.

(Continued)

Primary Examiner — Ekaterina Poliakova-Georgantas
(74) Attorney, Agent, or Firm — Wolf, Greenfield & Sacks, P.C.

(57) ABSTRACT

Aspects of the disclosure provide compounds, compositions, and methods for modulating the expression or activity of plasma prekallikrein (PKK). In some aspects, the compounds, compositions, and methods of the disclosure can be used to reduce the expression of PKK mRNA in a cell or animal. In some aspects, the compounds, compositions, and methods of the disclosure can be used to reduce the expression of PKK protein in a cell or animal.

36 Claims, No Drawings
Specification includes a Sequence Listing.

(56) References Cited

OTHER PUBLICATIONS

Invitation to Pay Additional Fees for App. No. PCT/US2022/77381 dated Nov. 28, 2022.
[No Author Listed], Homo sapiens chromosome 4, GRCh38.p14 Primary Assembly. NCBI Reference Sequence: NC_000004.12. Feb. 3, 2014, entry version 12; Aug. 29, 2002, entry version 1. 3 pages.
[No Author Listed], *Homo sapiens* kallikrein B1 (KLKB1), RefSeqGene (LRG_565) on chromosome 4. NCBI Reference Sequence: NG_012095. 2. Feb. 26, 2014, entry version 2; May 21, 2009, entry version 1. 15 pages.
[No Author Listed], *Homo sapiens* kallikrein B1 (KLKB1), transcript variant 1, mRNA. NCBI Reference Sequence: NM_000892.5. Nov. 23, 2018, entry version 5; Mar. 24, 1999, entry version 1. 5 pages.
[No Author Listed], *Homo sapiens* kallikrein B1 (KLKB1), transcript variant X2, mRNA. NCBI Reference Sequence: XM_017008181. 1. Jun. 6, 2016, entry version 1. 2 pages.
[No Author Listed], *Homo sapiens* kallikrein B1 (KLKB1), transcript variant 2, mRNA. NCBI Reference Sequence: NM_001318394. 2. May 31, 2019, entry version 2; Jan. 8, 2016, entry version 1. 4 pages.
[No Author Listed], *Homo sapiens* kallikrein B1 (KLKB1), transcript variant 3, mRNA. NCBI Reference Sequence: NM_001318396. 2. May 31, 2019, entry version 2; Jan. 8, 2016, entry version 1. 4 pages.
Cichon et al., Increased activity of coagulation factor XII (Hageman factor) causes hereditary angioedema type III. Am J Hum Genet. Dec. 2006;79(6):1098-104. doi: 10.1086/509899. Epub Oct. 18, 2006.
Gigli et al., Interaction of Plasma Kallikrein with the CI Inhibitor. The Journal of Immunology. Mar. 1970;104(3):574-81.
Kaplan et al., Pathways for bradykinin formation and inflammatory disease. J Allergy Clin Immunol. Feb. 2002;109(2):195-209. doi: 10.1067/mai.2002.121316.
Maurer et al., Hereditary angioedema: an update on available therapeutic options. J Dtsch Dermatol Ges. Sep. 2010;8(9):663-72. doi: 10.1111/j. 1610-0387.2010.07450.x. Epub Jun. 29, 2010.
Pawluczyk et al., Kallikrein gene 'knock-down' by small interfering RNA transfection induces a profibrotic phenotype in rat mesangial cells. J Hypertens. Jan. 2008;26(1):93-101. doi: 10.1097/HJH. 0b013e3282f0ca68.
Schmaier, The contact activation and kallikrein/kinin systems: pathophysiologic and physiologic activities. J Thromb Haemost. Jan. 2016;14(1):28-39. doi: 10.1111/jth. 13194. Epub Jan. 11, 2016.
Zuraw, Clinical practice. Hereditary angioedema. N Engl J Med. Sep. 4, 2008;359(10):1027-36. doi: 10.1056/NEJMcp0803977.
International Search Report and Written Opinion for App. No. PCT/US2022/77381 dated Feb. 14, 2023.
PCT/US2022/77381, dated Feb. 14, 2023, International Search Report and Written Opinion.

SEQUENCE LISTING

```
Sequence total quantity: 630
SEQ ID NO: 1                  moltype = DNA  length = 2258
FEATURE                       Location/Qualifiers
source                        1..2258
                              mol_type = genomic DNA
                              organism = Homo sapiens
SEQUENCE: 1
agtgccacat tagaacagct tgaagaccgt tcattttaa  gtgacaagag actcacctcc  60
aagaagcaat tgtgttttca gaatgatttt attcaagcaa gcaacttatt tcatttcctt 120
gtttgctaca gtttcctgtg gatgtctgac tcaactctat gaaaacgcct tcttcagagg 180
tggggatgta gcttccatgt acaccccaaa tgcccaatac tgccagatga ggtgcacatt 240
ccacccaagg tgtttgctat tcagttttct tccagcaagt tcaatcaatg acatggagaa 300
aaggtttggt tgcttcttga agatagtgt  tacaggaacc ctgccaaaag tacatcgaac 360
aggtgcagtt tctggacatt ccttgaagca atgtggtcat caaataagtg cttgccatcg 420
agacatttat aaaggagttg atatgagagg agtcaatttt aatgtgtcta aggttagcag 480
tgttgaagaa tgccaaaaaa ggtgcaccag taacattcgc tgccagtttt tttcatatgc 540
cacgcaaaca tttcacaagg cagagtaccg gaacaattgc ctattaaagt acagtccgg  600
aggaacacct accgctataa aggtgctgag taacgtggaa tctggattct cactgaagcc 660
ctgtgccctt tcagaaattg gttgccacat gaacatcttc agcatcttg  cgttctcaga 720
tgtggatgtt gccagggttc tcactccaga tgcttttgtg tgtcggacca tctgcaccta 780
tcaccccaac tgcctcttct ttacattcta tacaaatgta tggaaaatcg agtcacaaag 840
```

```
aaatgtttgt cttcttaaaa catctgaaag tggcacacca agttcctcta ctcctcaaga    900
aaacaccata tctggatata gccttttaac ctgcaaaaga actttacctg aaccctgcca    960
ttctaaaatt tacccgggag ttgactttgg aggagaagaa ttgaatgtga cttttgttaa   1020
aggagtgaat gtttgccaag agacttgcac aaagatgatt cgctgtcagt ttttcactta   1080
ttctttactc ccagaagact gtaaggaaga gaagtgtaag tgtttcttaa gattatctat   1140
ggatggttct ccaactagga ttgcgtatgg gacacaaggg agctctggtt actctttgag   1200
attgtgtaac actggggaca actcgtctg cacaacaaaa acaagcacac gcattgttgg    1260
aggaacaaac tcttcttggg gagagtggcc ctggcaggtg agcctgcagg tgaagctgac   1320
agctcagagg cacctgtgtg gagggtcact cataggacac cagtgggtcc tcactgctga   1380
ccactgcttt gatgggcttc ccctgccagga tgtttggcgc atctatagtg gcatttttaaa 1440
tctgtcagac attacaaaag atacacctttt ctcacaaata aaagagatta ttattcacca   1500
aaactataaa gtctcagaag ggaatcatga tatcgccttg ataaaactcc aggctccttt   1560
gaattacact gaattccaaa aaccaatatg cctaccttcc aaaggtgaca caagcacaat   1620
ttataccaac tgttgggtaa ccggatgggg cttctcgaag gagaaaggtg aaatccaaaa   1680
tattctacaa aaggtaaata ttcctttggt aacaaatgaa gaatgccaga aaagatatca   1740
agattataaa ataacccaac ggatggtctg tgctggctat aaagaagggg gaaaagatgc   1800
ttgtaaggga gattcaggtg gtccctttag ttgcaaacac aatggaatgt ggcgtttggt   1860
gggcatcacc agctggggtg aaggctgtgc ccgcagggag caacctggtg tctacaccaa   1920
agtcgctgag tacatggact ggattttaga gaaaacacag agcagtgatg gaaaagctca   1980
gatgcagtca ccagcatgag aagcagtcca gagtctaggc aattttttaca acctgagttc   2040
aagtcaaatt ctgagcctgg ggggtcctca tctgcaaagc atggagagtg gcatcttctt   2100
tgcatcctaa ggacgaaaaa cacagtgcac tcagagctgc tgaggacaat gtctggctga   2160
agcccgcttt cagcacgccg taaccagggg ctgacaatgc gaggtcgcaa ctgagatctc   2220
catgactgtg tgttgtgaaa taaaatggtg aaagatca                           2258

SEQ ID NO: 2            moltype = DNA   length = 30965
FEATURE                 Location/Qualifiers
source                  1..30965
                        mol_type = genomic DNA
                        organism = Homo sapiens
SEQUENCE: 2
agtgccacat tagaacagct tgaagaccgt tcatttttaa gtgacaagag actcacctcc     60
aagaagcaat tgtgttttca ggtagcaaat ttttattatt ctgattgttt ccaaataaac    120
tataattttt aagtataatt tttttacttta tgagaaaatt aatcatttat attctaattt    180
cctgagtatg tagagagtat agataatgtt cctttatgta gaaatatttta aatgtaagat    240
gattttaaat cagaaagaat atttgattga tttaaaattt ttaaatgggc tttaatatttt    300
tcagaggttt tctttactta gggattttg gactgacatt attgccatta tttattaatt     360
ttgttttgc ccaaatcaag aggttggcata attgtttact ctctctctac caattccctt    420
tccaacatta ctagccacag agttggccaa tgaacaataa acacaacagt agtctggagg    480
tctcaatttg tatcttggga agcattataa attttccaac tccctagaca caaatgtacc    540
aaaaaaaaac ccttgttttc tataccagta attgtgtgct ttgtcttgca attcagacat    600
ttacaagaaa atctaaatca ccttaaatta agatttatgt taaatgtggt ctaaaaccag    660
cagagttatg tattgttttc tttttagaa tgattttatt caagcaagca acttatttca     720
tttccttgtt tgctacagtt tcctgtggta agtgaattat ctataaaaca tggaattcag    780
gctaagacag gagtagccaa gcaagtggca ccacccctgg agaaagctat tgaacataca    840
gcttcggggg tggagattgt ccctgatgat tcaggacacg tgtctattta atgttccaca    900
acaaggacca cttgtcaggt atattgctgt agacatatgt tgcagaccag aggaaggagc    960
tcagaagtag gaatgtcttg ggacttgtgt taacaaaaac ttctgttcgc agatgacact   1020
ctgcaaagca aaacttgaaa caaaaaaaaa ttagtcctct atttttatta tcaacagtaa   1080
aaaattaaac tttatctgaa aattcaaaag agtgctaggc attttatagt gtctgggtcc   1140
aatccaagta tctgttagga acaccataca tagttttact ctggaccgct agggaaccat   1200
ttcaaaaatg aaagtaactg gtttaaattt aacttagcaa accatgcatt ggatagttc    1260
taggtgaata gcttttcaaca ccagatttag atctcatttc tctattaatt tcattaattt   1320
ttggagaata aaaatgattc tggacatttc attaatcatt acagagggag ttttctctgt   1380
gtcccacaa ggcatgattc tgggtctatg gtgacttaag agggccacac aacaatgagt   1440
atttaatttt cctcagatgt atggctacaa taaacatcta taggtaaggt ttacattcat   1500
aaagagacct ttttttttcc aggaaaaaag acttttattc cccctaaatc acaactcccc   1560
tgtgtctgtc cctcaaccct gatttctctt ctaaaccgta atttacaaac ccatgtgcaa   1620
acccactgaa aggtgagaag gagcataagc cagagacact gggaaccaca gccaactaca   1680
gggggttttt catttttttg ttttgttttg ttttttggca aaataaatca tgattatgc    1740
taggaaaatc agggatgtaa gtaagcaaaa atttagaaac tacatattgc atgtagtccc    1800
caaattcaga aacagtcatc gttaaacatc tttatttag tctttcagat attttttctac    1860
atataccctat ttgcacattt cacaaaaaag agttattaac tgtggacact ctttgacttg   1920
cattttccac ttatagctat cttttttggtgc aaataagtaa tatattttgg agcttgctat   1980
tcttctctttt ttatggtatt tttgtgtgca cattcttatg ctcttattca gttatttctg   2040
tagaatacaa tttttgaaat aaaaatacta gattcaaagg tgtgaatatt tttgaaggtt   2100
ttgtggtgtg gtatcatgaa attaggtttc agaaagttta ctccatagtt gacttttcct   2160
accagctaat aagagtgctc atttacccca cttaggccaa ctctaacagg cttctgttgc   2220
tttgcatcct gacatattta tcttttctgga aacagtgtcc taatttattt ctgcagagct   2280
actgcctctc agttttggtc catgtggttc tggtgaccct gattcttctg ctgaaccaga   2340
aagtgcacac atcctcctgg ctgtggtgac ccaatcagag ccaacgtctt gcaatgaagc   2400
ttttctttag acatctagaa ataagactct tatgtttttt ttttccaatt tgacttgaaa   2460
cttaagacaa tacacaggcc tgagttgttg gtactatttt gctactacgt ggagcttgag   2520
agtaatggta acaccaagac tggagcaagt ggaaggacag atattgtcca ctgatgctat   2580
cagttgagca caatgtgcag ttactttttta agccagattc accatgggct ttttggctcc   2640
tgaaccaata gatttcattt gttttcaagc cactttgtac taggttttcc atcatttgca   2700
atcaaaacca gtatacaaac actggttatt aatttttca ttttttgctaa tctcaggat    2760
aaaatggctt ctagttgttt taacttggct atatttgtga ttcttcccat tttcatatac   2820
ttactaatca cttctatttc ttttgtaaat tatcttttca tatttgttat ctaattctttt  2880
```

```
aaaatttgag tactttaatt ctcattattg tttgtggaat tgttaaacaa gactgaataa   2940
tctgcccaaa gtccatggac atgggggccc atgtaaaagc tttgaaagcc accatcatta   3000
tgagataaat tatataatag tactttacat aggctccaaa atacagcaca gacacagcta   3060
tcattgtcat ggtcatcatt atcatcatga tcaccaactt atgaggataa gcaagaacac   3120
ctactagaag tttctttcca ttcagcaaca aaattggtgt ctttctagtc actcccttcc   3180
ctgactgtca catgcagtt cacagaggct cagttgcaga atgagaagct ctgggccagg    3240
acctgccatt gtatgcatcc ttgcatggga actgggggct ggaagaggag tgactgcttg   3300
ataattatga gtcagtcaaa accaccaact gtctgaaaaa ataggcctt tttgtaacta    3360
gtattgtcac taaaccaact cctccatgtt ttgtgcatac atgaaatcta ggcaatacac   3420
ttgtattccc aaaagcttcc acttgaagag atctgtgctc tttccaaata taaaccttac   3480
ccgagaggtg gtcatcttgg ccacacctca gagagggaga gaggcagtct tgttgggttg   3540
ggtggtcata atgggctca gggccaaatc cccaggggt aggatagtgc agagaagatg     3600
gcactctcca gtgcttaata aaatgcacgt ggtctaagct gcccactccc tcaaaggcaa   3660
taaaaaatag gtactattta aattgaagag taactactgc cccagggaat ggacaggttg   3720
tcattggaat agccatggtt aatggtccca gttgacaact gaaatgaatg tgctacctga   3780
acaggaaagc ttattaacca gatttcaaag acagtctttc ccgtaaaatc caaatttaca   3840
aattaaagcc agtaaagaca ccgaattctc taataatatg tgggtgcag tatattttag    3900
agctgggaat aattccaaac agcaaatagt tcaaaattta ttttcaattt agcatatgca   3960
tgcatttgct taaactgtct taaaaatgag taaaaaatac tgtcagtttg tttcaatcat   4020
actgagatga ggaacaatgt ttagcattgc atgctagaaa aggacacagg attgggagtc   4080
agggctgggt gaccgtcaca ggactttcac taactgtgtg gatcttgggc aagtctgtgt   4140
gccctgagac tcagttattt aacttttctt taaaaaacat agtccagatg cagataacaa   4200
agcctgcctc taatttccct tacagaattg tgaagaactg gtggagatgt ttgttacaaa   4260
agtgttttga aaatagagca aatattattc tttttaaggc atgatgtttt catagcatgt   4320
caggcaacag gaaaaaacta agttaggatt ttattttatt gtggggaatt tatgtgcaaa   4380
ttattgtgca atttaatgaa agaagccaa tgttttatac agaagtaccc agaaaattaa    4440
ataacactat acattgttca aatagttgcc ttaatatatt ttattttctc agcataatta   4500
gagttgtatt atacaggtct ttgagtagtc agtcagtggg agaagttaag acaacagata   4560
tctttttatt aaaattatta tatgaattat cgcaaattaa ttttatggt tctgtcacag    4620
gatgtctgac tcaactctat gaaaacgcct tcttcagagg tgggatgta gcttccatgt    4680
acaccccaaa tgcccaatac tgccagatga ggtgcacatt ccacccaagg tgtttgctat   4740
tcagtttct tccagcaagt tcaatcaatg acatggagaa aaggtaaaag ttggtatttc    4800
attattggag aagctgtttt tcaaaactga atcagttttg tgcagaaagg tgtagtataa   4860
ctgagagttc ttcctcacac ggggttcaag gaccagcttc agcaaaatcc cgtcaagtgg   4920
ttcttacaaa tgcagattcc taggccacaa cccagatctg ctgaaccaaa gtttcttgtg   4980
accaggaatc tgcattttaa acaatcactg tgtttcttta aagtagtaga agctagtcat   5040
tttctattca aagcctcaaa atgcttgaat atcattgggc taagggattg tctcaagaaa   5100
gagtctaaca ggtgcacatt tcatctgaat aaagaaacag atttaactgt gtgacccatg   5160
atcacattag cggatagcac agtccaaaga aaataacata agacaagcat tttgctgaga   5220
atgtaattga gaaagatcta gaacttgtga ttttgggaca gggcagttct aaatggggcc   5280
tatagtgagc cagtttgggc acctgtgca tgatgctatg tatggtgtgt gtgtgtatgt    5340
gtgcttgtgc ttgtgtgaat atgtattatt aactggaaat ttgtaaaagt attggaaaaa   5400
tagtacttac gattttgtgt gtgtgtgtga tggagtctcg ctttgtagcc caggctgagg   5460
tgcagtggcg tgatctcggc tcactgcaac ttccacctcc caggttcaag cgattctcct   5520
gcctcagcct cccaagtagc tgggattaca ggcacgcacc accacgtcca gctaattttt   5580
gtagttttag tagagacggg gtttcaccac attggccagg ctggccttga actcctgacc   5640
tcgtgatcca cctgcctcta cctcctaatg tgctgggatt acaggcatga gccaccgcac   5700
ccagcggtaa ttacaatttt tattaggtca gagagatgct tattaatcac gagccacagt   5760
ttcatcttaa tgattttttcc ttttgattaa tatccagagt aagcttttct ttgttgttcc   5820
catttccatg ttcataactc tttactcatc ttcactctat gtgagtttac caactagaaa   5880
ttggatagtc atttctctgat cccacatgtt aaacttgtag agaaaactca gattgtatgt   5940
gaggatcatc atatttaaaag tggaggaagg ttctagaatt cttataaata atgaaattaa   6000
catgaaggtg gacatctaag acagagggaa gtcttccatt aagtgcagac tacaaggagt   6060
taataagcaa gatgaacacg atatacaaat ccagctctta tcactaagtt aacttttaa    6120
gtaaatgaaa gtatttgcaa aaataattac caattgacaa catagttgcc tgaaagttta   6180
agaacacagg aaaaatcatt aactctttaa tatggttgat ttcctgtact taaaaaatgt   6240
gagtgtaaag aaaacgcagt gatggagtta gatattatgg ggtgttataa aattagctct   6300
aagagtgttc tttccagcaa gtattgggga agctatatta ttttccttat tcctggtttt   6360
atttgttagt gtgtagaaaa tgctagacat ttcctcaatg tatgttatt attctacttc    6420
ctaagtaaag ctactttaa aataggtttg gttgcttctt gaaagatagt gttacaggaa     6480
ccctgccaaa agtacatcga acaggtgcag tttctggaca ttccttgaag caatgtggtc   6540
atcaaataag tggtaagttg tgaatttctt agctacattt gagttaatat tggatctcgc   6600
ttagaacagc ttttgctcaa agtttgtact gctacagctt tttggaaggc atcactcata   6660
aagataggag atggggcagt attctggaca caaaagaggg acccatattc atctggacac   6720
ttctattgtc tttataaatc aacacatact taatgagcct ctattattta tgaggttagc   6780
gctcaagtgt aagatttgca gaaaatgaat ccaataatt gtgtctcgtt tccagataag    6840
aatttttaag aaaacacaag ggaacatctc tctcaagttc acttgagggt aatttttaca   6900
tcagtgattc tcaaccagca gtgattttgt ctcttccact ggggacattt gacaatgtct   6960
ggagacattt ttggtggcta caactaggga ggatgcttact aagtagaggc               7020
cagaatgttt gaatgctgac caacattcta caaggcacag ggcagtcgtc cacagcaaat   7080
aattttctgg cccaaaacgt caacagtgct gacatcaaga aactctgtga tataccacta   7140
ggcccaaatt gaagaactga gttctgcaaa tcttgctaag aataatactt cctaaaggaa   7200
acttgaggac taggatgcta gagaactttg attctgacat ctgaagctac tgatgtcttg   7260
ggaaacagtt tccaatgtca tcctaataaa tttaagacaa atgaactatt tctcaaacat   7320
gactgggact gataagaaag tgaaagtgc tgaaaagatt caactgatgg gttgtcagaa     7380
tcttaaaata actgctgtta ttctatgtat gactatatat cattactatt ttattttcat   7440
tatgcacaat taattttgta ggttcaaatt tcagatgttt ttaaatttgt catcctttcc   7500
tccctcattg atatcacctc ttcaatacgt acacactttg agcctgctgt ttgcatttta   7560
accagttatc aaaggatggc aatgccttca ttataaatgt gggcctgact tagccagtat   7620
```

```
aataggtgta gtctacgtga ggtggagtac atttcctatt ttaaaagatc aattttttatg   7680
ttaatccaat ttggtataaa ttattcgagt aagtgctatt tctgattgtt gtatcttgta   7740
gcaaaattta aagaaaaagt aatttgtgcc tttctcaata ttcctgttat tgttcatgta   7800
ttctaaaact cactgttact cacttagctt gcttttaatg ttttttaaag tgaaaaattg   7860
ttcccaagta cataaaatct ctacactcaa gaacaattct agtcaaaagc atttagagct   7920
tccgtatgaa cacttaaaga gttttttattt gtaagagtcg catcccaact cttagcctgt   7980
tcttttctca catgcagaaa aataggaaag agacttcgtt tccacagtct gcaaattcct   8040
gtgtttaaga accacagtga ataatccacc tccctgccca actcatcgta ctgtcatata   8100
gttttcctga cagtttgtgt attttctgtc tttcccaccc ttaaatttag ttttatgact   8160
tcaaccatac ttcttaggag tggaaaggta tctgtagtag attatggttt attccacata   8220
atcttgggga ataaaacttt aaaaaagtat acagtttata cttctggtta cattacttcc   8280
ttaaccaaaa gtctaaccaa gaaatttgaa tcttttaaaaa aaaaagaggc cgggcgcggt   8340
ggctcacgcc tgtaatccca gcactttggg aggccgagac gggcggatca cgaggtcagg   8400
agatcgagac catcctgct gacacggtga aaccccgtct ctactaaaaa tacaaaaatt   8460
agccgggcgt ggtggcgcgc gcctgtagtc ccagctactc gggaggctga ggcaggagaa   8520
tggcgtgaac ccgggaggcg gagcttgcag tgagtcgaga tcgcgccact gcgctccagc   8580
ctgggcgaca gagcgagact ccgtctcaaa aaaaaaaaaa aaaaaagag cctaattttg   8640
cttcactgtc tgtgaaaaga attatctgta tctttttgcat gtaagacaaa tctcaatgaa   8700
aagggtgctt aaatagaagt taacactatt ttaaagcaag aatggaagtg gtttcatcat   8760
gcgtaaacaa caactctcca cattttgtaa tgattgatct ggatgcaatt tgtcatcaga   8820
caggagaagt cgaaagcaaa gaaataacac tgggagatag agaagctctt tcattcaatg   8880
cgaaaggtca aaggcacatc agtttcttta ataatgcaaa cctcagcaca cattatcagt   8940
gtcctcatta ttattgcctt gtttatttcc cactgctcat tgataatttc aacgtgaaat   9000
ttacctgtat tgctgcatgc atcttgcagt ttaagaagtg aagtaaccca atttcaaagc   9060
tagtgcttta gggaaaatat tggattgtat ttacttcaag cagagttcga taatttatgt   9120
acataataaa aattttaaat ccccttagtta atatagcagt tgccaaaact gggctattat   9180
cattctaaac taccaaccca aatggtagta ggtatctaat ctacctctag aaagaaaatg   9240
gactgtattt gctctatgta ttttttcttgt acagcttgcc atcgagacat ttataaagga   9300
gttgatatga gaggagtcaa ttttaatgtg tctaaggtta gcagtgttga agaatgccaa   9360
aaaaggtgca ccagtaacat tcgctgccag tttttttcat atgccacgca aacatttcac   9420
aaggcagagt accggtgagt acaattcaag gtgtgtgttc tttgtattgg tgcctccagg   9480
atttcactgt attcttctta acctcttttg ttcccaaact aaaaaccaaa cagggctttt   9540
attctaacca ctttcctcat ttacttactc tattttattt tttatctttt tatttatttta   9600
tttatttatt gagatggagt cgcgctctgt cgcccaggct agagtgcagt ggcgtaatct   9660
cgactcacta caacctccgc ttcccgggtt caagcgattc tcctgcctca gcctcccgag   9720
tagctgggat tacaggcgtc cgccaccatg cctggctaat ttttgtattt ttagtagagt   9780
cggggtttta ctatgttggt caggctggtc tcgaactcct gatcttgtga tccacccacc   9840
tcagcctccc aaagcgctgg gattacaggc atgagccact gcgcctcgcc cttcattttt   9900
taattaaata attcatttaa tttcattttgt ttctctactt tttcccctg gcatgtaatt   9960
gtaccgcatc ttcaaagcct gacatcctct tcccctactt ctccaaagct gattcttgca   10020
ggtctttcct caaataccgt ccctccaaa agcccatttc tgagcattct cttttaagtc   10080
acactcagct ctgtttattt cattcataga gctaatcaca atttgatatt aacttgtgat   10140
ttttttcctt attttttaaat cttattttta tttgcataga tgtatggggt acaagtgtaa   10200
ttttgttact ttgatgtatt ttacagtggt aaagtctggg cttttggtat atccatcact   10260
ggagtcatgt acattgtacc cactaagcta ttttttcaacg cccgcccct tcccaccttct   10320
ctgtcacctt cccagtctct actgtctatc gctccatgct ctactcaatt ttggtgtcat   10380
tttttcctga agcaaatttt tggtgtcatt ttttctgaag tcatttttctg aagtctgtgt   10440
cattttttcgc tttcctgaag cgaattttgg tgtcattttt cctgaagttc cgtttgcccc   10500
acacataggc cttgcttata gaatgagggt ttagtgtcac ggagtctcct gcctcattct   10560
caccctaact tttcctttac cccttgtcga ggggaaggat gtccattagg ttaataatgc   10620
agacccctaa cccactcatt atcagggtca ttgtttttcc actgtgcatt ttaatactaa   10680
ctgttacctg cactgctccc tgcccctcaa agtgcagaaa gcaaagtaac ctcttttctt   10740
cccattcagg aacaattgcc tattaaagta cagtcccgga ggaacaccta ccgctataaa   10800
ggtgctgagt aacgtggaat ctggattctc actgaagccc tgtgcccttt cagaaattgg   10860
taattgtagg actacttcac tttgtgattg tggtaggtgg aataggagcc cccagagacg   10920
tccctgtgct gagccctggg acctgtgcgt gtgttcccat agctggcaaa agcgtttctg   10980
tcaatggcat gcagttacgg gcttcgagat ggggagttta ctctggattt tctgaatggg   11040
cccaatgtac tcacagggtt gagtgctcac aaggctcata agaaaagag agaggcggaa   11100
ggctcagagc cagagagaga ggtttgaagg tattacactg ctggctttga agatgaaggt   11160
ccgtgagcca aggaatgcag gcggcctcta gaagttgaaa agggcgagga aagagtttcc   11220
ctgtggagcg tcctggagga agaagccctg ctgatgtctt gatttagcc cagtaagacc   11280
caatctctag aacagtaaga taattaattt gtgttgtttt taaccactaa gtttgtggtt   11340
atgccctag agcagcagtt ataggaaact agtacagtga tactgttaga gttataggac   11400
agtgatatag gacagtgata ctgttatagt tataggacag tatacagtg atactgttag   11460
agttatagga cagtgatata ggacagtgat attgttatag ttataggaaa ctagtacagt   11520
gatactgtta gagttatagg tacagtgata ttgttatagt tataggaaac tagtacagtg   11580
atactgttac aggtacagtg atataggaca gtgatactgt tataggaaac tagtacagtg   11640
atactgttag agttataggt acagtgacat aggacagtga tactgttata gttataggaa   11700
actagtacag tgatactgtt agagttatag gtagagttat aggacagt gatactgtta   11760
tagttataga aaactagtac agtgatactg ttatagttat aggacagtga tataggacag   11820
tgatattgtt atagttatag gaaactagta cagtgatact gttagagtta taggtacagt   11880
gatataggac agtgatattg ttatagttat aggaaactag tacagtgata ctgttagagt   11940
tataggtaca gtgatattgt tatagttata ggaaactagt acagtgatac tgttataggt   12000
acagtgatat aggacagtga tactgttata ggaaactagt acagtgagtt   12060
ataggtacag tgacatagga cagtgatact gttatagtta taggaaacta gtacagtgat   12120
actgttagag ttataggtac agtgatatag gacagtgata ctgttatagt tataggaaac   12180
tagtacagtg atactgttat agttatagga cagtgatatt gttatagtta taggaaacta   12240
gtacagtgat actgttagag ttataggtac agtgatatag gacagtgata ttgttatagt   12300
tataggaaac tagtacagtg atactgttat agttatagga cagtgatata ggacagtgat   12360
```

```
attgttatag ttataggaaa ctagtacggt gatactgtta tagttatagg tacagtgata  12420
ttgttatagt tataggaaac tagtacagtg atactgttag agttataggt acagtgatat  12480
aggacagtga tattgttata gttataggaa actagtacag tgatactgtt atagttgtag  12540
gacagtgata ttgttatagt tataggaaac tagtacagtg atactgttag agttataggt  12600
acagtgatat aggacagtga tactgttata gttataggac agtgatattc ttatagttac  12660
cgtggtatag ttatagttaa aggtacagtg atattgttat agttataggc cagtgatatt  12720
gttatagtta taggacagtg atgtagttac agtgatatag gtacagtgat attgttatag  12780
ttataggaca gtgatatagt tataggacag tgatattgtt acagttatag gtacagtgac  12840
gttgtaatag ttataggaca gtgatattgt tatagttata ggtacagtga tgttgtagca  12900
aaactgtaag gtcattcctt ggttgtgtcc ctatctagtg aaatgactct accagggqta  12960
gggaaataaa actctgtcgt ttcacacata aaggtaattt caatggaatt atccagaaaa  13020
ttgccatgac attccacctc atttagcatg tcaggatgtt aatgacaaga tgttactaaa  13080
agcaaatccc ttacgccaga ttttccgcag tactgggtgc tggctctgtg cctgccctg   13140
tattgggtgc tgggctagga tttccctgtg gaagattggg aaggttggtt acaaggtggc  13200
tattttcctg tctcctcttt gcgacagcac accttctcca tggctgtgtgc caggttcacg  13260
tgtactggtg atttaatttt aacgttcata ttatttttt ctgggagagt ttttgaaggc  13320
tgccaggagg caggactcga tgcaaacatg ctccattctg tacccagccc tgttgctgga  13380
aggattttgct gcacttaccc agggaacagg caagctgtg ctgtgggctct gggctgtcac  13440
agctgctgtc cacacctggg agagcaccct ggatggctca tctgtgtact tgctttcttg  13500
ttaaattgca gtgagttcac atgtgattta atcggatcaa atggcctta cagactgata  13560
aaaatatggc tgtttcaggt ggtgttttga gctgctaagg gcgtggcttt tcactgagta  13620
cgtggtcccc gttcctcagg gaacacccag tagccacatg cctcctaaac ctagagtagg  13680
gctgtctcct ggcctaactg cccaaatgag attcataagt tagggatgat ctgtagttat  13740
cactacagat ttgtccttgg tttcaccaag gatttttccta attttacaaa caaaaccccct  13800
aaggctcctg gaaggagggt agaagtgaag gtgctccggg ggcaacacag ctgatgagct  13860
gaaccagaac tcgaccccttg ggtcacacac atttcacagt cctcactcca cctttttgttt  13920
ttttaatgga tttaatggtg ttttaaagcc tcctgcctct caacacatat gaattcatta  13980
tatttacaga tttccttctc ttgtggtcca tcttcctgca tagatcttga gagatgtcag  14040
gctaaccacg tttcctcagt taatttaaca aaaccatttg caactctgac atggaaaatt  14100
cctaccatgt gacttattaa tttatcaatt gagatggtac acatattttc aagccaaaag  14160
gaggaaaaca taaattggaa aaaaaaggtt tttttatttt tatcacctct ggggaagaaa  14220
gtctgataaa cgaagctggt tgataaaatt gcaattaggg gaagcaacat catggtttct  14280
gttcggaggc taaccagatg gcatacttga aatagagaat gtcctagaaa tcaactggtt  14340
gcttggccaa aatatctata aatagtgccc aacatattag ataggaaaag caaagtaaaa  14400
acaattttaa caggttagga cattgggctg aagtattgca tatatttaat gtcatgtgcg  14460
tccgtgtgaa gagaccacta acaggcttt gtgtgagcaa gaaagctttt taatcacctg  14520
ggtgcaggca ggctgagtcc gaaaagagag tcagtgaagg gagatggggt ggggacgttt  14580
tataggattt gggtaggtag tggaaaatta cagtcaaagg gggttgttct ctggcgggca  14640
gcggtgggg gtcacaaggt gctcagtggg ggagctttcg agccaggaga aggaatttca  14700
caaggtaacg tcatcagtta aggcaggaac cggccatttt cacttctttt gtctttcttc  14760
agttacttca ggtcatctag atgtatacgt gcaggcctgg gcccagaggc ctgacattcc  14820
tgtcttctta tattaataag aaaaagaaaa cgaaatagtg gtaaagtgtt ggggtggcga  14880
aagttttgtg gggtggtatg gagagataat gggcgatgtt tctcagggct gcttcgaggg  14940
ggattagggg cggcgtggga acctacagtg ggagagatga agctgaagga atattttatg  15000
gtaagggtg atattgtggg gttgttagaa gcagcatttg tcatatagaa tgattggtga  15060
tggcctggat atggttttgt gtgaaatgag aaactaaatg gaagacacaa ggtctgaata  15120
agagaaggag aaaaacaggt gttaaaggac taagaattgg gagaacccag gacatctaat  15180
tagagagtgc ctaaggggt tcagtgtaat tacttgcttg gttggtgagt tttgggctc  15240
tatccttgac agagtcctcc ttttaagtt ggaggctgag cttggtgagg tgtgttttta  15300
aaagaccatt agtctgttct acctttcctg aagattgagg atggtgaggg gtatgaaggt  15360
tttactgaat accaagagcc tgagaaactg ctttgggtat ttgactaata aaggccgatc  15420
tgttatcgga ttgtatagag atggaaaggc caaactgagg aattatgtct gacagaaggg  15480
aagaaatgac cacggtggcc ttctcagacc ctgtgggaaa ggcctctacc catccagtga  15540
aagtgtctac ccagaccaag aggtatttta gtttcctgac tccgggtatg tgagtaaagt  15600
caatctgcca gtcctgggcg gggcaaatc cccgagcttg atgtgtaggg aagggaggqg  15660
gcctgagcaa tccctgagga ggagtggagt agcagatgga acactgagca gttattttt  15720
gaggatagat ttttacgacg gaaggaaaa gtgaggtttt aagaggtggg ttagtggctt  15780
gtaacttaca tggaagagtt tatgaaatga tgacagaata gaatgggcct gtgaggctgg  15840
aggagatatt ttccttggtc caagaattat ttgccttgtg tgggaagaa ttgataggtg  15900
gaagttcaa tgggggagta gatgggagtg acagatgaga aagaaaaaaa ctggctgtga  15960
gggatagaag ttggaatgct cgctgctttt ttagctacct tatcagcata ggcattgtcc  16020
tgagcagtgg gatctgatgc ctttggtgg cccttgcagt gaatggcttc agcttccttt  16080
ggaagtaaag tggccttgag aggagttttt attaaagagg cattaagatg gagaaccctt  16140
gtgtagtgag gaaacctcct tcagcccata taaccgcatg gtggtgcaga atatggaagg  16200
catatttaga gtcagtataa atattgacac gtagtccctt tgcaagagtg agggcctgag  16260
ttaaggcaat gagttcagct tgctgagagg tagtggagcg gggcagagca gtagcctcag  16320
tgatagatgt ggaagatact acagcatagc ctgcctttgc tggtgagtgg tgattaggcc  16380
tggtggaact gccatcaata aaccaagtgt gatcaggta aggaacagga aagaggaaa  16440
tatgggaaa ttggagtgat gtcagttgga tcagagagat acagtcatgg gggtggggggc  16500
cagcctaaaa cagtaaggtc aagttgtttg aacagaaagg ctacagggcg tggtcctggc  16560
tcttgtgtaa gaattttgac tgcgcagccc tgcacttcgg ctgtgtgtaa tgaaagggt  16620
tgggatgagt tagggagagc tagtgtggga gcagttccta gggctgtttt taaggaatgg  16680
caagaggagt ggctaaagga tttaggatct tgggggtcag ctagcttgc ttttgtgagt  16740
ttatataatg gtttagtcag gatggtaaaa cttagtatcc aaaggcggaa gtacttaacc  16800
atacctagga agaaaaggag ttgttttgta gaagggggttg gggtttggga gatgagccag  16860
acacaatcag cagggagagc acatgtgttt tcatgaagaa ttatgccgag ataggtaatg  16920
gatgaggaag aaatttgggc ttgactgaag taatgggggc tgtcctcgaa gccttgtggc  16980
agtacagccc aagtaagttg ctgaggctga cgggtgtcag ggtcagtcca agtgaaagcg  17040
aagagaggct gggatgaagg gtgcaaagga atagtaaaga aagcatgttt gagatccaga  17100
```

```
acagaataat gggttgtgga gggaggtatt gaggatagga gagtatatgg ctttggtacc   17160
atggggtgaa taggcaagac aatttggtta atgaggcaca gatcctgaac taacctgtaa   17220
ggcttgtccg gttttggac aggtaaaatg ggggaattgt aaggagagtt tataggcttc    17280
aaaaggccac gctgtaacag gtgagtgata acaggcttta atcctttaa agcatgctgt    17340
gggatgggat attggcattg agcggggtaa gtgtgattag gttttaatgg gatggtaagg   17400
ggtgcacgat aggttgccaa ggagggagca gaggtgtcct atacttgtgg attaaggtgg   17460
ggacacacaa ggggaggatg tgaaggaggc tttgaactgg ggaaagggtg gcattgaggt   17520
gtggctgtgg cctaagaaca gtcagggaag cggataattg agttaaaatg cctcgaccta   17580
gtaagggagc tgggcaggtg gtgataacta aaaaggagtg cataaaagaa tgttgtccaa   17640
gttggcacca gagttgggga gttttaagag gtttagaagc ctggcggtca atacctacaa   17700
cagttatgga ggcaagggaa acaggccctt gaaaagaacg taatgtggag tgggtagcct   17760
ctgtattaat taagaagggg atggatttac cctccactgt aagagttacc taaagcatct   17820
gtgatggtcc aggaggcttc taaggtgatc gggcagcgtc agtcttcagc cgctaagcca   17880
agaagatctg ggaagcagtc agtcagagag ccttggcca gagttccagg ggctctggga    17940
gtggcagcca ggccagttag acagtccgat ttctagtggg gtcccacaca gatgagacac   18000
agcttaggag gaatcccagg ctgcgggcat tccttggccc attggccaga tttctggcac   18060
ttgaaacaag atcctgatgg aggaggtcct gtaggaatgc ttgaccactg cagtttaggc   18120
atttttgaagt ttttgtgtgt gctggagatg tggctgggtt ttgtctcaca gcagaggcaa  18180
ggaatcgcaa ctcagaaata cattgctact tggctgcctc tattattgta catcttgaag   18240
gcgaggttaa ttaagtcctc ttgtggggtt tgagggctgg aatctaattt ttggagtttt   18300
tttttgtttg ttttttggtt ttttttttt aatgtcagga gctgactggg tgataaaatg    18360
catattgaga ataagaggcc ttctgaccct tctgggtcta gggctgtaaa gcgtctcagg   18420
gttgctgcca aacggccat gaactgggct gggttttca tatttgatga aaaagagcct     18480
aaacgctaac tgatttggga gaggtcgat aaataaaaag gaacattaat cttgactatg    18540
cctttagctc caaccacctc tttaagagga aattgttggg caggtgggg agggctagtc    18600
gtggaatgaa actgtaagct ggaccgggtg tgaggagggg aggtgataga aggattatag   18660
ggtggaggag cagaggctga ggaagaattg ggatctggct tggcctggca aggagcagcc   18720
tggggaggag gggagaggtc agatgggtcc ataggaaaagg aggattggaa agactcagca  18780
acacttgggg ttgggattga gaggacagat gggttgggat tgaggggaca gatgggaggg   18840
aagaaaggaa gatttgggac aagttgcatt gggaacagag actagggagg gaccaatgtg   18900
taaaagaatg cctggacgtc aggcacctca gaccgtttgc ccatttatg acaagaatta    18960
tctagatctt gtaggatgga aaaatcgaaa gtgccgtttt ctggctattt ggaaccattg   19020
tcgagtttgt attggggtta agcagcattg cagaagaaaa taaggcattt aggttttagg   19080
tcaggtgtga gttgaagagg ttttaagttc ttgagaacat aggctaaggg agaagaggga   19140
ggaatggaag gtggaaagtt gcctatagtg aaggaggcaa gcccagagaa aagagagggt   19200
agagacatgg agagaagggg tgggggggtg cttgccccca ggaaagtggt tcttgccact   19260
aagggtgaag gatcaaggca ggcattcgcg cggtgatcag atacctctga aacgtgggtg   19320
aataatcaag caggtgtccc tgcagtgatt aaacagcaag gaaagactat cttcccaagt   19380
ccatgaccag tgccagagtt ttgggttcat ggataaaacg cgtctcctct gtctctacca   19440
gaaaatgaaa ggaattgaaa ttaagaagag ggagagattg aaggatggcg ccaagattga   19500
aaggaaaaag aggttgaggg atagggagag aggttggata agagagtaaa aagaggctgc   19560
ttacccaatt taaaatcggt gagatgttcc ttgggcttgt tggtctgagg accagaggtc   19620
atgggtggat cttttctcatg gagcaaagag cagggggaca gggggattgat ttcccaaggg  19680
aggtccctg atctgagtca cagcaccaaa tatcacgtgt gtccatgcga agagaccacc    19740
aaacaggctt tgtgtgagca agaaagcttt ttaatcacct gggtgcaggc gggctgagtc   19800
caaaagaga gtcagtgaag ggagataggg gtggggacgt tttataggat ttgggtaggt    19860
agtggaaaat tacagtcaaa ggggttgtt ctctggcggg caggggtggg gggtcacaag    19920
gtgctcagtg ggggagcttc tgagccagga gaaggaattt cacaaggtaa cgtcatcagt   19980
taaggcagga accggccatt ttcacttctt ttgtcattct tcagttactt caggccatct   20040
ggatgtatgc atgtaggctt gggcccagag gcctgacatt taacatggat aaatgtaaag   20100
ttcttagaat catacataca cttttggaaaa gatgggggctt aatcgcactt tataagactt  20160
gaaggatgtt tgagaatcac tatgaaactg ctgaaaatac caagaaaatt taattcttat   20220
gtatataaat aatgtgtctg ttttacatga atcccttcta caagcttggt atttaatatg   20280
gcatatattg ttttttcata gtagatttaa aattttgat atctaattta gataacataa     20340
aattaaccct ttgaaagtgt acaactccgt ggttttagt atatccacct gattgcacaa    20400
cgatcaccac tgtctagttc cagaacattt ttatcaccac aaaagaaagg ctgtatccag   20460
gccgggcacg gtggctcacg cctgtaatcc cagcactttg ggaggccgag gcgggcggat   20520
cacggggtca ggagattgaa accatcctgg gtaacacggt gaagcccctat ctgtactaaa  20580
gatacaaaaa aattagctgg gcatgatggc agatgcctgt agtcccagct actcaggagg   20640
ctgaggcagg agaatggcct gaacccagga agcggagctt gcagtgagcc aagattgcgc   20700
cactgcactc cagcctgggc gacagagcaa gactccatct cacaaaaaaa taataaaaat   20760
aaaataaaaa aaaaaagaa aggctgtctt tctcctttcc cattggccgt ctttctccat    20820
tccctactcc tccaatcccc tggcaaccac taaatctact ttccatgtct gtggacttga   20880
ctcttcggga cattttacat aaatggaatc atgcaatgca gcacattttg catctggctt   20940
ttttcacctg gcgtgttttc aaggctcatt cgtattctag catatatcaa tactttgttc   21000
ctatttagga ctaaataaga ttctattgta tgaataaaac atattttgtt tatatactta   21060
gtttgatgaa catttgagtt gtttctggat ttttttttt ttttttttgc ctcttatgaa    21120
taatgctgct atggacaaca gttttgggt aggcatgcat tttaaattct cttatgtata    21180
tacttaggat taaaattgct ggatcacaga gtaactccat gtttaacttt ttgatgaatt   21240
gccaaactgt ttttgagagc agctacacaa tgttacattc ttaccagcaa caattgaggg   21300
cttcagtctc tctacaacct taacaacact tgttattgtc tttgtaatta ttgccttct    21360
aggcagtgtg aagtggtgtc tcactgtggt tttgatatgc atttccctaa tgactaacaa   21420
tgttgtgtat cttttcgtgt gctcattttc aatttgaata cattctttgg gaaaatctct   21480
gtttaaatct tttggccatt aaaaataatt gggttatttt cattgttgag ttgtatgaac   21540
tcttttatata ctctggatac tacactctta tgacatatat tattttcaaa aatttctgt   21600
gcatctgcag gtcatctttt cacttttactg atggtgttct ttgaagcacc aaagttttta  21660
aacttgatga aatccagtct ggcttttattc ttgcacgtgc tttacctaaa acgccaaaac   21720
ctaattcatg gttttgaaga ttttgcttta tgatttgttc ttagaggttt atagtttag    21780
ctcttacatt taggcatttg atgcatttta aattaaattt tgtatatggt gtaaagtagc   21840
```

```
aatccaactt aattcttgca tgtgggtatt cagttattcc attgtcttga aacccttttc   21900
aaaatcaatt gtctataaat gtaagagttt attttggac catcagttct atcctgttga    21960
cctatatatg cctatcctaa tgccagttac acacagtctt gattaccata actttgcagt   22020
aagttttgaa ctcagacagt ctgagtgctt ttattttgtc cttttcaag attaatttgg    22080
ttattccgga tcttttgcat ttccatatga attttaggat ggttgtcaat ttctgcaata   22140
gaaaagcagc aggattttga tagagagtgc attgaatctg tagaccaatg agtatcaatg   22200
gaattatgtg ttatcaaatt tagtaaacta cataaacgat atgtacacaa ctaaaacaaa   22260
actaagagat aagatcatat taatgtaatg ataataaaag tggattgtct cctgttctaa   22320
ttttaataag cacaaggcat ttttgttaat cacttcttat taaagaattt tttataaat    22380
tcaggaaaat acaacaaaaa aacccttaca ttcctaaggc ctcagagtca gagtaatata   22440
aaggaaatgt aaacacatgc tgagtaatgc aagcatttgg caatggtggt gactggagct   22500
gggagcacag ctttattc tctgaaatag gaatttgccc cttagagtta gaccaatttt    22560
gccttcctct aaatggcaaa cagtttggag atactttaaa ggacattttt tcacttagga   22620
tgtttagtac tatgaataat aaatagtcac aatttcctta actatggtga caaaatacaa   22680
gcaaatttag cctcatgtca tttcctaagg aacatcttct ctctgtgagt tcacaggttg   22740
ccacatgaac atcttccagc atcttgcgtt ctcagatgtg gatgttgcca gggttctcac   22800
tccagatgct tttgtgtgtc ggaccatctg cacctatcac cccaactgcc tcttctttac   22860
attctataca aatgtatgga aaatcgagtc acaaaggcga gtatgcatgg aaaatcgcat   22920
cacaaaggcg agtatgcatg gggagcactt gctgctgtac tttcatcact tttatagtct   22980
gagttcttaa aagtttcgtt catttccctc aaaacacttg aacctgcagt ttcagtaggt   23040
actgttctgc caggtgcaga ttagttaaga gattagcaga cttctctgcc tatcttctct   23100
tactttaaaa caaatgttac cattgaatca aggaagcaat agccatgaaa aaaaagaagg   23160
atctgacgcc tttgaatgaa gattcaaaac atgatcttca tgttttgtat tagcttggag   23220
taaaatccac ttgctggcaa tatagccctt aagcttgttg cctcttctct ttgtttcaga   23280
aactagagcc ctgtttattc tgatcaaggc tctggcccac tgtctttatc tcagataacc   23340
caccctcttc tgcacacagc atggagctaa gagaaggggtg tctagttatg taatatcatc   23400
ggcagcataa attcccagaa tttgttcttt gattttttg tttgttttc cagttagaag     23460
gtggaacttc atcattgtcc tcttttcagg ttgtctgtgc ctattagttt tctccagagg   23520
gagaggtggc ttgatttaca tttaatctct gcaatttatt agagtcctgt agttggattt   23580
actttgaaga gagtttccca gaagaataaa atttgctgcg ttgctttttg ggtgtgagct   23640
gcttttgtat ttgcctaatg cctttaatgc aaatttcttt cttctctct tgctttttt     23700
taaaaaaat agaaatgttt gtcttcttaa aacatctgaa agtggcacac caagttcctc    23760
tactcctcaa gaaaacacca tatctggata tagccttta acctgcaaaa gaactttacc    23820
tggtaatgtg atttgataat aatattacat aaaatgtaac ctatttcatg actttttaaca  23880
gcaacagtga tgaaacaatc ctcaaggtaa cagaaacttg tgtaaatgtc gttcattgct   23940
tttcccatct gatatctttt tgtgtttata attgacacag aaccctgcca ttctaaaatt   24000
tacccgggag ttgactttgg aggagaagaa ttgaatgtga cttttgttaa aggagtgaat   24060
gtttgccaag agacttgcac aaagatgatt cgctgtcagt ttttcactta ttctttactc   24120
ccagaagct gtaaggaaga gaagtaaagg aaattttatt tttcaaagac agttgacatg   24180
accatttcat attctctttc cccctgtgaa ggcttactct ttctactgtt catttcatct   24240
aggtgtaagt gtttcttaag attatctatg gatggttctc caactaggat tgcgtatggg   24300
acacaaggga gctctggtta ctcttttgaga ttgtgtaaca ctggggacaa ctctggtgag  24360
taacctcact ttttcgtgga cctgtcaggg atgtctgtca tgttgatagt ttgcttagtc   24420
ttaaggaatt atgtgtcttg ttctccttgg ttagaaggga ctttgattca cttctaattc   24480
caaccattag cgtcaacgct ctcttttcag tctgcacaac aaaaacaagc acacgcattg   24540
ttggaggaac aaactcttct tggggagagt ggccctggca ggtgagcctg caggtgaagc   24600
tgacagctca gaggcacctg tgtggagggt cactcatagg acaccagtgg tcctcactg    24660
ctgcccactg ctttgatggg taagtgttgg atgcatctca tccagagtct tatcttggct   24720
tttcattttg aaggatctat gatcagctgc ttcaccgcca tgtgacttta tgaatagaga   24780
cgtgttaaag cggggatggt attcacaaca tttaacttat agggtccaag cactgaccaa   24840
cctgaccatt agaacagagt gtggtctctg tacagggcag atggcgctga gtgggtattc   24900
tccacagaaa gagaaacgaa gacagtaccc cactcctcca acccaccacc caccaccaat   24960
cccaccacca attccaccac caatcctgcc acccaccacc aatctcacca ccaatcccac   25020
caccaatcct accacccacc atcaatctca gcaccaatcc caccaccaat cccaccacca   25080
atcccaccac ctacccacc accaatcccg ccacccaccc caatcccacc caccgatccc    25140
gccaccaatc ccaccaccaa tcccaccccc taccccacca ccaatcccgc cacccacgac   25200
caatcccacc accgatcccg ccaccaacca ccaatcccac caccaatccc accaccaatc   25260
cctgatgtgt tcttcaaaga cttatttgtc aggcccatag aaatgttact tcttgctctc   25320
tgattcataa atatactaag tcataataat ttttaaaagt gagagtttcg tactctgtat   25380
atttcaatgt atataatttg atctatttca atttattggt caaatagtag acatgttagg   25440
taagtcttaa aatactgagg ctttggagtt agacagaaca tggcttaagt gacagctttg   25500
ctgcttatta gaggtgtggc cctagaagat ttgtaaatcc ctctgagctt tatttgatct   25560
aaaatatgaa tagtaatagt cccgaatttg taacgttgtt gggaagatta agtgacacat   25620
ttaaaatgct tagtactgtg tgtagaacat aaacacttca aaaaatgtaa actgtgattt   25680
ctatattcaa taagaaatgt agaaatggac aaagcatata aaaagcaaaa gaaatactag   25740
aagacacttg attttttctca aaaataaaca caccaagtat ttttgtttta gtgaaattca   25800
tgcttacatg ctgtatacta ggattgaaca tactgccacc aaaatatagc agtcggtggt   25860
acatgtgggt ggagcaagac ccctccacct tgtcatcgtg tgaagggggct ctgccataca  25920
tgaccttgca tgtgacttta aggtggttgg cctggaagaa aagtcccaag atgggaaata   25980
gtaggtgtct ttttactaa atgcactcca atttgggacc aaaaattttc attcttgaag    26040
gctcagtatt gtgagtttat aagagataat agacataaaa gtgtaatgat ttcattgcaa   26100
ataaaaaag gccccttgc acctgatatc tccatcattt ttctagaatt ttgtgcacac    26160
atgccttgca ctacttggtg atgataaaga tttccagatc tttgcacaga ataaggcttt   26220
gcttttagatc agaattttgg atgtacttag tatacattca tcttttaaat aatctattta   26280
cattttcata ctttccaaaa tacagatata ttttattttta tttatatatt tatttaatttt  26340
atttttgag atggagtctc tctctgttgc ccagagtaga gtgcagtggc acaatcttgg    26400
ttcactgcag cctctgcctc ccgggttcaa gcgattctcc tgcctcagcc tcctgagtag   26460
ctgggattac aggcgcgcgc cacacctggc taatttttgt attttagta gagacgaggt    26520
ttcatcatgt tggtcaggct ggtctcgaac tcctggcctc aagggatcca cccacctcgg   26580
```

```
cctcccgaag tgctgggatt acaggtgtgg gccactgtgc ccagctgtat agagatattt    26640
taaacaacac taaagtcctc ctactttgac taattagaag agcattagaa gatcagcctg    26700
acttcttgac agttctgaat ttagtggagc aatgaggttc agctttggtg aatgagctta    26760
attttttccat gataaactgc tagtttcttc ccactacagt gtctctcaaa aatgggacag    26820
caacattctt tttgttttca cttgcagtaa gcatgatgca attacataaa tgtacacttt    26880
tcaatttgtt aaatagaatc ttcagagatt cactactgcc gctattggtg atgaaaaatt    26940
accagaagga ggaattaggt aggagaaaat gtgtcctatg tatttccttc ccagttcttt    27000
gaaagagagt gataggaaaa aggaacacta ttgaaggaag gactgcccag tttcaaacag    27060
gtatttattt ttctctccta ggcttcccct gcaggatgtt tggcgcatct atagtggcat    27120
tttaaatctg tcagacatta caaaagatac acctttctca caaataaaag agattattat    27180
tcaccaaaac tataaagtct cagaagggaa tcatgatatc gccttgataa aactccaggc    27240
tcctttgaat tacactggta tgtagcatat gtaagaaggt ggagagcaga attgcgctgg    27300
ttgatatttt catatcagtt tgaacaagag ggcagaccta gagagactgt cgtcgttttc    27360
tgactggtgg agttgaggga aacgtgaggg ttgctgggaa gtgaagaccc cgcgacttgc    27420
cgtgaaatct cttctactta aagagcaaga catgtgaatt aattctttca gggagggata    27480
caactgcatg caggtgatgg aaataatggg cgtgggaaat gtctgtgccg tctgagaggc    27540
actgggcttg ctttgacaag agtagcagaa ctgtcattgc tttgggctta gggatattcg    27600
aatgtgtgag ggcaagtggg atcagatatc tacttccagg tataatttgg gtaggaaaga    27660
gactcatgca gaaagaagcc ctggaaggcc agagcatcgt ggtcagaggt gttgcctttg    27720
gagggtcatt gctgccagga gccgaatacc cactgtatcc aataacattc atggtcagga    27780
atggtggctc acacctgtaa tcccaacact tgggatgcc caggtgggag gattgcttga    27840
ggccaggagt ttgagaccag cctgggcaac acagtgagac cccgtctcta cataaaatta    27900
gaaaaaaaca attaactggg tgtggtggtg tgcacctgta gtcccagcta gtcaagaggc    27960
tgagacaaga ggatctcttg agcccaggag ctcaaggctg tagtgagcca agatcgtgcc    28020
actgcacaca aacaattatg tgacctcggg caagttgctt tacctcttta cacctcttaa    28080
tttccttatc tgtaaaatga ggatgtaaat ttcttcctgg gtctgttgta ataattaata    28140
catcaaagca cttcatgtct ggaacagtga agatacccta ctatgactat taaggatagt    28200
atacatggaa taagcacag gaacttctaa atgcttttga ccatagattt aggttctgag    28260
ttttaagaat ttaactcagg aaattgtaac accaaaaatg tcatgtgaaa aatggtggtg    28320
acaaattttc ttgaatcatt agcctctagag gttgggcaga aagcaaaaaa ttattcttga    28380
tgctactcta tagaaagaga agacagaaaa agagaaagat gtattttaa agtctatatc    28440
cataactttta tttgaccaaa ctctaatttta aaaattatgt ttcagaattc caaaaaccaa    28500
tatgcctacc ttccaaaggt gacacaagca caatttatac caactgttgg gtaaccggat    28560
ggggctcctc gaaggagaaa ggtaagcatg acgctttaaa tattgcttct agagtaagtc    28620
tcacatgttg aaatacatgg agtgggtcgt tttaatcggt ttctgtctga aattatatct    28680
aaactcttta tcttcctat ctatttattc ccaatatttt attcagttat tcttaaaaaa    28740
tgtattttttg ctttggcttg aaaaaaaatt ttagggagac ttttaagcat cttacttcat    28800
tataaagatc agttgcttga ctttgcatga agcagattgg gcccttctag ggctgacaag    28860
cccgtgcaag accaccccgct cctcagtgtt agtagcgttc ccgtctccca aaaccatgtt    28920
ctcccttgat gctaatggcc gggagcacag gcaggtgtgt cgtctcacta tggagaataa    28980
tatttgtgtc attctttaca gaagaaggta gcttgccaaa ctgtctccat cttttcccgat    29040
tcagtctttt gttcaagtaa ttcacatttt tagattttt attggtaatc tgagacaaga    29100
agaaatttaa agtaatcttc actaagccat gaaagctccc aacattgttc tccatgagag    29160
atgctggcct gcatttattc aaaaacaaaa gaccccctg ttgccaaagc tcggagggct    29220
tttcagaaac gatatagttg taaattataa ttttgaatat ataaagcaaa aaatgaaaa    29280
gtgagaactt ccaggctttg gattgttgta ggtgataaat ataaaatggg atttctgggg    29340
ggctgctact gagatgaggg gatggcagaa aacatgcaag caaggtctct ggtcagccca    29400
gggtgctggg cttgtcccaa caccacgtag gcaataagag gacagtacag ggtgccgtct    29460
ctctccctct tcctctctct gtctctctct ctctgtgtgt gtgtgtgtgt gtgtgtgtaa    29520
cactaccttc ccaatttta ctgtctattt gtattcaaag ataaggtcct tatgaaaaat    29580
acactgctct gattcacttt aaaacttatt tccatattta ttatttattg tgggaataat    29640
aatattccca atattattat ttattattta agttattatt attaacttcc ctctgaggtt    29700
atatattggt tactcacagg tgaaatccaa aatattctac aaaaggtaaa tattcctttg    29760
gtaacaaatg aagaatgcca gaaagatat caagattata aaataaccca acggatggtc    29820
tgtgctggct ataaagaagg gggaaaagat gcttgtaagg taactcatga gattatgaaa    29880
aacacaatg gctgcttgag aaaattcatt tcaaaatata ttttccaata gcataattca    29940
atcatagttt ttaaaaaaat tcagagacaa atgatctgat aaattgataa gcaacttta    30000
acaaattgaa tatacataat atatttat attattattg atatatgtca caatctatgc    30060
atgtgctatt taagagggc aaatatacat gcaataattg tgctagaata taaaacatt    30120
agacttcatc attggggatga tgatatcaag atttctttgt tagattttatt tcagataga     30180
aagggggatac gaaaaatgca ggcacatgag atacttggag aactttaaga aagagtgagt    30240
gtgtgtgtgt gtgtgtgtgt gtgtgtgtgt gtgtctggca agcaaggtct tgcacacaca    30300
cagcactttg ggaggccaat gcaggtggat cacttgagcc taggaatttg agaccagtct    30360
gggcaatgtg atgaaaccca tctctacaaa aaaatatgaa atatctgtg tgtgtgtgtt    30420
gctgtgtagt ggactacaga actttagagg cagtcactta tttgaatccc attgtcgtaa    30480
ctttctacta ttttatttt ccactgtgac tcagggagat tcaggtggtc ccttagtttg    30540
caaacacaat ggaatgtggc gtttggtggg catcaccagc tggggtgaag gctgtgcccg    30600
cagggagcaa cctggtgtct acaccaaagt cgctgagtac atggactgga ttttagagaa    30660
aacacagagc agtgatggaa aagctcagat gcagtcacca gcatgagagg cagtccagag    30720
tctaggcaat ttttacaacc tgagttcaag tcaattctg agcctggggg gtcctcatct    30780
gcaaagcatg gagagtggca tcttcttttgc atcctaagga cgaaaacac agtgcactca    30840
gagctgctga ggacaatgtc tggctgaagc ccgctttcag cacgccgtaa ccaggggctg    30900
acaatgcgag gtcgcaactg agatctccat gactgtgtgt tgtgaaataa aatggtgaaa    30960
gatca                                                                30965

SEQ ID NO: 3        moltype = DNA   length = 3050
FEATURE             Location/Qualifiers
source              1..3050
                    mol_type = genomic DNA
``` organism = Homo sapiens
SEQUENCE: 3

```
caggtgcatg ccaccgtgcc tggctaattt ttgtaatttt tcttgtacag ttggggtttg    60
gccatgtttc ccaggctaaa ttaagacatt taaatcactc aggcacaact aatttttttca   120
tattgccaca tcttcctagg agtgggattg tgcttcagtt ttttcagctg tctatgcctt   180
aattttgact cccatcaata atgcttgatg ttgtagccag tgttggttta ttattaccaa   240
aagcaatgct gttctggaaa ggcaaggact gcagtgtctc atatgatgca attggacgga   300
acctcaagac gacatttgct cccagcaaag ggcattcagc agaacaagga ccaatcagaa   360
ttcatccaac aatcattttc agtgtcatct aagactggca ggtaatagct tacatgtgcg   420
attgtgactt tcatgtgagg atgagatggt ccacaactgc ggggaaagca accttcctgt   480
cctcaatctc ttgtttttaa aagatatttc attccttatt catgtgctta tttatttatc   540
gttttactct ttcattcata aaagtctgcc aagttctatt gagggagctg gggaaagaca   600
gcaagcaagc cccagtccta ccagcaaggt gttacagaca gtgggcgtct gaaaacaac    660
agagaaatgg acaaggaggt aacagaatgg cagggagtga aagcgttac gcagaaagac    720
aaagaatggt gaagagacag gaggtggaag agatggaagg tgccttttca gatgagatgc    780
ttgctggagg atggtatcct gaggagatga tgtttgagca gtggtctgat tgaaaatgat    840
tttattcaag caagcaactt atttcatttc cttgtttgct acagtttcct gtggatgtct    900
gactcaactc tatgaaaacg ccttcttcag aggtggggat gtagcttcca tgtacacccc   960
aaatgcccaa tactgccaga tgaggtgcac attccaccca aggtgtttgc tattcagttt  1020
tcttccagca agttcaatca atgacatgga gaaaaggttt ggttgcttct tgaaagatag  1080
tgttacagga accctgccaa aagtacatcg aacaggtgca gtttctggac attccttgaa  1140
gcaatgtggt catcaaataa gtgcttgcca tcgagacatt tataaaggag ttgatatgag  1200
aggagtcaat tttaatgtgt ctaaggttag cagtgttgaa gaatgccaaa aaaggtgcac  1260
cagtaacatt cgctgccagt tttttcata tgccacgcaa acatttcaca aggcagagta  1320
ccggaacaat tgcctattaa agtacagtcc cggaggaaca cctaccgcta taaaggtgct  1380
gagtaacgtg gaatctggat tctcactgaa gccctgtgcc ctttcagaaa ttggtaattg  1440
taggactact tcactttgtg attgtggttg ccacatgaac atcttccagc atcttgcgtt  1500
ctcagatgtg gatgttgcca gggttctcac tccagatgct tttgtgtgtc ggaccatctg  1560
cacctatcac cccaactgcc tcttcttcac attctataca aatgtatgga aaatcgagtc  1620
acaaagaaat gtttgtcttc ttaaaacatc tgaaagtggc acaccaagtt cctctactcc  1680
tcaagaaaac accatatctg gatatagcct tttaacctgc aaaagaactt tacctgaacc  1740
ctgccattct aaaatttacc cgggagttga ctttggagga gaagaattga atgtgacttt  1800
tgttaaagga gtgaatgttt gccaagagac ttgcacaaag atgattcgct gtcagttttt  1860
cacttattct ttactcccag aagactgtaa ggaagaaga tgtaagtgtt tcttaagatt  1920
atctatggat ggttctccaa ctaggattgc gtatgggaca caaggggagc ctggttactc  1980
tttgagattg tgtaacactg gggacaactc tgtctgcaca acaaaaacaa gcacacgcat  2040
tgttggagga acaaactctt cttggggaga gtggccctgg caggtgagcc tgcaggtgaa  2100
gctgacagct cagaggcacc tgtgtggagg gtcactcata ggacgaccagt gggtcctcac  2160
tgctgcccac tgctttgatg ggcttcccct gcaggatgtt tggcgcatct atagtggcat  2220
tttaaatctg tcagacatta caaaagatac accttttctca caaataaaag agattattat  2280
tcaccaaaac tataaagtct cagaaggaa tcatgatatc gccttgataa aactccaggc  2340
tcctttgaat tacactgaat tccaaaaacc aatatgccta ccttccaaag gtgacacaag  2400
cacaatttat accaactgtt gggtaaccgg atgggcttc tcgaaggaga aaggtgaaat  2460
ccaaatatt ctacaaaagg taaatattcc tttggtaaca aatgaagaat gccagaaaag  2520
atatcaagat tataaaataa cccaacggat ggtctgtgct ggctataaag aagggggaaa  2580
agatgcttgt aagggagatt caggtggtcc cttagtttgc aaacacaatg gaatgtggcg  2640
tttggtgggc atcaccagct ggggtgaagg ctgtgccgc gtggtgtcta  2700
caccaaagtc gctgagtaca tggactggat tttagagaaa acacagagca gtgatggaaa  2760
agctcagatg cagtcaccag catgagaagc agtccagagt ctaggcaatt tttacaacct  2820
gagttcaagt caaattctga gcctgggggg tcctcatctg caaagcatgg agagtggcat  2880
cttctttgca tcctaaggac gaaaaacaca gtgcactcag agctgctgag gacaatgtct  2940
ggctgaagcc cgctttcagc acgccgtaac caggggctga caatgcgagg tcgcaactga  3000
gatctccatg actgtgtgtt gtgaaataaa atggtgaaag atcacgatta             3050
```

```
SEQ ID NO: 4           moltype = DNA   length = 42764
FEATURE                Location/Qualifiers
source                 1..42764
                       mol_type = genomic DNA
                       organism = Homo sapiens
SEQUENCE: 4
caggtgcatg ccaccgtgcc tggctaattt ttgtaatttt tcttgtacag ttggggtttg    60
gccatgtttc ccaggctaaa ttaagacatt taaatcactc aggcacaact aatttttttca   120
tattgccaca tcttcctagg agtgggattg tgcttcagtt ttttcagctg tctatgcctt   180
aattttgact cccatcaata atgcttgatg ttgtagccag tgttggttta ttattaccaa   240
aagcaatgct gttctggaaa ggcaaggact gcagtgtctc atatgatgca attggacgga   300
acctcaagac gacatttgct cccagcaaag ggcattcagc agaacaagga ccaatcagaa   360
ttcatccaac aatcattttc agtgtcatct aagactggca ggtaatagct tacatgtgcg   420
attgtgactt tcatgtgagg atgagatggt ccacaactgc ggggaaagca accttcctgt   480
cctcaatctc ttgtttttaa aagatatttc attccttatt catgtgctta tttatttatc   540
gttttactct ttcattcata aaagtctgcc aagttctatt gagggagctg gggaaagaca   600
gcaagcaagc cccagtccta ccagcaaggt gttacagaca gtgggcgtct gaaaacaac    660
agagaaatgg acaaggaggt aacagaatgg cagggagtga aagcgttac gcagaaagac    720
aaagaatggt gaagagacag gaggtggaag agatggaagg tgccttttca gatgagatgc    780
ttgctggagg atggtatcct gaggagatga tgtttgagca gtggtctgat tgaagtgagt   840
cacgtgggga tctgggacaa ggggaggtgg agagggctcc atcctggcac gtgtctaagg   900
ggaggttctg gagaaaaatc ctctttcaag cacgtgcagt ttgttggaat attcagtgct   960
ttgggatggt aggggtgaaa tccccatgtt cttttttggc cttgtccaga gatgactctc  1020
aggtccttcc ccgtgaccca tctcaaagcc agcgctggag cacttccctg ctgtcaatcc  1080
ctcttaacgc tctgaatctc tctgacatct ccttatgctg accgcagagg aaaactctgc  1140
```

```
ttttaatggg ctcatgtaat aagatttggc ccactctgat tgactccatt ttgattggca 1200
caaagccaag tgtttagtaa tcttaacccc atctgcagaa ttgcttttct catgtaacat 1260
aatcatgggc agatgtgata tctcgtttta ttcactgtcc ccaggatttg agtgggagat 1320
ttgggagaat gttttagaat tctacttacc acgcctcttt tcaatttagt tctgatttgg 1380
ttcacctgaa tctacagagg ttttttttagt tttattgtgc tactagaatg taacatgttt 1440
cactgtaaga aaactccaac taaacctaga agcatattta aataggttaa aagtctgtaa 1500
tctcacctttt tagaaaaaca aaccctgagg gtttctgctg tgatgtgaag gcagggtgct 1560
tttgtcccag ttgttttgtt gttgttgttg ttgttcttgt tttctgctga gcctggtagc 1620
tgatgaaatc taaaatataa actctttttct actgcacaaa gtggagagat ttgttgacta 1680
ctgctgcacc acttgatatc ctaaaagaca gcacaacatg catatttaaa atatgctact 1740
tccttctcac cagaaaatat tttattggca acattatcct acatttctaa taaatgtagt 1800
tctgcattcc agtaatatac ataaaatatt tatttaagaa tcgactccaa aaactctaat 1860
gtactaatca agatgatata ctgtaatttc aaagaataga aaacaaagga gatttagtgg 1920
gcaggtcatt gtggtcttta aatattttaa aagcagaaaa aggagaatca gttgttttgt 1980
gtgggtctag tacgtaaatc taggactgaa ggatagaagt ttgcaaggag gtgtatttca 2040
gtatacagga agttttttc ttttcttaaa aataaaatta aaatagagct ccctgagctc 2100
tgaaataaaa taaaattaaa atagagctcc ctgagttgga gcaggctgct taggaaacca 2160
gtttctcctc agtcgaagta ttttgacagg aaggtctaaa gtctatgtca gaagtgttat 2220
ccagcagatt tcagccaacc ttatctgtag agtcagatag taaatcttct ggcttttga 2280
ggccatgctg cctctgtagc aacttcttaa ctctgccatt gtaaggtgaa agcaggcata 2340
gacagcaagt gaatgaatgg ccatggctgt gtttcaataa aactttattt acaaaaacag 2400
gtgcaaagcc aaatgtggtc tgtgaactgt ggtttgtcaa gcctgatata ttgcatttcc 2460
tgaattgggt gggaatagga cctaaacatc aagccagtcc cttccaaatc taagatttca 2520
gtgttatatg attctttggt agggtgtagg aaggcataga tatcatttgc taaaatatcc 2580
ctctaggagg agctatccat acccatccat tattcactgt gcctgcaagc aactctaata 2640
aaaaaaagtt ctgttagatg aggtttcaac tacatgccac taaatactgg gaatgttata 2700
agcatttttt aaaatggaaa cctgtgcata aactgtgtga ccctaaaatg aaatttaggg 2760
cctttttgagt gcagcatttt tctaccttttt tttatgtatc atttacaaat aaaaaattata 2820
tatatctact gtgtacaaga tagtgttttg atatacatgt acattgtgaa atgattacca 2880
tagtcaagct aattaacatg tccattattt tacatagtgt gtgtgtgtgt gtgtgtgtgc 2940
gcatgtgtgt gtgctgagaa cccatcagat ctattctcta gtgaagttca tgtatacgat 3000
acagtattat gaactatagt caccatgttt gcattagtca gggttctcta gaaggacaga 3060
actaatagga tagatgtaca tataaagggg agtttattaa agagtattga ctcacacgat 3120
cacaaggtga agtcccacaa tagtctgcct gcaggctgag gagcaaggaa gccagtctaa 3180
gtcccaaaac ctcaaaagca agaaagtcaa cagtgcagcc ttcagtctgt ggtcaaaggt 3240
ccaagagccc ttggcaaacc actggtgtaa ctccaagagt ccaaaagctg aagaacttgg 3300
agtacaaagt tcaagggcag gaaacatcca gcacaggaga aagatgaggg ccagaagact 3360
tagccagtct agtccttcca cgttcctctg cctgcttttta tcctagcccg gctggcagct 3420
gagatggtgc ccacccagat tgagggtggg tctgcctcct ccagtcaact gactcaaata 3480
ttaatctcct ttggcaacac cctcacagac acatccagga acaatacttg gcatccttca 3540
atccagtcaa gccgacactc aatattaacc atcacaagtc caccccttgt ctacttgaac 3600
ccatacgcat ctccctgaaat catatataat cttcaaataa agataataat aaggtcataa 3660
ttatgttagg taatacataa tacagctatc cttcgtacaa ccagaagtgt accaatcccc 3720
aacccaaatg ctgttacata aagttaacaa catttaaatg ctgatttgaa gtaaataaat 3780
cttatgtcac atgataaagg aaaagaaag gaaataaaat gaagatattt tcttagtaca 3840
agtgtataca tacacaaaca tgttcctaac aaaaataagga ggaaatatga caattacagt 3900
cctcatttct gcagctggtc acgtgggcat agccggtatt gatgactacc ttcttctact 3960
acccattctg tattccttttt gccttcagca agcatctcag caggttgtgg ttttttacct 4020
ggtgagtga cccaaacatt cattcctaag gggtctgggc cttatgtagc actgcctgga 4080
ttgggctgtt gtagtttccc attgacctta atcacagggc atggtaatac taagagttgc 4140
ctgaagggat ctcctgtatt ccttgcatac tcttccttac ctccactgtg gagtaataga 4200
ctaacttcat cttgatagtc caggtcaatc accacagcca acactgcaac tcccttctga 4260
gcctgttgac ttagaggtaa aaggatctca aagtgtccag gtgcaagct taacttccag 4320
tttaatggaa tccttgttgt gtcttctggt ggcagcattt ttccctctga aactaacaca 4380
actaagcaag cagaaggtaa tgtattggga acaggaagca aaaatttgc tagtggatag 4440
ctaggggtga tggtgagtgg tgccacttcc acttctgccc cttgattcct agacctgtga 4500
atcctggcta tgggagaaac ggtgccatat attggatgtt gattcagagc atacatagcc 4560
ttctggagaa ttttgcccca gccctgcaaa gtattgtccc ctagttggca ttgtaattgt 4620
gacttcaaaa ggccattcca ccgttctatc aatacagctg cttcaggatg acgggaaaca 4680
atgttgtaca ttagatcctc caacttattc acactgcata attggaactt tggaccttt 4740
gaccaaaacc acccccatagc tggcactccc catactctgg ctaccaccat tctactctct 4800
gttagcatga ctttgacttt tttagattct gcatgtagtt gtaagtgcct ctcttcagat 4860
gatcatatga ttttttatcct tcattttgtg aatgtgtat atagcattta ttgagttgca 4920
tatgttgaac catccttgca tcctaggctc agttgatcat gatcctttta atgtgttgtt 4980
gaatttagtc tggctaatat tttcttcagg atttctggat ctatgttcat caggaatatt 5040
gatctataat tttaatttta tttattgtg atgtccttgt ttggctctgc tatcaaagta 5100
atgctggcct cattaaatga gattggaagt gtttcctcct tttcaattat ttgaaagagt 5160
ttgagaagga ttggtgttaa ttcttttaaat gtttatagac ttcaccaatg aagacatcag 5220
gtgctgagct tttctttagtt gagagttttt attttctgatt caacctcctt actcattatt 5280
ggtttgttca gattttctat ttcttcctga ttcagtcttg gtaggttgta tgttcctagg 5340
aatttatccta tttcttctac attatttaat tagttgatgt actgtttttc atagtagtct 5400
catgattttc tgtatttctg tggtatccat tgtaatcttt cctccttcat ttataatttt 5460
atttgagttt ttttcttttt tctcctaatt aggctaaaga tttcttgatt tatcttttta 5520
aaaacaataa cagtgtcatt gacctttttct gttgttttctc tagtctctat ttcatttatc 5580
tctgctctga tctttattat tttcttctt cctctgtctt tgggcttagt tttttttttt 5640
tactttctta ttgcttcagg tgtaaagtta ggatatttca gatctttcca ttttcttaag 5700
gtaggtattt atcgctataa acttccttct tagaactgct tttgctgcat cccataaatt 5760
ttcaatgcca caaattttgt ttctctttttc atttttctca agacattttt tgattttcct 5820
tttgatttct tcttttgactc attggttgtt caggagtatg ttaattttca tgtatttgtg 5880
```

```
aattttccat ttttccttct gttactgagt tctactttta tgccattatg gttggaaaag   5940
atacttgata tgatttcaat ccttaaattt gttaagatgt tttccatggc ctaacatata   6000
acctatcctg gagagtgttc tgtgtgcact taaaaagaat gtgcattctg ctgcttttga   6060
aaggaatgtt ctgcacatgt ccgttaggtc tattggttta tagcattttg aaatccacag   6120
tttccttgtt gattttctgt ccaggtgatc tattcattgt tgaaagcatg ttgctattta   6180
tttctccttt agttatgtta atatttgctt tatagattta gatgcactga ttttgggtac   6240
atgtgtattt acaattgtta tatcctctta atgaattcac cctttaccca ttatataatg   6300
accttctctg tctcttgtga cagtatttga cttaaactct atctcatctg ttataaggat   6360
agccacctct gctttcgttt ggttatcatg tgaatgcaat ctcttttca tcccttcact   6420
tccagcttat gtctgtcctt aaagctaaag ttagtctctt acaggcagca tatagttaga   6480
tcttgttttt tattcactca tccactctct cttttgattg gataatttaa tacatttaca   6540
tctaaagtaa ttattggtag gtaaaggctt actactatca tgttgttaat tgttttctga   6600
ttgttttgta gttcctttgt tgcttctttt tgtctcactg tcttccttg tgacttaata   6660
actttttgg agcaatttgc tttggttcct ttctctttat gttttgtata tctactacag   6720
acttttttctt tgtggttatc atgaggttta cataaaatat ttcatagtta taaccatcca   6780
ttttaatctg gtaacaactt tgactgcatt taaaaatact gtatttaac ttctcctcct   6840
cccacatttt attattcatg ccatagttta tatcttttgt atgttgtgta ttcattagca   6900
aattgttgta gttatagtta tttgttaata cttttgtttt ttaactttta tactagagtt   6960
aaaagtgact gttgcacaat aacagtattg gagtattctg tatttgactg tataagaata   7020
cctttaaatag agtttattc tttcatttgt tttcatgtta gttagtgtcc ttttgtttaa   7080
acttgagaat tcccttttagc attttttgta aggcaggttt aatggtgttg aaatcccaca   7140
gcttttattt gtctggtgat atgattttgtt cctgaacttc cacccaaatc tcatctcgaa   7200
ttgcaatccc caggtgtcaa aggagggacc tgttgggaga tgattggatc acgaggtgtt   7260
ttccccccatt atgttctcat gatagtgagg gtgttctcat gagatctgat ggtttaaaag   7320
tggtggttac ccgtgcgcac atgctctctc tctctcctgc tgccttgtga agaaggtacc   7380
tgcttccccct tcaccttcca ccataattgt aagtttcctg aggcctcccc agccatgagg   7440
aactgtgagt catttagacc tcttttgttt ataaattacc cagtctcagg tgatatcttt   7500
tagcagtgtg aaaataaaca atacagagaa ttggtactgg cagagtgagg tactgctata   7560
aagacaacct gaaaatgtga aggcaacttt gaaactgggt aacaggcaga ggttggaaca   7620
gtttggaggg cttagaagat aggaagatgt gggaaagttt gaaacttcct agagacttgt   7680
tgaatggttt tgaccaaaat gctgatagtc gtattgacaa tgaagtccag gctgagatgt   7740
tctcagatgg agacgagaaa ctattgggaa ctggagcaaa ggccattctt gctatgcttt   7800
agcagagact ggcagcattt tgccctgcc ctagagatct gtggagcttt gaacttgaga   7860
gagatgattt agggtatctg tcagaataaa tttctaagca gaaaagcatt caaatataac   7920
ctggcttttt ctgaaagcat acagtcaagt catatgcgtt cacaaagaga tggtatgaaa   7980
ttggaactta tgtttaaaag ggaagcaaag cataaaagtt tggaaatttt gcagcctgac   8040
catgtggtag aaaagaaaaa ccaatttttct gaggaggaat tcaagccggc tgcagaaatt   8100
tacataagta atcaggagct gaatgttaat tgccaaacaa tggggaaatg tctccagggc   8160
atttcagagg tcttcaaggc agcccctccc attacaggcc cagaggccta ggagggaaaa   8220
atggtttcat gggccctgct gctctgtgca gccttgggac ttggtgccct gtgcccagc   8280
cactccagct ccagctgtga ctaaaagggt ccatagctca ggctgtcgct tcaagggtgc   8340
aagccccaag ccttggtggc ttccacgtgc tctgggtct gcgagttcac agaaaacaag   8400
agctgagctt tgagagcctc tgcctagatt tcacaggatg tgtggaaaca cctggctgtc   8460
caggcagaag cctgctgcag ggacccagcc ctcatggaga acctctatta gggcagtgca   8520
gaggtgaact gtgggttgg agcccacaca cagagacccc actggagcac tgcccagtgg   8580
agctgtgaaa agagttcccc catcttccag atgccagaat ggtagatcca ctgactggaa   8640
agttgcaggc actcagtgcc gggccatgaa ggcagccgta gggctgtac cctgcaaagc   8700
cacagggaca gagctgccca aggcttaac agcccacacc ttgcatcagc atgccctggg   8760
tgtgagacag gggctccaag gagattattg tggagcttta aaatttaatg acttccctgc   8820
taggttttgc atatgcttgg gacctgtggc ccctttattt tggccaattt ctcccatttg   8880
gaatgggaac atttacccaa ttcctgtacc cacattgtgt tttggaagta actaacttgt   8940
ttttatttt aaaggctcat tgagggaagg gacttgcctt gtctcaaatg agactttgga   9000
ctcggacttt tgggttactg tggaatgagt taagactttg ggggactgtt ggaaagacat   9060
cattggtttt gaaatctgaa aaggacatga gatttgggaa aggccagggg aagaatgata   9120
tggtttggct ctgtgtcctc atccaaatct cgtcttgaat tgtaatcccc acatgggatt   9180
acatgggagg ggcctggtga gaggtgattg gatcatggag gtggtttccc ctgtgctgtg   9240
atctcatgat agtgagggat ttaaaagtga cagtttcccc tgcacataca cactctctct   9300
ctcgtatcac cttgtgaaga aggtgtctgc ttcccctctg ccttccatcg tgattataag   9360
tttcctgagg cctccccagc catgggtaac tgtgagtcag ttaaacctct tttgtttata   9420
aattacccag tctcaggtag tatctttaca gcagtgtgaa actgactaa tacatctggg   9480
aaattctttt tgtctccttc ctttctgaag gacagctttg cctgatatta tattcttggt   9540
tgccaggttt tgtactttca atactttgaa tatatcatcc cactctctct tggcctacat   9600
gatttctgct gagaaatcca ccaataatct tatgaagctt cccttgtatg tgaagaattg   9660
cttttctctt gcttctttga aaattctctc tttgtcattg tgaggatttc cttttcttt   9720
ttttttttt agatgagtc tagctctgtt gtccaggctg gagtgcagtg tgcagtggcg   9780
caatctcggc tcactgcaag ctccgtctcc tgggttcaca ccattttcct gtctcagcct   9840
ctggagtagc tgagactaca ggtgcccacc accacgcctg gctaaatttt tttttgtattt   9900
ttagtagaga tggggttca ctgtgttagc caggatggtc tcgatctcct gacctcatga   9960
tccacccatc ttggcctcc aaagtgctgg gattacaggc atgagccact gcacctggcc  10020
gaggatctct ttatatttaa tctatttgga gttcttttgg gcttcataaa tctggatgtt  10080
tatttcattt atgtctccaa attttgagag ttttctattc ttattttttt aaataagttt  10140
ctgcaacttt ctctttctct acttcttctg gaactcttct aatgcatatt aattttctta  10200
acagtgtcct ataagtcttg tcagctttct gcaattttta tcattccttt tattactctg  10260
actgggtaat ttcaaatgac ctgtatctga gcatgctgat tcttttctct gcttgatcta  10320
gtctgctgtc gaagctgttt gtgaattttt tcaattcagt cattttgttc tttagcttcca  10380
gaatttctgt ttcattcttt tttatggttc ctatctatct ttttgttgaa cttcaattt  10440
tgctcatgta ttgttttcct gattttgttt actgtctatc tatattgttt tgtagcttat  10500
tgagcttct taaggcaatt attttagct cttgtcatgc agtaaagatc tccatttctt  10560
tagggtcacc tcctgctgct ttattccctt cctttggtgg tttcttgttt cccgattat  10620
```

```
ttgtgatcag tgtggccttg cactgaagta ggcacctatt tcagtctttta catactagct   10680
tcagcagaga aagccattca ctagtcagat tgaccagaga ttgttggtgg gctgtctgtt   10740
ggggtctatg cacaggattt ctgctggagt tctaaggtgg gaaggctgg attctgggtt   10800
cattcactgt ggttgtctgt attctgtgca caaggactgg cttgaagcat ggatccttgg   10860
gggctgactt ggcactgaaa tgagccttaa gcctgcgtct gcaggggca gcctaacatg   10920
gggatcacct ggcacctgag ttcatgggga taggcctgtt cctgagttta ttcaggctgt   10980
cctgggaaca aggtccactg gggtgagccc agcatctggg tccacatggc ccagcatgga   11040
gccaagatct ctggaggctg acctggtgct ggatctgcag gggatggcct ggattctagg   11100
cccatggtg ccaacttgga gcctggggtt gctgggcta acgtggaggc tagatagagt   11160
cttgggggcc aggctagagc tggagcaggc ctgaagtcta ggttttgtgt ggccatcttg   11220
gagcctgaag ccccaggggc tgacctggtc tggggtgagc atggggctga ggccacagag   11280
gctggtctgg cctgtggcag gcctgaatcc tggtgctggg gttactgga gtgggcttgg   11340
tgcttgggat ctgtggtgaa gttaggttct atcttaactg tccctcctcc atgcaagagg   11400
gcatctctct ccatactgtg ctgcccaggc ttgaaggtga gatgacaccg gtaatgtgaa   11460
attgtccttc ctatacactt ctatgtgtct tttcttattt ctgtgctgca accaggtggc   11520
ataacctctc acctgattcc ttagctctag tgaagttatt ttcgtgcatg gatacttgtt   11580
cgaattgatg tttctgcaag ggatgagcgc tagaaactcc tgttctgaca aactcctatt   11640
cctattcttg ctgacatcac tccctgaaat agttaatata cttaacagct gaacacggat   11700
aggatgttca tggaatatgt tgacaggaca aaaagttgaa actgttggca gaaacccaaa   11760
gtcaatattg aagccaagca aaatattgcc tgcagtgcca cattagaaca gcttgaagac   11820
cgttcatttt taagtgacaa gagactcacc tccaagaagc aattgtgttt tcaggtagca   11880
aattttttatt attctgattg tttccaaata aactataatt tttaagtata atttttttact   11940
ttatgagaaa attaatcatt tatattctaa tttcctgagt atgtagagag tatagataat   12000
gttcctttat gtagaaatat ttaaatgtaa gatgattta aatcagaaag aatatttgat   12060
tgatttaaaa ttttttaaatg ggctttaata ttttcagagg ttttctttac ttagggattt   12120
tggactgac attattgcca ttatttatta attttgtttt tgcccaaatc aagaggtttc   12180
ataattgttt actctctctc taccaattcc ctttccaaca ttactagcca cagagttggc   12240
caatgaacaa taaacacaac agtagtctgg aggtctcaat ttgtatcttg ggaagcatta   12300
taaattttcc aactccctag acacaaatgt accaaaaaaa aacccttgtt ttctatacca   12360
gtaattgtgt gcttttgtctt gcaattcaga catttacaag aaaatctaaa tcaccttaaa   12420
ttaagattta tgttaaatgt ggtctaaaac cagcagagtt atgtattgtt ttctttttta   12480
gaatgatttt attcaagcaa gcaacttatt tcatttcctt gtttgctaca gtttcctgtg   12540
gtaagtgaat tatctataaa acatggaatt caggctaaga caggagtagc caagcaagtg   12600
gcaccacccc tggagaaagc tattgaacat acagcttcgg gggtggagat tgtccctgat   12660
gattcaggac acgtgtctat ttaatgttcc acaacaagga ccacttgtca ggtatattgc   12720
tgtagacata tgttgcagac cagaggaagg agctcagaag taggaatgtc ttgggacttg   12780
tgttaacaaa aacttctgtt cgcagatgac actctgcaaa gcaaaacttg aaacaaaaaa   12840
aaattagtcc tctatttta ttatcaacag taaaaaatta aacttttatct gaaaattcaa   12900
aagagtgcta ggcattttat agtgtctggg tccaatccaa gtatctgtta ggaacaccat   12960
acatagtttt actctggacc gctagggaac catttcaaaa atgaaagtaa ctggtttaaa   13020
tttaacttag caaaccatgc atttggatag ttctaggtga atagctttca acaccagatt   13080
tagatctcat ttctctatta atttcattaa tttttggaga ataaaaatga ttctggacat   13140
ttcattaatc attacagagg gagtttttctc tgtgtcccca caaggcatga tctgggtct   13200
atggtgactt aagagggcca cacaacaatg agtatttaat tttcctcaga tgtatggcta   13260
caataaacat ctataggtaa ggtttacatt cataaagaga ccttttttttt tccaggaaaa   13320
aagactttta ttccccctaa atcacaactc ccctgtgtct gtccctcaac cctgattctc   13380
cttctaaacc gtaatttaca aacccatgtg caaacccact gaaaggtgag aaggagcata   13440
agccagagac actgggaacc acagccaact acaggggtt tttcatttttt ttgttttgtt   13500
ttgtttttttg gcaaaataaa tcatgattat ggctaggaaa atcagggatg taagtaagca   13560
aaaatttaga aactacatat tgcatgtagt ccccaaattc agaaacagtc atcgttaaac   13620
atcttttatt tagtctttca gatatttttc tacatataccc tatttgcaca tttcacaaaa   13680
aagagttatt aactgtggac actctttgac ttgcattttc cacttatagc tatcttttgg   13740
tgcaaataag taatatattt tggagcttgc tattcttctc ttttttatggt attttttgtgt   13800
gcacattctt atgctcttat tcagttattt ctgtagaata caattttttga aataaaaata   13860
ctagattcaa aggtgtgaat attttttgaag gttttgtggt gtggtatcat gaaattaggt   13920
ttcagaaagt ttactccata gttgacttttt tctaccagct aataagagtg ctcatttacc   13980
ccacttaggc caactctaac aggcttctgt tgctttgcat cctgacatat ttatctttct   14040
ggaaacagtg tcctaattta tttctgcaga gctactgcct tcagttttg gtccatgtgg   14100
ttctggtgac cctgattctt ctgctgaacc agaaagtgca cacatcctcc tggctgtgt   14160
gacccaatca gagccaacgt cttgcaatga agcttttctt tagacatcta gaaataagac   14220
tcttatgttt tttttttcca atttgacttg aaacttaaga caatacacag gcctgagttg   14280
ttggtactat tttgctacta cgtggagctt gagagtaatg gtaacaccaa gactggagca   14340
agtggaagga gacatattgt ccactgatgc tatcagttga gcacaatgtg cagttacttt   14400
ttaagccaga ttcaccatgg gcttttttggc tcctgaacca atagattttca tttgttttca   14460
agccactttg tactaggttt tccatcattt gcaatcaaaa ccagtataca aacactggtt   14520
atttaatttt tcattttgc taatctcagg gataaaatgg cttctagttg ttttaacttg   14580
gctatatttg tgattcttcc cattttcata tacttactaa tcacttctat ttcttttgta   14640
aattatcttt ttcatatttgt tatctaattc tttaaatttt gagtacttta attctcatta   14700
ttgtttgtgg aattgttaaa caagactgaa taatctgccc aaagtccatg gacatgggg   14760
cccatgtaaa agctttgaaa gccaccatca ttatgagata aattatataa tagtacttta   14820
cataggctcc aaaatacagc acagacacag ctatcattgt catggtcatc attatcatca   14880
tgatcaccaa cttatgagga taagcaagaa cacctactag aagtttcttt ccattcagca   14940
acaaaattgg tgtcttttcta gtcactccct tccctgactg tcacatagca gttcacagag   15000
gctcagttgc agaatgagaa gctctgggcc aggacctgcc attgtatgca tccttgcatg   15060
ggaactgggg gctggaagag gagtgactgc ttgataatta tgagtcagtc aaaaccacca   15120
actgtctgaa aaaaataggc cttttttgtaa ctagtattgt cactaaacca actcctccat   15180
gttttgtgca tacatgaaat ctaggcaata cacttgtatt cccaaaagct tccacttgaa   15240
gagatctgtg ctctttccaa atataaacct tacccgagag tggtcatct tggccacacc   15300
tcagagaggg agagaggcag tcttgttggg ttgggtggtc ataatgggc tcagggccaa   15360
```

```
atccccaggg ggtaggatag tgcagagaag atggcactct ccagtgctta ataaaatgca  15420
cgtggtctaa gctgcccact ccctcaaagg caataaaaaa taggtactat ttaaattgaa  15480
gagtaactac tgcccagggg aatggacagg ttgtcattgg aatagccatg gttaatggtc  15540
ccagttgaca actgaaatga atgtgctacc tgaacaggaa agcttattaa ccagatttca  15600
aagacagtct ttcccggtaa atccaaattt acaaattaaa gccagtaaag acaccgaatt  15660
ctctaataat atgtgggggtg cagtatattt tagagctggg aataattcca aacagcaaat  15720
agttcaaaat ttattttcaa tttagcatat gcatgcattt gcttaaactg tcttaaaaat  15780
gagtaaaaaa tactgtcagt ttgtttcaat catactgaga tgaggaacaa tgtttagcat  15840
tgcatgctag aaaaggacac aggattggga gtcagggctg ggtgaccgtc acaggacttt  15900
cactaactgt gtggatcttg ggcaagtctg tgtgccctga gactcagtta tttaactttc  15960
ttttaaaaaa catagtccag atgcagataa caaagcctgc ctctaatttc ccttacagaa  16020
ttgtgagaag ctggtggaga tgtttgttac aaaagtgttt tgaaaataga gcaaatatta  16080
ttcttttaa ggcatgatgt tttcatagca tgtcaggcaa caggaaaaaa ctaagttagg  16140
attttatttt attgtgggga atttatgtgc aaattattgt gcaatttaat gaaaataagc  16200
caatgtttta tacagaagta cccagaaaat taaataacac tatacattgt tcaaatagtt  16260
gccttaatat attttatttt ctcagcataa ttagagttgt attatacagg tctttgagta  16320
gtcagtcagt gggagaagtt aagacaacag atatcttttt attaaaatta ttatatgaat  16380
tatcgcaaat taattttttat ggttctgtca caggatgtct gactcaactc tatgaaaacg  16440
ccttcttcag aggtggggat gtagcttcca tgtacacccc aaatgcccaa tactgccaga  16500
tgaggtgcac attccaccca aggtgtttgc tattcagttt tcttccagca agttcaatca  16560
atgacatgga gaaaggtaa aagttggtat ttcattattg gagaagctgt ttttcaaaac  16620
tgaatcagtt ttgtgcagaa aggtgtagta taactgagga ttcttcctca cacggggttc  16680
aaggaccagc ttcagcaaaa tcccgtcaag tggttcttac aaatgcagat tcctaggcca  16740
caacccagat ctgctgaacc aaagtttctt gtgaccagga atctgcattt taaacaatca  16800
ctgtgtttct ttaaagtagt agaagctagt cattttctat tcaaagcctc aaaatgcttg  16860
aatatcattg ggctaaggga ttgtctcaag aaagagtcta acagtgcac atttcatctg  16920
aataaagaaa cagatttaac tgtgtgaccc atgatcacat tagcggatag cacagtccaa  16980
agaaaataac ataagacaag cattttgctg agaatgtaat tgagaaagat ctagaacttg  17040
tgattttggg acagggcagt tctaaatggg gcctatagtg agccagtttg ggcacctgtg  17100
gcatgatgct atgtatggtg tgtgtgtgta tgtgtgcttg tgcttgtgtg aaatatgtatt  17160
attaactgga aatttgtaaa agtattggaa aaatagtact tacgattttg tgtgtgtgtg  17220
tgatggagtc tcgctttgta gcccaggctg gagtgcagtg gcgtgatctc ggctcactgc  17280
aacttccacc tcccaggttc aagcgattct cctgcctcag cctcccaagt agctgggatt  17340
acaggcagtg accaccacgt ccagctaatt tttgtagttt tagtagagac ggggttttcac  17400
cacattggcc aggctggcct tgaactcctg acctcgtgat ccacctgcct ctacctccta  17460
atgtgctggg attacaggca tgagccaccg cacccagcgg taattacaat ttttattagg  17520
tcagagagat gcttattaat cacgagccac agtttcatct taatgatttt tccttttgat  17580
taatatccag agtaagcttt tctttgttgt tcccatttcc atgttcataa ctcttttactc  17640
atcttcactc tatgtgagtt taccaactag aaattggata gtcattctct gatcccacat  17700
gttaaacttg tagagaaaac tcagattgta tgtgaggatc atcatattaa aagtggagga  17760
aggttctaga attcttataa ataatgaaat taacatgaag gtggacatct aagacagagg  17820
gaagtcttcc attaagtgca gactacaagg agttaataag caagatgaac acgatataca  17880
aatccagctc ttatcactaa gttaactttt taagtaaatg aaagtatttg caaaagtttgt  17940
taccaattga gaacatagtt gcctgaaagt ttaagaacac aggaaaaatc attaactctt  18000
taatatggtt gatttcctgt acttaaaaaa tgtgagtgta aagaaaacgc agtgatggag  18060
ttagatatta tgggggtgtta taaaattagc tctaagagtg ttcttttccag caagtattgg  18120
ggaagctata ttatttttcct tattcctggt tttatttgtt agtgtgtaga aaatgctaga  18180
cattccctca atgtatgttt attattctac ttcctaagta aagctacttt taaaataggt  18240
ttggttgctt cttgaaagat agtgttacag gaacctgcc aaaagtacat cgaacaggtg  18300
cagtttctgg acattccttg aagcaatgtg gtcatcaaat aagtggtaag ttgtgaattt  18360
cttagctaca ttgagttaa tattggatct cgcttagaac agcttttgct caaagtttgt  18420
actgctacag cttttggaa ggcatcactc ataaagatag gagatggggc agtattctgc  18480
acacaaaaga gggacccata ttcatctgga cacttctatt gtctttataa atcaacacat  18540
acttaatgag cctctattat ttatgaggtt agcgctcaag tgtaagattt gcagaaaatg  18600
aatcaaata attgtgtctc gtttccagat aagaattttt agaaaaacac aagggaacat  18660
ctctctcaag ttcacttgag ggtaattttt acatcagtga ttctcaacca gcagtgatttt  18720
tgtctcttcc actggggaca tttgacaatg tctggagaca ttttttggtgg ctacaactag  18780
ggaggatgct attagcattt actaagtaga ggccagaatg tttgaatgct gaccaacatt  18840
ctacaaggca cagggcagtc gtccacagca aataattttc tggcccaaaa cgtcaacagt  18900
gctgacatca agaaactctg tgatatacca ctaggcccaa attgaagaac tgagttctgc  18960
aaatcttgct aagaataata cttcctaaag gaaacttgag gactaggatg ctagagaact  19020
ttgattctga catctgaagc tactgatgtc ttgggaaaca gtttccaatg ctatcctaat  19080
aaatttaaga caaatgaact atttctcaaa catgactggg actgataaga aagtgaaaag  19140
tgctgaaaag attcaactga tgggttgtca gaatcttaaa ataactgctg ttattctatg  19200
tatgactata tatcattact attttatttt cattatgcac aattaatttt gtaggttcaa  19260
atttcagatg ttttttaaatt tgtcatcctt tcctccctca ttgatatcac ctcttcaata  19320
cgtacacact ttgagcctgc tgtttgcatt ttaaccagtt atcaaaggat ggcaatgcct  19380
tcattataaa tgtgggcctg acttagccag tataataggt gtagtctacg tgaggtggag  19440
tacatttcct attttaaaag atcaattttt atgttaatcc aatttggtat aaattattcg  19500
agtaagtgct atttctgatt gttgtatctt gtagcaaaat ttaaagaaaa agtaatttgt  19560
gcctttctca atattcctgt tatttgttcat gtattctaaa actcactgtt actcacttag  19620
cttgcttta atgtttttta aagtgaaaaa ttgttcccaa gtacataaaa tctctacact  19680
caagaacaat tctagtcaaa agcatttaga gcttccgtat gaacacttaa agagttttta  19740
tttgtaagag tcgcatccca actcttagcc tgttctttttc tcacatgcag aaaaatagga  19800
aagagacttc gtttcacacag tctgcaaatt cctgtgtttta agaaccacag tgaataatcc  19860
acctccctgc ccaactcatc gtactgtcat atagtttttcc tgcagtttg tgtatttttct  19920
gtctttccca ccccttaaatt tagttttatg acttcaacca tacttcttag gagtggaaag  19980
gtatctgtat tagattatgg tttattccac ataatcttgg ggaataaaac tttaaaaaag  20040
tatacagttt atacttctgg ttacattact tccttaacca aaagtctaac caagaaattt  20100
```

```
gaatctttaa aaaaaaaga ggccgggcgc ggtggctcac gcctgtaatc ccagcacttt    20160
gggaggccga gacgggcgga tcacgaggtc aggagatcga gaccatcctg gctgacacgg    20220
tgaaaccccg tctctactaa aaatacaaaa attagccggg cgtggtggcg cgcgcctgta    20280
gtcccagcta ctcgggaggc tgaggcagga gaatggcgtg aacccgggag gcggagcttg    20340
cagtgagtcg agatcgcgcc actgcgctcc agcctgggcg acagagcgag actccgtctc    20400
aaaaaaaaaa aaaaaaaaaa gagcctaatt ttgcttcact gtctgtgaaa agaattatct    20460
gtatctttg catgtaagac aaatctcaat gaaaagggtg cttaaataga agttaacact    20520
atttaaagc aagaatggaa gtggtttcat catgcgtaaa caacaactct ccacattttg    20580
taatgattga tctggatgca atttgtcatc agacaggaga agtcgaaagc aaagaaataa    20640
cactgggaga tagagaagct cttttcattca atgcgaaagg tcaaaggcac atcagtttct    20700
ttaataatgc aaacctcagc acacattatc agtgtcctca ttattattgc cttgtttatt    20760
tcccactgct cattgataat ttcaacgtga aatttacctg tattgctgca tgcatcttgc    20820
agtttaagaa gtgaagtaac ccaatttcaa agctagtgct ttagggaaaa tattggattg    20880
tatttacttc aagcagagtt cgataattta tgtacataat aaaaattta aatccctag    20940
ttaatatagc agttgccaaa actgggctat tatcattcta aactaccaac ccaaatggta    21000
gtgggtatct aatctacctc tagaaagaaa atggactgta tttgctctat gtatttttct    21060
tgtacagctt gccatcgaga catttataaa ggagttgata tgagaggagt caattttaat    21120
gtgtctaagg ttagcagtgt tgaagaatgc caaaaaaggt gcaccagtaa cattcgctgc    21180
cagttttttt catatgccac gcaaacattt cacaaggcag agtaccggtg agtacaattc    21240
aaggtgtgtg ttctttgtat tggtgcctcc aggatttcac tgtattcttc ttaacctctt    21300
ttgttcccaa actaaaaacc aaacagggct tttattctaa ccactttcct catttactta    21360
ctctatttta tttttatttat ttatttattt attgagatgg agtcgcgctc    21420
tgtcgcccag gctagagtgc agtggcgtaa tctcgactca ctacaacctc cgcttcccgg    21480
gttcaagcga ttctcctgcc tcagcctccc gagtagctgg gattacaggc gtccgccacc    21540
atgcctggct aattttttgta tttttagtag agtcggggtt ttactatgtt ggtcaggctg    21600
gtctcgaact cctgatcttg tgatccaccc acctcagcct cccaaagcgc tgggattaca    21660
ggcatgagcc actgcgcctc gcccttcatt tttaattaa ataattcatt taatttcatt    21720
tgtttctcta ctcttttccc ctggcatgta attgtaccgc atcttcaaag cctgacatcc    21780
tcttcccctaa ctttctccaaa gctgattctt gcaggtcttt cctcaaatac cgtcccctcc    21840
aaaagcccat ttctgagcat tctctcttaa gtcacactca gctctgttta tttcattcat    21900
agagctaatc acaatttgat attaacttgt gattttttc cttatttta aatcttattt    21960
ttatttgcat agatgtatgg ggtacaagtg taatttttgtt actttgatgt attttacagt    22020
ggtaaagtct gggcttttgg tatatccatc actggagtca tgtacattgt acccactaag    22080
ctatttttca acgcccgccc ccttcccacc tctctgtcac cttcccagtc tctactgtct    22140
atcgctccat gctctactca attttggtgt cattttttcc tgaagcaaaa ttttggtgtc    22200
atttttctg aagtcatttt ctgaagtctg tgtcattttt cgctttcctg aagcgaattt    22260
tggtgtcatt tttcctgaag ttccgtttgc cccacacata ggccttgctt atagaatgag    22320
ggtttagtgt cacggagtct cctgcctcat tctcaccccta acttttcctt tacccctttg    22380
cgaggggaag gatgtccatt aggttaataa tgcagaccec taacccactc attatcaggg    22440
tcattgtttt tccactgtgc attttaatac taactgttac ctgcactgct ccctgccct    22500
caaagtgcag aaagcaaagt aacctctttt cttcccattc aggaacaatt gcctattaaa    22560
gtacagtccc ggaggaacac ctaccgctat aaaggtgctg agtaacgtgg aatctggatt    22620
ctcactgaag ccctgtgccc tttcagaaat tggtaattgt aggactactt cactttgtaa    22680
ttgtggtagg tggaatagga gccccccagag acgtccctgt gctgagccct gggacctgtg    22740
cgtgtgttcc catagctggc aaaagcgttt ctgtcaatgg catgcagtta cgggcttcga    22800
gatgggagt ttactctgga ttttctgaat gggcccaatg tactcacagg gttgagtgct    22860
cacaagcgctc ataagaaaaa gagagaggcg gaaggctgaa agcagagag agaggtttga    22920
aggtattaca ctgctggctt tgaagatgaa ggtccgtgag ccaaggaatg caggcggcct    22980
ctagaagttg aaaagggcga ggaaagagtt tccctgtgga gcgtcctgga ggaagaagcc    23040
ctgctgatgt cttgatttta gcccagtaag acccaatctc tagaacagta agataattaa    23100
tttgtgttgt ttttaaccac taagtttgtg gttatgcccc tagagcagca gttataggaa    23160
actagtacag tgatactgtt agagttatag gacagtgata taggacagtg atactgtat    23220
agttataggaa aactagtaca gtgatactgt tagagttata ggacagtgat ataggacagt    23280
gatattgtta tagttatagg aaactagtac agtgatactg ttagagttat aggtacagtg    23340
atattgttat agttatagga aactagtaca tacaggtaca gtgatataggg    23400
acagtgatac tgttagagga aactagtaca gtgatactgt tagagttata ggtacagtga    23460
cataggacag tgatactgtt atagttatag gaaactagta cagtgatact gttagagtta    23520
taggtagagt gatataggac agtgatactg ttatagttat agaaaactag tacagtgata    23580
ctgttatagt tataggacag tgatatagga cagtgatatt gttatagtta taggaaacta    23640
gtacagtgat actgttagag ttataggtac agtgatatag gacagtgata ttgttatagt    23700
tataggaaac tagtacagtg atactgttag agttataggt acagtgatat tgttatagtt    23760
ataggaaact agtacagtga tactgttata ggtacagtga tataggacag tgatactgtt    23820
ataggaaact agtacagtga tactgttaga gttataggta cagtgacata ggacagtgat    23880
actgttatag ttataggaaa ctagtacagt gatactgtta gagttataggt tacagtgatt    23940
taggacagtg atactgttat agttatagga aactagtaca gtgatactgt tatagttata    24000
ggacagtgat attgttatag ttataggaaa ctagtacagt gatactgtta gagttatagg    24060
tacagtgata taggacagtg atattgttat agttatagga aactagtaca gtgatactgt    24120
tatagttata ggacagtgat ataggacagt gatattgtta gttataggt aaactagtac    24180
ggtgatactgt ttatagtttat aggtacagtg atattgttat agttatagga aactagtaca    24240
gtgatactgt tagagttata ggtacagtga tataggacag tgatattgtt atagttatag    24300
gaaactagta cagtgatact gttatagttg taggacagtg atattgttat agttatagga    24360
aactagtaca gtgatactgt tagagttata ggtacagtga tataggacag tgatactgtt    24420
atagttatag gacagtgata ttcttatagt taccgtggta tagttatagt taaaggtaca    24480
gtgatgttat taggtacagt gatattgttat agttataggt acagtgatat agttataggg    24540
tacagtgata taggtacagt gatattgtta tagttatagg acagtgatat agttatagga    24600
cagtgatatt gttacagtta taggtacagt gacgttgtaa tagttatagg acagtgatat    24660
tgttatagtt ataggtacag tgatgttgta gcaaactgt aaggtcattc cttggttgtg    24720
tccctatcta gtgaaatgac tctaccaggg gtagggaaat aaaactctgt cgtttcacac    24780
ataaaggtaa tttcaatgga attatccaga aaattgccat gacattccac ctcatttagc    24840
```

```
atgtcaggat gttaatgaca agatgttact aaaagcaaat cccttacggc cagttttccg  24900
cagtactggg tgctggctct gtgcctggcc ctgtattggg tgctgggcta ggatttccct  24960
gtggaagatt gggaaggttg gttacaaggt ggctattttc ctgtctcctc tttgcgacag  25020
cacaccttcc ccatggtgtg tgccaggttc acgtgtactg gtgatttaat tttaacgttc  25080
atattatttt tttctgggag agttttttgaa ggctgccagg aggcaggact cgatgcaaac  25140
atgctccatt ctgtacccag ccctgttgct ggaaggattt gctgcactta cccagggaac  25200
aggcaagctc gtgctgtggc tctgggctgt cacagctgct gtccacacct gggagagcac  25260
cctggatggc tcatctgtgt acttgctttc ttgttaaatt gcagtgagtt cacatgtgat  25320
ttaatcggat caaatggcct ttacagactg ataaaaatat ggctgtttca ggtggtgttt  25380
tgagctgcta agggcgtggc ttttcactga gtacgtggtc cccgttcctc agggaacacc  25440
cagtagccac atgcctccta aacctagagt agggctgtct cctggcctaa ctgcccaaat  25500
gagattcata agttagggat gatctgtagt tatcactaca gatttgtcct tggtttcacc  25560
aaggattttc ctaattttac aaacaaaacc cctaaggctc ctggaaggag ggtagaagtg  25620
aaggtgctcc gggggcaaca cagctgatga gctgaaccag aactcgaccc ttgggtcaca  25680
cacatttcac agtgctcact ccacccttttg ttttttttaat ggatttaatg gtgttttaaa  25740
gcctcctgcc tctcaacaca tatgaattca ttatatttac agatttcctt ctcttgtggt  25800
ccatcttcct gcatagatct tgagagatgt caggctaacc acgtttcctc agttaattta  25860
acaaaaccat ttgcaactct gacatgaaaa attcctacca tgtgacttat taatttatca  25920
attgagatgg tacacatatt ttcaagccaa aaggaggaaa acataaattg gaaaaaaaag  25980
gtttttttat ttttatcacc tctggggaag aaagtctgat aaacgaagct ggttgataaa  26040
attgcaatta ggggaagcaa catcatggtt tctgttcgga ggctaaccag atggcatact  26100
tgaaatagag aatgtcctag aaatcaactg gttgcttggc caaaatatct ataaatagtg  26160
cccaacatat tagataggaa aagcaaagta aaaacaattt taacaggtta ggacattggg  26220
ctgaagtatt gcatatattt aatgtcatgt gcgtccgtgt gaagagacca ctaaacaggc  26280
tttgtgtgag caagaaagct ttttaatcac ctgggtgcag gcaggctgag tccgaaaaga  26340
gagtcagtga agggagatgg ggtggggacg ttttatagga tttgggtagg tagtggaaaa  26400
ttacagtcaa aggggggttgt tctctgcgg gcagcggtgg gggtcacaa ggtgctcagt  26460
gggggagctt ctgagccagg agaaggaatt tcacaaggta acgtcatcag ttaaggcagg  26520
aaccggccat tttcacttct tttgtctttc ttcagttact tcaggtcatc tagatgtata  26580
cgtgcaggcc tgggcccaga ggcctgacat tcctgtcttc ttatattaat aagaaaaaga  26640
aaacgaaata gtggtaaagt gttggggtgg cgaaagttt tggggtggt atggagagat  26700
aatgggcgat gtttctcagg gctgcttcga gcgggattag gggcggcctg ggaacctaca  26760
gtgggagaga tgaagctgaa ggaatatttt atggtaaggg gtgatattgt ggggttgtta  26820
gaagcagcat ttgtcatata gaatgattgg tgatggcctg gatatggttt tgtgtgaaat  26880
gagaaactaa atgaagaca caaggtctga ataagaagga gagaaaaaca ggtgttaaag  26940
gactaagaat tgggaggacc caggacatct aattagagag tgcctaaggg ggttcagtgt  27000
aattacttgc ttggttggtg agttttgggg ctctatcctt gacagagtcc tccttttttaa  27060
gttggaggct gagcttggtg aggtgtgttt ttaaaagacc attagtctgt tctaccttttc  27120
ctgaagattg aggatggtga ggggtatgaa ggtttactg aataccaaga gcctgagaaa  27180
ctgcttgggt gatttgacta ataaaggccg gtctgttatc ggattgtata gagatgaaa  27240
ggccaaactg aggaattatg tctgacagaa gggaagaaat gaccacggtg gccttctcag  27300
accctgtggg aaaggcctct accccatccag tgaaagtgtc tacccagacc aagaggtatt  27360
ttagttttcct gactccgggt atgtgagtaa agtcaatctg cctcctgg gcgggggcaa  27420
atccccgagc ttgatgtgta gggaaggag gggcctgag caatccctga ggaggagtgg  27480
agtagcagat ggaacactga gcagttattt tttgaggata gatttttacg acggaaagga  27540
aaagtgaggt tttaagaggt gggttagtgg cttgaactt acatgaaga gtttatgaaa  27600
tgatgacaga ataagatggg cctgtgaggc tggaggagat attttccttg gtccaagaat  27660
tatttgcctt gtgtgggaag agattgatag gtgaagttc caatggggga gtagatggga  27720
gtgacagatg aggaagaaaa aaactggctg tgagggatag aagttggaat gctcgctgct  27780
tttttagcta cccttatcagc ataggcattg tcctgagcag tgggatctga tgccttttgg  27840
tggccccttgc agtgaatggc ttcagcttcc tttggaagta aagtggcctt gagaggagtt  27900
tttattaaag aggcattaag atggagaacc cttgtgtagt gaggaaacct ccttcagccc  27960
atataaccgc atggtggtgc agaatatgga aggcatattt agagtcagta taaatattga  28020
cacgtagtcc ctttgcaaga gtgagggcct gagttaaggc aatgagttca gcttgctgag  28080
aggtagtgga gcggggcaga gcagtagcct cagtgataga tgtggaagat actacagcat  28140
agcctgcctt tgctggtgag tggtgattag gcctggtgga actgccatca ataaaccaag  28200
tgtgatcagg gtaaggaaca ggaaagaagg aaatatgggg aaatgagtg gatgtcaggt  28260
ggatcagaga gatacagtca tgggggtggg ggccagccta aaacagtaag gtcaagttgt  28320
ttgaacagaa aggctacagg gcgtgtcct ggctcttgtg taagaatttt gactgcgcag  28380
ccctgcactt cggctgtgtg taatgaaaag ggttgggatg agttagggag agctagtgtg  28440
ggagcagttt ctagggctgt ttttaaggaa tggcaagagg agtggctaaa ggatttagga  28500
tctttgggggt cagctagctt tgcttttgtg agtttatata atggtttagt caggatggta  28560
aaacttagta tccaaaggcg gaagtactta accataccta ggaagaaaag gagttgtttt  28620
gtagaagggg ttggggtttg ggagatgagc cagacaagaa cagcagggag agcacatgtg  28680
ttttcatgaa gaattatgcc gagataggta atggatgagg aagaaatttg ggcttgactg  28740
aagtaatggg ggctgtcctc gaagccttgt ggcagtacag cccaagtaag ttgctgaggc  28800
tgacgggtgt cagggtcagt ccaagtgaaa gcgaagagag gctgggatga agggtgcaaa  28860
ggaatagtaa agaaagcatg tttgagatcc agaacagaat aatggttgt ggagggaggt  28920
attgaggata ggagagtata tggctttggt accatgggt gaataggcaa gacaatttgg  28980
ttaatgaggc acagatcctg aactaacctg taaggcttgt ccggtttttg gacaggtaaa  29040
atgggggaat tgtaaggaga gtttataggc ttcaaaaggc cacgctgtaa caggtgagtg  29100
ataacaggct ttaatccttt taaagcatgc tgtgggatgg gatattggca ttgagcgggg  29160
taagtgtgat taggttttaa tgggatggta aggggtgcac gataggttgc caaggaggga  29220
gcagagtgt cctatacttg tggattaagg tggggacaca caagggaggg atgtgaagga  29280
ggctttgaac tggggaaagg gtggcattga ggtgtggctg tggcctaaga acagtcaggg  29340
aagcggataa ttgagttaaa atgcctcgac ctagtaaggg agctgggcag gtggtgataa  29400
ctaaaaagga gtgcataaaa gaatgttgtc caagttggca ccagagttgg ggagttttaa  29460
gaggtttaga agcctggcgg tcaataccta caacagttat ggaggcaagg gaaacaggcc  29520
cttgaaaaga acgtaatgtg gagtgggtag cctctgtatt aattaagaag gggatggatt  29580
```

```
taccctccac tgtaagagtt acctaaagca tctgtgatgg tccaggaggc ttctaaggtg   29640
atcgggcagc gtcagtcttc agccgctaag ccaagaagat ctgggaagca gtcagtcaga   29700
gagccttggg ccagagttcc aggggctctg ggagtggcag ccaggccagt tagacagtcc   29760
gatttctagt ggggtcccac acagatgaga cacagcttag gaggaatccc aggctgcggg   29820
cattccttgg cccattggcc agatttctgg cacttgaaac aagatcctga tggaggaggt   29880
cctgtaggaa tgcttgacca ctgcagttta ggcattttga agtttttgtg tgtgctggag   29940
atgtggctgg gttttgtctc acagcagagg caaggaatcg caactcagaa atacattgct   30000
acttggctgc ctctattatt gtacatcttg aaggcgaggt taattaagtc ctcttgtggg   30060
gtttgagggc tggaatctaa ttttttggagt ttttttttgt ttgttttttg gtttttttt   30120
tttaatgtca ggagctgact gggtgataaa atgcatattg agaataagag gccttctgac   30180
ccttctgggt ctagggctgt aaagcgtctc agggttgctg ccaaacgggc catgaactgg   30240
gctgggtttt tcatatttga tgaaaaagag cctaaacgct aactgatttg ggagaggtcg   30300
gataaataaa aaggaacatt aatcttgact atgcctttag ctccaaccac ctctttaaga   30360
ggaaattgtt gggcaggtgg gggagggcta gtcgtggaat gaaactgtaa gctggaccgg   30420
gtgtgaggag gggaggtgat agaaggatta tagggtgagg gagcagaggc tgaggaagaa   30480
ttgggatctg gcttggcctg gcaaggagca gcctggggag gaggggagag gtcagatggg   30540
tccatagaaa aggaggattg gaaagactca gcaacacttg gggttgggat tgagaggaca   30600
gatgggttgg gattgagggg acagatggga gggaaagaag gaagatttgg gacaagttgc   30660
attgggaaca gagactaggg agggaccaat gtgtaaaaga atgcctggac gtcaggcacc   30720
tcagaccgtt tgcccatttt atgacaagaa ttatctagat cttgtaggat ggaaaaatcg   30780
aaagtgccgt tttctggcta tttgaaacca ttgtcgagtt tgtattgggg ttaagcagca   30840
ttgcagaaga aaataaggca tttaggtttt aggtcaggtg tgagttgaag aggttttaag   30900
ttcttgagaa cataggctaa gggagaagaa ggaggaatga agggtggaaa gttgcctata   30960
gtgaaggagg caagcccaga gaaaagagag ggtagagaca tggagagaag gggtgggggg   31020
gtgcttgccc ccaggaaagt ggttcttgcc actaaggggtg aaggatcaag gcaggcattc   31080
gcgcggtgat cagataccte tgaaacgtgg gtgaataatc aagcaggtgt ccctgccagtg   31140
attaaacagc aaggaaagac tatcttccca agtccatgac cagtgccaga gttttgggtt   31200
catggataaa acgcgtctcc tctgtctcta ccagaaaatg aaaggaattg aaattaagag   31260
aagggagaga ttgaaggatg gcgccaagat tgaaaggaaa aagaggttga gggataggga   31320
gagaggttgg ataagagagt aaaaagaggc tgcttaccca atttaaaatc ggtgagatgt   31380
tccttgggct tgttggtctg aggaccagag gtcatgggtg gatctttctc atggagcaaa   31440
gagcaggggg acaggggatt gatttcccaa gggaggtccc ctgatctgag tcacagcacc   31500
aaatatcacg tgtgtccatg cgaagagacc accaaacagg ctttgtgtga gcaagaaagc   31560
tttttaatca cctgggtgca ggcgggctga gtccaaaaag agagtcagtg aaggagata   31620
ggggtgggga cgttttatag gatttgggta ggtagtggaa aattacagtc aaaggggggtt   31680
gttctctggc gggcagggt gggggtcac aaggtgctca gtgggggagc ttctgagcca   31740
ggagaaggaa tttcacaagg taacgtcatc agttaaggca ggaaccggcc attttcactt   31800
cttttgtcat tcttcagtta cttcaggcca tctggatgta tgcatgtagg cttgggccca   31860
gaggcctgac atttaacatg gataaatgta aagttcttag aatcatacat acactttgga   31920
aaagatgggg cttaatcgca cttttataaga cttgaaggat gtttgagaat cactatgaaa   31980
ctgctgaaaa taccaagaaa atttaattct tatgtatata aataatgtgt ctgttttaca   32040
tgaatccctt ctacaagctt ggtatttaat atggcatata ttgttttttc atagtagatt   32100
taaaattttt gatatctaat ttagataaca taaaattaac ccttttgaaag tgtacaactc   32160
cgtggttttt agtatatcca cctgattgca caacgatcac cactgtctag ttccagaaca   32220
tttttatcac cacaaaagaa aggctgtatc caggccgggc acggtggctc acgcctgtaa   32280
tcccagcact ttgggaggcc gaggcgggcg gatcacgggg tcaggagatt gaaaccatcc   32340
tgggtaacac ggtgaaaccc tatctgtact aaagatacaa aaaaattagc tgggcatgat   32400
ggcagatgcc tgtagtccca gctactcagg aggctgaggc aggagaatgg cctgaaccca   32460
ggaagcggag cttgcagtga gccaagattg cgccactgca ctccagcctg ggcgacagag   32520
caagactcca tctcacaaaa aaataataaa aataaaataa aaaaaaaaa gaaaggctgt   32580
cttcctcctt tcccattggc cgtctttctc cattccctac tcctccaatc ccctggccaa   32640
cactaaatct actttccatg tctgtggact tgactcttcg ggacattta cataaatgaa   32700
atcatgcaat gcagcacatt ttgcatctgg ctttttttcac ctggcgtgtt ttcaaggctc   32760
attcgtattc tagcatatat caatactttg ttcctatttta ggactaaata agattctatt   32820
gtatgaataa aacatatttt gtttatatac ttagtttgat gaacatttga gttgtttctg   32880
gatttttttt tttttttttt tgcctcttat gaataatgct gctatggaca acagtttttg   32940
ggtaggcatg catttttaaat tctcttatgt atatacttag gattaaaatt gctggatcac   33000
agagtaactc catgtttaac tttttgatga attgccaaac tgttttgag agcagctaca   33060
caatgttaca ttcttaccag caacaattga gggcttcagt ctctctacaa ccttaacaac   33120
acttgttatt gtctttgtaa ttattgcctt tctaggcagt gtgaagtggt gtctcactgt   33180
ggttttgata tgcatttccc taatgactaa caatgttgtg tatctttttcg tgtgctcatt   33240
ttcaatttga atacattctt tgggaaaatc tctgttaaaa tcttttggcc attaaaaata   33300
attgggttat tttcattgtt gagttgtatg aactcttat atatctgga tactacactc   33360
ttatgacata tattattttc aaaaattttc tgtgcatctg caggtcatct tttcacttta   33420
ctgatggtgt tctttgaagc accaaagttt ttaaacttga tgaaatccag tctggcttta   33480
ttcttgcacg tgctttacct aaaacgccaa aacctaattc atggtttga agattttgc   33540
ttatgatttg ttcttagagg tttatagttt tagctcttac atttaggcat ttgatgcatt   33600
ttaaattaaa ttttatatat ggtgtaaagt agcaatccaa cttaattctt gcatgtgggt   33660
attcagttat tccattgtct tgaaaccctt ttcaaaatca attgtctata aatgtaagag   33720
tttattttg gaccatcagt tctatcctgt tgacctatat atgcctatcc taatgccagt   33780
tacacacagt cttgattacc ataacttgc agtaagtttt gaactcagac agtctgagtg   33840
cttttatttt gtccttttttc aagattaatt tggttattcc ggatcttttg catttccata   33900
tgaatttag atggttgtc aatttctgca atagaaaagc agcaggattt tgatagagag   33960
tgcattgaat ctgtagacca atgagtatca atggaattat gtgttatcaa atttagtaaa   34020
ctacataaac gatatgtaca caactaaaac aaaactaaga tataagatca tattaatgta   34080
atgataataa aagtgggattg tctcctgttc taatttaat aggcacaagg cattttttgtt   34140
aatcacttct tattaaagaa ttttttataa tattcaggaa aatacaacaa aaaacccctt   34200
acattcctaa ggcctcagag tcagagtaat ataaggaaa tgtaaacaca tgctgagtaa   34260
tgcaagcatt tggcaatggt ggtgactgga gctgggagca cagcttttat ttctctgaaa   34320
```

```
taggaatttg cccccttagag ttagaccaat tttgccttcc tctaaatggc aaacagtttg   34380
gagatacttt aaaggacatt ttttcactta ggatgtttag tactatgaat aataaatagt   34440
cacaatttcc ttaactatgg tgacaaaata caagcaaatt tagcctcatg tcatttccta   34500
aggaacatct tctctctgtg agttcacagg ttgccacatg aacatcttcc agcatcttgc   34560
gttctcagat gtggatgttg ccagggttct cactccagat gcttttgtgt gtcggaccat   34620
ctgcacctat caccccaact gcctcttctt tacattctat acaaatgtat ggaaaatcga   34680
gtcacaaagg cgagtatgca tggaaaatcg catcacaaag gcgagtatgc atggggagca   34740
cttgctgctg tactttcatc acttttatag tctgagttct taaaagtttc gttcatttcc   34800
ctcaaaacac ttgaacctgc agtttcagta ggtactgttc tgccaggtgc agattagtta   34860
agagattagc agacttctct gcctatcttc tcttacttta aaacaaatgt taccattgaa   34920
tcaaggaagc aatagccatg agaaaaaaga aggatctgac gcctttgaat gaagattcaa   34980
aacatgatct tcatgttttg tattagcttg gagtaaaatc cacttgctgg caatatagcc   35040
cttaagcttg ttgcctcttc tctttgtttc agaaactaga gccctgttta ttctgatcaa   35100
ggctctggcc cactgtcttt atctcagata acccaccctc ttctgcacac agcatggagc   35160
taagagaagg gtgtcctagtt atgtaatatc atcggcagca taaattccca gaatttgttc   35220
tttgattttt ttgtttgttt ttccagttag aaggtggaac ttcatcattg tcctcttttc   35280
aggttgtctg tgcctattag ttttctccag agggagaggt ggcttgattt acatttaatc   35340
tctgcaattt attagagtcc tgtagttgga tttactttga agagagtttc ccagaagaat   35400
aaaatttgct gcgttgcttt ttgggtgtga gctgcttttg tatttgccta atgcctttaa   35460
tgcaaatttc tttctttctc tcttgctttt ttttaaaaaa aatagaaatg tttgtcttct   35520
taaaacatct gaaagtggca caccaagttc ctctactcct caagaaaaca ccatatctgg   35580
atatagcctt ttaacctgca aaagaacttt acctggtaat gtgatttgat aataatatta   35640
cataaaatgt aacctatttc atgactttta acagcaacag tgatgaaaca atcctcaagg   35700
taacagaaac ttgtgtaaat gtcgttcatt gcttttccca tctgatatct ttttgtgttt   35760
ataattgaca cagaaccctg ccattctaaa atttacccgg gagttgactt tggaggagaa   35820
gaattgaatg tgacttttgt taaaggagtg aatgtttgcc aagagacttg cacaaagatg   35880
attcgctgtc agttttttcac ttattcttta ctcccagaag actgtaagga agagaagtaa   35940
aggaaatttt atttttcaaa gacagttgac atgaccattt catattctct ttccccctgt   36000
gaaggcttac tctttctact gttcatttca tctaggtgta agtgtttctt aagattatct   36060
atggatggtt ctccaactag gattgcgtat gggacacaag gggagctctgg ttactctttg   36120
agattgtgta acactgggga caactctggt gagtaacctc acttttttcgt ggacctgtca   36180
gggatgtctg tcatgttgat agtttgctta gtcttaagga attatgtgtc ttgttctcct   36240
tggttagaag ggactttgat tcacttctaa ttccaaccat tagcgtcaac gctctctttt   36300
cagtctgcac aacaaaaaca agcacacgca ttgttggagg aacaaactct tcttggggag   36360
agtggccctg gcaggtgagc ctgcaggtga agctgacagc tcagaggcac ctgtgtggag   36420
ggtcactcat aggacaccag tgggtcctca ctgctgccca ctgctttgat gggtaagtgt   36480
tggatgcatc tcatccagag tcttatcttg gcttttcatt ttgaaggatc tatgatcagc   36540
tgcttcaccg ccatgtgact ttatgaatag agacgtgtta aagcggggat ggtattcaca   36600
acatttaact tatagggtcc aagcactgac caacctgacc attagaacag agtgtggtct   36660
ctgtacaggg cagatggcgc tgagtgggta ttctccacag aaagagaaac gaagacagta   36720
ccccactcct ccaacccacc acccaccacc aatcccacca ccaattccac caccaatcct   36780
gccacccacc accaatctca ccaccaatcc caccaccaat cctaccaccc accatcaatc   36840
tcagcaccaa tcccaccacc aatcccacca ccaatcaccc caccacccac accaccaatc   36900
ccgccaccca cgaccaatcc caccaccgat cccgccacca atcccaccac caatcccacc   36960
acctacccca ccaccaatcc cgccacccac gaccaatccc accaccgatc cgccaccaa   37020
ccaccaatcc caccaccaat cccaccacca atccctgatg tgttcttcaa agacttattt   37080
gtcaggccca tagaaatgtt aacttcttgct ctttgattca taaatatact aagtcataat   37140
aatttttaaa agtgagagtt tcgtactctg tatatttcaa tgtatataat ttgatctatt   37200
tcaatttatt ggtcaaatag tagacatgtt aggtaagtct taaaatactg aggctttgga   37260
gttagacaga acatggctta agtgacagct ttgctgctta ttagaggtgt ggccctagaa   37320
gatttgtaaa tccctctgag ctttatttga tctaaaatat gaatagtaat agtcccgaat   37380
ttgtaacgtt gttgggaaga ttaagtgaca catttaaaat gcttagtact gtgtgtagaa   37440
cataaacact tcaaaaaatg taaactgtga tttctatatt caataagaaa tgtagaaatg   37500
gacaaagcat ataaaaagca aaagaaatac tagaagacac ttgattttc tcaaaaataa   37560
acacaccaag tattttttgtt ttagtgaaat tcatgcttac atgctgtata ctaggattga   37620
acatactgcc accaaaatat agcagtcggt ggtacatgtg ggtggagcaa gacccctcca   37680
ccttgtcatc gtgtgaaggg gctctgccat acatgacctt gcatgtgact ttaaggtggt   37740
tggcctggaa gaaaagtccc aagatgggaa atagtaggtg tcttttttac taaatgcact   37800
ccaatttggg accaaaaatt ttcattcttg aaggctcagt attgtgagtt tataagagat   37860
aatagacata aaagtgtaat gatttcattg caaataaaaa aaggcccctt tgcacctgat   37920
atctccatca tttttctaga attttgtgca cacatgcctt gcactacttg gtgatgataa   37980
agatttccag atctttgcac agaataaggc tttgctttag atcagaattt tggatgtact   38040
tagtatacat tcatctttta aataatctat ttacatttttc atactttcca aaatacagat   38100
atattttatt ttatttatat attttatttaa tttattttaa gagatggagt tctctctctgt   38160
tgcccagagt agagtgcagt ggcacaatct tggttcactg cagcctctgc ctcccgggtt   38220
caagcgattc tcctgcctca gcctcctgag tagctgggat tacaggcgcg cgccacacct   38280
ggctaatttt tgtattttta gtagagacga ggtttcatca tgttggtcag gctggtctcg   38340
aactcctggc ctcaagggat ccacccacct cggcctcccg aagtgctggg attacaggtg   38400
tgggccactg tgcccagctg tatagagata ttttaaacaa cactaaagtc ctcctacttt   38460
gactaattag aagagcatta gaagatcagc ctgacttctt gacagttctg aatttagtgg   38520
agcaatgagg ttcagctttg gtgaatgagc ttaattttc catgataaac tgctagtttc   38580
ttcccactac agtgtctctc aaaaatggga cagcaacatt ctttttgttt tcacttgcag   38640
taagcatgat gcaattacat aaatgtacac ttttcaattt gttaaataga atcttcagag   38700
attcactact gccgctattg gtgatgaaaa attaccagaa gaggaatta ggtaggagaa   38760
aatgtgtcct atgtatttcc ttcccagttc tttgaaagag agtgatagga aaaggaaca   38820
ctattgaagg aaggactgcc cagtttcaaa caggtattta ttttttctctc ctaggcttcc   38880
cctgcaggat gtttggcgca tctatagtgg catttttaaat ctgtcagaca ttacaaaaga   38940
tacacccttc tcacaaataa aagagattat tattcaccaa aactataaag tctcagaagg   39000
gaatcatgat atcgccttga taaaactcca ggctcctttg aattacactg gtatgtagca   39060
```

```
tatgtaagaa ggtggagagc agaattgcgc tggttgatat tttcatatca gtttgaacaa    39120
gagggcagac ctagagagac tgtcgtcgtt ttctgactgg tggagttgag ggaaacgtga    39180
gggttgctgg gaagtgaaga ccccgcgact tgccgtgaaa tctcttctac ttaaagagca    39240
agacatgtga attaattctt tcagggaggg atacaactgc atgcaggtga tggaaataat    39300
gggcgttggga aatgtctgtg ccgtctgaga ggcactgggc ttgctttgac aagagtagca    39360
gaactgtcat tgctttgggc ttagggatat tcgaatgtgt gagggcaagt gggatcagat    39420
atctacttcc aggtataatt tgggtaggaa agagactcat gcagaaagaa gccctggaag    39480
gccagagcat cgtggtcaga ggtgttgcct ttggagggtc attgctgcca ggagccgaat    39540
acccactgta tccaataaca ttcatggtca ggaatggtgg ctcacacctg taatcccaac    39600
actttgggat gcccaggtgg gaggattgct tgaggccagg agtttgagac cagcctgggc    39660
aacacagtga gaccccgtct ctacataaaa ttagaaaaaa acaattaact gggtgtggtg    39720
gtgtgcacct gtagtcccag ctagtcaaga ggctgagaca agaggatctc ttgagcccag    39780
gagctcaagg ctgtagtgag ccaagatcgt gccactgcac acaaacaatt atgtgacctc    39840
gggcaagttg ctttacctct ttacacctct taatttcctt atctgtaaaa tgaggatgat    39900
aatttcttcc tgggtctgtt gtaataatta atacatcaaa gcacttcatg tctgaacag    39960
tgaagatacc ctgctatgac tattaaggat agtatacatg gaataagaca caggaacttc    40020
taaatgctt tgaccataga tttaggttct gagttttaag aatttaactc aggaaattgt    40080
aacaccaaaa atgtcatgtg aaaaatggtg gtgacaaatt ttcttgaatc attagccta    40140
gaggttgggc agaaagcaaa aaattattcc tgatgctact ctatagaaag agaagacaga    40200
aaaagagaaa gatgtatttt taaagtctat atccataact ttatttgacc aaactctaat    40260
ttaaaatta tgtttcagaa ttccaaaaac caatatgcct accttccaaa ggtgacacaa    40320
gcacaattta taccaactgt tgggtaaccg gatggggcctt ctcgaaggag aaaggtaagc    40380
atgacgcttt aaatattgct tctagagtaa gtctcacatg ttgaaataca tggagtgggt    40440
cgttttaatc ggtttctgtc tgaaattata tctaaactct ttatctttcc tatctattta    40500
ttcccaaata tttattcagt tattcttaaa aaatgtattt ttgctttggc ttgaaaaaaa    40560
attttaggga gactttttaag catcttactt cattataaag atcagttgct tgacttttga    40620
tgaagcagat tgggccttc tagggctgac aagcccgtgc aagaccaccc gctcctcagt    40680
gttagtagcg ttcccgtctc ccaaaaccat gttctccctt gatgctaatg gccgggagca    40740
caggcaggtg tgtcgtctca ctatggagaa taatatttgt gtcattcttt acagaagaag    40800
gtagcttgcc aaactgtctc catctttccc gattcagtct tttgttcaag taattcacat    40860
ttttagattt tttattggta atctgagaca agaagaaatt taaagtaatc ttcactaagc    40920
catgaaagct cccaacattg ttctccatga gagatgctgg cctgcattta ttcaaaaaca    40980
aaagacccct ctgttgccaa agctcggagg gcttttcaga aacgatatag ttgtaaatta    41040
taattttgaa tatataaagc aaaaaaatga aaagtgagaa cttccaggct ttggattgtt    41100
gtaggtgata aatataaat gggatttctg gggggctgct actgagatga gggggatggca    41160
gaaaacatgg aagcaaggtc tctggtcagc ccagggtgct gggcttgtcc caacaccacg    41220
taggcaataa gaggacagta cagggtgccg tctctctccc tcttcctctc tctgtctctc    41280
tctctctgtg tgtgtgtg tgtgtgtg taacactacc ttcccaattt ttactgtcta    41340
tttgtattca aagataaggt ccttatgaaa aatacactgc tctgattcac tttaaaactt    41400
atttccatat ttattattta ttgtgggaat aataatattc ccaatattat tatttattat    41460
ttaagttatt attattaact tccctctgag gttatatatt ggttactcac aggtgaaatc    41520
caaaatattc tacaaaaggt aaatattcct ttggtaacaa atgaagaatg ccagaaaaga    41580
tatcaagatt ataaaataac ccaacggatg gtctgtgctg gctataaaga aggggggaaa    41640
gatgcttgta aggtaactca tgagattatg aaaaacacaa taggctgctt gagaaaattc    41700
atttcaaaat atattttcca atagcataat tcaatcatag ttttttaaaaa aattcagaga    41760
caaatgatct gataaattga taagcaactt ttaacaaatt gaatatacat aatatatatt    41820
tatattattt atgatatatg tcacaatcta tgcatgtgct atttaagagg ggcaaatata    41880
catgcaataa ttgtgctaga atataaaaac attagacttc atcattggga tgatgatatc    41940
aagatttctt tgttagattt atttcagata gaaaagggga tacgaaaaat gcaggcacat    42000
gagatacttg gagaactttta agaaagagtg agtgtgtgtg tgtgtgtgtg tgtgtgtgtg    42060
tgtgtgtctg gcaagcaagg tcttgcacac acacagcact ttgggaggcc aatgcaggtg    42120
gatcacttga gcctaggaat ttgagaccag tctgggcaat gtgatgaaac ccatctctac    42180
aaaaaaatat gaaagtatct gtgtgtgtgt gttgctgtgt agtggactac agaactttag    42240
aggcagtcac ttatttgaat cccattgtcg taactttcta ctattttatt tttccactgt    42300
gactcaggga gattcaggtg gtcccttagt ttgcaaacaa aatgaaatgt ggcgtttggt    42360
gggcatcacc agctggggtg aaggctgtgc ccgcagggag caacctggtg tctacaccaa    42420
agtcgctgag tacatggact ggattttaga gaaaacacag agcagtgatg gaaaagctca    42480
gatgcagtca ccagcatgag aagcagtcca gagtctaggc aatttttaca acctgagttc    42540
aagtcaaatt ctgagcctgg ggggtcctca tctgcaaagc atggagagtg gcatcttctt    42600
tgcatcctaa ggacgaaaaa cacagtgcac tcagagctgc tgaggacaat gtctggctga    42660
agcccgcttt cagcacgccg taaccagggg ctgacaatgc gaggtcgcaa ctgagatctc    42720
catgactgtg tgttgtgaaa taaaatggtg aaagatcacg atta                    42764
```

SEQ ID NO: 5        moltype = DNA  length = 2187
FEATURE           Location/Qualifiers
source            1..2187
                  mol_type = genomic DNA
                  organism = Homo sapiens
SEQUENCE: 5

```
agtgccacat tagaacagct tgaagaccgt tcatttttaa gtgacaagag actcacctcc     60
aagaagcaat tgtgttttca gtttcctgtg agggagtttt ctctgtgtcc ccacaaggca    120
tgattctggg tctatggtga cttaagaggg ccacacaaca atgagtattt aattttcctc    180
agatgtatgg ctacaataaa catctatagg atgtctgact caactctatg aaaacgcctt    240
cttcagaggt ggggatgtag cttccatgta caccccaaat gcccaatact gccagatgag    300
gtgcacattc cacccaaggt gtttgctatt cagtttttctt ccagcaagtt caatcaatga    360
catggagaaa aggtttggtt gcttcttgaa agatagtgtt acaggaaccc tgccaaaagt    420
acatcgaaca ggtgcagttt ctggacattc cttgaagcaa tgtggtcatc aaataagtgc    480
ttgccatcga gacatttata aaggagttga tatgagagga gtcaatttta atgtgtctaa    540
ggttagcagt gttgaagaat gccaaaaaag gtgcaccagt aacattcgct gccagttttt    600
```

```
ttcatatgcc acgcaaacat ttcacaaggc agagtaccgg aacaattgcc tattaaagta    660
cagtcccgga ggaacaccta ccgctataaa ggtgctgagt aacgtggaat ctggattctc    720
actgaagccc tgtgcccttt cagaaattgg ttgccacatg aacatcttcc agcatcttgc    780
gttctcagat gtggatgttg ccagggttct cactccagat gctttgtgt gtcggaccat     840
ctgcacctat caccccaact gcctcttctt tacattctat acaaatgtat ggaaaatcga    900
gtcacaaaga aatgtttgtc ttcttaaaac atctgaaagt ggcacaccaa gttcctctac    960
tcctcaagaa aacaccatat ctggatatag ccttttaacc tgcaaaagaa ctttacctga   1020
accctgccat tctaaaattt acccgggagt tgactttgga ggagaagaat tgaatgtgac   1080
ttttgttaaa ggagtgaatg tttgccaaga gacttgcaca aagatgattc gctgtcagtt   1140
tttcacttat tctttactcc cagaagactg taaggaagag aagtgtaagt gtttcttaag   1200
attatctatg gatggttctc caactaggat tgcgtatggg acacaaggga gctctggtta   1260
ctctttgaga ttgtgtaaca ctggggacaa ctctgtctgc acaacaaaaa caagcacacg   1320
cattgttgga ggaacaaact cttcttgggg agagtggccc tggcaggtga gcctgcaggt   1380
gaagctgaca gctcagaggc acctgtgtgg agggtcactc ataggacacc agtgggtcct   1440
cactgctgcc cactgctttg atgggcttcc cctgcaggat gtttggcgca tctatagtgt   1500
catttaaat ctgtcagaca ttacaaaaga tacacctttc tcacaaataa aagagattat    1560
tattcaccaa aactataaag tctcagaagg gaatcatgat atcgccttga taaaactcca   1620
ggctcctttg aattacactg aattccaaaa accaatatgc ctaccttcca aaggtgacac   1680
aagcacaatt tataccaact gttgggtaac cggatgggc ttctcgaagg agaaagggag    1740
attcaggtgg tccctagtt tgcaaacaca atggaatgtg gcgtttggtg ggcatcacca    1800
gctggggtga aggctgtgcc cgcagggagc aacctggtgt ctacaccaaa gtcgctgagt   1860
acatggactg gattttagag aaaacacaga gcagtgatgg aaaagctgag atgcagtcac   1920
cagcatgaga agcagtccag agtctaggca attttttacaa cctgagttca agtcaaattc   1980
tgagcctggg gggtcctcat ctgcaaagca tggagagtgg catcttcttt gcatcctaag   2040
gacgaaaaac acagtgcact cagagctgct gaggacaatg tctggctgaa gcccgctttc   2100
agcacgccgt aaccaggggc tgacaatgcg aggtcgcaac tgagatctcc atgactgtgt   2160
gttgtgaaat aaaatggtga aagatca                                       2187

SEQ ID NO: 6            moltype = DNA  length = 2289
FEATURE                 Location/Qualifiers
source                  1..2289
                        mol_type = genomic DNA
                        organism = Homo sapiens
SEQUENCE: 6
agtgccacat tagaacagct tgaagaccgt tcattttaa gtgacaagag actcacctcc      60
aagaagcaat tgtgttttca gaatgatttt attcaagcaa gcaacttatt tcatttcctt    120
gtttgctaca gtttcctgtg gatgtctgac tcaactctat gaaaacgcct tcttcagagg    180
tggggatgta gcttccatgt acaccccaaa tgcccaatac tgccagatga ggtgcacatt    240
ccacccaagg tgtttgctat tcagtttct tccagcaagt tcaatcaatg acatggagaa     300
aaggtttggt tgcttcttga agatagtgt tacaggaacc ctgccaaaag tacatcgaac    360
aggtgcagtt tctggacatt ccttgaagca atgtggtcat caaataagtg cttgccatcg    420
agacatttat aaaggagttg atatgagagg agtcaatttt aatgtgtcta aggttagcag    480
tgttgaagaa tgcaaaaaa ggtgcaccag taacattcgc tgccagtttt tttcatatgc     540
cacgcaaaca tttcacaagg cagagtaccg gaacaattgc ctattaaagt acagtcccgg    600
aggaacacct accgctataa aggtgctgag taacgtggaa tctggattct cactgaagcc    660
ctgtgccctt tcagaaattg gttgccacat gaacatcttc cagcatcttg cgttctcaga    720
tgtggatgtt gccagggttc tcactccaga tgcttttgtg tgtcggacca tctgcaccta    780
tcaccccaac tgcctcttct ttacattcta tacaaatgta tggaaaatcg agtcacaaag    840
gcgagtatgc atggaaaatc gcatcacaaa gaaatgtttg tcttcttaaa acatctgaaa    900
gtggcacacc aagttcctct actcctcaag aaaacaccat atctggatat agccttttaa    960
cctgcaaaag aactttacct gaaccctgcc atttctaaaat ttacccggga gttgacttta   1020
gaggagaaga attgaatgtg acttttgtta aaggagtgaa tgtttgccaa gagacttgca   1080
caaagatgat tcgctgtcag ttttcactt attcttact cccagaagac tgtaaggaag    1140
agaagtgtaa gtgtttctta agattatcta tggatggttc tccaactagg attgcgtatg   1200
ggacacaagg gagctctggt tactctttga gattgtgtaa cactggggac aactctgtct   1260
gcacaacaaa aacaagcaca cgcattgttg gaggaacaaa ctcttcttgg ggagagtggc   1320
cctggcaggt gagcctgcag gtgaagctga cagctcagag gcacctgtgt ggagggtcac   1380
tcataggaca ccagtgggtc ctcactgctg cccactgctt tgatgggctt ccctgcagg    1440
atgtttggcg catctatagt ggcattttaa atctgtcaga cattacaaaa gatacacctt   1500
tctcacaaat aaaagagatt attattcacc aaaactataa agtctcagaa gggaatcatg   1560
atatcgcctt gataaaactc caggctcctt tgaattacac tgaattccaa aaaccaatat   1620
gcctaccttc caaaggtgac acaagcacaa tttataccaa ctgttgggta accggatggg   1680
gcttctcgaa ggagaaaggt gaaatccaaa atattctaca aaaggtaaat attcctttgg   1740
taacaaatga agaatgccag aaaagatatc aagattataa aataacccaa cggatggtct   1800
gtgctggcta taagaaggg ggaaaagatg cttgtaaggg agattcaggt ggtccctag     1860
tttgcaaaca caatggaatg tggcgtttgg tgggcatcac cagctggggt gaaggctgtg   1920
cccgcaggga gcaacctggt gtctacacca agtcgctga gtacatggac tggattttag    1980
agaaaacaca gagcagtgat ggaaaagctc agatgcagtc caccagcatga gaagcagtcc   2040
agagtctagg caatttttac aacctgagtt caagtcaaat tctgagcctg ggggtcctcc   2100
atctgcaaag catggagagt ggcatcttct ttgcatccta aggacgaaaa acacagtgca   2160
ctcagagctg ctgaggacaa tgtctggctg aagcccgctt tcagcacgcc gtaaccaggg   2220
gctgacaatg cgaggtcgca actgagatct ccatgactgt gtgttgtgaa ataaaatggt   2280
gaaagatca                                                          2289

SEQ ID NO: 7            moltype =  length = 
SEQUENCE: 7
000

SEQ ID NO: 8            moltype =  length = 
```

```
SEQUENCE: 8
000

SEQ ID NO: 9              moltype =    length =
SEQUENCE: 9
000

SEQ ID NO: 10             moltype = RNA   length = 21
FEATURE                   Location/Qualifiers
source                    1..21
                          mol_type = other RNA
                          organism = synthetic construct
SEQUENCE: 10
ttacatcccc acctctgaag a                                              21

SEQ ID NO: 11             moltype = RNA   length = 21
FEATURE                   Location/Qualifiers
source                    1..21
                          mol_type = other RNA
                          organism = synthetic construct
SEQUENCE: 11
tctacatccc cacctctgaa g                                              21

SEQ ID NO: 12             moltype = RNA   length = 21
FEATURE                   Location/Qualifiers
source                    1..21
                          mol_type = other RNA
                          organism = synthetic construct
SEQUENCE: 12
agctacatcc ccacctctga a                                              21

SEQ ID NO: 13             moltype = RNA   length = 21
FEATURE                   Location/Qualifiers
source                    1..21
                          mol_type = other RNA
                          organism = synthetic construct
SEQUENCE: 13
aagctacatc cccacctctg a                                              21

SEQ ID NO: 14             moltype = RNA   length = 21
FEATURE                   Location/Qualifiers
source                    1..21
                          mol_type = other RNA
                          organism = synthetic construct
SEQUENCE: 14
taagctacat ccccacctct g                                              21

SEQ ID NO: 15             moltype = RNA   length = 21
FEATURE                   Location/Qualifiers
source                    1..21
                          mol_type = other RNA
                          organism = synthetic construct
SEQUENCE: 15
tgaagctaca tccccacctc t                                              21

SEQ ID NO: 16             moltype = RNA   length = 21
FEATURE                   Location/Qualifiers
source                    1..21
                          mol_type = other RNA
                          organism = synthetic construct
SEQUENCE: 16
tggaagctac atccccacct c                                              21

SEQ ID NO: 17             moltype = RNA   length = 21
FEATURE                   Location/Qualifiers
source                    1..21
                          mol_type = other RNA
                          organism = synthetic construct
SEQUENCE: 17
atggaagcta catccccacc t                                              21

SEQ ID NO: 18             moltype = RNA   length = 21
FEATURE                   Location/Qualifiers
source                    1..21
                          mol_type = other RNA
                          organism = synthetic construct
SEQUENCE: 18
tatggaagct acatccccac c                                              21
```

| | | |
|---|---|---|
| SEQ ID NO: 19<br>FEATURE<br>source | moltype = RNA length = 21<br>Location/Qualifiers<br>1..21<br>mol_type = other RNA<br>organism = synthetic construct | |
| SEQUENCE: 19<br>acatggaagc tacatcccca c | | 21 |
| SEQ ID NO: 20<br>FEATURE<br>source | moltype = RNA length = 21<br>Location/Qualifiers<br>1..21<br>mol_type = other RNA<br>organism = synthetic construct | |
| SEQUENCE: 20<br>tacatggaag ctacatcccc a | | 21 |
| SEQ ID NO: 21<br>FEATURE<br>source | moltype = RNA length = 21<br>Location/Qualifiers<br>1..21<br>mol_type = other RNA<br>organism = synthetic construct | |
| SEQUENCE: 21<br>ttacatggaa gctacatccc c | | 21 |
| SEQ ID NO: 22<br>FEATURE<br>source | moltype = RNA length = 21<br>Location/Qualifiers<br>1..21<br>mol_type = other RNA<br>organism = synthetic construct | |
| SEQUENCE: 22<br>taccttgggt ggaatgtgca c | | 21 |
| SEQ ID NO: 23<br>FEATURE<br>source | moltype = RNA length = 21<br>Location/Qualifiers<br>1..21<br>mol_type = other RNA<br>organism = synthetic construct | |
| SEQUENCE: 23<br>acaccttggg tggaatgtgc a | | 21 |
| SEQ ID NO: 24<br>FEATURE<br>source | moltype = RNA length = 21<br>Location/Qualifiers<br>1..21<br>mol_type = other RNA<br>organism = synthetic construct | |
| SEQUENCE: 24<br>aacaccttgg gtggaatgtg c | | 21 |
| SEQ ID NO: 25<br>FEATURE<br>source | moltype = RNA length = 21<br>Location/Qualifiers<br>1..21<br>mol_type = other RNA<br>organism = synthetic construct | |
| SEQUENCE: 25<br>tcaaacacct tgggtggaat g | | 21 |
| SEQ ID NO: 26<br>FEATURE<br>source | moltype = RNA length = 21<br>Location/Qualifiers<br>1..21<br>mol_type = other RNA<br>organism = synthetic construct | |
| SEQUENCE: 26<br>agcaaacacc ttgggtggaa t | | 21 |
| SEQ ID NO: 27<br>FEATURE<br>source | moltype = RNA length = 21<br>Location/Qualifiers<br>1..21<br>mol_type = other RNA<br>organism = synthetic construct | |
| SEQUENCE: 27<br>aatagcaaac accttgggtg g | | 21 |
| SEQ ID NO: 28<br>FEATURE<br>source | moltype = RNA length = 21<br>Location/Qualifiers<br>1..21<br>mol_type = other RNA<br>organism = synthetic construct | |
| SEQUENCE: 28<br>taatagcaaa caccttgggt g | | 21 |

```
SEQ ID NO: 29           moltype = RNA  length = 21
FEATURE                 Location/Qualifiers
source                  1..21
                        mol_type = other RNA
                        organism = synthetic construct
SEQUENCE: 29
tgaatagcaa acaccttggg t                                              21

SEQ ID NO: 30           moltype = RNA  length = 21
FEATURE                 Location/Qualifiers
source                  1..21
                        mol_type = other RNA
                        organism = synthetic construct
SEQUENCE: 30
actgaatagc aaacaccttg g                                              21

SEQ ID NO: 31           moltype = RNA  length = 21
FEATURE                 Location/Qualifiers
source                  1..21
                        mol_type = other RNA
                        organism = synthetic construct
SEQUENCE: 31
aactgaatag caaacacctt g                                              21

SEQ ID NO: 32           moltype = RNA  length = 21
FEATURE                 Location/Qualifiers
source                  1..21
                        mol_type = other RNA
                        organism = synthetic construct
SEQUENCE: 32
aaactgaata gcaaacacct t                                              21

SEQ ID NO: 33           moltype = RNA  length = 21
FEATURE                 Location/Qualifiers
source                  1..21
                        mol_type = other RNA
                        organism = synthetic construct
SEQUENCE: 33
aaaactgaat agcaaacacc t                                              21

SEQ ID NO: 34           moltype = RNA  length = 21
FEATURE                 Location/Qualifiers
source                  1..21
                        mol_type = other RNA
                        organism = synthetic construct
SEQUENCE: 34
taaaactgaa tagcaaacac c                                              21

SEQ ID NO: 35           moltype = RNA  length = 21
FEATURE                 Location/Qualifiers
source                  1..21
                        mol_type = other RNA
                        organism = synthetic construct
SEQUENCE: 35
agaaaactga atagcaaaca c                                              21

SEQ ID NO: 36           moltype = RNA  length = 21
FEATURE                 Location/Qualifiers
source                  1..21
                        mol_type = other RNA
                        organism = synthetic construct
SEQUENCE: 36
tggaagaaaa ctgaatagca a                                              21

SEQ ID NO: 37           moltype = RNA  length = 21
FEATURE                 Location/Qualifiers
source                  1..21
                        mol_type = other RNA
                        organism = synthetic construct
SEQUENCE: 37
taacttgctg gaagaaaact g                                              21

SEQ ID NO: 38           moltype = RNA  length = 21
FEATURE                 Location/Qualifiers
source                  1..21
                        mol_type = other RNA
                        organism = synthetic construct
SEQUENCE: 38
```

```
tcttttctcc atgtcattga t                                              21

SEQ ID NO: 39          moltype = RNA   length = 21
FEATURE                Location/Qualifiers
source                 1..21
                       mol_type = other RNA
                       organism = synthetic construct
SEQUENCE: 39
aaacctttc tccatgtcat t                                               21

SEQ ID NO: 40          moltype = RNA   length = 21
FEATURE                Location/Qualifiers
source                 1..21
                       mol_type = other RNA
                       organism = synthetic construct
SEQUENCE: 40
taaacctttt ctccatgtca t                                              21

SEQ ID NO: 41          moltype = RNA   length = 21
FEATURE                Location/Qualifiers
source                 1..21
                       mol_type = other RNA
                       organism = synthetic construct
SEQUENCE: 41
tacctttttt ggcattcttc a                                              21

SEQ ID NO: 42          moltype = RNA   length = 21
FEATURE                Location/Qualifiers
source                 1..21
                       mol_type = other RNA
                       organism = synthetic construct
SEQUENCE: 42
tggtgcacct tttttggcat t                                              21

SEQ ID NO: 43          moltype = RNA   length = 21
FEATURE                Location/Qualifiers
source                 1..21
                       mol_type = other RNA
                       organism = synthetic construct
SEQUENCE: 43
accaatttct gaaagggcac a                                              21

SEQ ID NO: 44          moltype = RNA   length = 21
FEATURE                Location/Qualifiers
source                 1..21
                       mol_type = other RNA
                       organism = synthetic construct
SEQUENCE: 44
aaccaatttc tgaaagggca c                                              21

SEQ ID NO: 45          moltype = RNA   length = 21
FEATURE                Location/Qualifiers
source                 1..21
                       mol_type = other RNA
                       organism = synthetic construct
SEQUENCE: 45
tcaagatgct ggaagatgtt c                                              21

SEQ ID NO: 46          moltype = RNA   length = 21
FEATURE                Location/Qualifiers
source                 1..21
                       mol_type = other RNA
                       organism = synthetic construct
SEQUENCE: 46
aggaacttgg tgtgccactt t                                              21

SEQ ID NO: 47          moltype = RNA   length = 21
FEATURE                Location/Qualifiers
source                 1..21
                       mol_type = other RNA
                       organism = synthetic construct
SEQUENCE: 47
taggaacttg gtgtgccact t                                              21

SEQ ID NO: 48          moltype = RNA   length = 21
FEATURE                Location/Qualifiers
source                 1..21
                       mol_type = other RNA
                       organism = synthetic construct
```

```
SEQUENCE: 48
agaggaactt ggtgtgccac t                                              21

SEQ ID NO: 49          moltype = RNA  length = 21
FEATURE                Location/Qualifiers
source                 1..21
                       mol_type = other RNA
                       organism = synthetic construct
SEQUENCE: 49
tagaggaact tggtgtgcca c                                              21

SEQ ID NO: 50          moltype = RNA  length = 21
FEATURE                Location/Qualifiers
source                 1..21
                       mol_type = other RNA
                       organism = synthetic construct
SEQUENCE: 50
ttagaggaac ttggtgtgcc a                                              21

SEQ ID NO: 51          moltype = RNA  length = 21
FEATURE                Location/Qualifiers
source                 1..21
                       mol_type = other RNA
                       organism = synthetic construct
SEQUENCE: 51
taggagtaga ggaacttggt g                                              21

SEQ ID NO: 52          moltype = RNA  length = 21
FEATURE                Location/Qualifiers
source                 1..21
                       mol_type = other RNA
                       organism = synthetic construct
SEQUENCE: 52
tgaggagtag aggaacttgg t                                              21

SEQ ID NO: 53          moltype = RNA  length = 21
FEATURE                Location/Qualifiers
source                 1..21
                       mol_type = other RNA
                       organism = synthetic construct
SEQUENCE: 53
ttgaggagta gaggaacttg g                                              21

SEQ ID NO: 54          moltype = RNA  length = 21
FEATURE                Location/Qualifiers
source                 1..21
                       mol_type = other RNA
                       organism = synthetic construct
SEQUENCE: 54
tttgaggagt agaggaactt g                                              21

SEQ ID NO: 55          moltype = RNA  length = 21
FEATURE                Location/Qualifiers
source                 1..21
                       mol_type = other RNA
                       organism = synthetic construct
SEQUENCE: 55
tcttgaggag tagaggaact t                                              21

SEQ ID NO: 56          moltype = RNA  length = 21
FEATURE                Location/Qualifiers
source                 1..21
                       mol_type = other RNA
                       organism = synthetic construct
SEQUENCE: 56
ttcttgagga gtagaggaac t                                              21

SEQ ID NO: 57          moltype = RNA  length = 21
FEATURE                Location/Qualifiers
source                 1..21
                       mol_type = other RNA
                       organism = synthetic construct
SEQUENCE: 57
tttcttgagg agtagaggaa c                                              21

SEQ ID NO: 58          moltype = RNA  length = 21
FEATURE                Location/Qualifiers
source                 1..21
                       mol_type = other RNA
```

-continued

```
                        organism = synthetic construct
SEQUENCE: 58
tttcttgag gagtagagga a                                              21

SEQ ID NO: 59           moltype = RNA   length = 21
FEATURE                 Location/Qualifiers
source                  1..21
                        mol_type = other RNA
                        organism = synthetic construct
SEQUENCE: 59
ttgttttctt gaggagtaga g                                             21

SEQ ID NO: 60           moltype = RNA   length = 21
FEATURE                 Location/Qualifiers
source                  1..21
                        mol_type = other RNA
                        organism = synthetic construct
SEQUENCE: 60
tgtgttttct tgaggagtag a                                             21

SEQ ID NO: 61           moltype = RNA   length = 21
FEATURE                 Location/Qualifiers
source                  1..21
                        mol_type = other RNA
                        organism = synthetic construct
SEQUENCE: 61
tggtgttttc ttgaggagta g                                             21

SEQ ID NO: 62           moltype = RNA   length = 21
FEATURE                 Location/Qualifiers
source                  1..21
                        mol_type = other RNA
                        organism = synthetic construct
SEQUENCE: 62
tcttttgcag gttaaaaggc t                                             21

SEQ ID NO: 63           moltype = RNA   length = 21
FEATURE                 Location/Qualifiers
source                  1..21
                        mol_type = other RNA
                        organism = synthetic construct
SEQUENCE: 63
agggttcagg taaagttctt t                                             21

SEQ ID NO: 64           moltype = RNA   length = 21
FEATURE                 Location/Qualifiers
source                  1..21
                        mol_type = other RNA
                        organism = synthetic construct
SEQUENCE: 64
tagggttcag gtaaagttct t                                             21

SEQ ID NO: 65           moltype = RNA   length = 21
FEATURE                 Location/Qualifiers
source                  1..21
                        mol_type = other RNA
                        organism = synthetic construct
SEQUENCE: 65
tcagggttca ggtaaagttc t                                             21

SEQ ID NO: 66           moltype = RNA   length = 21
FEATURE                 Location/Qualifiers
source                  1..21
                        mol_type = other RNA
                        organism = synthetic construct
SEQUENCE: 66
tgcagggttc aggtaaagtt c                                             21

SEQ ID NO: 67           moltype = RNA   length = 21
FEATURE                 Location/Qualifiers
source                  1..21
                        mol_type = other RNA
                        organism = synthetic construct
SEQUENCE: 67
tggcagggtt caggtaaagt t                                             21

SEQ ID NO: 68           moltype = RNA   length = 21
FEATURE                 Location/Qualifiers
source                  1..21
```

```
                            mol_type = other RNA
                            organism = synthetic construct
SEQUENCE: 68
atggcagggt tcaggtaaag t                                                 21

SEQ ID NO: 69           moltype = RNA  length = 21
FEATURE                 Location/Qualifiers
source                  1..21
                        mol_type = other RNA
                        organism = synthetic construct
SEQUENCE: 69
taatggcagg gttcaggtaa a                                                 21

SEQ ID NO: 70           moltype = RNA  length = 21
FEATURE                 Location/Qualifiers
source                  1..21
                        mol_type = other RNA
                        organism = synthetic construct
SEQUENCE: 70
agaatggcag ggttcaggta a                                                 21

SEQ ID NO: 71           moltype = RNA  length = 21
FEATURE                 Location/Qualifiers
source                  1..21
                        mol_type = other RNA
                        organism = synthetic construct
SEQUENCE: 71
tagaatggca gggttcaggt a                                                 21

SEQ ID NO: 72           moltype = RNA  length = 21
FEATURE                 Location/Qualifiers
source                  1..21
                        mol_type = other RNA
                        organism = synthetic construct
SEQUENCE: 72
ttagaatggc agggttcagg t                                                 21

SEQ ID NO: 73           moltype = RNA  length = 21
FEATURE                 Location/Qualifiers
source                  1..21
                        mol_type = other RNA
                        organism = synthetic construct
SEQUENCE: 73
tttagaatgg cagggttcag g                                                 21

SEQ ID NO: 74           moltype = RNA  length = 21
FEATURE                 Location/Qualifiers
source                  1..21
                        mol_type = other RNA
                        organism = synthetic construct
SEQUENCE: 74
ttttagaatg gcagggttca g                                                 21

SEQ ID NO: 75           moltype = RNA  length = 21
FEATURE                 Location/Qualifiers
source                  1..21
                        mol_type = other RNA
                        organism = synthetic construct
SEQUENCE: 75
attttagaat ggcagggttc a                                                 21

SEQ ID NO: 76           moltype = RNA  length = 21
FEATURE                 Location/Qualifiers
source                  1..21
                        mol_type = other RNA
                        organism = synthetic construct
SEQUENCE: 76
aattttagaa tggcagggtt c                                                 21

SEQ ID NO: 77           moltype = RNA  length = 21
FEATURE                 Location/Qualifiers
source                  1..21
                        mol_type = other RNA
                        organism = synthetic construct
SEQUENCE: 77
aaattttaga atggcagggt t                                                 21

SEQ ID NO: 78           moltype = RNA  length = 21
FEATURE                 Location/Qualifiers
```

-continued

```
source                   1..21
                         mol_type = other RNA
                         organism = synthetic construct
SEQUENCE: 78
taaattttag aatggcaggg t                                              21

SEQ ID NO: 79            moltype = RNA   length = 21
FEATURE                  Location/Qualifiers
source                   1..21
                         mol_type = other RNA
                         organism = synthetic construct
SEQUENCE: 79
ttaaatttta gaatggcagg g                                              21

SEQ ID NO: 80            moltype = RNA   length = 21
FEATURE                  Location/Qualifiers
source                   1..21
                         mol_type = other RNA
                         organism = synthetic construct
SEQUENCE: 80
tgtaaatttt agaatggcag g                                              21

SEQ ID NO: 81            moltype = RNA   length = 21
FEATURE                  Location/Qualifiers
source                   1..21
                         mol_type = other RNA
                         organism = synthetic construct
SEQUENCE: 81
tcgggtaaat tttagaatgg c                                              21

SEQ ID NO: 82            moltype = RNA   length = 21
FEATURE                  Location/Qualifiers
source                   1..21
                         mol_type = other RNA
                         organism = synthetic construct
SEQUENCE: 82
tccgggtaaa ttttagaatg g                                              21

SEQ ID NO: 83            moltype = RNA   length = 21
FEATURE                  Location/Qualifiers
source                   1..21
                         mol_type = other RNA
                         organism = synthetic construct
SEQUENCE: 83
tacattcaat tcttctcctc c                                              21

SEQ ID NO: 84            moltype = RNA   length = 21
FEATURE                  Location/Qualifiers
source                   1..21
                         mol_type = other RNA
                         organism = synthetic construct
SEQUENCE: 84
tcacattcaa ttcttctcct c                                              21

SEQ ID NO: 85            moltype = RNA   length = 21
FEATURE                  Location/Qualifiers
source                   1..21
                         mol_type = other RNA
                         organism = synthetic construct
SEQUENCE: 85
agtcacattc aattcttctc c                                              21

SEQ ID NO: 86            moltype = RNA   length = 21
FEATURE                  Location/Qualifiers
source                   1..21
                         mol_type = other RNA
                         organism = synthetic construct
SEQUENCE: 86
tgcaaacatt cactccttta a                                              21

SEQ ID NO: 87            moltype = RNA   length = 21
FEATURE                  Location/Qualifiers
source                   1..21
                         mol_type = other RNA
                         organism = synthetic construct
SEQUENCE: 87
actgacagcg aatcatcttt g                                              21

SEQ ID NO: 88            moltype = RNA   length = 21
```

-continued

```
FEATURE                 Location/Qualifiers
source                  1..21
                        mol_type = other RNA
                        organism = synthetic construct
SEQUENCE: 88
aactgacagc gaatcatctt t                                      21

SEQ ID NO: 89           moltype = RNA   length = 21
FEATURE                 Location/Qualifiers
source                  1..21
                        mol_type = other RNA
                        organism = synthetic construct
SEQUENCE: 89
aaactgacag cgaatcatct t                                      21

SEQ ID NO: 90           moltype = RNA   length = 21
FEATURE                 Location/Qualifiers
source                  1..21
                        mol_type = other RNA
                        organism = synthetic construct
SEQUENCE: 90
aaaactgaca gcgaatcatc t                                      21

SEQ ID NO: 91           moltype = RNA   length = 21
FEATURE                 Location/Qualifiers
source                  1..21
                        mol_type = other RNA
                        organism = synthetic construct
SEQUENCE: 91
aaaaactgac agcgaatcat c                                      21

SEQ ID NO: 92           moltype = RNA   length = 21
FEATURE                 Location/Qualifiers
source                  1..21
                        mol_type = other RNA
                        organism = synthetic construct
SEQUENCE: 92
ttgaaaaact gacagcgaat c                                      21

SEQ ID NO: 93           moltype = RNA   length = 21
FEATURE                 Location/Qualifiers
source                  1..21
                        mol_type = other RNA
                        organism = synthetic construct
SEQUENCE: 93
agtgaaaaac tgacagcgaa t                                      21

SEQ ID NO: 94           moltype = RNA   length = 21
FEATURE                 Location/Qualifiers
source                  1..21
                        mol_type = other RNA
                        organism = synthetic construct
SEQUENCE: 94
aagtgaaaaa ctgacagcga a                                      21

SEQ ID NO: 95           moltype = RNA   length = 21
FEATURE                 Location/Qualifiers
source                  1..21
                        mol_type = other RNA
                        organism = synthetic construct
SEQUENCE: 95
taagtgaaaa actgacagcg a                                      21

SEQ ID NO: 96           moltype = RNA   length = 21
FEATURE                 Location/Qualifiers
source                  1..21
                        mol_type = other RNA
                        organism = synthetic construct
SEQUENCE: 96
ataagtgaaa aactgacagc g                                      21

SEQ ID NO: 97           moltype = RNA   length = 21
FEATURE                 Location/Qualifiers
source                  1..21
                        mol_type = other RNA
                        organism = synthetic construct
SEQUENCE: 97
aataagtgaa aaactgacag c                                      21
```

```
SEQ ID NO: 98          moltype = RNA   length = 21
FEATURE                Location/Qualifiers
source                 1..21
                       mol_type = other RNA
                       organism = synthetic construct
SEQUENCE: 98
aagaataagt gaaaaactga c                                                    21

SEQ ID NO: 99          moltype = RNA   length = 21
FEATURE                Location/Qualifiers
source                 1..21
                       mol_type = other RNA
                       organism = synthetic construct
SEQUENCE: 99
aaagaataag tgaaaactg a                                                     21

SEQ ID NO: 100         moltype = RNA   length = 21
FEATURE                Location/Qualifiers
source                 1..21
                       mol_type = other RNA
                       organism = synthetic construct
SEQUENCE: 100
tagtaaagaa taagtgaaaa a                                                    21

SEQ ID NO: 101         moltype = RNA   length = 21
FEATURE                Location/Qualifiers
source                 1..21
                       mol_type = other RNA
                       organism = synthetic construct
SEQUENCE: 101
tgagtaaaga ataagtgaaa a                                                    21

SEQ ID NO: 102         moltype = RNA   length = 21
FEATURE                Location/Qualifiers
source                 1..21
                       mol_type = other RNA
                       organism = synthetic construct
SEQUENCE: 102
tggagtaaag aataagtgaa a                                                    21

SEQ ID NO: 103         moltype = RNA   length = 21
FEATURE                Location/Qualifiers
source                 1..21
                       mol_type = other RNA
                       organism = synthetic construct
SEQUENCE: 103
tgggagtaaa gaataagtga a                                                    21

SEQ ID NO: 104         moltype = RNA   length = 21
FEATURE                Location/Qualifiers
source                 1..21
                       mol_type = other RNA
                       organism = synthetic construct
SEQUENCE: 104
ttgggagtaa agaataagtg a                                                    21

SEQ ID NO: 105         moltype = RNA   length = 21
FEATURE                Location/Qualifiers
source                 1..21
                       mol_type = other RNA
                       organism = synthetic construct
SEQUENCE: 105
tctgggagta aagaataagt g                                                    21

SEQ ID NO: 106         moltype = RNA   length = 21
FEATURE                Location/Qualifiers
source                 1..21
                       mol_type = other RNA
                       organism = synthetic construct
SEQUENCE: 106
ttctgggagt aaagaataag t                                                    21

SEQ ID NO: 107         moltype = RNA   length = 21
FEATURE                Location/Qualifiers
source                 1..21
                       mol_type = other RNA
                       organism = synthetic construct
SEQUENCE: 107
tttctgggag taaagaataa g                                                    21
```

```
SEQ ID NO: 108         moltype = RNA   length = 21
FEATURE                Location/Qualifiers
source                 1..21
                       mol_type = other RNA
                       organism = synthetic construct
SEQUENCE: 108
tcttctggga gtaaagaata a                                                   21

SEQ ID NO: 109         moltype = RNA   length = 21
FEATURE                Location/Qualifiers
source                 1..21
                       mol_type = other RNA
                       organism = synthetic construct
SEQUENCE: 109
agtcttctgg gagtaaagaa t                                                   21

SEQ ID NO: 110         moltype = RNA   length = 21
FEATURE                Location/Qualifiers
source                 1..21
                       mol_type = other RNA
                       organism = synthetic construct
SEQUENCE: 110
tagtcttctg ggagtaaaga a                                                   21

SEQ ID NO: 111         moltype = RNA   length = 21
FEATURE                Location/Qualifiers
source                 1..21
                       mol_type = other RNA
                       organism = synthetic construct
SEQUENCE: 111
tttacagtct tctgggagta a                                                   21

SEQ ID NO: 112         moltype = RNA   length = 21
FEATURE                Location/Qualifiers
source                 1..21
                       mol_type = other RNA
                       organism = synthetic construct
SEQUENCE: 112
tcttacagtc ttctgggagt a                                                   21

SEQ ID NO: 113         moltype = RNA   length = 21
FEATURE                Location/Qualifiers
source                 1..21
                       mol_type = other RNA
                       organism = synthetic construct
SEQUENCE: 113
tccttacagt cttctgggag t                                                   21

SEQ ID NO: 114         moltype = RNA   length = 21
FEATURE                Location/Qualifiers
source                 1..21
                       mol_type = other RNA
                       organism = synthetic construct
SEQUENCE: 114
taagaaacac ttacacttct c                                                   21

SEQ ID NO: 115         moltype = RNA   length = 21
FEATURE                Location/Qualifiers
source                 1..21
                       mol_type = other RNA
                       organism = synthetic construct
SEQUENCE: 115
ttaagaaaca cttacacttc t                                                   21

SEQ ID NO: 116         moltype = RNA   length = 21
FEATURE                Location/Qualifiers
source                 1..21
                       mol_type = other RNA
                       organism = synthetic construct
SEQUENCE: 116
tttaagaaac acttacactt c                                                   21

SEQ ID NO: 117         moltype = RNA   length = 21
FEATURE                Location/Qualifiers
source                 1..21
                       mol_type = other RNA
                       organism = synthetic construct
SEQUENCE: 117
```

```
tataatctta agaaacactt a                                             21

SEQ ID NO: 118         moltype = RNA   length = 21
FEATURE                Location/Qualifiers
source                 1..21
                       mol_type = other RNA
                       organism = synthetic construct
SEQUENCE: 118
atcctagttg gagaaccatc c                                             21

SEQ ID NO: 119         moltype = RNA   length = 21
FEATURE                Location/Qualifiers
source                 1..21
                       mol_type = other RNA
                       organism = synthetic construct
SEQUENCE: 119
aatcctagtt ggagaaccat c                                             21

SEQ ID NO: 120         moltype = RNA   length = 21
FEATURE                Location/Qualifiers
source                 1..21
                       mol_type = other RNA
                       organism = synthetic construct
SEQUENCE: 120
tagagctccc ttgtgtccca t                                             21

SEQ ID NO: 121         moltype = RNA   length = 21
FEATURE                Location/Qualifiers
source                 1..21
                       mol_type = other RNA
                       organism = synthetic construct
SEQUENCE: 121
tcagagctcc cttgtgtccc a                                             21

SEQ ID NO: 122         moltype = RNA   length = 21
FEATURE                Location/Qualifiers
source                 1..21
                       mol_type = other RNA
                       organism = synthetic construct
SEQUENCE: 122
aaccagagct cccttgtgtc c                                             21

SEQ ID NO: 123         moltype = RNA   length = 21
FEATURE                Location/Qualifiers
source                 1..21
                       mol_type = other RNA
                       organism = synthetic construct
SEQUENCE: 123
taaccagagc tcccttgtgt c                                             21

SEQ ID NO: 124         moltype = RNA   length = 21
FEATURE                Location/Qualifiers
source                 1..21
                       mol_type = other RNA
                       organism = synthetic construct
SEQUENCE: 124
ttaaccagag ctcccttgtg t                                             21

SEQ ID NO: 125         moltype = RNA   length = 21
FEATURE                Location/Qualifiers
source                 1..21
                       mol_type = other RNA
                       organism = synthetic construct
SEQUENCE: 125
tagtaaccag agctcccttg t                                             21

SEQ ID NO: 126         moltype = RNA   length = 21
FEATURE                Location/Qualifiers
source                 1..21
                       mol_type = other RNA
                       organism = synthetic construct
SEQUENCE: 126
agagtaacca gagctccctt g                                             21

SEQ ID NO: 127         moltype = RNA   length = 21
FEATURE                Location/Qualifiers
source                 1..21
                       mol_type = other RNA
                       organism = synthetic construct
```

```
SEQUENCE: 127
tcaaagagta accagagctc c                                              21

SEQ ID NO: 128          moltype = RNA   length = 21
FEATURE                 Location/Qualifiers
source                  1..21
                        mol_type = other RNA
                        organism = synthetic construct
SEQUENCE: 128
tccagtgtta cacaatctca a                                              21

SEQ ID NO: 129          moltype = RNA   length = 21
FEATURE                 Location/Qualifiers
source                  1..21
                        mol_type = other RNA
                        organism = synthetic construct
SEQUENCE: 129
tcccagtgtt acacaatctc a                                              21

SEQ ID NO: 130          moltype = RNA   length = 21
FEATURE                 Location/Qualifiers
source                  1..21
                        mol_type = other RNA
                        organism = synthetic construct
SEQUENCE: 130
tgtccccagt gttacacaat c                                              21

SEQ ID NO: 131          moltype = RNA   length = 21
FEATURE                 Location/Qualifiers
source                  1..21
                        mol_type = other RNA
                        organism = synthetic construct
SEQUENCE: 131
tcccaagaag agtttgttcc t                                              21

SEQ ID NO: 132          moltype = RNA   length = 21
FEATURE                 Location/Qualifiers
source                  1..21
                        mol_type = other RNA
                        organism = synthetic construct
SEQUENCE: 132
tccccaagaa gagtttgttc c                                              21

SEQ ID NO: 133          moltype = RNA   length = 21
FEATURE                 Location/Qualifiers
source                  1..21
                        mol_type = other RNA
                        organism = synthetic construct
SEQUENCE: 133
ttccccaaga agagtttgtt c                                              21

SEQ ID NO: 134          moltype = RNA   length = 21
FEATURE                 Location/Qualifiers
source                  1..21
                        mol_type = other RNA
                        organism = synthetic construct
SEQUENCE: 134
tctccccaag aagagtttgt t                                              21

SEQ ID NO: 135          moltype = RNA   length = 21
FEATURE                 Location/Qualifiers
source                  1..21
                        mol_type = other RNA
                        organism = synthetic construct
SEQUENCE: 135
ttctccccaa gaagagtttg t                                              21

SEQ ID NO: 136          moltype = RNA   length = 21
FEATURE                 Location/Qualifiers
source                  1..21
                        mol_type = other RNA
                        organism = synthetic construct
SEQUENCE: 136
actctcccca agaagagttt g                                              21

SEQ ID NO: 137          moltype = RNA   length = 21
FEATURE                 Location/Qualifiers
source                  1..21
                        mol_type = other RNA
```

```
                        organism = synthetic construct
SEQUENCE: 137
tcactctccc caagaagagt t                                                     21

SEQ ID NO: 138          moltype = RNA  length = 21
FEATURE                 Location/Qualifiers
source                  1..21
                        mol_type = other RNA
                        organism = synthetic construct
SEQUENCE: 138
tccactctcc ccaagaagag t                                                     21

SEQ ID NO: 139          moltype = RNA  length = 21
FEATURE                 Location/Qualifiers
source                  1..21
                        mol_type = other RNA
                        organism = synthetic construct
SEQUENCE: 139
agggccactc tccccaagaa g                                                     21

SEQ ID NO: 140          moltype = RNA  length = 21
FEATURE                 Location/Qualifiers
source                  1..21
                        mol_type = other RNA
                        organism = synthetic construct
SEQUENCE: 140
tagggccact ctccccaaga a                                                     21

SEQ ID NO: 141          moltype = RNA  length = 21
FEATURE                 Location/Qualifiers
source                  1..21
                        mol_type = other RNA
                        organism = synthetic construct
SEQUENCE: 141
tcagggccac tctccccaag a                                                     21

SEQ ID NO: 142          moltype = RNA  length = 21
FEATURE                 Location/Qualifiers
source                  1..21
                        mol_type = other RNA
                        organism = synthetic construct
SEQUENCE: 142
ttggtgtcct atgagtgacc c                                                     21

SEQ ID NO: 143          moltype = RNA  length = 21
FEATURE                 Location/Qualifiers
source                  1..21
                        mol_type = other RNA
                        organism = synthetic construct
SEQUENCE: 143
actggtgtcc tatgagtgac c                                                     21

SEQ ID NO: 144          moltype = RNA  length = 21
FEATURE                 Location/Qualifiers
source                  1..21
                        mol_type = other RNA
                        organism = synthetic construct
SEQUENCE: 144
tccactggtg tcctatgagt g                                                     21

SEQ ID NO: 145          moltype = RNA  length = 21
FEATURE                 Location/Qualifiers
source                  1..21
                        mol_type = other RNA
                        organism = synthetic construct
SEQUENCE: 145
acccactggt gtcctatgag t                                                     21

SEQ ID NO: 146          moltype = RNA  length = 21
FEATURE                 Location/Qualifiers
source                  1..21
                        mol_type = other RNA
                        organism = synthetic construct
SEQUENCE: 146
tacccactgg tgtcctatga g                                                     21

SEQ ID NO: 147          moltype = RNA  length = 21
FEATURE                 Location/Qualifiers
source                  1..21
```

```
                              mol_type = other RNA
                              organism = synthetic construct
SEQUENCE: 147
tgaagcccat caaagcagtg g                                              21

SEQ ID NO: 148                moltype = RNA   length = 21
FEATURE                       Location/Qualifiers
source                        1..21
                              mol_type = other RNA
                              organism = synthetic construct
SEQUENCE: 148
acagatttaa aatgccacta t                                              21

SEQ ID NO: 149                moltype = RNA   length = 21
FEATURE                       Location/Qualifiers
source                        1..21
                              mol_type = other RNA
                              organism = synthetic construct
SEQUENCE: 149
tacagattta aaatgccact a                                              21

SEQ ID NO: 150                moltype = RNA   length = 21
FEATURE                       Location/Qualifiers
source                        1..21
                              mol_type = other RNA
                              organism = synthetic construct
SEQUENCE: 150
tgacagattt aaaatgccac t                                              21

SEQ ID NO: 151                moltype = RNA   length = 21
FEATURE                       Location/Qualifiers
source                        1..21
                              mol_type = other RNA
                              organism = synthetic construct
SEQUENCE: 151
ttgacagatt taaaatgcca c                                              21

SEQ ID NO: 152                moltype = RNA   length = 21
FEATURE                       Location/Qualifiers
source                        1..21
                              mol_type = other RNA
                              organism = synthetic construct
SEQUENCE: 152
tctgacagat ttaaaatgcc a                                              21

SEQ ID NO: 153                moltype = RNA   length = 21
FEATURE                       Location/Qualifiers
source                        1..21
                              mol_type = other RNA
                              organism = synthetic construct
SEQUENCE: 153
ttctgacaga tttaaaatgc c                                              21

SEQ ID NO: 154                moltype = RNA   length = 21
FEATURE                       Location/Qualifiers
source                        1..21
                              mol_type = other RNA
                              organism = synthetic construct
SEQUENCE: 154
tgtctgacag atttaaaatg c                                              21

SEQ ID NO: 155                moltype = RNA   length = 21
FEATURE                       Location/Qualifiers
source                        1..21
                              mol_type = other RNA
                              organism = synthetic construct
SEQUENCE: 155
tgtaatgtct gacagattta a                                              21

SEQ ID NO: 156                moltype = RNA   length = 21
FEATURE                       Location/Qualifiers
source                        1..21
                              mol_type = other RNA
                              organism = synthetic construct
SEQUENCE: 156
tcttttgtaa tgtctgacag a                                              21

SEQ ID NO: 157                moltype = RNA   length = 21
FEATURE                       Location/Qualifiers
```

-continued

```
source                  1..21
                        mol_type = other RNA
                        organism = synthetic construct
SEQUENCE: 157
atatcatgat tcccttctga g                                              21

SEQ ID NO: 158          moltype = RNA  length = 21
FEATURE                 Location/Qualifiers
source                  1..21
                        mol_type = other RNA
                        organism = synthetic construct
SEQUENCE: 158
tcgatatcat gattcccttc t                                              21

SEQ ID NO: 159          moltype = RNA  length = 21
FEATURE                 Location/Qualifiers
source                  1..21
                        mol_type = other RNA
                        organism = synthetic construct
SEQUENCE: 159
tgcgatatca tgattccctt c                                              21

SEQ ID NO: 160          moltype = RNA  length = 21
FEATURE                 Location/Qualifiers
source                  1..21
                        mol_type = other RNA
                        organism = synthetic construct
SEQUENCE: 160
aggcgatatc atgattccct t                                              21

SEQ ID NO: 161          moltype = RNA  length = 21
FEATURE                 Location/Qualifiers
source                  1..21
                        mol_type = other RNA
                        organism = synthetic construct
SEQUENCE: 161
aattcaaagg agcctggagt t                                              21

SEQ ID NO: 162          moltype = RNA  length = 21
FEATURE                 Location/Qualifiers
source                  1..21
                        mol_type = other RNA
                        organism = synthetic construct
SEQUENCE: 162
taattcaaag gagcctggag t                                              21

SEQ ID NO: 163          moltype = RNA  length = 21
FEATURE                 Location/Qualifiers
source                  1..21
                        mol_type = other RNA
                        organism = synthetic construct
SEQUENCE: 163
ttaattcaaa ggagcctgga g                                              21

SEQ ID NO: 164          moltype = RNA  length = 21
FEATURE                 Location/Qualifiers
source                  1..21
                        mol_type = other RNA
                        organism = synthetic construct
SEQUENCE: 164
tgtaattcaa aggagcctgg a                                              21

SEQ ID NO: 165          moltype = RNA  length = 21
FEATURE                 Location/Qualifiers
source                  1..21
                        mol_type = other RNA
                        organism = synthetic construct
SEQUENCE: 165
ttgtaattca aaggagcctg g                                              21

SEQ ID NO: 166          moltype = RNA  length = 21
FEATURE                 Location/Qualifiers
source                  1..21
                        mol_type = other RNA
                        organism = synthetic construct
SEQUENCE: 166
agtgtaattc aaaggagcct g                                              21

SEQ ID NO: 167          moltype = RNA  length = 21
```

-continued

| | | |
|---|---|---|
| FEATURE | Location/Qualifiers | |
| source | 1..21 | |
| | mol_type = other RNA | |
| | organism = synthetic construct | |
| SEQUENCE: 167 | | |
| tagtgtaatt caaaggagcc t | | 21 |
| | | |
| SEQ ID NO: 168 | moltype = RNA length = 21 | |
| FEATURE | Location/Qualifiers | |
| source | 1..21 | |
| | mol_type = other RNA | |
| | organism = synthetic construct | |
| SEQUENCE: 168 | | |
| tcagtgtaat tcaaaggagc c | | 21 |
| | | |
| SEQ ID NO: 169 | moltype = RNA length = 21 | |
| FEATURE | Location/Qualifiers | |
| source | 1..21 | |
| | mol_type = other RNA | |
| | organism = synthetic construct | |
| SEQUENCE: 169 | | |
| tgaattcagt gtaattcaaa g | | 21 |
| | | |
| SEQ ID NO: 170 | moltype = RNA length = 21 | |
| FEATURE | Location/Qualifiers | |
| source | 1..21 | |
| | mol_type = other RNA | |
| | organism = synthetic construct | |
| SEQUENCE: 170 | | |
| attggttttt ggaattcagt g | | 21 |
| | | |
| SEQ ID NO: 171 | moltype = RNA length = 21 | |
| FEATURE | Location/Qualifiers | |
| source | 1..21 | |
| | mol_type = other RNA | |
| | organism = synthetic construct | |
| SEQUENCE: 171 | | |
| tattggtttt tggaattcag t | | 21 |
| | | |
| SEQ ID NO: 172 | moltype = RNA length = 21 | |
| FEATURE | Location/Qualifiers | |
| source | 1..21 | |
| | mol_type = other RNA | |
| | organism = synthetic construct | |
| SEQUENCE: 172 | | |
| tatattggtt tttggaattc a | | 21 |
| | | |
| SEQ ID NO: 173 | moltype = RNA length = 21 | |
| FEATURE | Location/Qualifiers | |
| source | 1..21 | |
| | mol_type = other RNA | |
| | organism = synthetic construct | |
| SEQUENCE: 173 | | |
| tcatattggt ttttggaatt c | | 21 |
| | | |
| SEQ ID NO: 174 | moltype = RNA length = 21 | |
| FEATURE | Location/Qualifiers | |
| source | 1..21 | |
| | mol_type = other RNA | |
| | organism = synthetic construct | |
| SEQUENCE: 174 | | |
| ttaggcatat tggttttttgg a | | 21 |
| | | |
| SEQ ID NO: 175 | moltype = RNA length = 21 | |
| FEATURE | Location/Qualifiers | |
| source | 1..21 | |
| | mol_type = other RNA | |
| | organism = synthetic construct | |
| SEQUENCE: 175 | | |
| tgtaggcata ttggtttttg g | | 21 |
| | | |
| SEQ ID NO: 176 | moltype = RNA length = 21 | |
| FEATURE | Location/Qualifiers | |
| source | 1..21 | |
| | mol_type = other RNA | |
| | organism = synthetic construct | |
| SEQUENCE: 176 | | |
| aggtaggcat attggttttt g | | 21 |

| | | |
|---|---|---|
| SEQ ID NO: 177 | moltype = RNA length = 21 | |
| FEATURE | Location/Qualifiers | |
| source | 1..21<br>mol_type = other RNA<br>organism = synthetic construct | |
| SEQUENCE: 177 | | |
| aaggtaggca tattggtttt t | | 21 |
| | | |
| SEQ ID NO: 178 | moltype = RNA length = 21 | |
| FEATURE | Location/Qualifiers | |
| source | 1..21<br>mol_type = other RNA<br>organism = synthetic construct | |
| SEQUENCE: 178 | | |
| taaggtaggc atattggttt t | | 21 |
| | | |
| SEQ ID NO: 179 | moltype = RNA length = 21 | |
| FEATURE | Location/Qualifiers | |
| source | 1..21<br>mol_type = other RNA<br>organism = synthetic construct | |
| SEQUENCE: 179 | | |
| tgaaggtagg catattggtt t | | 21 |
| | | |
| SEQ ID NO: 180 | moltype = RNA length = 21 | |
| FEATURE | Location/Qualifiers | |
| source | 1..21<br>mol_type = other RNA<br>organism = synthetic construct | |
| SEQUENCE: 180 | | |
| tggaaggtag gcatattggt t | | 21 |
| | | |
| SEQ ID NO: 181 | moltype = RNA length = 21 | |
| FEATURE | Location/Qualifiers | |
| source | 1..21<br>mol_type = other RNA<br>organism = synthetic construct | |
| SEQUENCE: 181 | | |
| tcacctttgg aaggtaggca t | | 21 |
| | | |
| SEQ ID NO: 182 | moltype = RNA length = 21 | |
| FEATURE | Location/Qualifiers | |
| source | 1..21<br>mol_type = other RNA<br>organism = synthetic construct | |
| SEQUENCE: 182 | | |
| ttgtcacctt tggaaggtag g | | 21 |
| | | |
| SEQ ID NO: 183 | moltype = RNA length = 21 | |
| FEATURE | Location/Qualifiers | |
| source | 1..21<br>mol_type = other RNA<br>organism = synthetic construct | |
| SEQUENCE: 183 | | |
| tgtgtcacct tggaaggta g | | 21 |
| | | |
| SEQ ID NO: 184 | moltype = RNA length = 21 | |
| FEATURE | Location/Qualifiers | |
| source | 1..21<br>mol_type = other RNA<br>organism = synthetic construct | |
| SEQUENCE: 184 | | |
| ttgtgtcacc tttggaaggt a | | 21 |
| | | |
| SEQ ID NO: 185 | moltype = RNA length = 21 | |
| FEATURE | Location/Qualifiers | |
| source | 1..21<br>mol_type = other RNA<br>organism = synthetic construct | |
| SEQUENCE: 185 | | |
| ttgatgccca ccaaacgcca c | | 21 |
| | | |
| SEQ ID NO: 186 | moltype = RNA length = 21 | |
| FEATURE | Location/Qualifiers | |
| source | 1..21<br>mol_type = other RNA<br>organism = synthetic construct | |
| SEQUENCE: 186 | | |
| ttccctgcgg gcacagcctt c | | 21 |

```
SEQ ID NO: 187          moltype = RNA   length = 21
FEATURE                 Location/Qualifiers
source                  1..21
                        mol_type = other RNA
                        organism = synthetic construct
SEQUENCE: 187
accaggttgc tccctgcggg c                                                   21

SEQ ID NO: 188          moltype = RNA   length = 21
FEATURE                 Location/Qualifiers
source                  1..21
                        mol_type = other RNA
                        organism = synthetic construct
SEQUENCE: 188
taccaggttg ctccctgcgg g                                                   21

SEQ ID NO: 189          moltype = RNA   length = 21
FEATURE                 Location/Qualifiers
source                  1..21
                        mol_type = other RNA
                        organism = synthetic construct
SEQUENCE: 189
acaccaggtt gctccctgcg g                                                   21

SEQ ID NO: 190          moltype = RNA   length = 21
FEATURE                 Location/Qualifiers
source                  1..21
                        mol_type = other RNA
                        organism = synthetic construct
SEQUENCE: 190
tacaccaggt tgctccctgc g                                                   21

SEQ ID NO: 191          moltype = RNA   length = 21
FEATURE                 Location/Qualifiers
source                  1..21
                        mol_type = other RNA
                        organism = synthetic construct
SEQUENCE: 191
agacaccagg ttgctccctg c                                                   21

SEQ ID NO: 192          moltype = RNA   length = 21
FEATURE                 Location/Qualifiers
source                  1..21
                        mol_type = other RNA
                        organism = synthetic construct
SEQUENCE: 192
tagacaccag gttgctccct g                                                   21

SEQ ID NO: 193          moltype = RNA   length = 21
FEATURE                 Location/Qualifiers
source                  1..21
                        mol_type = other RNA
                        organism = synthetic construct
SEQUENCE: 193
ttagacacca ggttgctccc t                                                   21

SEQ ID NO: 194          moltype = RNA   length = 21
FEATURE                 Location/Qualifiers
source                  1..21
                        mol_type = other RNA
                        organism = synthetic construct
SEQUENCE: 194
tgtagacacc aggttgctcc c                                                   21

SEQ ID NO: 195          moltype = RNA   length = 21
FEATURE                 Location/Qualifiers
source                  1..21
                        mol_type = other RNA
                        organism = synthetic construct
SEQUENCE: 195
ttgtagacac caggttgctc c                                                   21

SEQ ID NO: 196          moltype = RNA   length = 21
FEATURE                 Location/Qualifiers
source                  1..21
                        mol_type = other RNA
                        organism = synthetic construct
SEQUENCE: 196
```

```
agcgactttg gtgtagacac c                                          21

SEQ ID NO: 197          moltype = RNA  length = 21
FEATURE                 Location/Qualifiers
source                  1..21
                        mol_type = other RNA
                        organism = synthetic construct
SEQUENCE: 197
tcagtccatg tactcagcga c                                          21

SEQ ID NO: 198          moltype = RNA  length = 21
FEATURE                 Location/Qualifiers
source                  1..21
                        mol_type = other RNA
                        organism = synthetic construct
SEQUENCE: 198
tccagtccat gtactcagcg a                                          21

SEQ ID NO: 199          moltype = RNA  length = 21
FEATURE                 Location/Qualifiers
source                  1..21
                        mol_type = other RNA
                        organism = synthetic construct
SEQUENCE: 199
atccagtcca tgtactcagc g                                          21

SEQ ID NO: 200          moltype = RNA  length = 21
FEATURE                 Location/Qualifiers
source                  1..21
                        mol_type = other RNA
                        organism = synthetic construct
SEQUENCE: 200
tctgtgtttt ctctaaaatc c                                          21

SEQ ID NO: 201          moltype = RNA  length = 21
FEATURE                 Location/Qualifiers
source                  1..21
                        mol_type = other RNA
                        organism = synthetic construct
SEQUENCE: 201
ttctgtgttt tctctaaaat c                                          21

SEQ ID NO: 202          moltype = RNA  length = 21
FEATURE                 Location/Qualifiers
source                  1..21
                        mol_type = other RNA
                        organism = synthetic construct
SEQUENCE: 202
tctctgtgtt ttctctaaaa t                                          21

SEQ ID NO: 203          moltype = RNA  length = 21
FEATURE                 Location/Qualifiers
source                  1..21
                        mol_type = other RNA
                        organism = synthetic construct
SEQUENCE: 203
tgctctgtgt tttctctaaa a                                          21

SEQ ID NO: 204          moltype = RNA  length = 21
FEATURE                 Location/Qualifiers
source                  1..21
                        mol_type = other RNA
                        organism = synthetic construct
SEQUENCE: 204
ttgctctgtg ttttctctaa a                                          21

SEQ ID NO: 205          moltype = RNA  length = 21
FEATURE                 Location/Qualifiers
source                  1..21
                        mol_type = other RNA
                        organism = synthetic construct
SEQUENCE: 205
tatcactgct ctgtgttttc t                                          21

SEQ ID NO: 206          moltype = RNA  length = 21
FEATURE                 Location/Qualifiers
source                  1..21
                        mol_type = other RNA
                        organism = synthetic construct
```

-continued

```
SEQUENCE: 206
ttccatcact gctctgtgtt t                                             21

SEQ ID NO: 207          moltype = RNA   length = 21
FEATURE                 Location/Qualifiers
source                  1..21
                        mol_type = other RNA
                        organism = synthetic construct
SEQUENCE: 207
tttccatcac tgctctgtgt t                                             21

SEQ ID NO: 208          moltype = RNA   length = 21
FEATURE                 Location/Qualifiers
source                  1..21
                        mol_type = other RNA
                        organism = synthetic construct
SEQUENCE: 208
tgctcagaat ttgacttgaa c                                             21

SEQ ID NO: 209          moltype = RNA   length = 21
FEATURE                 Location/Qualifiers
source                  1..21
                        mol_type = other RNA
                        organism = synthetic construct
SEQUENCE: 209
aggctcagaa tttgacttga a                                             21

SEQ ID NO: 210          moltype = RNA   length = 21
FEATURE                 Location/Qualifiers
source                  1..21
                        mol_type = other RNA
                        organism = synthetic construct
SEQUENCE: 210
taggctcaga atttgacttg a                                             21

SEQ ID NO: 211          moltype = RNA   length = 21
FEATURE                 Location/Qualifiers
source                  1..21
                        mol_type = other RNA
                        organism = synthetic construct
SEQUENCE: 211
tcaggctcag aatttgactt g                                             21

SEQ ID NO: 212          moltype = RNA   length = 21
FEATURE                 Location/Qualifiers
source                  1..21
                        mol_type = other RNA
                        organism = synthetic construct
SEQUENCE: 212
tccaggctca gaatttgact t                                             21

SEQ ID NO: 213          moltype = RNA   length = 21
FEATURE                 Location/Qualifiers
source                  1..21
                        mol_type = other RNA
                        organism = synthetic construct
SEQUENCE: 213
tccccaggct cagaatttga c                                             21

SEQ ID NO: 214          moltype = RNA   length = 21
FEATURE                 Location/Qualifiers
source                  1..21
                        mol_type = other RNA
                        organism = synthetic construct
SEQUENCE: 214
tctccatgct ttgcagatga g                                             21

SEQ ID NO: 215          moltype = RNA   length = 21
FEATURE                 Location/Qualifiers
source                  1..21
                        mol_type = other RNA
                        organism = synthetic construct
SEQUENCE: 215
tactctccat gctttgcaga t                                             21

SEQ ID NO: 216          moltype = RNA   length = 21
FEATURE                 Location/Qualifiers
source                  1..21
                        mol_type = other RNA
```

```
                        organism = synthetic construct
SEQUENCE: 216
tcactctcca tgctttgcag a                                              21

SEQ ID NO: 217          moltype = RNA   length = 21
FEATURE                 Location/Qualifiers
source                  1..21
                        mol_type = other RNA
                        organism = synthetic construct
SEQUENCE: 217
tccactctcc atgctttgca g                                              21

SEQ ID NO: 218          moltype = RNA   length = 21
FEATURE                 Location/Qualifiers
source                  1..21
                        mol_type = other RNA
                        organism = synthetic construct
SEQUENCE: 218
tgccactctc catgctttgc a                                              21

SEQ ID NO: 219          moltype = RNA   length = 21
FEATURE                 Location/Qualifiers
source                  1..21
                        mol_type = other RNA
                        organism = synthetic construct
SEQUENCE: 219
atgccactct ccatgctttg c                                              21

SEQ ID NO: 220          moltype = RNA   length = 21
FEATURE                 Location/Qualifiers
source                  1..21
                        mol_type = other RNA
                        organism = synthetic construct
SEQUENCE: 220
tatgccactc tccatgcttt g                                              21

SEQ ID NO: 221          moltype = RNA   length = 21
FEATURE                 Location/Qualifiers
source                  1..21
                        mol_type = other RNA
                        organism = synthetic construct
SEQUENCE: 221
agatgccact ctccatgctt t                                              21

SEQ ID NO: 222          moltype = RNA   length = 21
FEATURE                 Location/Qualifiers
source                  1..21
                        mol_type = other RNA
                        organism = synthetic construct
SEQUENCE: 222
tattgtcctc agcagctctg a                                              21

SEQ ID NO: 223          moltype = RNA   length = 21
FEATURE                 Location/Qualifiers
source                  1..21
                        mol_type = other RNA
                        organism = synthetic construct
SEQUENCE: 223
tctacatccc cacttctgaa g                                              21

SEQ ID NO: 224          moltype = RNA   length = 21
FEATURE                 Location/Qualifiers
source                  1..21
                        mol_type = other RNA
                        organism = synthetic construct
SEQUENCE: 224
agctacatcc ccatctctga a                                              21

SEQ ID NO: 225          moltype = RNA   length = 21
FEATURE                 Location/Qualifiers
source                  1..21
                        mol_type = other RNA
                        organism = synthetic construct
SEQUENCE: 225
taagctacat ccctacctct g                                              21

SEQ ID NO: 226          moltype = RNA   length = 21
FEATURE                 Location/Qualifiers
source                  1..21
```

```
                        mol_type = other RNA
                        organism = synthetic construct
SEQUENCE: 226
tgaagctaca tcctcacctc t                                              21

SEQ ID NO: 227          moltype = RNA   length = 21
FEATURE                 Location/Qualifiers
source                  1..21
                        mol_type = other RNA
                        organism = synthetic construct
SEQUENCE: 227
tggaagctac atctccacct c                                              21

SEQ ID NO: 228          moltype = RNA   length = 21
FEATURE                 Location/Qualifiers
source                  1..21
                        mol_type = other RNA
                        organism = synthetic construct
SEQUENCE: 228
atggaagcta cattcccacc t                                              21

SEQ ID NO: 229          moltype = RNA   length = 21
FEATURE                 Location/Qualifiers
source                  1..21
                        mol_type = other RNA
                        organism = synthetic construct
SEQUENCE: 229
tacatggaag ctatatcccc a                                              21

SEQ ID NO: 230          moltype = RNA   length = 21
FEATURE                 Location/Qualifiers
source                  1..21
                        mol_type = other RNA
                        organism = synthetic construct
SEQUENCE: 230
taatagcaaa cactttgggt g                                              21

SEQ ID NO: 231          moltype = RNA   length = 21
FEATURE                 Location/Qualifiers
source                  1..21
                        mol_type = other RNA
                        organism = synthetic construct
SEQUENCE: 231
tgaatagcaa acatcttggg t                                              21

SEQ ID NO: 232          moltype = RNA   length = 21
FEATURE                 Location/Qualifiers
source                  1..21
                        mol_type = other RNA
                        organism = synthetic construct
SEQUENCE: 232
actgaatagc aaataccttg g                                              21

SEQ ID NO: 233          moltype = RNA   length = 21
FEATURE                 Location/Qualifiers
source                  1..21
                        mol_type = other RNA
                        organism = synthetic construct
SEQUENCE: 233
taaaactgaa tagtaaacac c                                              21

SEQ ID NO: 234          moltype = RNA   length = 21
FEATURE                 Location/Qualifiers
source                  1..21
                        mol_type = other RNA
                        organism = synthetic construct
SEQUENCE: 234
taaacctttt ctctatgtca t                                              21

SEQ ID NO: 235          moltype = RNA   length = 21
FEATURE                 Location/Qualifiers
source                  1..21
                        mol_type = other RNA
                        organism = synthetic construct
SEQUENCE: 235
taacactatc ttttaagaag c                                              21

SEQ ID NO: 236          moltype = RNA   length = 21
FEATURE                 Location/Qualifiers
```

```
source                  1..21
                        mol_type = other RNA
                        organism = synthetic construct
SEQUENCE: 236
tctgtaacac tattttttcaa g                                             21

SEQ ID NO: 237          moltype = RNA  length = 21
FEATURE                 Location/Qualifiers
source                  1..21
                        mol_type = other RNA
                        organism = synthetic construct
SEQUENCE: 237
aattgactcc tcttatatca a                                              21

SEQ ID NO: 238          moltype = RNA  length = 21
FEATURE                 Location/Qualifiers
source                  1..21
                        mol_type = other RNA
                        organism = synthetic construct
SEQUENCE: 238
aaaattgact cctttcatat c                                              21

SEQ ID NO: 239          moltype = RNA  length = 21
FEATURE                 Location/Qualifiers
source                  1..21
                        mol_type = other RNA
                        organism = synthetic construct
SEQUENCE: 239
ttaaaattga ctcttctcat a                                              21

SEQ ID NO: 240          moltype = RNA  length = 21
FEATURE                 Location/Qualifiers
source                  1..21
                        mol_type = other RNA
                        organism = synthetic construct
SEQUENCE: 240
attaaaattg acttctctca t                                              21

SEQ ID NO: 241          moltype = RNA  length = 21
FEATURE                 Location/Qualifiers
source                  1..21
                        mol_type = other RNA
                        organism = synthetic construct
SEQUENCE: 241
acattaaaat tgattcctct c                                              21

SEQ ID NO: 242          moltype = RNA  length = 21
FEATURE                 Location/Qualifiers
source                  1..21
                        mol_type = other RNA
                        organism = synthetic construct
SEQUENCE: 242
tcattcttca acattgctaa c                                              21

SEQ ID NO: 243          moltype = RNA  length = 21
FEATURE                 Location/Qualifiers
source                  1..21
                        mol_type = other RNA
                        organism = synthetic construct
SEQUENCE: 243
tggcattctt caatactgct a                                              21

SEQ ID NO: 244          moltype = RNA  length = 21
FEATURE                 Location/Qualifiers
source                  1..21
                        mol_type = other RNA
                        organism = synthetic construct
SEQUENCE: 244
ttttggcatt ctttaacact g                                              21

SEQ ID NO: 245          moltype = RNA  length = 21
FEATURE                 Location/Qualifiers
source                  1..21
                        mol_type = other RNA
                        organism = synthetic construct
SEQUENCE: 245
tagaatccag atttcacgtt a                                              21

SEQ ID NO: 246          moltype = RNA  length = 21
```

```
FEATURE                 Location/Qualifiers
source                  1..21
                        mol_type = other RNA
                        organism = synthetic construct
SEQUENCE: 246
ttcagtgaga atctagattc c                                              21

SEQ ID NO: 247          moltype = RNA   length = 21
FEATURE                 Location/Qualifiers
source                  1..21
                        mol_type = other RNA
                        organism = synthetic construct
SEQUENCE: 247
taaagttctt ttgtaggtta a                                              21

SEQ ID NO: 248          moltype = RNA   length = 21
FEATURE                 Location/Qualifiers
source                  1..21
                        mol_type = other RNA
                        organism = synthetic construct
SEQUENCE: 248
ttcaggtaaa gttttttgc a                                               21

SEQ ID NO: 249          moltype = RNA   length = 21
FEATURE                 Location/Qualifiers
source                  1..21
                        mol_type = other RNA
                        organism = synthetic construct
SEQUENCE: 249
taatggcagg gtttaggtaa a                                              21

SEQ ID NO: 250          moltype = RNA   length = 21
FEATURE                 Location/Qualifiers
source                  1..21
                        mol_type = other RNA
                        organism = synthetic construct
SEQUENCE: 250
aattttagaa tggtagggtt c                                              21

SEQ ID NO: 251          moltype = RNA   length = 21
FEATURE                 Location/Qualifiers
source                  1..21
                        mol_type = other RNA
                        organism = synthetic construct
SEQUENCE: 251
taaagtcaac tcctgggtaa a                                              21

SEQ ID NO: 252          moltype = RNA   length = 21
FEATURE                 Location/Qualifiers
source                  1..21
                        mol_type = other RNA
                        organism = synthetic construct
SEQUENCE: 252
tcaaagtcaa ctctcgggta a                                              21

SEQ ID NO: 253          moltype = RNA   length = 21
FEATURE                 Location/Qualifiers
source                  1..21
                        mol_type = other RNA
                        organism = synthetic construct
SEQUENCE: 253
tccaaagtca acttccgggt a                                              21

SEQ ID NO: 254          moltype = RNA   length = 21
FEATURE                 Location/Qualifiers
source                  1..21
                        mol_type = other RNA
                        organism = synthetic construct
SEQUENCE: 254
ttcaattctt ctcttccaaa g                                              21

SEQ ID NO: 255          moltype = RNA   length = 21
FEATURE                 Location/Qualifiers
source                  1..21
                        mol_type = other RNA
                        organism = synthetic construct
SEQUENCE: 255
attcaattct tcttctccaa a                                              21
```

```
SEQ ID NO: 256          moltype = RNA   length = 21
FEATURE                 Location/Qualifiers
source                  1..21
                        mol_type = other RNA
                        organism = synthetic construct
SEQUENCE: 256
tttggcaaac atttactcct t                                                   21

SEQ ID NO: 257          moltype = RNA   length = 21
FEATURE                 Location/Qualifiers
source                  1..21
                        mol_type = other RNA
                        organism = synthetic construct
SEQUENCE: 257
actgacagcg aattatcttt g                                                   21

SEQ ID NO: 258          moltype = RNA   length = 21
FEATURE                 Location/Qualifiers
source                  1..21
                        mol_type = other RNA
                        organism = synthetic construct
SEQUENCE: 258
agtgaaaaac tgatagcgaa t                                                   21

SEQ ID NO: 259          moltype = RNA   length = 21
FEATURE                 Location/Qualifiers
source                  1..21
                        mol_type = other RNA
                        organism = synthetic construct
SEQUENCE: 259
aataagtgaa aaattgacag c                                                   21

SEQ ID NO: 260          moltype = RNA   length = 21
FEATURE                 Location/Qualifiers
source                  1..21
                        mol_type = other RNA
                        organism = synthetic construct
SEQUENCE: 260
tccttacagt cttttgggag t                                                   21

SEQ ID NO: 261          moltype = RNA   length = 21
FEATURE                 Location/Qualifiers
source                  1..21
                        mol_type = other RNA
                        organism = synthetic construct
SEQUENCE: 261
taaccagagc tcctttgtgt c                                                   21

SEQ ID NO: 262          moltype = RNA   length = 21
FEATURE                 Location/Qualifiers
source                  1..21
                        mol_type = other RNA
                        organism = synthetic construct
SEQUENCE: 262
ttaaccagag ctctcttgtg t                                                   21

SEQ ID NO: 263          moltype = RNA   length = 21
FEATURE                 Location/Qualifiers
source                  1..21
                        mol_type = other RNA
                        organism = synthetic construct
SEQUENCE: 263
agagtaacca gagttccctt g                                                   21

SEQ ID NO: 264          moltype = RNA   length = 21
FEATURE                 Location/Qualifiers
source                  1..21
                        mol_type = other RNA
                        organism = synthetic construct
SEQUENCE: 264
tctcaaagag taatcagagc t                                                   21

SEQ ID NO: 265          moltype = RNA   length = 21
FEATURE                 Location/Qualifiers
source                  1..21
                        mol_type = other RNA
                        organism = synthetic construct
SEQUENCE: 265
tcccagtgtt acataatctc a                                                   21
```

```
SEQ ID NO: 266          moltype = RNA   length = 21
FEATURE                 Location/Qualifiers
source                  1..21
                        mol_type = other RNA
                        organism = synthetic construct
SEQUENCE: 266
tttgttcctc caataatgcg t                                                     21

SEQ ID NO: 267          moltype = RNA   length = 21
FEATURE                 Location/Qualifiers
source                  1..21
                        mol_type = other RNA
                        organism = synthetic construct
SEQUENCE: 267
tagtttgttc ctctaacaat g                                                     21

SEQ ID NO: 268          moltype = RNA   length = 21
FEATURE                 Location/Qualifiers
source                  1..21
                        mol_type = other RNA
                        organism = synthetic construct
SEQUENCE: 268
agagtttgtt ccttcaacaa t                                                     21

SEQ ID NO: 269          moltype = RNA   length = 21
FEATURE                 Location/Qualifiers
source                  1..21
                        mol_type = other RNA
                        organism = synthetic construct
SEQUENCE: 269
taagagtttg ttcttccaac a                                                     21

SEQ ID NO: 270          moltype = RNA   length = 21
FEATURE                 Location/Qualifiers
source                  1..21
                        mol_type = other RNA
                        organism = synthetic construct
SEQUENCE: 270
agaagagttt gtttctccaa c                                                     21

SEQ ID NO: 271          moltype = RNA   length = 21
FEATURE                 Location/Qualifiers
source                  1..21
                        mol_type = other RNA
                        organism = synthetic construct
SEQUENCE: 271
agggccactc tcctcaagaa g                                                     21

SEQ ID NO: 272          moltype = RNA   length = 21
FEATURE                 Location/Qualifiers
source                  1..21
                        mol_type = other RNA
                        organism = synthetic construct
SEQUENCE: 272
tagggccact ctctccaaga a                                                     21

SEQ ID NO: 273          moltype = RNA   length = 21
FEATURE                 Location/Qualifiers
source                  1..21
                        mol_type = other RNA
                        organism = synthetic construct
SEQUENCE: 273
tcagggccac tcttcccaag a                                                     21

SEQ ID NO: 274          moltype = RNA   length = 21
FEATURE                 Location/Qualifiers
source                  1..21
                        mol_type = other RNA
                        organism = synthetic construct
SEQUENCE: 274
tagtgaccct ccatacaggt g                                                     21

SEQ ID NO: 275          moltype = RNA   length = 21
FEATURE                 Location/Qualifiers
source                  1..21
                        mol_type = other RNA
                        organism = synthetic construct
SEQUENCE: 275
```

```
tatgagtgac ccttcacaca g                                               21

SEQ ID NO: 276          moltype = RNA   length = 21
FEATURE                 Location/Qualifiers
source                  1..21
                        mol_type = other RNA
                        organism = synthetic construct
SEQUENCE: 276
tctatgagtg accttccaca c                                               21

SEQ ID NO: 277          moltype = RNA   length = 21
FEATURE                 Location/Qualifiers
source                  1..21
                        mol_type = other RNA
                        organism = synthetic construct
SEQUENCE: 277
tcctatgagt gactctccac a                                               21

SEQ ID NO: 278          moltype = RNA   length = 21
FEATURE                 Location/Qualifiers
source                  1..21
                        mol_type = other RNA
                        organism = synthetic construct
SEQUENCE: 278
ttcctatgag tgatcctcca c                                               21

SEQ ID NO: 279          moltype = RNA   length = 21
FEATURE                 Location/Qualifiers
source                  1..21
                        mol_type = other RNA
                        organism = synthetic construct
SEQUENCE: 279
acccactggt gtcttatgag t                                               21

SEQ ID NO: 280          moltype = RNA   length = 21
FEATURE                 Location/Qualifiers
source                  1..21
                        mol_type = other RNA
                        organism = synthetic construct
SEQUENCE: 280
tacccactgg tgttctatga g                                               21

SEQ ID NO: 281          moltype = RNA   length = 21
FEATURE                 Location/Qualifiers
source                  1..21
                        mol_type = other RNA
                        organism = synthetic construct
SEQUENCE: 281
tcttttgtaa tgtttgacag a                                               21

SEQ ID NO: 282          moltype = RNA   length = 21
FEATURE                 Location/Qualifiers
source                  1..21
                        mol_type = other RNA
                        organism = synthetic construct
SEQUENCE: 282
atatcatgat tcctttctga g                                               21

SEQ ID NO: 283          moltype = RNA   length = 21
FEATURE                 Location/Qualifiers
source                  1..21
                        mol_type = other RNA
                        organism = synthetic construct
SEQUENCE: 283
aattcaaagg agcttggagt t                                               21

SEQ ID NO: 284          moltype = RNA   length = 21
FEATURE                 Location/Qualifiers
source                  1..21
                        mol_type = other RNA
                        organism = synthetic construct
SEQUENCE: 284
taattcaaag gagtctggag t                                               21

SEQ ID NO: 285          moltype = RNA   length = 21
FEATURE                 Location/Qualifiers
source                  1..21
                        mol_type = other RNA
                        organism = synthetic construct
```

```
SEQUENCE: 285
tcccaccaaa cgctacattc c                                              21

SEQ ID NO: 286         moltype = RNA   length = 21
FEATURE                Location/Qualifiers
source                 1..21
                       mol_type = other RNA
                       organism = synthetic construct
SEQUENCE: 286
tgcccaccaa acgtcacatt c                                              21

SEQ ID NO: 287         moltype = RNA   length = 21
FEATURE                Location/Qualifiers
source                 1..21
                       mol_type = other RNA
                       organism = synthetic construct
SEQUENCE: 287
tatgcccacc aaatgccaca t                                              21

SEQ ID NO: 288         moltype = RNA   length = 21
FEATURE                Location/Qualifiers
source                 1..21
                       mol_type = other RNA
                       organism = synthetic construct
SEQUENCE: 288
ttccctgcgg gcatagcctt c                                              21

SEQ ID NO: 289         moltype = RNA   length = 21
FEATURE                Location/Qualifiers
source                 1..21
                       mol_type = other RNA
                       organism = synthetic construct
SEQUENCE: 289
accaggttgc tccttgcggg c                                              21

SEQ ID NO: 290         moltype = RNA   length = 21
FEATURE                Location/Qualifiers
source                 1..21
                       mol_type = other RNA
                       organism = synthetic construct
SEQUENCE: 290
taccaggttg ctctctgcgg g                                              21

SEQ ID NO: 291         moltype = RNA   length = 21
FEATURE                Location/Qualifiers
source                 1..21
                       mol_type = other RNA
                       organism = synthetic construct
SEQUENCE: 291
acaccaggtt gcttcctgcg g                                              21

SEQ ID NO: 292         moltype = RNA   length = 21
FEATURE                Location/Qualifiers
source                 1..21
                       mol_type = other RNA
                       organism = synthetic construct
SEQUENCE: 292
agacaccagg ttgttccctg c                                              21

SEQ ID NO: 293         moltype = RNA   length = 21
FEATURE                Location/Qualifiers
source                 1..21
                       mol_type = other RNA
                       organism = synthetic construct
SEQUENCE: 293
atgtactcag cgattttggt g                                              21

SEQ ID NO: 294         moltype = RNA   length = 21
FEATURE                Location/Qualifiers
source                 1..21
                       mol_type = other RNA
                       organism = synthetic construct
SEQUENCE: 294
tccatgtact cagtgacttt g                                              21

SEQ ID NO: 295         moltype = RNA   length = 21
FEATURE                Location/Qualifiers
source                 1..21
                       mol_type = other RNA
```

```
                        organism = synthetic construct
SEQUENCE: 295
tagtccatgt acttagcgac t                                              21

SEQ ID NO: 296          moltype = RNA   length = 21
FEATURE                 Location/Qualifiers
source                  1..21
                        mol_type = other RNA
                        organism = synthetic construct
SEQUENCE: 296
tccagtccat gtattcagcg a                                              21

SEQ ID NO: 297          moltype = RNA   length = 21
FEATURE                 Location/Qualifiers
source                  1..21
                        mol_type = other RNA
                        organism = synthetic construct
SEQUENCE: 297
ttaaaatcca gtctatgtac t                                              21

SEQ ID NO: 298          moltype = RNA   length = 21
FEATURE                 Location/Qualifiers
source                  1..21
                        mol_type = other RNA
                        organism = synthetic construct
SEQUENCE: 298
tctaaaatcc agttcatgta c                                              21

SEQ ID NO: 299          moltype = RNA   length = 21
FEATURE                 Location/Qualifiers
source                  1..21
                        mol_type = other RNA
                        organism = synthetic construct
SEQUENCE: 299
ttctgtgttt tctttaaaat c                                              21

SEQ ID NO: 300          moltype = RNA   length = 21
FEATURE                 Location/Qualifiers
source                  1..21
                        mol_type = other RNA
                        organism = synthetic construct
SEQUENCE: 300
tgctctgtgt tttttctaaa a                                              21

SEQ ID NO: 301          moltype = RNA   length = 21
FEATURE                 Location/Qualifiers
source                  1..21
                        mol_type = other RNA
                        organism = synthetic construct
SEQUENCE: 301
ttccatcact gctttgtgtt t                                              21

SEQ ID NO: 302          moltype = RNA   length = 21
FEATURE                 Location/Qualifiers
source                  1..21
                        mol_type = other RNA
                        organism = synthetic construct
SEQUENCE: 302
tctccatgct ttgtagatga g                                              21

SEQ ID NO: 303          moltype = RNA   length = 21
FEATURE                 Location/Qualifiers
source                  1..21
                        mol_type = other RNA
                        organism = synthetic construct
SEQUENCE: 303
tccactctcc atgttttgca g                                              21

SEQ ID NO: 304          moltype = RNA   length = 21
FEATURE                 Location/Qualifiers
source                  1..21
                        mol_type = other RNA
                        organism = synthetic construct
SEQUENCE: 304
agatgccact ctctatgctt t                                              21

SEQ ID NO: 305          moltype = RNA   length = 23
FEATURE                 Location/Qualifiers
source                  1..23
```

```
                        mol_type = other RNA
                        organism = synthetic construct
SEQUENCE: 305
tagtgtaatt caaaggagcc tgg                                          23

SEQ ID NO: 306          moltype = RNA   length = 23
FEATURE                 Location/Qualifiers
source                  1..23
                        mol_type = other RNA
                        organism = synthetic construct
SEQUENCE: 306
accaatttct gaaagggcac agg                                          23

SEQ ID NO: 307          moltype = RNA   length = 23
FEATURE                 Location/Qualifiers
source                  1..23
                        mol_type = other RNA
                        organism = synthetic construct
SEQUENCE: 307
tcacattcaa ttcttctcct cca                                          23

SEQ ID NO: 308          moltype = RNA   length = 23
FEATURE                 Location/Qualifiers
source                  1..23
                        mol_type = other RNA
                        organism = synthetic construct
SEQUENCE: 308
aagtgaaaaa ctgacagcga acc                                          23

SEQ ID NO: 309          moltype = RNA   length = 23
FEATURE                 Location/Qualifiers
source                  1..23
                        mol_type = other RNA
                        organism = synthetic construct
SEQUENCE: 309
aatcctagtt ggagaaccat ccg                                          23

SEQ ID NO: 310          moltype = RNA   length = 23
FEATURE                 Location/Qualifiers
source                  1..23
                        mol_type = other RNA
                        organism = synthetic construct
SEQUENCE: 310
tcaaagagta accagagctc cct                                          23

SEQ ID NO: 311          moltype = RNA   length = 23
FEATURE                 Location/Qualifiers
source                  1..23
                        mol_type = other RNA
                        organism = synthetic construct
SEQUENCE: 311
tacagattta aaatgccact gcg                                          23

SEQ ID NO: 312          moltype = RNA   length = 23
FEATURE                 Location/Qualifiers
source                  1..23
                        mol_type = other RNA
                        organism = synthetic construct
SEQUENCE: 312
tgtaattcaa aggagcctgg agt                                          23

SEQ ID NO: 313          moltype = RNA   length = 23
FEATURE                 Location/Qualifiers
source                  1..23
                        mol_type = other RNA
                        organism = synthetic construct
SEQUENCE: 313
tcatattggt ttttggaatt cag                                          23

SEQ ID NO: 314          moltype = RNA   length = 21
FEATURE                 Location/Qualifiers
source                  1..21
                        mol_type = other RNA
                        organism = synthetic construct
SEQUENCE: 314
tcttcagagg tggggatgta a                                            21

SEQ ID NO: 315          moltype = RNA   length = 21
FEATURE                 Location/Qualifiers
```

```
source                  1..21
                        mol_type = other RNA
                        organism = synthetic construct
SEQUENCE: 315
cttcagaggt ggggatgtag a                                              21

SEQ ID NO: 316          moltype = RNA   length = 21
FEATURE                 Location/Qualifiers
source                  1..21
                        mol_type = other RNA
                        organism = synthetic construct
SEQUENCE: 316
ttcagaggtg gggatgtagc t                                              21

SEQ ID NO: 317          moltype = RNA   length = 21
FEATURE                 Location/Qualifiers
source                  1..21
                        mol_type = other RNA
                        organism = synthetic construct
SEQUENCE: 317
tcagaggtgg ggatgtagct t                                              21

SEQ ID NO: 318          moltype = RNA   length = 21
FEATURE                 Location/Qualifiers
source                  1..21
                        mol_type = other RNA
                        organism = synthetic construct
SEQUENCE: 318
cagaggtggg gatgtagctt a                                              21

SEQ ID NO: 319          moltype = RNA   length = 21
FEATURE                 Location/Qualifiers
source                  1..21
                        mol_type = other RNA
                        organism = synthetic construct
SEQUENCE: 319
agaggtgggg atgtagcttc a                                              21

SEQ ID NO: 320          moltype = RNA   length = 21
FEATURE                 Location/Qualifiers
source                  1..21
                        mol_type = other RNA
                        organism = synthetic construct
SEQUENCE: 320
gaggtgggga tgtagcttcc a                                              21

SEQ ID NO: 321          moltype = RNA   length = 21
FEATURE                 Location/Qualifiers
source                  1..21
                        mol_type = other RNA
                        organism = synthetic construct
SEQUENCE: 321
aggtgggat gtagcttcca t                                               21

SEQ ID NO: 322          moltype = RNA   length = 21
FEATURE                 Location/Qualifiers
source                  1..21
                        mol_type = other RNA
                        organism = synthetic construct
SEQUENCE: 322
ggtgggatg tagcttccat a                                               21

SEQ ID NO: 323          moltype = RNA   length = 21
FEATURE                 Location/Qualifiers
source                  1..21
                        mol_type = other RNA
                        organism = synthetic construct
SEQUENCE: 323
gtgggatgt agcttccatg t                                               21

SEQ ID NO: 324          moltype = RNA   length = 21
FEATURE                 Location/Qualifiers
source                  1..21
                        mol_type = other RNA
                        organism = synthetic construct
SEQUENCE: 324
tgggatgta gcttccatgt a                                               21

SEQ ID NO: 325          moltype = RNA   length = 21
```

```
FEATURE                 Location/Qualifiers
source                  1..21
                        mol_type = other RNA
                        organism = synthetic construct
SEQUENCE: 325
ggggatgtag cttccatgta a                                              21

SEQ ID NO: 326          moltype = RNA   length = 21
FEATURE                 Location/Qualifiers
source                  1..21
                        mol_type = other RNA
                        organism = synthetic construct
SEQUENCE: 326
gtgcacattc cacccaaggt a                                              21

SEQ ID NO: 327          moltype = RNA   length = 21
FEATURE                 Location/Qualifiers
source                  1..21
                        mol_type = other RNA
                        organism = synthetic construct
SEQUENCE: 327
tgcacattcc acccaaggtg t                                              21

SEQ ID NO: 328          moltype = RNA   length = 21
FEATURE                 Location/Qualifiers
source                  1..21
                        mol_type = other RNA
                        organism = synthetic construct
SEQUENCE: 328
gcacattcca cccaaggtgt t                                              21

SEQ ID NO: 329          moltype = RNA   length = 21
FEATURE                 Location/Qualifiers
source                  1..21
                        mol_type = other RNA
                        organism = synthetic construct
SEQUENCE: 329
cattccaccc aaggtgtttg a                                              21

SEQ ID NO: 330          moltype = RNA   length = 21
FEATURE                 Location/Qualifiers
source                  1..21
                        mol_type = other RNA
                        organism = synthetic construct
SEQUENCE: 330
attccaccca aggtgtttgc t                                              21

SEQ ID NO: 331          moltype = RNA   length = 21
FEATURE                 Location/Qualifiers
source                  1..21
                        mol_type = other RNA
                        organism = synthetic construct
SEQUENCE: 331
ccacccaagg tgtttgctat t                                              21

SEQ ID NO: 332          moltype = RNA   length = 21
FEATURE                 Location/Qualifiers
source                  1..21
                        mol_type = other RNA
                        organism = synthetic construct
SEQUENCE: 332
cacccaaggt gtttgctatt a                                              21

SEQ ID NO: 333          moltype = RNA   length = 21
FEATURE                 Location/Qualifiers
source                  1..21
                        mol_type = other RNA
                        organism = synthetic construct
SEQUENCE: 333
acccaaggtg tttgctattc a                                              21

SEQ ID NO: 334          moltype = RNA   length = 21
FEATURE                 Location/Qualifiers
source                  1..21
                        mol_type = other RNA
                        organism = synthetic construct
SEQUENCE: 334
ccaaggtgtt tgctattcag t                                              21
```

| | | |
|---|---|---|
| SEQ ID NO: 335 | moltype = RNA length = 21 | |
| FEATURE | Location/Qualifiers | |
| source | 1..21 | |
| | mol_type = other RNA | |
| | organism = synthetic construct | |
| SEQUENCE: 335 | | |
| caaggtgttt gctattcagt t | | 21 |
| | | |
| SEQ ID NO: 336 | moltype = RNA length = 21 | |
| FEATURE | Location/Qualifiers | |
| source | 1..21 | |
| | mol_type = other RNA | |
| | organism = synthetic construct | |
| SEQUENCE: 336 | | |
| aaggtgtttg ctattcagtt t | | 21 |
| | | |
| SEQ ID NO: 337 | moltype = RNA length = 21 | |
| FEATURE | Location/Qualifiers | |
| source | 1..21 | |
| | mol_type = other RNA | |
| | organism = synthetic construct | |
| SEQUENCE: 337 | | |
| aggtgtttgc tattcagttt t | | 21 |
| | | |
| SEQ ID NO: 338 | moltype = RNA length = 21 | |
| FEATURE | Location/Qualifiers | |
| source | 1..21 | |
| | mol_type = other RNA | |
| | organism = synthetic construct | |
| SEQUENCE: 338 | | |
| ggtgtttgct attcagtttt a | | 21 |
| | | |
| SEQ ID NO: 339 | moltype = RNA length = 21 | |
| FEATURE | Location/Qualifiers | |
| source | 1..21 | |
| | mol_type = other RNA | |
| | organism = synthetic construct | |
| SEQUENCE: 339 | | |
| gtgtttgcta ttcagttttc t | | 21 |
| | | |
| SEQ ID NO: 340 | moltype = RNA length = 21 | |
| FEATURE | Location/Qualifiers | |
| source | 1..21 | |
| | mol_type = other RNA | |
| | organism = synthetic construct | |
| SEQUENCE: 340 | | |
| ttgctattca gttttcttcc a | | 21 |
| | | |
| SEQ ID NO: 341 | moltype = RNA length = 21 | |
| FEATURE | Location/Qualifiers | |
| source | 1..21 | |
| | mol_type = other RNA | |
| | organism = synthetic construct | |
| SEQUENCE: 341 | | |
| cagttttctt ccagcaagtt a | | 21 |
| | | |
| SEQ ID NO: 342 | moltype = RNA length = 21 | |
| FEATURE | Location/Qualifiers | |
| source | 1..21 | |
| | mol_type = other RNA | |
| | organism = synthetic construct | |
| SEQUENCE: 342 | | |
| atcaatgaca tggagaaaag a | | 21 |
| | | |
| SEQ ID NO: 343 | moltype = RNA length = 21 | |
| FEATURE | Location/Qualifiers | |
| source | 1..21 | |
| | mol_type = other RNA | |
| | organism = synthetic construct | |
| SEQUENCE: 343 | | |
| aatgacatgg agaaaaggtt t | | 21 |
| | | |
| SEQ ID NO: 344 | moltype = RNA length = 21 | |
| FEATURE | Location/Qualifiers | |
| source | 1..21 | |
| | mol_type = other RNA | |
| | organism = synthetic construct | |
| SEQUENCE: 344 | | |
| atgacatgga gaaaaggttt a | | 21 |

| SEQ ID NO: 345 | moltype = RNA length = 21 |
| FEATURE | Location/Qualifiers |
| source | 1..21 |
| | mol_type = other RNA |
| | organism = synthetic construct |

SEQUENCE: 345
tgaagaatgc caaaaaggt a                                              21

| SEQ ID NO: 346 | moltype = RNA length = 21 |
| FEATURE | Location/Qualifiers |
| source | 1..21 |
| | mol_type = other RNA |
| | organism = synthetic construct |

SEQUENCE: 346
aatgccaaaa aaggtgcacc a                                             21

| SEQ ID NO: 347 | moltype = RNA length = 21 |
| FEATURE | Location/Qualifiers |
| source | 1..21 |
| | mol_type = other RNA |
| | organism = synthetic construct |

SEQUENCE: 347
tgtgcccttt cagaaattgg t                                             21

| SEQ ID NO: 348 | moltype = RNA length = 21 |
| FEATURE | Location/Qualifiers |
| source | 1..21 |
| | mol_type = other RNA |
| | organism = synthetic construct |

SEQUENCE: 348
gtgcccttc agaaattggt t                                              21

| SEQ ID NO: 349 | moltype = RNA length = 21 |
| FEATURE | Location/Qualifiers |
| source | 1..21 |
| | mol_type = other RNA |
| | organism = synthetic construct |

SEQUENCE: 349
gaacatcttc cagcatcttg a                                             21

| SEQ ID NO: 350 | moltype = RNA length = 21 |
| FEATURE | Location/Qualifiers |
| source | 1..21 |
| | mol_type = other RNA |
| | organism = synthetic construct |

SEQUENCE: 350
aaagtggcac accaagttcc t                                             21

| SEQ ID NO: 351 | moltype = RNA length = 21 |
| FEATURE | Location/Qualifiers |
| source | 1..21 |
| | mol_type = other RNA |
| | organism = synthetic construct |

SEQUENCE: 351
aagtggcaca ccaagttcct a                                             21

| SEQ ID NO: 352 | moltype = RNA length = 21 |
| FEATURE | Location/Qualifiers |
| source | 1..21 |
| | mol_type = other RNA |
| | organism = synthetic construct |

SEQUENCE: 352
agtggcacac caagttcctc t                                             21

| SEQ ID NO: 353 | moltype = RNA length = 21 |
| FEATURE | Location/Qualifiers |
| source | 1..21 |
| | mol_type = other RNA |
| | organism = synthetic construct |

SEQUENCE: 353
gtggcacacc aagttcctct a                                             21

| SEQ ID NO: 354 | moltype = RNA length = 21 |
| FEATURE | Location/Qualifiers |
| source | 1..21 |
| | mol_type = other RNA |
| | organism = synthetic construct |

SEQUENCE: 354

```
tggcacacca agttcctcta a                                                      21

SEQ ID NO: 355          moltype = RNA   length = 21
FEATURE                 Location/Qualifiers
source                  1..21
                        mol_type = other RNA
                        organism = synthetic construct
SEQUENCE: 355
caccaagttc ctctactcct a                                                      21

SEQ ID NO: 356          moltype = RNA   length = 21
FEATURE                 Location/Qualifiers
source                  1..21
                        mol_type = other RNA
                        organism = synthetic construct
SEQUENCE: 356
accaagttcc tctactcctc a                                                      21

SEQ ID NO: 357          moltype = RNA   length = 21
FEATURE                 Location/Qualifiers
source                  1..21
                        mol_type = other RNA
                        organism = synthetic construct
SEQUENCE: 357
ccaagttcct ctactcctca a                                                      21

SEQ ID NO: 358          moltype = RNA   length = 21
FEATURE                 Location/Qualifiers
source                  1..21
                        mol_type = other RNA
                        organism = synthetic construct
SEQUENCE: 358
caagttcctc tactcctcaa a                                                      21

SEQ ID NO: 359          moltype = RNA   length = 21
FEATURE                 Location/Qualifiers
source                  1..21
                        mol_type = other RNA
                        organism = synthetic construct
SEQUENCE: 359
aagttcctct actcctcaag a                                                      21

SEQ ID NO: 360          moltype = RNA   length = 21
FEATURE                 Location/Qualifiers
source                  1..21
                        mol_type = other RNA
                        organism = synthetic construct
SEQUENCE: 360
agttcctcta ctcctcaaga a                                                      21

SEQ ID NO: 361          moltype = RNA   length = 21
FEATURE                 Location/Qualifiers
source                  1..21
                        mol_type = other RNA
                        organism = synthetic construct
SEQUENCE: 361
gttcctctac tcctcaagaa a                                                      21

SEQ ID NO: 362          moltype = RNA   length = 21
FEATURE                 Location/Qualifiers
source                  1..21
                        mol_type = other RNA
                        organism = synthetic construct
SEQUENCE: 362
ttcctctact cctcaagaaa a                                                      21

SEQ ID NO: 363          moltype = RNA   length = 21
FEATURE                 Location/Qualifiers
source                  1..21
                        mol_type = other RNA
                        organism = synthetic construct
SEQUENCE: 363
ctctactcct caagaaaaca a                                                      21

SEQ ID NO: 364          moltype = RNA   length = 21
FEATURE                 Location/Qualifiers
source                  1..21
                        mol_type = other RNA
                        organism = synthetic construct
```

```
SEQUENCE: 364
tctactcctc aagaaaacac a                                                   21

SEQ ID NO: 365          moltype = RNA   length = 21
FEATURE                 Location/Qualifiers
source                  1..21
                        mol_type = other RNA
                        organism = synthetic construct
SEQUENCE: 365
ctactcctca agaaaacacc a                                                   21

SEQ ID NO: 366          moltype = RNA   length = 21
FEATURE                 Location/Qualifiers
source                  1..21
                        mol_type = other RNA
                        organism = synthetic construct
SEQUENCE: 366
agcctttaa cctgcaaaag a                                                    21

SEQ ID NO: 367          moltype = RNA   length = 21
FEATURE                 Location/Qualifiers
source                  1..21
                        mol_type = other RNA
                        organism = synthetic construct
SEQUENCE: 367
aaagaacttt acctgaaccc t                                                   21

SEQ ID NO: 368          moltype = RNA   length = 21
FEATURE                 Location/Qualifiers
source                  1..21
                        mol_type = other RNA
                        organism = synthetic construct
SEQUENCE: 368
aagaacttta cctgaaccct a                                                   21

SEQ ID NO: 369          moltype = RNA   length = 21
FEATURE                 Location/Qualifiers
source                  1..21
                        mol_type = other RNA
                        organism = synthetic construct
SEQUENCE: 369
agaactttac ctgaaccctg a                                                   21

SEQ ID NO: 370          moltype = RNA   length = 21
FEATURE                 Location/Qualifiers
source                  1..21
                        mol_type = other RNA
                        organism = synthetic construct
SEQUENCE: 370
gaactttacc tgaaccctgc a                                                   21

SEQ ID NO: 371          moltype = RNA   length = 21
FEATURE                 Location/Qualifiers
source                  1..21
                        mol_type = other RNA
                        organism = synthetic construct
SEQUENCE: 371
aactttacct gaaccctgcc a                                                   21

SEQ ID NO: 372          moltype = RNA   length = 21
FEATURE                 Location/Qualifiers
source                  1..21
                        mol_type = other RNA
                        organism = synthetic construct
SEQUENCE: 372
actttacctg aaccctgcca t                                                   21

SEQ ID NO: 373          moltype = RNA   length = 21
FEATURE                 Location/Qualifiers
source                  1..21
                        mol_type = other RNA
                        organism = synthetic construct
SEQUENCE: 373
tttacctgaa ccctgccatt a                                                   21

SEQ ID NO: 374          moltype = RNA   length = 21
FEATURE                 Location/Qualifiers
source                  1..21
                        mol_type = other RNA
```

-continued

```
                         organism = synthetic construct
SEQUENCE: 374
ttacctgaac cctgccattc t                                              21

SEQ ID NO: 375           moltype = RNA   length = 21
FEATURE                  Location/Qualifiers
source                   1..21
                         mol_type = other RNA
                         organism = synthetic construct
SEQUENCE: 375
tacctgaacc ctgccattct a                                              21

SEQ ID NO: 376           moltype = RNA   length = 21
FEATURE                  Location/Qualifiers
source                   1..21
                         mol_type = other RNA
                         organism = synthetic construct
SEQUENCE: 376
acctgaaccc tgccattcta a                                              21

SEQ ID NO: 377           moltype = RNA   length = 21
FEATURE                  Location/Qualifiers
source                   1..21
                         mol_type = other RNA
                         organism = synthetic construct
SEQUENCE: 377
cctgaaccct gccattctaa a                                              21

SEQ ID NO: 378           moltype = RNA   length = 21
FEATURE                  Location/Qualifiers
source                   1..21
                         mol_type = other RNA
                         organism = synthetic construct
SEQUENCE: 378
ctgaaccctg ccattctaaa a                                              21

SEQ ID NO: 379           moltype = RNA   length = 21
FEATURE                  Location/Qualifiers
source                   1..21
                         mol_type = other RNA
                         organism = synthetic construct
SEQUENCE: 379
tgaaccctgc cattctaaaa t                                              21

SEQ ID NO: 380           moltype = RNA   length = 21
FEATURE                  Location/Qualifiers
source                   1..21
                         mol_type = other RNA
                         organism = synthetic construct
SEQUENCE: 380
gaaccctgcc attctaaaat t                                              21

SEQ ID NO: 381           moltype = RNA   length = 21
FEATURE                  Location/Qualifiers
source                   1..21
                         mol_type = other RNA
                         organism = synthetic construct
SEQUENCE: 381
aaccctgcca ttctaaaatt t                                              21

SEQ ID NO: 382           moltype = RNA   length = 21
FEATURE                  Location/Qualifiers
source                   1..21
                         mol_type = other RNA
                         organism = synthetic construct
SEQUENCE: 382
accctgccat tctaaaattt a                                              21

SEQ ID NO: 383           moltype = RNA   length = 21
FEATURE                  Location/Qualifiers
source                   1..21
                         mol_type = other RNA
                         organism = synthetic construct
SEQUENCE: 383
ccctgccatt ctaaaattta a                                              21

SEQ ID NO: 384           moltype = RNA   length = 21
FEATURE                  Location/Qualifiers
source                   1..21
```

```
                        mol_type = other RNA
                        organism = synthetic construct
SEQUENCE: 384
cctgccattc taaaatttac a                                           21

SEQ ID NO: 385          moltype = RNA  length = 21
FEATURE                 Location/Qualifiers
source                  1..21
                        mol_type = other RNA
                        organism = synthetic construct
SEQUENCE: 385
gccattctaa aatttacccg a                                           21

SEQ ID NO: 386          moltype = RNA  length = 21
FEATURE                 Location/Qualifiers
source                  1..21
                        mol_type = other RNA
                        organism = synthetic construct
SEQUENCE: 386
ccattctaaa atttacccgg a                                           21

SEQ ID NO: 387          moltype = RNA  length = 21
FEATURE                 Location/Qualifiers
source                  1..21
                        mol_type = other RNA
                        organism = synthetic construct
SEQUENCE: 387
ggaggagaag aattgaatgt a                                           21

SEQ ID NO: 388          moltype = RNA  length = 21
FEATURE                 Location/Qualifiers
source                  1..21
                        mol_type = other RNA
                        organism = synthetic construct
SEQUENCE: 388
gaggagaaga attgaatgtg a                                           21

SEQ ID NO: 389          moltype = RNA  length = 21
FEATURE                 Location/Qualifiers
source                  1..21
                        mol_type = other RNA
                        organism = synthetic construct
SEQUENCE: 389
ggagaagaat tgaatgtgac t                                           21

SEQ ID NO: 390          moltype = RNA  length = 21
FEATURE                 Location/Qualifiers
source                  1..21
                        mol_type = other RNA
                        organism = synthetic construct
SEQUENCE: 390
ttaaaggagt gaatgtttgc a                                           21

SEQ ID NO: 391          moltype = RNA  length = 21
FEATURE                 Location/Qualifiers
source                  1..21
                        mol_type = other RNA
                        organism = synthetic construct
SEQUENCE: 391
caaagatgat tcgctgtcag t                                           21

SEQ ID NO: 392          moltype = RNA  length = 21
FEATURE                 Location/Qualifiers
source                  1..21
                        mol_type = other RNA
                        organism = synthetic construct
SEQUENCE: 392
aaagatgatt cgctgtcagt t                                           21

SEQ ID NO: 393          moltype = RNA  length = 21
FEATURE                 Location/Qualifiers
source                  1..21
                        mol_type = other RNA
                        organism = synthetic construct
SEQUENCE: 393
aagatgattc gctgtcagtt t                                           21

SEQ ID NO: 394          moltype = RNA  length = 21
FEATURE                 Location/Qualifiers
```

```
source                  1..21
                        mol_type = other RNA
                        organism = synthetic construct
SEQUENCE: 394
agatgattcg ctgtcagttt t                                          21

SEQ ID NO: 395          moltype = RNA   length = 21
FEATURE                 Location/Qualifiers
source                  1..21
                        mol_type = other RNA
                        organism = synthetic construct
SEQUENCE: 395
gatgattcgc tgtcagtttt t                                          21

SEQ ID NO: 396          moltype = RNA   length = 21
FEATURE                 Location/Qualifiers
source                  1..21
                        mol_type = other RNA
                        organism = synthetic construct
SEQUENCE: 396
gattcgctgt cagttttca a                                           21

SEQ ID NO: 397          moltype = RNA   length = 21
FEATURE                 Location/Qualifiers
source                  1..21
                        mol_type = other RNA
                        organism = synthetic construct
SEQUENCE: 397
attcgctgtc agttttcac t                                           21

SEQ ID NO: 398          moltype = RNA   length = 21
FEATURE                 Location/Qualifiers
source                  1..21
                        mol_type = other RNA
                        organism = synthetic construct
SEQUENCE: 398
ttcgctgtca gttttcact t                                           21

SEQ ID NO: 399          moltype = RNA   length = 21
FEATURE                 Location/Qualifiers
source                  1..21
                        mol_type = other RNA
                        organism = synthetic construct
SEQUENCE: 399
tcgctgtcag ttttcactt a                                           21

SEQ ID NO: 400          moltype = RNA   length = 21
FEATURE                 Location/Qualifiers
source                  1..21
                        mol_type = other RNA
                        organism = synthetic construct
SEQUENCE: 400
cgctgtcagt tttcactta t                                           21

SEQ ID NO: 401          moltype = RNA   length = 21
FEATURE                 Location/Qualifiers
source                  1..21
                        mol_type = other RNA
                        organism = synthetic construct
SEQUENCE: 401
gctgtcagtt tttcacttat t                                          21

SEQ ID NO: 402          moltype = RNA   length = 21
FEATURE                 Location/Qualifiers
source                  1..21
                        mol_type = other RNA
                        organism = synthetic construct
SEQUENCE: 402
gtcagttttt cacttattct t                                          21

SEQ ID NO: 403          moltype = RNA   length = 21
FEATURE                 Location/Qualifiers
source                  1..21
                        mol_type = other RNA
                        organism = synthetic construct
SEQUENCE: 403
tcagttttc acttattctt t                                           21

SEQ ID NO: 404          moltype = RNA   length = 21
```

```
FEATURE              Location/Qualifiers
source               1..21
                     mol_type = other RNA
                     organism = synthetic construct
SEQUENCE: 404
tttttcactt attctttact a                                              21

SEQ ID NO: 405       moltype = RNA  length = 21
FEATURE              Location/Qualifiers
source               1..21
                     mol_type = other RNA
                     organism = synthetic construct
SEQUENCE: 405
ttttcactta ttctttactc a                                              21

SEQ ID NO: 406       moltype = RNA  length = 21
FEATURE              Location/Qualifiers
source               1..21
                     mol_type = other RNA
                     organism = synthetic construct
SEQUENCE: 406
tttcacttat tctttactcc a                                              21

SEQ ID NO: 407       moltype = RNA  length = 21
FEATURE              Location/Qualifiers
source               1..21
                     mol_type = other RNA
                     organism = synthetic construct
SEQUENCE: 407
ttcacttatt ctttactccc a                                              21

SEQ ID NO: 408       moltype = RNA  length = 21
FEATURE              Location/Qualifiers
source               1..21
                     mol_type = other RNA
                     organism = synthetic construct
SEQUENCE: 408
tcacttattc tttactccca a                                              21

SEQ ID NO: 409       moltype = RNA  length = 21
FEATURE              Location/Qualifiers
source               1..21
                     mol_type = other RNA
                     organism = synthetic construct
SEQUENCE: 409
cacttattct ttactcccag a                                              21

SEQ ID NO: 410       moltype = RNA  length = 21
FEATURE              Location/Qualifiers
source               1..21
                     mol_type = other RNA
                     organism = synthetic construct
SEQUENCE: 410
acttattctt tactcccaga a                                              21

SEQ ID NO: 411       moltype = RNA  length = 21
FEATURE              Location/Qualifiers
source               1..21
                     mol_type = other RNA
                     organism = synthetic construct
SEQUENCE: 411
cttattcttt actcccagaa a                                              21

SEQ ID NO: 412       moltype = RNA  length = 21
FEATURE              Location/Qualifiers
source               1..21
                     mol_type = other RNA
                     organism = synthetic construct
SEQUENCE: 412
ttattcttta ctcccagaag a                                              21

SEQ ID NO: 413       moltype = RNA  length = 21
FEATURE              Location/Qualifiers
source               1..21
                     mol_type = other RNA
                     organism = synthetic construct
SEQUENCE: 413
attctttact cccagaagac t                                              21
```

```
SEQ ID NO: 414         moltype = RNA  length = 21
FEATURE                Location/Qualifiers
source                 1..21
                       mol_type = other RNA
                       organism = synthetic construct
SEQUENCE: 414
ttctttactc ccagaagact a                                                   21

SEQ ID NO: 415         moltype = RNA  length = 21
FEATURE                Location/Qualifiers
source                 1..21
                       mol_type = other RNA
                       organism = synthetic construct
SEQUENCE: 415
ttactcccag aagactgtaa a                                                   21

SEQ ID NO: 416         moltype = RNA  length = 21
FEATURE                Location/Qualifiers
source                 1..21
                       mol_type = other RNA
                       organism = synthetic construct
SEQUENCE: 416
tactcccaga agactgtaag a                                                   21

SEQ ID NO: 417         moltype = RNA  length = 21
FEATURE                Location/Qualifiers
source                 1..21
                       mol_type = other RNA
                       organism = synthetic construct
SEQUENCE: 417
actcccagaa gactgtaagg a                                                   21

SEQ ID NO: 418         moltype = RNA  length = 21
FEATURE                Location/Qualifiers
source                 1..21
                       mol_type = other RNA
                       organism = synthetic construct
SEQUENCE: 418
gagaagtgta agtgtttctt a                                                   21

SEQ ID NO: 419         moltype = RNA  length = 21
FEATURE                Location/Qualifiers
source                 1..21
                       mol_type = other RNA
                       organism = synthetic construct
SEQUENCE: 419
agaagtgtaa gtgtttctta a                                                   21

SEQ ID NO: 420         moltype = RNA  length = 21
FEATURE                Location/Qualifiers
source                 1..21
                       mol_type = other RNA
                       organism = synthetic construct
SEQUENCE: 420
gaagtgtaag tgtttcttaa a                                                   21

SEQ ID NO: 421         moltype = RNA  length = 21
FEATURE                Location/Qualifiers
source                 1..21
                       mol_type = other RNA
                       organism = synthetic construct
SEQUENCE: 421
taagtgtttc ttaagattat a                                                   21

SEQ ID NO: 422         moltype = RNA  length = 21
FEATURE                Location/Qualifiers
source                 1..21
                       mol_type = other RNA
                       organism = synthetic construct
SEQUENCE: 422
ggatggttct ccaactagga t                                                   21

SEQ ID NO: 423         moltype = RNA  length = 21
FEATURE                Location/Qualifiers
source                 1..21
                       mol_type = other RNA
                       organism = synthetic construct
SEQUENCE: 423
gatggttctc caactaggat t                                                   21
```

```
SEQ ID NO: 424          moltype = RNA   length = 21
FEATURE                 Location/Qualifiers
source                  1..21
                        mol_type = other RNA
                        organism = synthetic construct
SEQUENCE: 424
atgggacaca agggagctct a                                                   21

SEQ ID NO: 425          moltype = RNA   length = 21
FEATURE                 Location/Qualifiers
source                  1..21
                        mol_type = other RNA
                        organism = synthetic construct
SEQUENCE: 425
tgggacacaa gggagctctg a                                                   21

SEQ ID NO: 426          moltype = RNA   length = 21
FEATURE                 Location/Qualifiers
source                  1..21
                        mol_type = other RNA
                        organism = synthetic construct
SEQUENCE: 426
ggacacaagg gagctctggt t                                                   21

SEQ ID NO: 427          moltype = RNA   length = 21
FEATURE                 Location/Qualifiers
source                  1..21
                        mol_type = other RNA
                        organism = synthetic construct
SEQUENCE: 427
gacacaaggg agctctggtt a                                                   21

SEQ ID NO: 428          moltype = RNA   length = 21
FEATURE                 Location/Qualifiers
source                  1..21
                        mol_type = other RNA
                        organism = synthetic construct
SEQUENCE: 428
acacaaggga gctctggtta a                                                   21

SEQ ID NO: 429          moltype = RNA   length = 21
FEATURE                 Location/Qualifiers
source                  1..21
                        mol_type = other RNA
                        organism = synthetic construct
SEQUENCE: 429
acaagggagc tctggttact a                                                   21

SEQ ID NO: 430          moltype = RNA   length = 21
FEATURE                 Location/Qualifiers
source                  1..21
                        mol_type = other RNA
                        organism = synthetic construct
SEQUENCE: 430
caagggagct ctggttactc t                                                   21

SEQ ID NO: 431          moltype = RNA   length = 21
FEATURE                 Location/Qualifiers
source                  1..21
                        mol_type = other RNA
                        organism = synthetic construct
SEQUENCE: 431
ggagctctgg ttactctttg a                                                   21

SEQ ID NO: 432          moltype = RNA   length = 21
FEATURE                 Location/Qualifiers
source                  1..21
                        mol_type = other RNA
                        organism = synthetic construct
SEQUENCE: 432
ttgagattgt gtaacactgg a                                                   21

SEQ ID NO: 433          moltype = RNA   length = 21
FEATURE                 Location/Qualifiers
source                  1..21
                        mol_type = other RNA
                        organism = synthetic construct
SEQUENCE: 433
```

```
tgagattgtg taacactggg a                                              21

SEQ ID NO: 434          moltype = RNA   length = 21
FEATURE                 Location/Qualifiers
source                  1..21
                        mol_type = other RNA
                        organism = synthetic construct
SEQUENCE: 434
gattgtgtaa cactggggac a                                              21

SEQ ID NO: 435          moltype = RNA   length = 21
FEATURE                 Location/Qualifiers
source                  1..21
                        mol_type = other RNA
                        organism = synthetic construct
SEQUENCE: 435
aggaacaaac tcttcttggg a                                              21

SEQ ID NO: 436          moltype = RNA   length = 21
FEATURE                 Location/Qualifiers
source                  1..21
                        mol_type = other RNA
                        organism = synthetic construct
SEQUENCE: 436
ggaacaaact cttcttgggg a                                              21

SEQ ID NO: 437          moltype = RNA   length = 21
FEATURE                 Location/Qualifiers
source                  1..21
                        mol_type = other RNA
                        organism = synthetic construct
SEQUENCE: 437
gaacaaactc ttcttgggga a                                              21

SEQ ID NO: 438          moltype = RNA   length = 21
FEATURE                 Location/Qualifiers
source                  1..21
                        mol_type = other RNA
                        organism = synthetic construct
SEQUENCE: 438
aacaaactct tcttggggag a                                              21

SEQ ID NO: 439          moltype = RNA   length = 21
FEATURE                 Location/Qualifiers
source                  1..21
                        mol_type = other RNA
                        organism = synthetic construct
SEQUENCE: 439
acaaactctt cttggggaga a                                              21

SEQ ID NO: 440          moltype = RNA   length = 21
FEATURE                 Location/Qualifiers
source                  1..21
                        mol_type = other RNA
                        organism = synthetic construct
SEQUENCE: 440
caaactcttc ttggggagag t                                              21

SEQ ID NO: 441          moltype = RNA   length = 21
FEATURE                 Location/Qualifiers
source                  1..21
                        mol_type = other RNA
                        organism = synthetic construct
SEQUENCE: 441
aactcttctt ggggagagtg a                                              21

SEQ ID NO: 442          moltype = RNA   length = 21
FEATURE                 Location/Qualifiers
source                  1..21
                        mol_type = other RNA
                        organism = synthetic construct
SEQUENCE: 442
actcttcttg gggagagtgg a                                              21

SEQ ID NO: 443          moltype = RNA   length = 21
FEATURE                 Location/Qualifiers
source                  1..21
                        mol_type = other RNA
                        organism = synthetic construct
```

```
SEQUENCE: 443
cttcttgggg agagtggccc t                                              21

SEQ ID NO: 444          moltype = RNA   length = 21
FEATURE                 Location/Qualifiers
source                  1..21
                        mol_type = other RNA
                        organism = synthetic construct
SEQUENCE: 444
ttcttgggga gagtggccct a                                              21

SEQ ID NO: 445          moltype = RNA   length = 21
FEATURE                 Location/Qualifiers
source                  1..21
                        mol_type = other RNA
                        organism = synthetic construct
SEQUENCE: 445
tcttgggag agtggccctg a                                               21

SEQ ID NO: 446          moltype = RNA   length = 21
FEATURE                 Location/Qualifiers
source                  1..21
                        mol_type = other RNA
                        organism = synthetic construct
SEQUENCE: 446
gggtcactca taggacacca a                                              21

SEQ ID NO: 447          moltype = RNA   length = 21
FEATURE                 Location/Qualifiers
source                  1..21
                        mol_type = other RNA
                        organism = synthetic construct
SEQUENCE: 447
ggtcactcat aggacaccag t                                              21

SEQ ID NO: 448          moltype = RNA   length = 21
FEATURE                 Location/Qualifiers
source                  1..21
                        mol_type = other RNA
                        organism = synthetic construct
SEQUENCE: 448
cactcatagg acaccagtgg a                                              21

SEQ ID NO: 449          moltype = RNA   length = 21
FEATURE                 Location/Qualifiers
source                  1..21
                        mol_type = other RNA
                        organism = synthetic construct
SEQUENCE: 449
actcatagga caccagtggg t                                              21

SEQ ID NO: 450          moltype = RNA   length = 21
FEATURE                 Location/Qualifiers
source                  1..21
                        mol_type = other RNA
                        organism = synthetic construct
SEQUENCE: 450
ctcataggac accagtgggt a                                              21

SEQ ID NO: 451          moltype = RNA   length = 21
FEATURE                 Location/Qualifiers
source                  1..21
                        mol_type = other RNA
                        organism = synthetic construct
SEQUENCE: 451
ccactgcttt gatgggcttc a                                              21

SEQ ID NO: 452          moltype = RNA   length = 21
FEATURE                 Location/Qualifiers
source                  1..21
                        mol_type = other RNA
                        organism = synthetic construct
SEQUENCE: 452
atagtggcat tttaaatctg t                                              21

SEQ ID NO: 453          moltype = RNA   length = 21
FEATURE                 Location/Qualifiers
source                  1..21
                        mol_type = other RNA
```

```
                        organism = synthetic construct
SEQUENCE: 453
tagtggcatt taaatctgt a                                                  21

SEQ ID NO: 454          moltype = RNA  length = 21
FEATURE                 Location/Qualifiers
source                  1..21
                        mol_type = other RNA
                        organism = synthetic construct
SEQUENCE: 454
agtggcattt taaatctgtc a                                                 21

SEQ ID NO: 455          moltype = RNA  length = 21
FEATURE                 Location/Qualifiers
source                  1..21
                        mol_type = other RNA
                        organism = synthetic construct
SEQUENCE: 455
gtggcatttt aaatctgtca a                                                 21

SEQ ID NO: 456          moltype = RNA  length = 21
FEATURE                 Location/Qualifiers
source                  1..21
                        mol_type = other RNA
                        organism = synthetic construct
SEQUENCE: 456
tggcatttta aatctgtcag a                                                 21

SEQ ID NO: 457          moltype = RNA  length = 21
FEATURE                 Location/Qualifiers
source                  1..21
                        mol_type = other RNA
                        organism = synthetic construct
SEQUENCE: 457
ggcattttaa atctgtcaga a                                                 21

SEQ ID NO: 458          moltype = RNA  length = 21
FEATURE                 Location/Qualifiers
source                  1..21
                        mol_type = other RNA
                        organism = synthetic construct
SEQUENCE: 458
gcattttaaa tctgtcagac a                                                 21

SEQ ID NO: 459          moltype = RNA  length = 21
FEATURE                 Location/Qualifiers
source                  1..21
                        mol_type = other RNA
                        organism = synthetic construct
SEQUENCE: 459
ttaaatctgt cagacattac a                                                 21

SEQ ID NO: 460          moltype = RNA  length = 21
FEATURE                 Location/Qualifiers
source                  1..21
                        mol_type = other RNA
                        organism = synthetic construct
SEQUENCE: 460
tctgtcagac attacaaaag a                                                 21

SEQ ID NO: 461          moltype = RNA  length = 21
FEATURE                 Location/Qualifiers
source                  1..21
                        mol_type = other RNA
                        organism = synthetic construct
SEQUENCE: 461
ctcagaaggg aatcatgata t                                                 21

SEQ ID NO: 462          moltype = RNA  length = 21
FEATURE                 Location/Qualifiers
source                  1..21
                        mol_type = other RNA
                        organism = synthetic construct
SEQUENCE: 462
agaagggaat catgatatcg a                                                 21

SEQ ID NO: 463          moltype = RNA  length = 21
FEATURE                 Location/Qualifiers
source                  1..21
```

```
                        mol_type = other RNA
                        organism = synthetic construct
SEQUENCE: 463
gaagggaatc atgatatcgc a                                              21

SEQ ID NO: 464          moltype = RNA   length = 21
FEATURE                 Location/Qualifiers
source                  1..21
                        mol_type = other RNA
                        organism = synthetic construct
SEQUENCE: 464
aagggaatca tgatatcgcc t                                              21

SEQ ID NO: 465          moltype = RNA   length = 21
FEATURE                 Location/Qualifiers
source                  1..21
                        mol_type = other RNA
                        organism = synthetic construct
SEQUENCE: 465
aactccaggc tcctttgaat t                                              21

SEQ ID NO: 466          moltype = RNA   length = 21
FEATURE                 Location/Qualifiers
source                  1..21
                        mol_type = other RNA
                        organism = synthetic construct
SEQUENCE: 466
actccaggct cctttgaatt a                                              21

SEQ ID NO: 467          moltype = RNA   length = 21
FEATURE                 Location/Qualifiers
source                  1..21
                        mol_type = other RNA
                        organism = synthetic construct
SEQUENCE: 467
ctccaggctc ctttgaatta a                                              21

SEQ ID NO: 468          moltype = RNA   length = 21
FEATURE                 Location/Qualifiers
source                  1..21
                        mol_type = other RNA
                        organism = synthetic construct
SEQUENCE: 468
tccaggctcc tttgaattac a                                              21

SEQ ID NO: 469          moltype = RNA   length = 21
FEATURE                 Location/Qualifiers
source                  1..21
                        mol_type = other RNA
                        organism = synthetic construct
SEQUENCE: 469
ccaggctcct ttgaattaca a                                              21

SEQ ID NO: 470          moltype = RNA   length = 21
FEATURE                 Location/Qualifiers
source                  1..21
                        mol_type = other RNA
                        organism = synthetic construct
SEQUENCE: 470
caggctcctt tgaattacac t                                              21

SEQ ID NO: 471          moltype = RNA   length = 21
FEATURE                 Location/Qualifiers
source                  1..21
                        mol_type = other RNA
                        organism = synthetic construct
SEQUENCE: 471
aggctccttt gaattacact a                                              21

SEQ ID NO: 472          moltype = RNA   length = 21
FEATURE                 Location/Qualifiers
source                  1..21
                        mol_type = other RNA
                        organism = synthetic construct
SEQUENCE: 472
ggctcctttg aattacactg a                                              21

SEQ ID NO: 473          moltype = RNA   length = 21
FEATURE                 Location/Qualifiers
```

```
                              -continued source                  1..21
                        mol_type = other RNA
                        organism = synthetic construct
SEQUENCE: 473
ctttgaatta cactgaattc a                                         21

SEQ ID NO: 474          moltype = RNA   length = 21
FEATURE                 Location/Qualifiers
source                  1..21
                        mol_type = other RNA
                        organism = synthetic construct
SEQUENCE: 474
cactgaattc caaaaaccaa t                                         21

SEQ ID NO: 475          moltype = RNA   length = 21
FEATURE                 Location/Qualifiers
source                  1..21
                        mol_type = other RNA
                        organism = synthetic construct
SEQUENCE: 475
actgaattcc aaaaaccaat a                                         21

SEQ ID NO: 476          moltype = RNA   length = 21
FEATURE                 Location/Qualifiers
source                  1..21
                        mol_type = other RNA
                        organism = synthetic construct
SEQUENCE: 476
tgaattccaa aaaccaatat a                                         21

SEQ ID NO: 477          moltype = RNA   length = 21
FEATURE                 Location/Qualifiers
source                  1..21
                        mol_type = other RNA
                        organism = synthetic construct
SEQUENCE: 477
gaattccaaa aaccaatatg a                                         21

SEQ ID NO: 478          moltype = RNA   length = 21
FEATURE                 Location/Qualifiers
source                  1..21
                        mol_type = other RNA
                        organism = synthetic construct
SEQUENCE: 478
tccaaaaacc aatatgccta a                                         21

SEQ ID NO: 479          moltype = RNA   length = 21
FEATURE                 Location/Qualifiers
source                  1..21
                        mol_type = other RNA
                        organism = synthetic construct
SEQUENCE: 479
ccaaaaacca atatgcctac a                                         21

SEQ ID NO: 480          moltype = RNA   length = 21
FEATURE                 Location/Qualifiers
source                  1..21
                        mol_type = other RNA
                        organism = synthetic construct
SEQUENCE: 480
caaaaaccaa tatgcctacc t                                         21

SEQ ID NO: 481          moltype = RNA   length = 21
FEATURE                 Location/Qualifiers
source                  1..21
                        mol_type = other RNA
                        organism = synthetic construct
SEQUENCE: 481
aaaaaccaat atgcctacct t                                         21

SEQ ID NO: 482          moltype = RNA   length = 21
FEATURE                 Location/Qualifiers
source                  1..21
                        mol_type = other RNA
                        organism = synthetic construct
SEQUENCE: 482
aaaccaata tgcctaccttt a                                         21

SEQ ID NO: 483          moltype = RNA   length = 21
```

-continued

```
FEATURE                 Location/Qualifiers
source                  1..21
                        mol_type = other RNA
                        organism = synthetic construct
SEQUENCE: 483
aaaccaatat gcctaccttc a                                              21

SEQ ID NO: 484          moltype = RNA   length = 21
FEATURE                 Location/Qualifiers
source                  1..21
                        mol_type = other RNA
                        organism = synthetic construct
SEQUENCE: 484
aaccaatatg cctaccttcc a                                              21

SEQ ID NO: 485          moltype = RNA   length = 21
FEATURE                 Location/Qualifiers
source                  1..21
                        mol_type = other RNA
                        organism = synthetic construct
SEQUENCE: 485
atgcctacct tccaaaggtg a                                              21

SEQ ID NO: 486          moltype = RNA   length = 21
FEATURE                 Location/Qualifiers
source                  1..21
                        mol_type = other RNA
                        organism = synthetic construct
SEQUENCE: 486
cctaccttcc aaaggtgaca a                                              21

SEQ ID NO: 487          moltype = RNA   length = 21
FEATURE                 Location/Qualifiers
source                  1..21
                        mol_type = other RNA
                        organism = synthetic construct
SEQUENCE: 487
ctaccttcca aaggtgacac a                                              21

SEQ ID NO: 488          moltype = RNA   length = 21
FEATURE                 Location/Qualifiers
source                  1..21
                        mol_type = other RNA
                        organism = synthetic construct
SEQUENCE: 488
taccttccaa aggtgacaca a                                              21

SEQ ID NO: 489          moltype = RNA   length = 21
FEATURE                 Location/Qualifiers
source                  1..21
                        mol_type = other RNA
                        organism = synthetic construct
SEQUENCE: 489
gtggcgtttg gtgggcatca a                                              21

SEQ ID NO: 490          moltype = RNA   length = 21
FEATURE                 Location/Qualifiers
source                  1..21
                        mol_type = other RNA
                        organism = synthetic construct
SEQUENCE: 490
gaaggctgtg cccgcaggga a                                              21

SEQ ID NO: 491          moltype = RNA   length = 21
FEATURE                 Location/Qualifiers
source                  1..21
                        mol_type = other RNA
                        organism = synthetic construct
SEQUENCE: 491
gcccgcaggg agcaacctgg t                                              21

SEQ ID NO: 492          moltype = RNA   length = 21
FEATURE                 Location/Qualifiers
source                  1..21
                        mol_type = other RNA
                        organism = synthetic construct
SEQUENCE: 492
cccgcaggga gcaacctggt a                                              21
```

| | | |
|---|---|---|
| SEQ ID NO: 493 | moltype = RNA  length = 21 | |
| FEATURE | Location/Qualifiers | |
| source | 1..21<br>mol_type = other RNA<br>organism = synthetic construct | |
| SEQUENCE: 493 | | |
| ccgcagggag caacctggtg t | | 21 |
| SEQ ID NO: 494 | moltype = RNA  length = 21 | |
| FEATURE | Location/Qualifiers | |
| source | 1..21<br>mol_type = other RNA<br>organism = synthetic construct | |
| SEQUENCE: 494 | | |
| cgcagggagc aacctggtgt a | | 21 |
| SEQ ID NO: 495 | moltype = RNA  length = 21 | |
| FEATURE | Location/Qualifiers | |
| source | 1..21<br>mol_type = other RNA<br>organism = synthetic construct | |
| SEQUENCE: 495 | | |
| gcagggagca acctggtgtc t | | 21 |
| SEQ ID NO: 496 | moltype = RNA  length = 21 | |
| FEATURE | Location/Qualifiers | |
| source | 1..21<br>mol_type = other RNA<br>organism = synthetic construct | |
| SEQUENCE: 496 | | |
| cagggagcaa cctggtgtct a | | 21 |
| SEQ ID NO: 497 | moltype = RNA  length = 21 | |
| FEATURE | Location/Qualifiers | |
| source | 1..21<br>mol_type = other RNA<br>organism = synthetic construct | |
| SEQUENCE: 497 | | |
| agggagcaac ctggtgtcta a | | 21 |
| SEQ ID NO: 498 | moltype = RNA  length = 21 | |
| FEATURE | Location/Qualifiers | |
| source | 1..21<br>mol_type = other RNA<br>organism = synthetic construct | |
| SEQUENCE: 498 | | |
| gggagcaacc tggtgtctac a | | 21 |
| SEQ ID NO: 499 | moltype = RNA  length = 21 | |
| FEATURE | Location/Qualifiers | |
| source | 1..21<br>mol_type = other RNA<br>organism = synthetic construct | |
| SEQUENCE: 499 | | |
| ggagcaacct ggtgtctaca a | | 21 |
| SEQ ID NO: 500 | moltype = RNA  length = 21 | |
| FEATURE | Location/Qualifiers | |
| source | 1..21<br>mol_type = other RNA<br>organism = synthetic construct | |
| SEQUENCE: 500 | | |
| ggtgtctaca ccaaagtcgc t | | 21 |
| SEQ ID NO: 501 | moltype = RNA  length = 21 | |
| FEATURE | Location/Qualifiers | |
| source | 1..21<br>mol_type = other RNA<br>organism = synthetic construct | |
| SEQUENCE: 501 | | |
| gtcgctgagt acatggactg a | | 21 |
| SEQ ID NO: 502 | moltype = RNA  length = 21 | |
| FEATURE | Location/Qualifiers | |
| source | 1..21<br>mol_type = other RNA<br>organism = synthetic construct | |
| SEQUENCE: 502 | | |
| tcgctgagta catggactgg a | | 21 |

```
SEQ ID NO: 503          moltype = RNA   length = 21
FEATURE                 Location/Qualifiers
source                  1..21
                        mol_type = other RNA
                        organism = synthetic construct
SEQUENCE: 503
cgctgagtac atggactgga t                                                   21

SEQ ID NO: 504          moltype = RNA   length = 21
FEATURE                 Location/Qualifiers
source                  1..21
                        mol_type = other RNA
                        organism = synthetic construct
SEQUENCE: 504
ggattttaga gaaaacacag a                                                   21

SEQ ID NO: 505          moltype = RNA   length = 21
FEATURE                 Location/Qualifiers
source                  1..21
                        mol_type = other RNA
                        organism = synthetic construct
SEQUENCE: 505
gattttagag aaaacacaga a                                                   21

SEQ ID NO: 506          moltype = RNA   length = 21
FEATURE                 Location/Qualifiers
source                  1..21
                        mol_type = other RNA
                        organism = synthetic construct
SEQUENCE: 506
attttagaga aaacacagag a                                                   21

SEQ ID NO: 507          moltype = RNA   length = 21
FEATURE                 Location/Qualifiers
source                  1..21
                        mol_type = other RNA
                        organism = synthetic construct
SEQUENCE: 507
ttttagagaa aacacagagc a                                                   21

SEQ ID NO: 508          moltype = RNA   length = 21
FEATURE                 Location/Qualifiers
source                  1..21
                        mol_type = other RNA
                        organism = synthetic construct
SEQUENCE: 508
tttagagaaa acacagagca a                                                   21

SEQ ID NO: 509          moltype = RNA   length = 21
FEATURE                 Location/Qualifiers
source                  1..21
                        mol_type = other RNA
                        organism = synthetic construct
SEQUENCE: 509
agaaaacaca gagcagtgat a                                                   21

SEQ ID NO: 510          moltype = RNA   length = 21
FEATURE                 Location/Qualifiers
source                  1..21
                        mol_type = other RNA
                        organism = synthetic construct
SEQUENCE: 510
aaacacagag cagtgatgga a                                                   21

SEQ ID NO: 511          moltype = RNA   length = 21
FEATURE                 Location/Qualifiers
source                  1..21
                        mol_type = other RNA
                        organism = synthetic construct
SEQUENCE: 511
aacacagagc agtgatggaa a                                                   21

SEQ ID NO: 512          moltype = RNA   length = 21
FEATURE                 Location/Qualifiers
source                  1..21
                        mol_type = other RNA
                        organism = synthetic construct
SEQUENCE: 512
```

```
gttcaagtca aattctgagc a                                              21

SEQ ID NO: 513          moltype = RNA   length = 21
FEATURE                 Location/Qualifiers
source                  1..21
                        mol_type = other RNA
                        organism = synthetic construct
SEQUENCE: 513
ttcaagtcaa attctgagcc t                                              21

SEQ ID NO: 514          moltype = RNA   length = 21
FEATURE                 Location/Qualifiers
source                  1..21
                        mol_type = other RNA
                        organism = synthetic construct
SEQUENCE: 514
tcaagtcaaa ttctgagcct a                                              21

SEQ ID NO: 515          moltype = RNA   length = 21
FEATURE                 Location/Qualifiers
source                  1..21
                        mol_type = other RNA
                        organism = synthetic construct
SEQUENCE: 515
caagtcaaat tctgagcctg a                                              21

SEQ ID NO: 516          moltype = RNA   length = 21
FEATURE                 Location/Qualifiers
source                  1..21
                        mol_type = other RNA
                        organism = synthetic construct
SEQUENCE: 516
aagtcaaatt ctgagcctgg a                                              21

SEQ ID NO: 517          moltype = RNA   length = 21
FEATURE                 Location/Qualifiers
source                  1..21
                        mol_type = other RNA
                        organism = synthetic construct
SEQUENCE: 517
gtcaaattct gagcctgggg a                                              21

SEQ ID NO: 518          moltype = RNA   length = 21
FEATURE                 Location/Qualifiers
source                  1..21
                        mol_type = other RNA
                        organism = synthetic construct
SEQUENCE: 518
ctcatctgca aagcatggag a                                              21

SEQ ID NO: 519          moltype = RNA   length = 21
FEATURE                 Location/Qualifiers
source                  1..21
                        mol_type = other RNA
                        organism = synthetic construct
SEQUENCE: 519
atctgcaaag catggagagt a                                              21

SEQ ID NO: 520          moltype = RNA   length = 21
FEATURE                 Location/Qualifiers
source                  1..21
                        mol_type = other RNA
                        organism = synthetic construct
SEQUENCE: 520
tctgcaaagc atggagagtg a                                              21

SEQ ID NO: 521          moltype = RNA   length = 21
FEATURE                 Location/Qualifiers
source                  1..21
                        mol_type = other RNA
                        organism = synthetic construct
SEQUENCE: 521
ctgcaaagca tggagagtgg a                                              21

SEQ ID NO: 522          moltype = RNA   length = 21
FEATURE                 Location/Qualifiers
source                  1..21
                        mol_type = other RNA
                        organism = synthetic construct
```

```
SEQUENCE: 522
tgcaaagcat ggagagtggc a                                                  21

SEQ ID NO: 523          moltype = RNA  length = 21
FEATURE                 Location/Qualifiers
source                  1..21
                        mol_type = other RNA
                        organism = synthetic construct
SEQUENCE: 523
gcaaagcatg gagagtggca t                                                  21

SEQ ID NO: 524          moltype = RNA  length = 21
FEATURE                 Location/Qualifiers
source                  1..21
                        mol_type = other RNA
                        organism = synthetic construct
SEQUENCE: 524
caaagcatgg agagtggcat a                                                  21

SEQ ID NO: 525          moltype = RNA  length = 21
FEATURE                 Location/Qualifiers
source                  1..21
                        mol_type = other RNA
                        organism = synthetic construct
SEQUENCE: 525
aaagcatgga gagtggcatc t                                                  21

SEQ ID NO: 526          moltype = RNA  length = 21
FEATURE                 Location/Qualifiers
source                  1..21
                        mol_type = other RNA
                        organism = synthetic construct
SEQUENCE: 526
tcagagctgc tgaggacaat a                                                  21

SEQ ID NO: 527          moltype = RNA  length = 21
FEATURE                 Location/Qualifiers
source                  1..21
                        mol_type = other RNA
                        organism = synthetic construct
SEQUENCE: 527
cttcagaagt ggggatgtag a                                                  21

SEQ ID NO: 528          moltype = RNA  length = 21
FEATURE                 Location/Qualifiers
source                  1..21
                        mol_type = other RNA
                        organism = synthetic construct
SEQUENCE: 528
ttcagagatg gggatgtagc t                                                  21

SEQ ID NO: 529          moltype = RNA  length = 21
FEATURE                 Location/Qualifiers
source                  1..21
                        mol_type = other RNA
                        organism = synthetic construct
SEQUENCE: 529
cagaggtagg gatgtagctt a                                                  21

SEQ ID NO: 530          moltype = RNA  length = 21
FEATURE                 Location/Qualifiers
source                  1..21
                        mol_type = other RNA
                        organism = synthetic construct
SEQUENCE: 530
agaggtgagg atgtagcttc a                                                  21

SEQ ID NO: 531          moltype = RNA  length = 21
FEATURE                 Location/Qualifiers
source                  1..21
                        mol_type = other RNA
                        organism = synthetic construct
SEQUENCE: 531
gaggtggaga tgtagcttcc a                                                  21

SEQ ID NO: 532          moltype = RNA  length = 21
FEATURE                 Location/Qualifiers
source                  1..21
                        mol_type = other RNA
```

```
                            organism = synthetic construct
SEQUENCE: 532
aggtgggaat gtagcttcca t                                              21

SEQ ID NO: 533          moltype = RNA  length = 21
FEATURE                 Location/Qualifiers
source                  1..21
                        mol_type = other RNA
                        organism = synthetic construct
SEQUENCE: 533
tggggatata gcttccatgt a                                              21

SEQ ID NO: 534          moltype = RNA  length = 21
FEATURE                 Location/Qualifiers
source                  1..21
                        mol_type = other RNA
                        organism = synthetic construct
SEQUENCE: 534
cacccaaagt gtttgctatt a                                              21

SEQ ID NO: 535          moltype = RNA  length = 21
FEATURE                 Location/Qualifiers
source                  1..21
                        mol_type = other RNA
                        organism = synthetic construct
SEQUENCE: 535
acccaagatg tttgctattc a                                              21

SEQ ID NO: 536          moltype = RNA  length = 21
FEATURE                 Location/Qualifiers
source                  1..21
                        mol_type = other RNA
                        organism = synthetic construct
SEQUENCE: 536
ccaaggtatt tgctattcag t                                              21

SEQ ID NO: 537          moltype = RNA  length = 21
FEATURE                 Location/Qualifiers
source                  1..21
                        mol_type = other RNA
                        organism = synthetic construct
SEQUENCE: 537
ggtgtttact attcagtttt a                                              21

SEQ ID NO: 538          moltype = RNA  length = 21
FEATURE                 Location/Qualifiers
source                  1..21
                        mol_type = other RNA
                        organism = synthetic construct
SEQUENCE: 538
atgacataga gaaaaggttt a                                              21

SEQ ID NO: 539          moltype = RNA  length = 21
FEATURE                 Location/Qualifiers
source                  1..21
                        mol_type = other RNA
                        organism = synthetic construct
SEQUENCE: 539
gcttcttaaa agatagtgtt a                                              21

SEQ ID NO: 540          moltype = RNA  length = 21
FEATURE                 Location/Qualifiers
source                  1..21
                        mol_type = other RNA
                        organism = synthetic construct
SEQUENCE: 540
cttgaaaaat agtgttacag a                                              21

SEQ ID NO: 541          moltype = RNA  length = 21
FEATURE                 Location/Qualifiers
source                  1..21
                        mol_type = other RNA
                        organism = synthetic construct
SEQUENCE: 541
ttgatataag aggagtcaat t                                              21

SEQ ID NO: 542          moltype = RNA  length = 21
FEATURE                 Location/Qualifiers
source                  1..21
```

```
                            mol_type = other RNA
                            organism = synthetic construct
SEQUENCE: 542
gatatgaaag gagtcaattt t                                          21

SEQ ID NO: 543              moltype = RNA   length = 21
FEATURE                     Location/Qualifiers
source                      1..21
                            mol_type = other RNA
                            organism = synthetic construct
SEQUENCE: 543
tatgagaaga gtcaatttta a                                          21

SEQ ID NO: 544              moltype = RNA   length = 21
FEATURE                     Location/Qualifiers
source                      1..21
                            mol_type = other RNA
                            organism = synthetic construct
SEQUENCE: 544
atgagagaag tcaattttaa t                                          21

SEQ ID NO: 545              moltype = RNA   length = 21
FEATURE                     Location/Qualifiers
source                      1..21
                            mol_type = other RNA
                            organism = synthetic construct
SEQUENCE: 545
gagaggaatc aattttaatg t                                          21

SEQ ID NO: 546              moltype = RNA   length = 21
FEATURE                     Location/Qualifiers
source                      1..21
                            mol_type = other RNA
                            organism = synthetic construct
SEQUENCE: 546
gttagcaatg ttgaagaatg a                                          21

SEQ ID NO: 547              moltype = RNA   length = 21
FEATURE                     Location/Qualifiers
source                      1..21
                            mol_type = other RNA
                            organism = synthetic construct
SEQUENCE: 547
tagcagtatt gaagaatgcc a                                          21

SEQ ID NO: 548              moltype = RNA   length = 21
FEATURE                     Location/Qualifiers
source                      1..21
                            mol_type = other RNA
                            organism = synthetic construct
SEQUENCE: 548
cagtgttaaa gaatgccaaa a                                          21

SEQ ID NO: 549              moltype = RNA   length = 21
FEATURE                     Location/Qualifiers
source                      1..21
                            mol_type = other RNA
                            organism = synthetic construct
SEQUENCE: 549
taacgtgaaa tctggattct a                                          21

SEQ ID NO: 550              moltype = RNA   length = 21
FEATURE                     Location/Qualifiers
source                      1..21
                            mol_type = other RNA
                            organism = synthetic construct
SEQUENCE: 550
ggaatctaga ttctcactga a                                          21

SEQ ID NO: 551              moltype = RNA   length = 21
FEATURE                     Location/Qualifiers
source                      1..21
                            mol_type = other RNA
                            organism = synthetic construct
SEQUENCE: 551
ttaacctaca aaagaacttt a                                          21

SEQ ID NO: 552              moltype = RNA   length = 21
FEATURE                     Location/Qualifiers
```

```
source                         1..21
                               mol_type = other RNA
                               organism = synthetic construct
SEQUENCE: 552
tgcaaaaaaa ctttacctga a                                                21

SEQ ID NO: 553                 moltype = RNA   length = 21
FEATURE                        Location/Qualifiers
source                         1..21
                               mol_type = other RNA
                               organism = synthetic construct
SEQUENCE: 553
tttacctaaa ccctgccatt a                                                21

SEQ ID NO: 554                 moltype = RNA   length = 21
FEATURE                        Location/Qualifiers
source                         1..21
                               mol_type = other RNA
                               organism = synthetic construct
SEQUENCE: 554
gaaccctacc attctaaaat t                                                21

SEQ ID NO: 555                 moltype = RNA   length = 21
FEATURE                        Location/Qualifiers
source                         1..21
                               mol_type = other RNA
                               organism = synthetic construct
SEQUENCE: 555
tttacccagg agttgacttt a                                                21

SEQ ID NO: 556                 moltype = RNA   length = 21
FEATURE                        Location/Qualifiers
source                         1..21
                               mol_type = other RNA
                               organism = synthetic construct
SEQUENCE: 556
ttacccgaga gttgactttg a                                                21

SEQ ID NO: 557                 moltype = RNA   length = 21
FEATURE                        Location/Qualifiers
source                         1..21
                               mol_type = other RNA
                               organism = synthetic construct
SEQUENCE: 557
tacccggaag ttgactttgg a                                                21

SEQ ID NO: 558                 moltype = RNA   length = 21
FEATURE                        Location/Qualifiers
source                         1..21
                               mol_type = other RNA
                               organism = synthetic construct
SEQUENCE: 558
ctttggaaga gaagaattga a                                                21

SEQ ID NO: 559                 moltype = RNA   length = 21
FEATURE                        Location/Qualifiers
source                         1..21
                               mol_type = other RNA
                               organism = synthetic construct
SEQUENCE: 559
tttggagaag aagaattgaa t                                                21

SEQ ID NO: 560                 moltype = RNA   length = 21
FEATURE                        Location/Qualifiers
source                         1..21
                               mol_type = other RNA
                               organism = synthetic construct
SEQUENCE: 560
aaggagtaaa tgtttgccaa a                                                21

SEQ ID NO: 561                 moltype = RNA   length = 21
FEATURE                        Location/Qualifiers
source                         1..21
                               mol_type = other RNA
                               organism = synthetic construct
SEQUENCE: 561
caaagataat tcgctgtcag t                                                21

SEQ ID NO: 562                 moltype = RNA   length = 21
```

```
FEATURE                 Location/Qualifiers
source                  1..21
                        mol_type = other RNA
                        organism = synthetic construct
SEQUENCE: 562
attcgctatc agtttttcac t                                              21

SEQ ID NO: 563          moltype = RNA  length = 21
FEATURE                 Location/Qualifiers
source                  1..21
                        mol_type = other RNA
                        organism = synthetic construct
SEQUENCE: 563
gctgtcaatt tttcacttat t                                              21

SEQ ID NO: 564          moltype = RNA  length = 21
FEATURE                 Location/Qualifiers
source                  1..21
                        mol_type = other RNA
                        organism = synthetic construct
SEQUENCE: 564
actcccaaaa gactgtaagg a                                              21

SEQ ID NO: 565          moltype = RNA  length = 21
FEATURE                 Location/Qualifiers
source                  1..21
                        mol_type = other RNA
                        organism = synthetic construct
SEQUENCE: 565
gacacaaagg agctctggtt a                                              21

SEQ ID NO: 566          moltype = RNA  length = 21
FEATURE                 Location/Qualifiers
source                  1..21
                        mol_type = other RNA
                        organism = synthetic construct
SEQUENCE: 566
acacaagaga gctctggtta a                                              21

SEQ ID NO: 567          moltype = RNA  length = 21
FEATURE                 Location/Qualifiers
source                  1..21
                        mol_type = other RNA
                        organism = synthetic construct
SEQUENCE: 567
caagggaact ctggttactc t                                              21

SEQ ID NO: 568          moltype = RNA  length = 21
FEATURE                 Location/Qualifiers
source                  1..21
                        mol_type = other RNA
                        organism = synthetic construct
SEQUENCE: 568
agctctgatt actctttgag a                                              21

SEQ ID NO: 569          moltype = RNA  length = 21
FEATURE                 Location/Qualifiers
source                  1..21
                        mol_type = other RNA
                        organism = synthetic construct
SEQUENCE: 569
tgagattatg taacactggg a                                              21

SEQ ID NO: 570          moltype = RNA  length = 21
FEATURE                 Location/Qualifiers
source                  1..21
                        mol_type = other RNA
                        organism = synthetic construct
SEQUENCE: 570
acgcattatt ggaggaacaa a                                              21

SEQ ID NO: 571          moltype = RNA  length = 21
FEATURE                 Location/Qualifiers
source                  1..21
                        mol_type = other RNA
                        organism = synthetic construct
SEQUENCE: 571
cattgttaga ggaacaaact a                                              21
```

```
SEQ ID NO: 572          moltype = RNA   length = 21
FEATURE                 Location/Qualifiers
source                  1..21
                        mol_type = other RNA
                        organism = synthetic construct
SEQUENCE: 572
attgttgaag gaacaaactc t                                                    21

SEQ ID NO: 573          moltype = RNA   length = 21
FEATURE                 Location/Qualifiers
source                  1..21
                        mol_type = other RNA
                        organism = synthetic construct
SEQUENCE: 573
tgttggaaga acaaactctt a                                                    21

SEQ ID NO: 574          moltype = RNA   length = 21
FEATURE                 Location/Qualifiers
source                  1..21
                        mol_type = other RNA
                        organism = synthetic construct
SEQUENCE: 574
gttggagaaa caaactcttc t                                                    21

SEQ ID NO: 575          moltype = RNA   length = 21
FEATURE                 Location/Qualifiers
source                  1..21
                        mol_type = other RNA
                        organism = synthetic construct
SEQUENCE: 575
cttcttgagg agagtggccc t                                                    21

SEQ ID NO: 576          moltype = RNA   length = 21
FEATURE                 Location/Qualifiers
source                  1..21
                        mol_type = other RNA
                        organism = synthetic construct
SEQUENCE: 576
ttcttggaga gagtggccct a                                                    21

SEQ ID NO: 577          moltype = RNA   length = 21
FEATURE                 Location/Qualifiers
source                  1..21
                        mol_type = other RNA
                        organism = synthetic construct
SEQUENCE: 577
tcttgggaag agtggccctg a                                                    21

SEQ ID NO: 578          moltype = RNA   length = 21
FEATURE                 Location/Qualifiers
source                  1..21
                        mol_type = other RNA
                        organism = synthetic construct
SEQUENCE: 578
cacctgtatg gagggtcact a                                                    21

SEQ ID NO: 579          moltype = RNA   length = 21
FEATURE                 Location/Qualifiers
source                  1..21
                        mol_type = other RNA
                        organism = synthetic construct
SEQUENCE: 579
ctgtgtgaag ggtcactcat a                                                    21

SEQ ID NO: 580          moltype = RNA   length = 21
FEATURE                 Location/Qualifiers
source                  1..21
                        mol_type = other RNA
                        organism = synthetic construct
SEQUENCE: 580
gtgtggaagg tcactcatag a                                                    21

SEQ ID NO: 581          moltype = RNA   length = 21
FEATURE                 Location/Qualifiers
source                  1..21
                        mol_type = other RNA
                        organism = synthetic construct
SEQUENCE: 581
tgtggagagt cactcatagg a                                                    21
```

```
SEQ ID NO: 582          moltype = RNA   length = 21
FEATURE                 Location/Qualifiers
source                  1..21
                        mol_type = other RNA
                        organism = synthetic construct
SEQUENCE: 582
gtggaggatc actcatagga a                                               21

SEQ ID NO: 583          moltype = RNA   length = 21
FEATURE                 Location/Qualifiers
source                  1..21
                        mol_type = other RNA
                        organism = synthetic construct
SEQUENCE: 583
actcataaga caccagtggg t                                               21

SEQ ID NO: 584          moltype = RNA   length = 21
FEATURE                 Location/Qualifiers
source                  1..21
                        mol_type = other RNA
                        organism = synthetic construct
SEQUENCE: 584
ctcatagaac accagtgggt a                                               21

SEQ ID NO: 585          moltype = RNA   length = 21
FEATURE                 Location/Qualifiers
source                  1..21
                        mol_type = other RNA
                        organism = synthetic construct
SEQUENCE: 585
tctgtcaaac attacaaaag a                                               21

SEQ ID NO: 586          moltype = RNA   length = 21
FEATURE                 Location/Qualifiers
source                  1..21
                        mol_type = other RNA
                        organism = synthetic construct
SEQUENCE: 586
ctcagaaagg aatcatgata t                                               21

SEQ ID NO: 587          moltype = RNA   length = 21
FEATURE                 Location/Qualifiers
source                  1..21
                        mol_type = other RNA
                        organism = synthetic construct
SEQUENCE: 587
aactccaagc tcctttgaat t                                               21

SEQ ID NO: 588          moltype = RNA   length = 21
FEATURE                 Location/Qualifiers
source                  1..21
                        mol_type = other RNA
                        organism = synthetic construct
SEQUENCE: 588
actccagact cctttgaatt a                                               21

SEQ ID NO: 589          moltype = RNA   length = 21
FEATURE                 Location/Qualifiers
source                  1..21
                        mol_type = other RNA
                        organism = synthetic construct
SEQUENCE: 589
ggaatgtagc gtttggtggg a                                               21

SEQ ID NO: 590          moltype = RNA   length = 21
FEATURE                 Location/Qualifiers
source                  1..21
                        mol_type = other RNA
                        organism = synthetic construct
SEQUENCE: 590
gaatgtgacg tttggtgggc a                                               21

SEQ ID NO: 591          moltype = RNA   length = 21
FEATURE                 Location/Qualifiers
source                  1..21
                        mol_type = other RNA
                        organism = synthetic construct
SEQUENCE: 591
```

```
atgtggcatt tggtgggcat a                                              21

SEQ ID NO: 592         moltype = RNA   length = 21
FEATURE                Location/Qualifiers
source                 1..21
                       mol_type = other RNA
                       organism = synthetic construct
SEQUENCE: 592
gaaggctatg cccgcaggga a                                              21

SEQ ID NO: 593         moltype = RNA   length = 21
FEATURE                Location/Qualifiers
source                 1..21
                       mol_type = other RNA
                       organism = synthetic construct
SEQUENCE: 593
gcccgcaagg agcaacctgg t                                              21

SEQ ID NO: 594         moltype = RNA   length = 21
FEATURE                Location/Qualifiers
source                 1..21
                       mol_type = other RNA
                       organism = synthetic construct
SEQUENCE: 594
cccgcagaga gcaacctggt a                                              21

SEQ ID NO: 595         moltype = RNA   length = 21
FEATURE                Location/Qualifiers
source                 1..21
                       mol_type = other RNA
                       organism = synthetic construct
SEQUENCE: 595
ccgcaggaag caacctggtg t                                              21

SEQ ID NO: 596         moltype = RNA   length = 21
FEATURE                Location/Qualifiers
source                 1..21
                       mol_type = other RNA
                       organism = synthetic construct
SEQUENCE: 596
gcagggaaca acctggtgtc t                                              21

SEQ ID NO: 597         moltype = RNA   length = 21
FEATURE                Location/Qualifiers
source                 1..21
                       mol_type = other RNA
                       organism = synthetic construct
SEQUENCE: 597
caccaaaatc gctgagtaca t                                              21

SEQ ID NO: 598         moltype = RNA   length = 21
FEATURE                Location/Qualifiers
source                 1..21
                       mol_type = other RNA
                       organism = synthetic construct
SEQUENCE: 598
caaagtcact gagtacatgg a                                              21

SEQ ID NO: 599         moltype = RNA   length = 21
FEATURE                Location/Qualifiers
source                 1..21
                       mol_type = other RNA
                       organism = synthetic construct
SEQUENCE: 599
agtcgctaag tacatggact a                                              21

SEQ ID NO: 600         moltype = RNA   length = 21
FEATURE                Location/Qualifiers
source                 1..21
                       mol_type = other RNA
                       organism = synthetic construct
SEQUENCE: 600
tcgctgaata catggactgg a                                              21

SEQ ID NO: 601         moltype = RNA   length = 21
FEATURE                Location/Qualifiers
source                 1..21
                       mol_type = other RNA
                       organism = synthetic construct
```

-continued

```
SEQUENCE: 601
agtacataga ctggatttta a                                              21

SEQ ID NO: 602         moltype = RNA    length = 21
FEATURE                Location/Qualifiers
source                 1..21
                       mol_type = other RNA
                       organism = synthetic construct
SEQUENCE: 602
gtacatgaac tggattttag a                                              21

SEQ ID NO: 603         moltype = RNA    length = 21
FEATURE                Location/Qualifiers
source                 1..21
                       mol_type = other RNA
                       organism = synthetic construct
SEQUENCE: 603
gattttaaag aaaacacaga a                                              21

SEQ ID NO: 604         moltype = RNA    length = 21
FEATURE                Location/Qualifiers
source                 1..21
                       mol_type = other RNA
                       organism = synthetic construct
SEQUENCE: 604
ttttagaaaa aacacagagc a                                              21

SEQ ID NO: 605         moltype = RNA    length = 21
FEATURE                Location/Qualifiers
source                 1..21
                       mol_type = other RNA
                       organism = synthetic construct
SEQUENCE: 605
aaacacaaag cagtgatgga a                                              21

SEQ ID NO: 606         moltype = RNA    length = 21
FEATURE                Location/Qualifiers
source                 1..21
                       mol_type = other RNA
                       organism = synthetic construct
SEQUENCE: 606
ctcatctaca aagcatggag a                                              21

SEQ ID NO: 607         moltype = RNA    length = 21
FEATURE                Location/Qualifiers
source                 1..21
                       mol_type = other RNA
                       organism = synthetic construct
SEQUENCE: 607
ctgcaaaaca tggagagtgg a                                              21

SEQ ID NO: 608         moltype = RNA    length = 21
FEATURE                Location/Qualifiers
source                 1..21
                       mol_type = other RNA
                       organism = synthetic construct
SEQUENCE: 608
aaagcataga gagtggcatc t                                              21

SEQ ID NO: 609         moltype = RNA    length = 22
FEATURE                Location/Qualifiers
source                 1..22
                       mol_type = other RNA
                       organism = synthetic construct
SEQUENCE: 609
caggctcctt tgaattacac ta                                             22

SEQ ID NO: 610         moltype = RNA    length = 24
FEATURE                Location/Qualifiers
source                 1..24
                       mol_type = other RNA
                       organism = synthetic construct
SEQUENCE: 610
tcctgtgccc tttcagaaat tggt                                           24

SEQ ID NO: 611         moltype = RNA    length = 23
FEATURE                Location/Qualifiers
source                 1..23
                       mol_type = other RNA
```

```
                              organism = synthetic construct
SEQUENCE: 611
cggaggagaa gaattgaatg tga                                                  23

SEQ ID NO: 612          moltype = RNA   length = 24
FEATURE                 Location/Qualifiers
source                  1..24
                        mol_type = other RNA
                        organism = synthetic construct
SEQUENCE: 612
tggttcgctg tcagtttttc actt                                                 24

SEQ ID NO: 613          moltype = RNA   length = 23
FEATURE                 Location/Qualifiers
source                  1..23
                        mol_type = other RNA
                        organism = synthetic construct
SEQUENCE: 613
cggatggttc tccaactagg att                                                  23

SEQ ID NO: 614          moltype = RNA   length = 22
FEATURE                 Location/Qualifiers
source                  1..22
                        mol_type = other RNA
                        organism = synthetic construct
SEQUENCE: 614
tggagctctg gttactcttt ga                                                   22

SEQ ID NO: 615          moltype = RNA   length = 24
FEATURE                 Location/Qualifiers
source                  1..24
                        mol_type = other RNA
                        organism = synthetic construct
SEQUENCE: 615
tcgcagtggc attttaaatc tgta                                                 24

SEQ ID NO: 616          moltype = RNA   length = 23
FEATURE                 Location/Qualifiers
source                  1..23
                        mol_type = other RNA
                        organism = synthetic construct
SEQUENCE: 616
tctccaggct cctttgaatt aca                                                  23

SEQ ID NO: 617          moltype = RNA   length = 21
FEATURE                 Location/Qualifiers
source                  1..21
                        mol_type = other RNA
                        organism = synthetic construct
SEQUENCE: 617
agggagcaac ctggtgtcta a                                                    21

SEQ ID NO: 618          moltype = RNA   length = 21
FEATURE                 Location/Qualifiers
source                  1..21
                        mol_type = other RNA
                        organism = synthetic construct
SEQUENCE: 618
cgctgagtac atggactgga t                                                    21

SEQ ID NO: 619          moltype = RNA   length = 22
FEATURE                 Location/Qualifiers
source                  1..22
                        mol_type = other RNA
                        organism = synthetic construct
SEQUENCE: 619
ctccaggctc ctttgaatta ca                                                   22

SEQ ID NO: 620          moltype = RNA   length = 24
FEATURE                 Location/Qualifiers
source                  1..24
                        mol_type = other RNA
                        organism = synthetic construct
SEQUENCE: 620
tctccaggct cctttgaatt acat                                                 24

SEQ ID NO: 621          moltype = RNA   length = 23
FEATURE                 Location/Qualifiers
source                  1..23
```

```
                        mol_type = other RNA
                        organism = synthetic construct
SEQUENCE: 621
tggaggagaa gaattgaatg tga                                              23

SEQ ID NO: 622          moltype = RNA  length = 24
FEATURE                 Location/Qualifiers
source                  1..24
                        mol_type = other RNA
                        organism = synthetic construct
SEQUENCE: 622
tggaggagaa gaattgaatg tgat                                             24

SEQ ID NO: 623          moltype = RNA  length = 23
FEATURE                 Location/Qualifiers
source                  1..23
                        mol_type = other RNA
                        organism = synthetic construct
SEQUENCE: 623
ctgaattcca aaaccaata tga                                               23

SEQ ID NO: 624          moltype = RNA  length = 15
FEATURE                 Location/Qualifiers
source                  1..15
                        mol_type = other RNA
                        organism = synthetic construct
SEQUENCE: 624
ttcctttgaa ttaca                                                       15

SEQ ID NO: 625          moltype = RNA  length = 23
FEATURE                 Location/Qualifiers
source                  1..23
                        mol_type = other RNA
                        organism = synthetic construct
SEQUENCE: 625
tgagaatcca gattccacgt tac                                              23

SEQ ID NO: 626          moltype = RNA  length = 23
FEATURE                 Location/Qualifiers
source                  1..23
                        mol_type = other RNA
                        organism = synthetic construct
SEQUENCE: 626
tcaagatgct ggaagatgtt cat                                              23

SEQ ID NO: 627          moltype = RNA  length = 23
FEATURE                 Location/Qualifiers
source                  1..23
                        mol_type = other RNA
                        organism = synthetic construct
SEQUENCE: 627
acaatctcaa agagtaacca gag                                              23

SEQ ID NO: 628          moltype = RNA  length = 22
FEATURE                 Location/Qualifiers
source                  1..22
                        mol_type = other RNA
                        organism = synthetic construct
SEQUENCE: 628
taacgtggaa tctggattct ca                                               22

SEQ ID NO: 629          moltype = RNA  length = 22
FEATURE                 Location/Qualifiers
source                  1..22
                        mol_type = other RNA
                        organism = synthetic construct
SEQUENCE: 629
tgaacatctt ccagcatctt ga                                               22

SEQ ID NO: 630          moltype = RNA  length = 23
FEATURE                 Location/Qualifiers
source                  1..23
                        mol_type = other RNA
                        organism = synthetic construct
SEQUENCE: 630
ctctggttac tctttgagat tgt                                              23
```

PREKALLIKREIN-MODULATING COMPOSITIONS AND METHODS OF USE THEREOF

CROSS-REFERENCE TO RELATED APPLICATIONS

This application claims the benefit of U.S. Provisional Application No. 63/251,571, filed Oct. 1, 2021; U.S. Provisional Application No. 63/252,554, filed Oct. 5, 2021; U.S. Provisional Application No. 63/270,504, filed Oct. 21, 2021; U.S. Provisional Application No. 63/283,175, filed Nov. 24, 2021; and U.S. Provisional Application No. 63/287,969, filed Dec. 9, 2021. The disclosure of each of the prior applications is considered part of and is incorporated by reference in its entirety in the disclosure of this application.

REFERENCE TO AN ELECTRONIC SEQUENCE LISTING

The contents of the electronic sequence listing (A127870009US05-SEQ-JIB.xml; Size: 638,286 bytes; and Date of Creation: Sep. 30, 2022) is herein incorporated by reference in its entirety.

BACKGROUND

Plasma prekallikrein (PKK) is a glycoprotein that participates in the surface-dependent activation of blood coagulation, fibrinolysis, kinin generation, and inflammation. PKK, which is encoded by the KLKB1 gene, is the precursor of plasma kallikrein (PK). PKK is present in plasma as a contact factor that forms non-covalent complexes with high molecular weight kininogen. PKK is converted to PK by Factor XIIa through the cleavage of an internal Arg-Ile peptide bond. PK is a member of the kinin-kallikrein pathway, which consists of several proteins that play a role in inflammation, blood pressure control, coagulation, and pain. PK liberates kinins from kininogens and also generates plasmin from plasminogen. For example, plasma kallikrein cleaves high molecular weight kininogen (HMWK) to generate bradykinin. The kinins, especially bradykinin, go on to induce downstream effects including vasodilation and edema (See, e.g., Schmaier. J. Thromb. Haemost 14: 28-39, 2016).

Certain mutations in PKK cause PKK deficiency, also known as Fletcher Factor deficiency, a rare coagulation deficiency characterized by a prolonged activated partial thromboplastin time (PTT). PKK deficiency has been linked to inflammatory and thrombotic disorders.

Mutations in PKK prevent the release of plasmin and kinins (e.g., bradykinin), and/or reduce fibrinolysis. This results in reduced vasodilation and increased blood clot formation, which in turn increase the likelihood of contracting inflammatory or thrombotic diseases. People with PKK deficiency are often asymptomatic, but still present a prolonged activated PTT, and are at risk of developing such diseases.

An inflammatory disorder occurs when the immune system mistakenly attacks the body's own cells or tissues. This causes abnormal inflammation that can result in chronic pain, redness, swelling, stiffness and damage to otherwise healthy body tissues. Inflammatory diseases include a vast array of disorders and conditions that are characterized by inflammation. Examples include rheumatoid arthritis, allergy, asthma, autoimmune diseases, coeliac disease, glomerulonephritis, hepatitis, inflammatory bowel disease, pre-perfusion injury and transplant rejection. It is estimated that over 1.36 million adults in the US suffer from rheumatoid arthritis and 3 million from inflammatory bowel disease.

Thrombosis is the formation of a blood clot inside a blood vessel, obstructing the flow of blood through the circulatory system. When a blood vessel is injured, the body uses platelets and fibrin to form a blood clot to prevent blood loss. Even when a blood vessel is not injured, blood clots may form in the body under certain conditions. In healthy people, homeostatic balance exists between procoagulant (clotting) forces and anticoagulant and fibrinolytic forces. Numerous genetic, acquired, and environmental factors can tip the balance in favor of coagulation, leading to the pathologic formation of thrombi in veins (e.g., deep venous thrombosis), arteries (e.g., myocardial infarction, ischemic stroke), or cardiac chambers. Thrombi can obstruct blood flow at the site of formation or detach and embolize to block a distant blood vessel (e.g., pulmonary embolism, embolic stroke). In the US alone, about 900,000 people are affected by blood clots each year, and about 100,000 of those people will die from blood clot-related complications.

Hereditary angioedema (HAE) is a rare inflammatory disease characterized by recurrent episodes of swelling around the head and extremities (Zuraw, B. L. N. Engl. J. Med. 359: 1027-36, 2008). Angioedema attacks occur with unpredictable frequency and are typically focused on the skin, and gastric, oropharyngeal, and laryngeal mucosas. Asphyxiation due to laryngeal swelling can result in mortality. HAE is caused by deficiency or malfunction of the serine protease inhibitor C1-INH (Kaplan, A. P. et al. J. Allergy Clin. Immunol. 109: 195-209, 2002). C1-INH is the primary inhibitor of coagulation factors 12 and 11 (Factor 11) of the intrinsic coagulation pathway as well as plasma kallikrein (Gigli, I. et al. J. Immunol. 104:574-581, 1970). C1-INH mediated inhibition of plasma kallikrein and Factor 12 results in inactivation of the kallikrein pathway and decreased levels of bradykinin (BK). C1-INH deficiency or dysfunction results in overproduction of BK, which is the mechanism by which HAE attacks are believed to occur. Type III HAE has been linked with mutations in the Factor 12 gene, which encodes coagulation protein Factor 12 (Cichon, S. et al. Am. J. Hum. Genet. 79: 1098-1104, 2006).

There is currently no cure for certain inflammatory conditions, such as HAE, or thrombotic conditions associated with dysregulation of PKK or other members of the kallikrein pathway. Accordingly, there is a need to find effective treatments for PKK related diseases.

SUMMARY

The present disclosure provides compounds, compositions, and methods for modulating the expression or activity of PKK. In certain embodiments, the compounds, compositions, and methods can be used to reduce the expression of PKK mRNA in a cell or animal. In certain embodiments, the compounds, compositions, and methods can be used to reduce the amount of PKK protein in a cell or animal.

In certain embodiments, the animal has an inflammatory or thrombotic disease, disorder or condition or a symptom thereof. In certain embodiments, the disease is hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct. Certain compounds, compositions and methods provided herein are directed to reducing an inflammatory or thrombotic disease, disorder or condition or a symptom thereof or hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct in an animal. In certain embodiments, the compounds and compositions provided herein are potent and tolerable and inhibit PKK expression, which can be used to treat, prevent, ameliorate, or slow progression of an inflammatory or thrombotic disease, disorder or condition or a symptom thereof or hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct.

In certain embodiments, the compounds and compositions comprise one or more features that are effective for increasing potency. In certain embodiments, the compounds and compositions comprise one or more features that are effective for increasing tolerability. In certain embodiments, compounds and compositions comprise one or more features that are effective for targeting the compound or composition to a cell or tissue. In certain embodiments, the compounds and compositions are more potent or have greater therapeutic value than compounds publicly disclosed.

DETAILED DESCRIPTION

It is to be understood that both the foregoing summary and the following detailed description are exemplary and explanatory only and are not restrictive of the embodiments, as claimed. The section headings used herein are for organizational purposes only and are not to be construed as limiting the subject matter described.

All documents, or portions of documents, cited in this application, including, but not limited to, patents, patent applications, articles, books, treatises, and GenBank, NCBI and other sequence reference records are hereby expressly incorporated by reference for the portions of the document discussed herein, as well as in their entirety as of the date of filing this application.

It is understood that the sequence set forth in each SEQ ID NO contained herein is independent of any modification to a sugar moiety, an internucleoside linkage, or a nucleobase even if shown in context with a modified compound. As such, compounds defined by a SEQ ID NO may comprise, independently, one or more modifications to a sugar moiety, an internucleoside linkage, or a nucleobase. Oligomeric compounds referenced by Compound Number or Ref ID NO indicate a combination of nucleobase sequence, chemical modification, and motif.

Herein, the use of the singular includes the plural unless specifically stated otherwise. For example, the articles "a" and "an" are used herein to refer to one or to more than one (i.e., to at least one) of the grammatical object of the article. By way of example, "an element" means one element or more than one element, e.g., a plurality of elements. As used herein, the use of "or" means "and/or" unless stated otherwise. Furthermore, the use of the term "including" as well as other forms, such as "includes" and "included", is not limiting and is used interchangeably with, the phrase "including but not limited to".

Definitions

Unless otherwise indicated, the following terms have the following meanings:

"Plasma prekallikrein" or "kallikrein B1," used interchangeably with the term "PKK," refers to any nucleic acid or protein of PKK. Exemplary nucleotide and amino acid sequences of PKK can be found, for example, at GenBank Accession No. NM_000892.5 (incorporated herein as SEQ ID NO: 1), NG_012095.2 truncated from 23529 . . . 54493 (incorporated herein as SEQ ID NO: 2), XM_017008181.1 (incorporated herein as SEQ ID NO: 3), NC_000004.12 truncated from 186215714 to 186258477 (incorporated herein as SEQ ID NO: 4), NM_001318394.2 (incorporated herein as SEQ ID NO: 5) and NM_001318396.2 (incorporated herein as SEQ ID NO: 6). Additional examples of PKK sequences are readily available through publicly available databases, e.g., GenBank, UniProt, and OMIM. Further information on PKK can be found, for example, at ncbi.nlm.nih.gov/gene/?term=PKK. PKK, as used herein, also refers to variations of the PKK gene including variants provided in the SNP database. Numerous sequence variations within the PKK gene have been identified and may be found at, for example, NCBI dbSNP and UniProt (see, e.g., ncbi.nlm.nih.gov/snp/?term=PKK). "PKK mRNA" means an mRNA encoding a PKK protein. PKK may be referred to in either upper or lower case.

"PKK specific inhibitor" refers to any agent capable of specifically inhibiting PKK RNA and/or PKK protein expression or activity at the molecular level. For example, PKK specific inhibitors include nucleic acids (including oligonucleotide compounds), peptides, antibodies, small molecules, and other agents capable of inhibiting the expression of PKK RNA and/or PKK protein.

"2'-O-methoxyethyl" or "2'-MOE" means a 2'-O(CH$_2$)$_2$—OCH$_3$ modification. A 2'-O-methoxyethyl modified sugar is a modified sugar with 2'-O(CH$_2$)$_2$—OCH$_3$ in the place of the 2'-OH group of a ribosyl ring.

"5' start site" means the nucleotide of the target nucleic acid or region which is aligned to the 3'-most nucleoside of an antisense oligonucleotide.

"3' stop site" means the nucleotide of the target nucleic acid or region which is aligned to the 5'-most nucleoside of an antisense oligonucleotide.

"About" means within ±10% of a value. For example, if it is stated, "a compound achieved about 70% inhibition of PKK", it is implied that PKK levels are inhibited within a range of 60% and 80%. When about is present before a series of numbers or a range, it is understood that "about" can modify each of the numbers in the series or range.

"Administer" or "administering" refers to routes of introducing a compound or composition provided herein to an individual to perform its intended function. An example, routes of administration that can be used include, but are not limited to, parenteral administration, such as subcutaneous, intravenous, or intramuscular injection or infusion.

"Ameliorate" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense oligonucleotide" or "antisense strand" means an oligonucleotide which includes a region that is complementary to a target nucleic acid, e.g., a PKK RNA or a region thereof.

"Complementarity" in reference to an oligonucleotide means the nucleobase sequence of such oligonucleotide or one or more regions thereof that is complementary to the nucleobase sequence of another oligonucleotide or nucleic acid or one or more regions thereof when the two nucleobase sequences are aligned in opposing directions. Complementary nucleobases, as described herein, are limited to the following pairs: adenine (A) and thymine (T), adenine (A) and uracil (U), and cytosine (C) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Composition" or "pharmaceutical composition" means a mixture of substances suitable for administering to an individual. For example, a composition may comprise one or more compounds or salt thereof and a sterile aqueous solution.

"Co-administration" means administration of two or more compounds in any manner in which the pharmacological effects of both are manifest in the patient. Co-administration does not require both compounds to be administered in a single pharmaceutical composition, in the same dosage form, by the same route of administration, or at the same time. The effects of both compounds need not manifest themselves at the same time. The effects need only be overlapping for a period of time and need not be coextensive. Co-administration includes parallel or sequential administration of the one or more compounds.

"Conjugate group" means a group of atoms that is attached to an oligonucleotide. A conjugate group is optionally attached to an oligonucleotide through a conjugate linker. A conjugate group may, for example, alter the distribution, targeting, or half-life of a compound into which it is incorporated. Conjugate groups include targeting moieties.

"Conjugate linker" means a group of atoms comprising at least one bond that connects a linked moiety to an oligonucleotide.

"Identity" in reference to an oligonucleotide means the nucleobase sequence of such oligonucleotide or one or more regions thereof that matches the nucleobase sequence of another oligonucleotide or nucleic acid or one or more regions thereof. Identity of an oligonucleotide to another oligonucleotide or nucleic acid need not require each nucleobase to match and may include one or more different nucleobases. By contrast, "fully identical" or "100% identity" in reference to oligonucleotides means that such oligonucleotides have the same nucleobase at each relative position over its length as the other oligonucleotide or nucleic acid.

"Individual" means a human or non-human animal selected for treatment or therapy.

"Inhibiting the expression or activity" with reference to a target nucleic acid or protein means to reduce or block the expression or activity of such target relative to the expression or activity in an untreated or control sample and does not necessarily indicate a total elimination of expression or activity.

As used herein, the term "internucleoside linkage" is the covalent linkage between adjacent nucleosides in an oligonucleotide. As used herein, "modified internucleoside linkage" means any internucleoside linkage other than a phosphodiester internucleoside linkage. "Phosphorothioate internucleoside linkage" is a modified internucleoside linkage in which one of the non-bridging oxygen atoms of a phosphodiester internucleoside linkage is replaced with a sulfur atom.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations as further described below. Unless otherwise indicated, chiral internucleoside linkages of modified oligonucleotides described herein can be stereorandom or in a particular stereochemical configuration.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

The term "isotopic variant" refers to a therapeutic agent (e.g., a compound and/or modified oligonucleotide disclosed herein) that contains an unnatural proportion of an isotope at one or more of the atoms that constitute such a therapeutic agent. In certain embodiments, an "isotopic variant" of a therapeutic agent contains unnatural proportions of one or more isotopes, including, but not limited to, hydrogen (H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine 123 ($^{123}$I), iodine-125 ($^{125}$I), iodine-127 ($^{127}$I), iodine-129 ($^{129}$I), and iodine-131 ($^{131}$I). In certain embodiments, an "isotopic variant" of a therapeutic agent contains unnatural proportions of one or more isotopes, including, but not limited to, hydrogen (H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine 123 ($^{123}$I), iodine-125 ($^{125}$I), iodine-127 ($^{127}$I), iodine-129 ($^{129}$I), and iodine-131 ($^{131}$I).

It will be understood that, in a therapeutic agent (e.g., a compound and/or modified oligonucleotide disclosed herein), any hydrogen can be $^2$H, for example, or any carbon can be $^{13}$C, for example, or any nitrogen can be $^{15}$N, for example, or any oxygen can be $^{18}$O, for example, where feasible according to the judgment of one of skill. In certain embodiments, an "isotopic variant" of a therapeutic agent contains unnatural proportions of deuterium (D).

"Mismatch" or "non-complementary" means a nucleobase of a first oligonucleotide or nucleic acid that is not complementary to the corresponding nucleobase of a second oligonucleotide or nucleic acid when the first oligonucleotide/nucleic acid and second oligonucleotide/nucleic acid are aligned in an antiparallel orientation. For example, nucleobases including, but not limited to, a universal nucleobase, inosine, and hypoxanthine, are capable of hybridizing with at least one nucleobase but are still mismatched or non-complementary with respect to the nucleobase to which they are hybridized. As another example, a nucleobase of a first oligonucleotide/nucleic acid that is not capable of hybridizing to the corresponding nucleobase of a second oligonucleotide/nucleic acid when the first and second oligonucleotides are aligned in an antiparallel orientation is a mismatch or non-complementary nucleobase.

"Modified oligonucleotide" means an oligonucleotide, wherein at least one sugar, nucleobase, or internucleoside linkage is modified.

"Modulating" refers to changing or adjusting a feature in a cell, tissue, organ or organism. For example, modulating PKK RNA can mean to increase or decrease the level of PKK RNA and/or PKK protein in a cell, tissue, organ or organism. A "modulator" effects the change in the cell, tissue, organ or organism. For example, a PKK compound can be a modulator that decreases the amount of PKK RNA and/or PKK protein in a cell, tissue, organ or organism.

"Motif" means the pattern of unmodified and modified sugar moieties, nucleobases, and/or internucleoside linkages, in an oligonucleotide.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Oligomeric Compound" means a compound comprising one or more oligonucleotides and optionally one or more additional features, such as a conjugate group or terminal group. Examples of oligomeric compounds include single-stranded and double-stranded compounds, such as, oligonucleotides, antisense oligonucleotides, interfering RNA compounds (RNAi compounds), microRNA targeting oligonucleotides, occupancy-based compounds (e.g., mRNA processing or translation blocking compounds and splicing compounds). RNAi compounds include double-stranded compounds (e.g., short-interfering RNA (siRNA) and double-stranded RNA (dsRNA)) and single-stranded compounds (e.g., single-stranded siRNA (ssRNA), single-stranded RNAi (ssRNAi), short hairpin RNA (shRNA) and microRNA mimics) which work at least in part through the RNA-induced silencing complex (RISC) pathway resulting in sequence specific degradation and/or sequestration of a target nucleic acid through a process known as RNA interference (RNAi). The term "RNAi compound" is meant to be equivalent to other terms used to describe nucleic acid compounds that are capable of mediating sequence-specific RNA interference, for example, interfering RNA (iRNA), iRNA agent, RNAi agent, short interfering oligonucleotide, short interfering nucleic acid, short interfering modified oligonucleotide, chemically modified siRNA, and others. Additionally, the term "RNAi" is meant to be equivalent to other terms used to describe sequence-specific RNA interference.

"Oligonucleotide" means a polymer of linked nucleosides, each of which can be modified or unmodified, independent from one another.

The term "oligomeric duplex" means a duplex formed by two oligomeric compounds having complementary nucleobase sequences. Each oligomeric compound of an oligomeric duplex may be referred to as a "duplexed oligomeric compound." The oligonucleotides of each oligomeric compound of an oligomeric duplex may include non-complementary overhanging nucleosides. In some embodiments, the terms "duplexed oligomeric compound" and "modified oligonucleotide" are used interchangeably. In other embodiments, the terms "oligomeric duplex" and "compound" are used interchangeably.

"Parenteral administration" means administration through injection or infusion. Parenteral administration includes subcutaneous administration, intravenous administration, intramuscular administration, intraarterial administration, intraperitoneal administration, or intracranial administration, e.g., intrathecal or intracerebroventricular administration.

"Pharmaceutically acceptable carrier or diluent" means any substance suitable for use in administering to an individual. In certain embodiments, a pharmaceutically acceptable carrier or diluent aids the administration of a compound to and absorption by an individual and can be included in the compositions of the present disclosure without causing a significant adverse toxicological effect on the patient. Non-limiting examples of pharmaceutically acceptable excipients include water, NaCl, normal saline solutions, and the like. For example, a pharmaceutically acceptable carrier can be a sterile aqueous solution, such as PBS or water-for-injection. One of skill in the art will recognize that other pharmaceutical excipients are useful in the present disclosure.

"Pharmaceutically acceptable salts" means or refers to physiologically and pharmaceutically acceptable salts of compounds, such as oligomeric compounds or oligonucleotides, i.e., salts that retain the desired biological activity of the parent compound and do not impart undesired toxicological effects thereto.

As used herein, a pharmaceutically acceptable salt is any salt of a compound provided herein which retains its biological properties and which is not toxic or otherwise undesirable for pharmaceutical use. The pharmaceutically acceptable salts of the therapeutic agents disclosed herein include salts that are prepared with relatively nontoxic acids or bases, depending on the particular substituents found on the compounds or modified oligonucleotides described herein.

When compounds of the present disclosure contain relatively acidic functionalities, base addition salts can be obtained by contacting the neutral form of such compounds with a sufficient amount of the desired base, either neat or in a suitable inert solvent.

When compounds of the present disclosure contain relatively basic functionalities, acid addition salts can be obtained by contacting the neutral form of such compounds with a sufficient amount of the desired acid, either neat or in a suitable inert solvent.

Thus, the compounds of the present disclosure may exist as salts, such as with pharmaceutically acceptable acids. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia, or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like (see, for example, Berge et al., "Pharmaceutical Salts," Journal of Pharmaceutical Science, 1977, 66, 1-19).

Pharmaceutically acceptable salts further include, by way of example only and without limitation, sodium, potassium, calcium, magnesium, ammonium, tetraalkylammonium, and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like. In some embodiments, the pharmaceutically acceptable salt of the compounds and modified oligonucleotides disclosed herein is a sodium or a potassium salt. In some embodiments, the pharmaceutically acceptable salt of the compounds and modified oligonucleotides disclosed herein is a sodium salt.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In embodiments, compounds of the present disclosure contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present disclosure.

"Pharmaceutical agent" means a compound that provides a therapeutic benefit when administered to an individual.

"Phosphorothioate linkage" means a modified phosphate linkage in which one of the non-bridging oxygen atoms is replaced with a sulfur atom.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligonucleotide.

"Prevent" refers to delaying or forestalling the onset, development or progression of a disease, disorder, or condition for a period of time.

"RNA interference compound" or "RNAi compound" means a compound that acts, at least in part, through an RNA-induced silencing complex (RISC) pathway or Ago2, but not through RNase H, to modulate a target nucleic acid and/or protein encoded by a target nucleic acid. RNAi compounds include, but are not limited to double-stranded siRNA, single-stranded siRNA, and microRNA, including microRNA mimics.

"Sense oligonucleotide" or "sense strand" means the strand of a double-stranded compound that includes a region that is substantially complementary to a region of the antisense strand of the compound.

"Specifically inhibit" with reference to a target nucleic acid or protein means to reduce or block expression or activity of the target nucleic acid or protein while minimizing or eliminating effects on non-target nucleic acids or proteins.

"Subunit" with reference to an oligonucleotide means a nucleotide, nucleoside, nucleobase or sugar or a modified nucleotide, nucleoside, nucleobase or sugar as provided herein.

"Target nucleic acid," "target RNA," and "nucleic acid target" all mean a nucleic acid capable of being targeted by compounds described herein.

"Target region" means a portion of a target nucleic acid to which one or more compounds is targeted.

"Targeting moiety" means a conjugate group that provides an enhanced affinity for a selected target, e.g., molecule, cell or cell type, compartment, e.g., a cellular or organ compartment, tissue, organ or region of the body, as, e.g., compared to a compound absent such a moiety.

"Terminal group" means a chemical group or group of atoms that is covalently linked to a terminus of an oligonucleotide.

"Therapeutically effective amount" or "effective amount" means an amount of a compound, pharmaceutical agent, or composition that provides a therapeutic benefit to an individual. A "therapeutically effective amount" or "effective amount" is an amount sufficient for a compound to accomplish a stated purpose relative to the absence of the compound (e.g., achieve the effect for which it is administered, treat, prevent or ameliorate a disease or reduce one or more symptoms of a disease or condition). An example of a "therapeutically effective amount" or "effective amount" is an amount sufficient to contribute to the treatment, prevention, amelioration, or reduction of a symptom or symptoms of a disease. A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The term "therapeutically effective amount," as used herein, refers to that amount of the therapeutic agent sufficient to provide a therapeutic benefit to an individual, such as treating, preventing or ameliorating the disease or disorder or symptom thereof, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

The terms "treating" or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters, including the results of a physical examination. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. In some instances, chronic administration may be required. For example, the compositions are administered to the subject in an amount and for a duration sufficient to treat the patient.

"Treat" refers to administering a compound or pharmaceutical composition to an animal in order to effect an alteration or improvement of a disease, disorder, or condition in the animal.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure (i.e., the R and S configurations for each asymmetric center). Therefore, single stereochemical isomers as well as enantiomeric and diastereomeric mixtures of the present compounds are within the scope of the disclosure.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the results of a synthetic method that is not designed to control the stereochemical configuration. In certain embodiments, a stereorandom chiral center is a stereorandom phosphorothioate internucleoside linkage.

Certain Embodiments

In certain aspects, the disclosure relates to methods, compounds and compositions for inhibiting PKK. In certain embodiments, PKK is specifically inhibited. In certain embodiments, PKK is specifically degraded. In certain embodiments, PKK expression is inhibited. In certain embodiments, PKK translation is inhibited. In certain embodiments, PKK activity is inhibited. In certain embodiments, PKK expression, translation, or activity is reduced by at least 10% relative to the expression, translation, or activity in an untreated or control sample. For example, in certain embodiments, PKK expression, translation, or activity is reduced by at least 10%, at least 20%, at least 30%, at least 40%, at least 50%, at least 60%, at least 70%, at least 80%, at least 90%, at least 95%, 10-50%, 25-50%, 25-75%, 50-75%, 50-99%, or 75-99% relative to the expression, translation, or activity in an untreated or control sample. In certain embodiments, PKK expression, translation, or activity is reduced as measured by any suitable assay, including but not limited to, an immunoassay, a hybridization-based assay, or a sequencing-based assay (e.g., RNA-Seq).

In certain aspects, the disclosure relates to compounds targeted to a PKK nucleic acid. In certain embodiments, the PKK nucleic acid has the sequence set forth in GENBANK Accession No. NM_000892.5 (incorporated herein as SEQ ID NO: 1), NG_012095.2 truncated from 23529 ... 54493 (incorporated herein as SEQ ID NO: 2), XM_017008181.1 (incorporated herein as SEQ ID NO: 3), NC_000004.12 truncated from 186215714 to 186258477 (incorporated herein as SEQ ID NO: 4), NM_001318394.2 (incorporated herein as SEQ ID NO: 5) and NM_001318396.2 (incorporated herein as SEQ ID NO: 6).

In certain embodiments, the compound is an oligomeric compound. In certain embodiments, the compound is single-stranded. In certain embodiments, the compound is double-stranded.

Certain embodiments provide a compound comprising a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequence of SEQ ID NOs: 10-313, 626, 627, and 628.

Certain embodiments provide a compound comprising a modified oligonucleotide (e.g., of 14 to 30, for example, 14 to 23, linked nucleosides in length) having a nucleobase sequence comprising the nucleobase sequence of any one of SEQ ID NOs: 10-313, 626, 627, and 628.

Certain embodiments provide a compound comprising a modified oligonucleotide having a nucleobase sequence selected from any one of SEQ ID NOs: 10-313, 626, 627, and 628.

In certain embodiments, the modified oligonucleotide has a nucleobase sequence that is at least 80%, at least 85%, at least 90%, or at least 95% complementary to SEQ ID NO: 1, 3, 5 or 6. In certain embodiments, the modified oligonucleotide comprises at least one modification selected from a modified internucleoside linkage, a modified sugar, and a modified nucleobase. In certain embodiments, the compound is double-stranded.

Certain embodiments provide a compound comprising a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequence of SEQ ID NOs: 10-631 and a second modified oligonucleotide (e.g., of 14 to 30, for example, 14 to 23, linked nucleosides in length) having a region of complementarity to the first modified oligonucleotide.

In certain embodiments, the compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequence provided in Tables 2-4, 6, and 8, and a second modified oligonucleotide (e.g., of 14 to 30, for example, 14 to 23, linked nucleosides in length) having a region of complementarity to the first modified oligonucleotide.

Certain embodiments provide a compound comprising a first modified oligonucleotide (e.g., of 14 to 30, for example, 14 to 23, linked nucleosides in length) having a nucleobase sequence comprising the nucleobase sequence of any one of SEQ ID NOs: 10-631 and a second modified oligonucleotide (e.g., of 14 to 30, for example, 14 to 23, linked nucleosides in length) having a region of complementarity to the first modified oligonucleotide.

Certain embodiments provide a compound comprising a first modified oligonucleotide having a nucleobase sequence selected from any one of SEQ ID NOs: 10-631 and a second modified oligonucleotide 19 to 23 linked nucleosides in length having a region of complementarity to the first modified oligonucleotide.

In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequences of SEQ ID NO: 307, 312 or 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequences of SEQ ID NO: 468, 611, 616, 619 or 629. In certain embodiments, a compound comprises a modified oligonucleotide having a nucleobase sequence selected from the nucleobase sequences of SEQ ID NO: 307, SEQ ID NO: 312 and SEQ ID NO: 626. In certain embodiments, a compound comprises a modified oligonucleotide having a nucleobase sequence selected from the nucleobase sequence of SEQ ID NO: 468, SEQ ID NO: 611, SEQ ID NO: 616, SEQ ID NO: 619 and SEQ ID NO: 629. In certain embodiments, the compound comprises a first modified oligonucleotide having a nucleobase sequence of SEQ ID NO: 312 and a second modified oligonucleotide having a nucleobase sequence of SEQ ID NO: 619. In certain embodiments, the compound comprises a first modified oligonucleotide having a nucleobase sequence of SEQ ID NO: 626 and a second modified oligonucleotide having a nucleobase sequence of SEQ ID NO: 629.

In certain embodiments, the modified oligonucleotide or first modified oligonucleotide of any preceding compound has at least 80%, at least 85%, at least 90%, or at least 95% complementarity or identity to SEQ ID NO: 1, 3, 5 or 6 over its length. In certain embodiments, the modified oligonucleotide or first modified oligonucleotide has at least 1, at least 2, at least 3 mismatches to a region of SEQ ID NO: 1, 3, 5 or 6. In certain embodiments, the region of complementarity between the first modified oligonucleotide or first strand and the second modified oligonucleotide or second strand is 14 to 30 linked nucleosides in length.

In certain embodiments, the region of complementarity between the first modified oligonucleotide or first strand and the second modified oligonucleotide or second strand is 14 to 23 linked nucleosides in length. In certain embodiments, the region of complementarity between the first modified oligonucleotide or first strand and the second modified oligonucleotide or second strand is 19 to 23 linked nucleosides in length. In certain embodiments, the region of complementarity between the first modified oligonucleotide or first strand and the second modified oligonucleotide or second strand is 21 to 23 linked nucleosides in length. In certain embodiments, the first modified oligonucleotide is fully complementary to the second modified oligonucleotide.

In certain embodiments, the modified oligonucleotide or first modified oligonucleotide of any preceding compound comprises at least one modification selected from a modified internucleoside linkage, a modified sugar, and a modified nucleobase. In certain embodiments, the second modified oligonucleotide of any preceding compound comprises at least one modification selected from the group consisting of a modified internucleoside linkage, a modified sugar, and a modified nucleobase. In certain embodiments, the modified internucleoside linkage is a phosphorothioate internucleoside linkage or a methylphosphonate internucleoside linkage. In certain embodiments, the phosphorothioate internucleoside linkage or methylphosphonate internucleoside linkage is at the 3' terminus of the first or second modified oligonucleotide or at the 5' terminus of the first modified oligonucleotide. In certain embodiments, the modified sugar comprises a modification selected from the group consisting of a halogen, an alkoxy group and a bicyclic sugar. In certain embodiments, the modified sugar comprises a 2'-F modification. In certain embodiments, the modified sugar comprises a 2'-OMe modification. In certain embodiments, each nucleoside of the first modified oligonucleotide comprises a modified sugar. In certain embodiments, each nucleoside of the second modified oligonucleotide comprises a modified sugar. In certain embodiments, the modified sugar comprises a modification selected from the group consisting of a halogen, an alkoxy group and a bicyclic sugar or a combination thereof. In certain embodiments, the modified sugar comprises a modification selected from the group consisting of 2'-MOE, 2'-F, and 2'-OMe or a combination thereof. In certain embodiments, the first modified oligonucleotide comprises no more than ten 2'-F sugar modifications. In certain embodiments, the second modified oligonucleotide comprises no more than five 2'-F sugar modifications.

In certain embodiments, the compound of any preceding embodiment comprises a conjugate group. In certain embodiments, the conjugate group is attached to the 5' end of the modified oligonucleotide. In certain embodiments, the conjugate group is a targeting moiety. In certain embodiments, the targeting moiety comprises one or more GalNAc. In certain embodiments, the modified oligonucleotide is the second modified oligonucleotide or sense oligonucleotide. In certain embodiments, the one or more GalNAc is attached to the 2' or 3' position of the ribosyl ring. In certain embodiments, the one or more GalNAc is attached to the 5' nucleoside of the modified oligonucleotide. In certain embodiments, the 5' nucleoside of a modified oligonucleotide is selected from the following Formulae or a salt, solvate, or hydrate thereof, wherein R is the portion of the modified oligonucleotide other than the 5' nucleoside:

Formula I

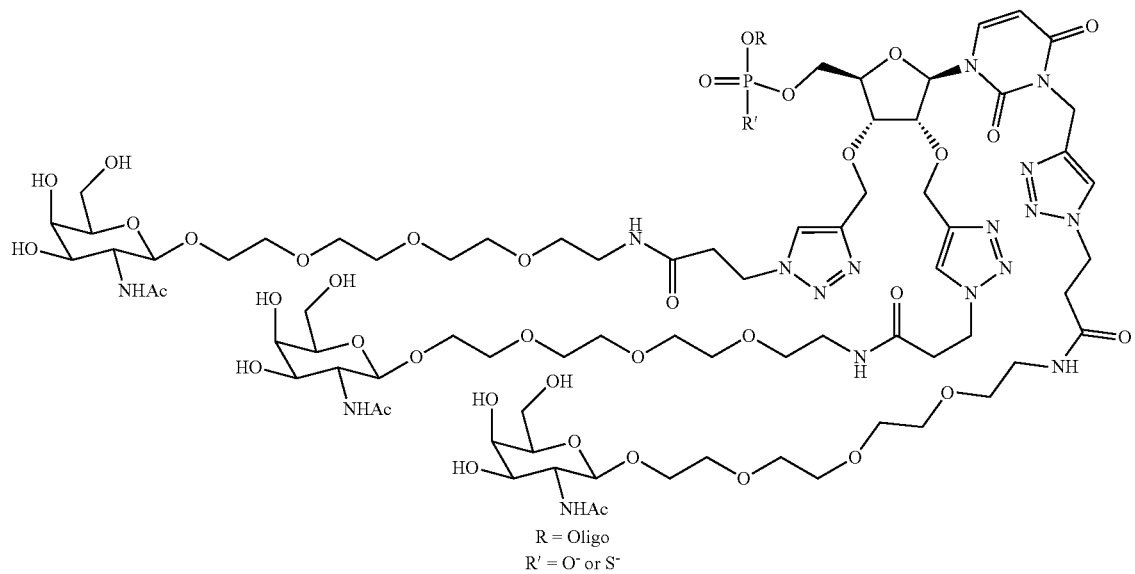

R = Oligo
R' = O⁻ or S⁻

-continued
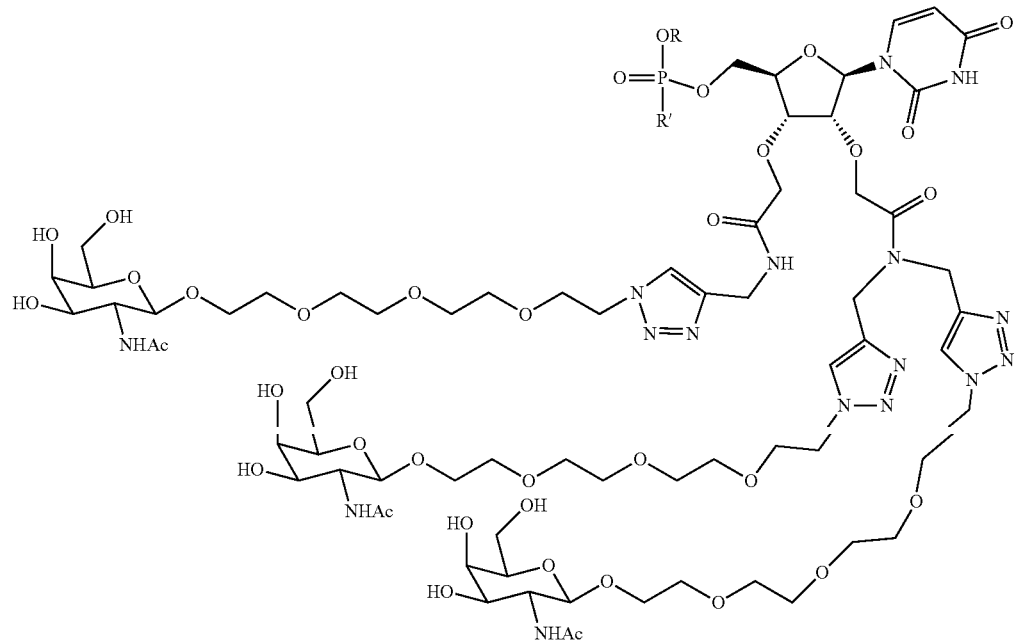
Formula II
R = Oligo
R' = O⁻ or S⁻
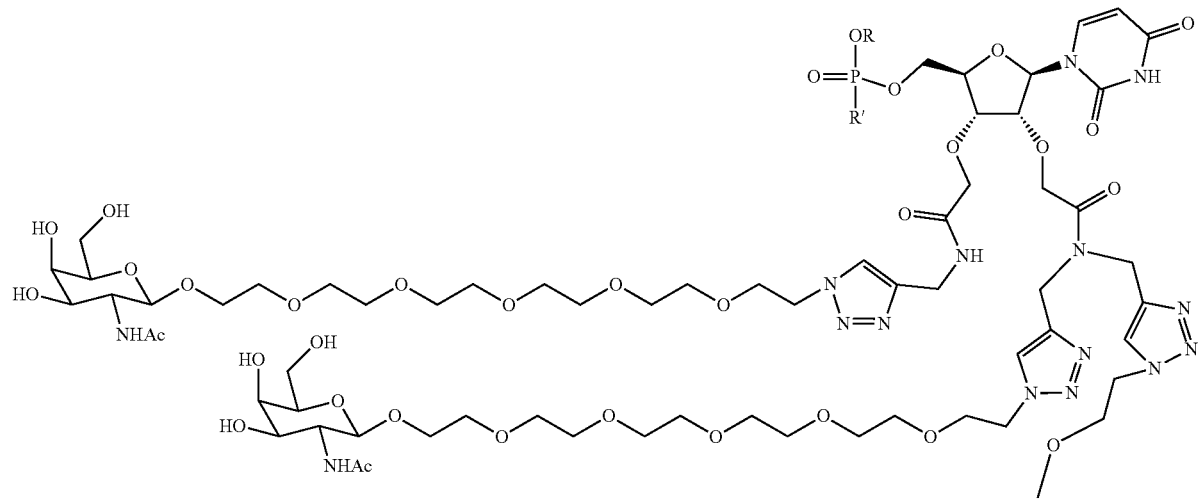
Formula III
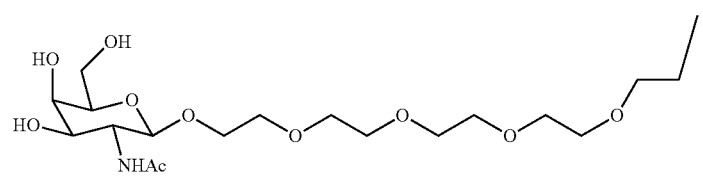
R = Oligo
R' = O⁻ or S⁻

-continued
Formula IV
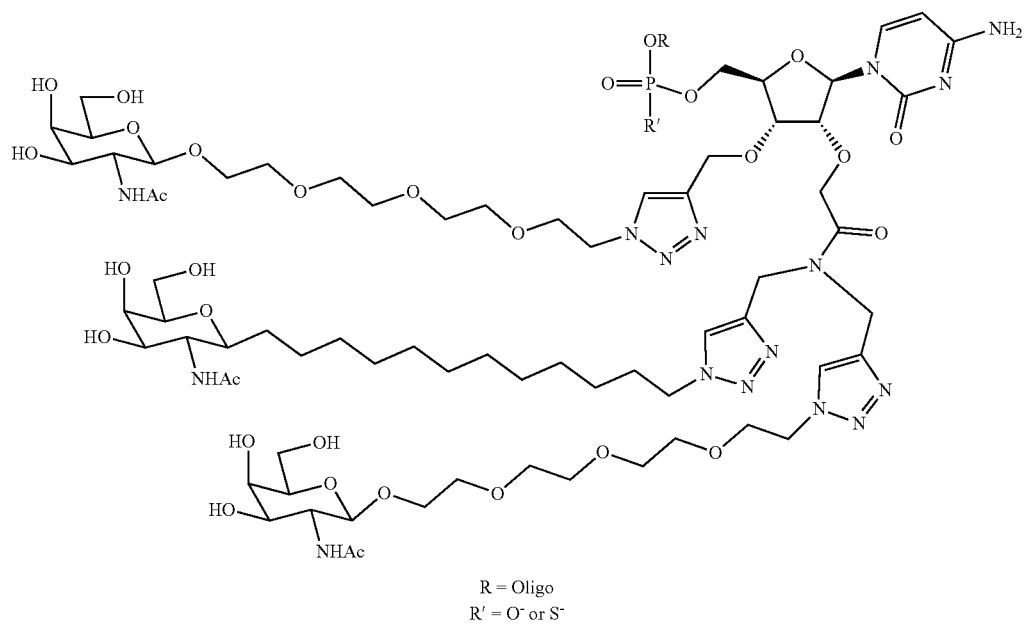
R = Oligo
R' = O⁻ or S⁻
Formula V
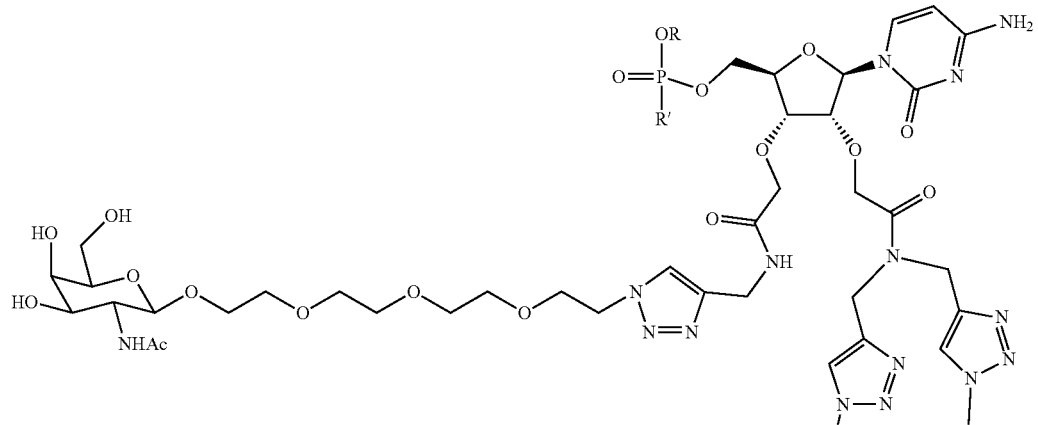
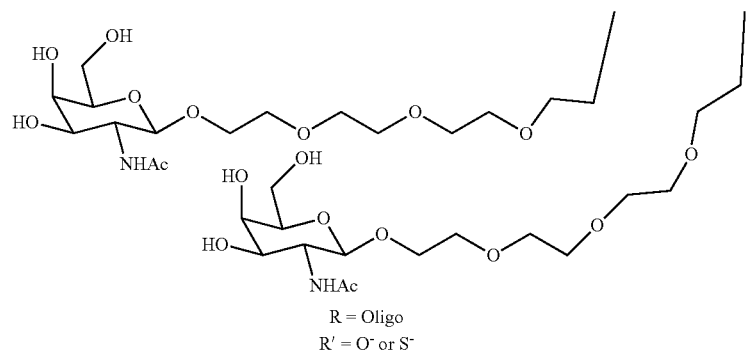
R = Oligo
R' = O⁻ or S⁻

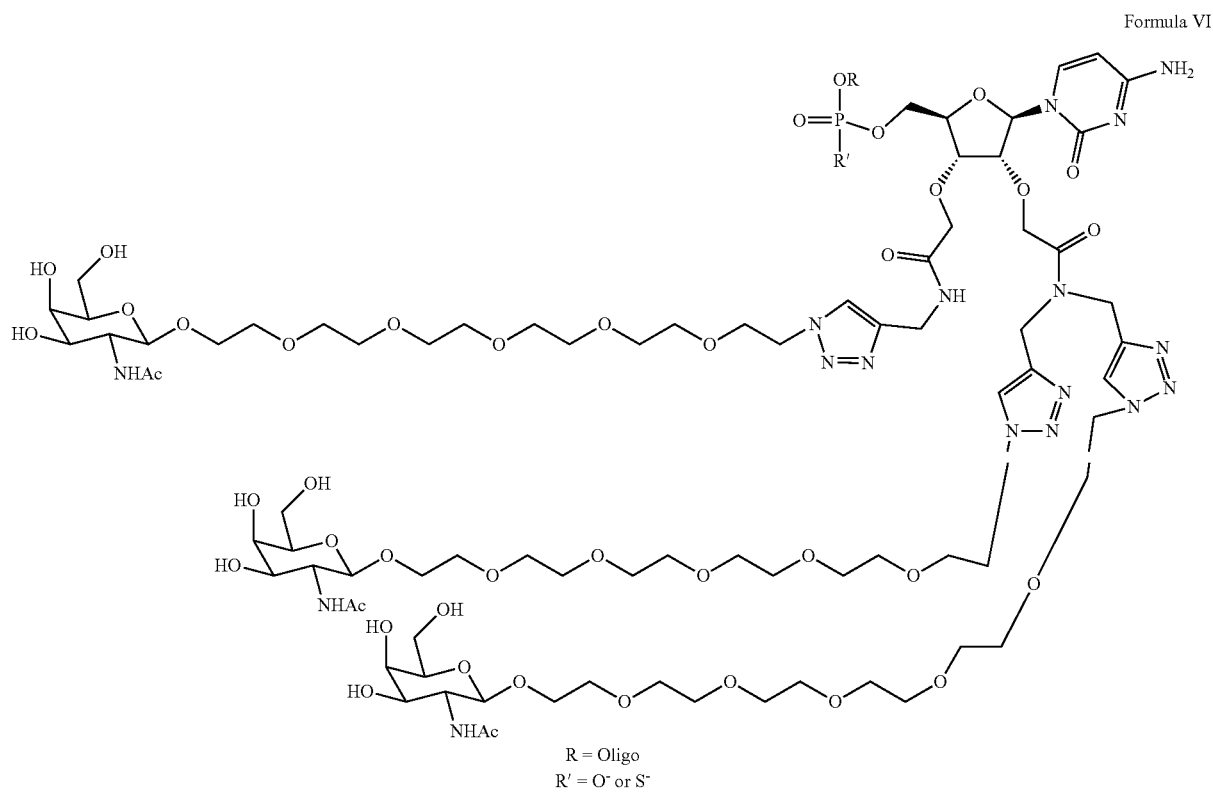
Formula VI
R = Oligo
R' = O⁻ or S⁻
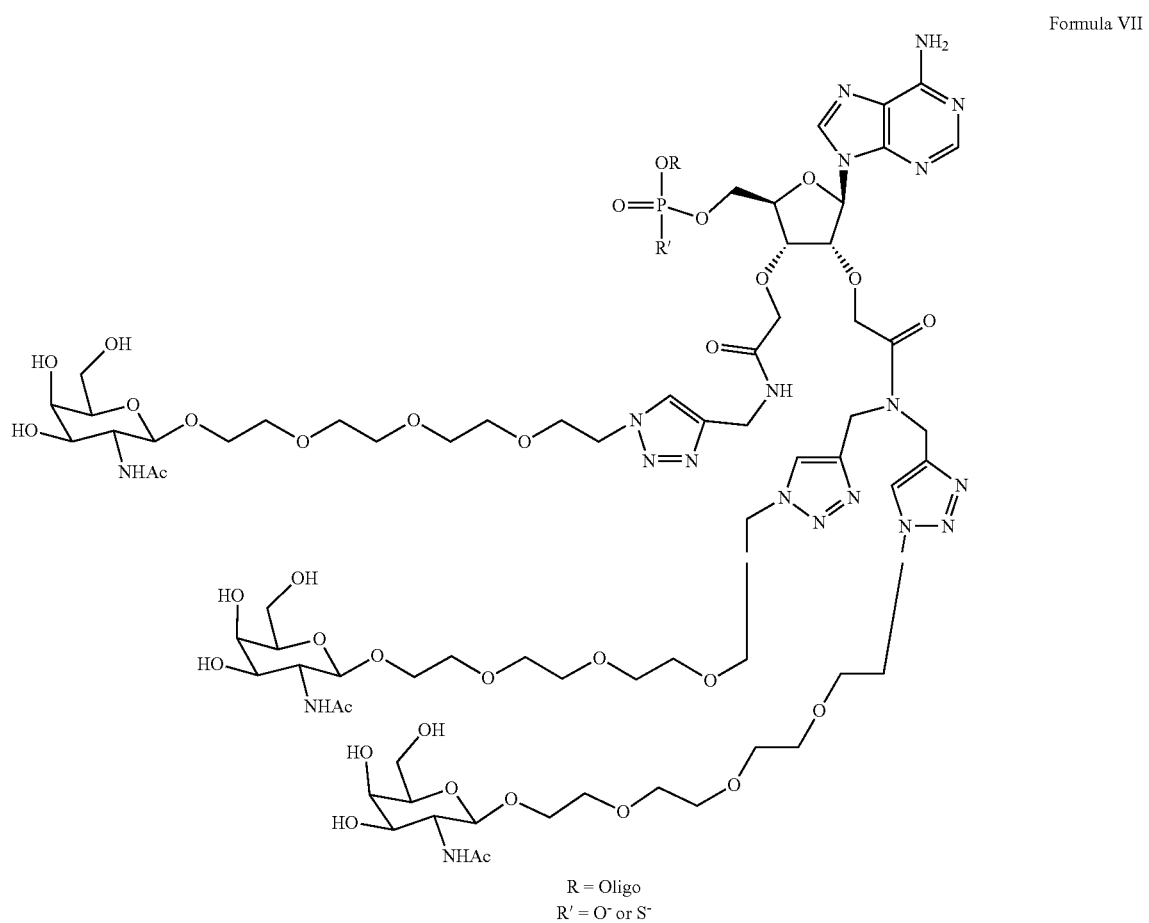
Formula VII
R = Oligo
R' = O⁻ or S⁻

-continued

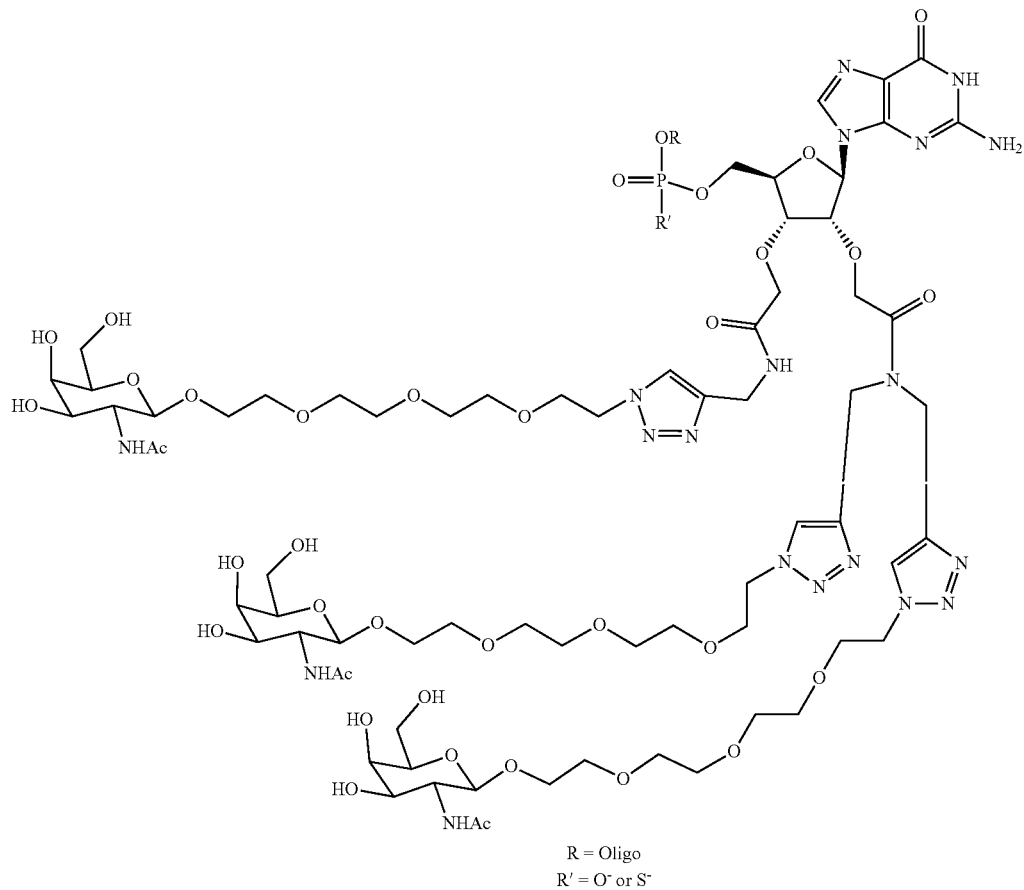

Formula VIII

R = Oligo
R' = O⁻ or S⁻

In certain embodiments, R' is O. In certain embodiments, R' is S. In certain embodiments, the 5' nucleoside of the modified oligonucleotide is Formula I and R' is O. In certain embodiments, the 5' nucleoside of the modified oligonucleotide is Formula I and R' is S. In certain embodiments, the 5' nucleoside of the modified oligonucleotide is Formula II and R' is O. In certain embodiments, the 5' nucleoside of the modified oligonucleotide is Formula II and R' is S. In certain embodiments, the 5' nucleoside of the modified oligonucleotide is Formula III and R' is O. In certain embodiments, the 5' nucleoside of the modified oligonucleotide is Formula III and R' is S. In certain embodiments, the 5' nucleoside of the modified oligonucleotide is Formula IV and R' is O. In certain embodiments, the 5' nucleoside of the modified oligonucleotide is Formula IV and R' is S. In certain embodiments, the 5' nucleoside of the modified oligonucleotide is Formula V and R' is O. In certain embodiments, the 5' nucleoside of the modified oligonucleotide is Formula V and R' is S. In certain embodiments, the 5' nucleoside of the modified oligonucleotide is Formula VI and R' is O. In certain embodiments, the 5' nucleoside of the modified oligonucleotide is Formula VI and R' is S. In certain embodiments, the 5' nucleoside of the modified oligonucleotide is Formula VII and R' is O. In certain embodiments, the 5' nucleoside of the modified oligonucleotide is Formula VII and R' is S. In certain embodiments, the 5' nucleoside of the modified oligonucleotide is Formula VIII and R' is O. In certain embodiments, the 5' nucleoside of the modified oligonucleotide is Formula VIII and R' is S.

Certain embodiments provide a compound comprising a first modified oligonucleotide selected from any one of Ref ID NOs: IA0812-821 and a second modified oligonucleotide 14 to 21 linked nucleosides in length fully complementary to the first modified oligonucleotide.

Certain embodiments provide a compound comprising a first modified oligonucleotide consisting of IA0813 and a second modified oligonucleotide consisting of IS1002.

Certain embodiments provide a compound comprising a first modified oligonucleotide consisting of IA0818 and a second modified oligonucleotide consisting of IS1007.

Certain embodiments provide a compound comprising a first modified oligonucleotide consisting of IA0818 and a second modified oligonucleotide consisting of IS1068.

Certain embodiments provide a compound comprising a first modified oligonucleotide selected from any one of Ref ID NOs: IA0864-866 and a second modified oligonucleotide 14 to 21 linked nucleosides in length fully complementary to the first modified oligonucleotide.

Certain embodiments provide a compound comprising a first modified oligonucleotide selected from Ref ID NOs: IA0818 and IA0864 and a second modified oligonucleotide selected from Ref ID NOs: IS1058 and IS1059.

Certain embodiments provide a compound comprising a first modified oligonucleotide consisting of IA0864 and a second modified oligonucleotide consisting of IS1059. Certain embodiments provide a compound comprising a first modified oligonucleotide consisting of IA0818 and a second modified oligonucleotide consisting of IS1058.

In certain embodiments, the compound comprises a first modified oligonucleotide consisting of IA0864 and a second modified oligonucleotide consisting of IS1059. In certain embodiments, the compound comprises a first modified oligonucleotide consisting of IA0818 and a second modified oligonucleotide consisting of IS1058.

In certain embodiments, the compound of any foregoing embodiment is in a pharmaceutically acceptable salt form. In certain embodiments, the pharmaceutically acceptable salt is a sodium salt. In certain embodiments, the pharmaceutically acceptable salt is a potassium salt.

In an aspect provided herein, is a modified oligonucleotide according to the following chemical structure:

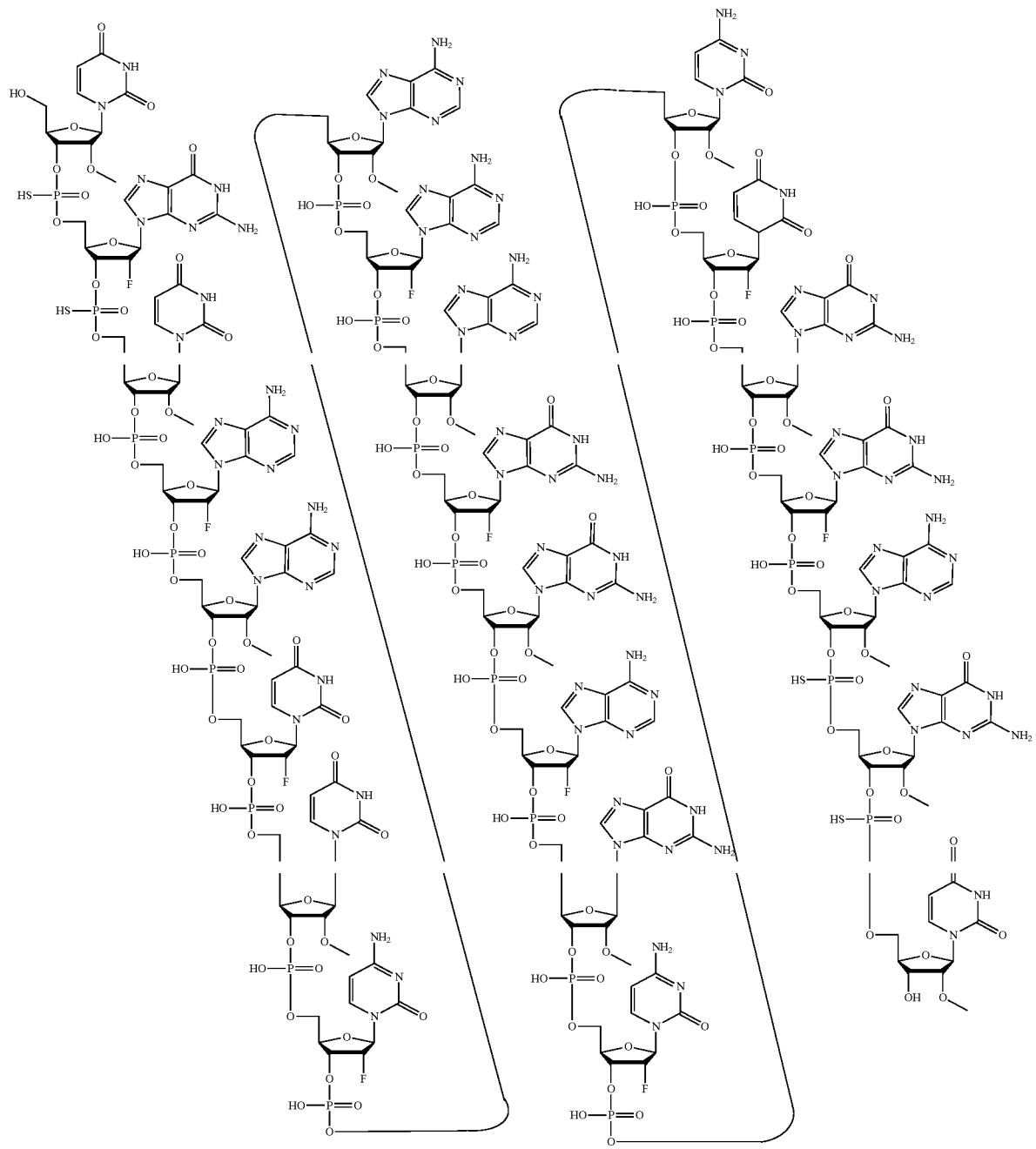

or a pharmaceutically acceptable salt or stereoisomer thereof. In certain embodiments, Ref ID NO: IA0818 is a modified oligonucleotide, or a pharmaceutically acceptable salt or stereoisomer thereof, according to the preceding chemical structure.
In an aspect provided herein, is a modified oligonucleotide according to the following chemical structure:
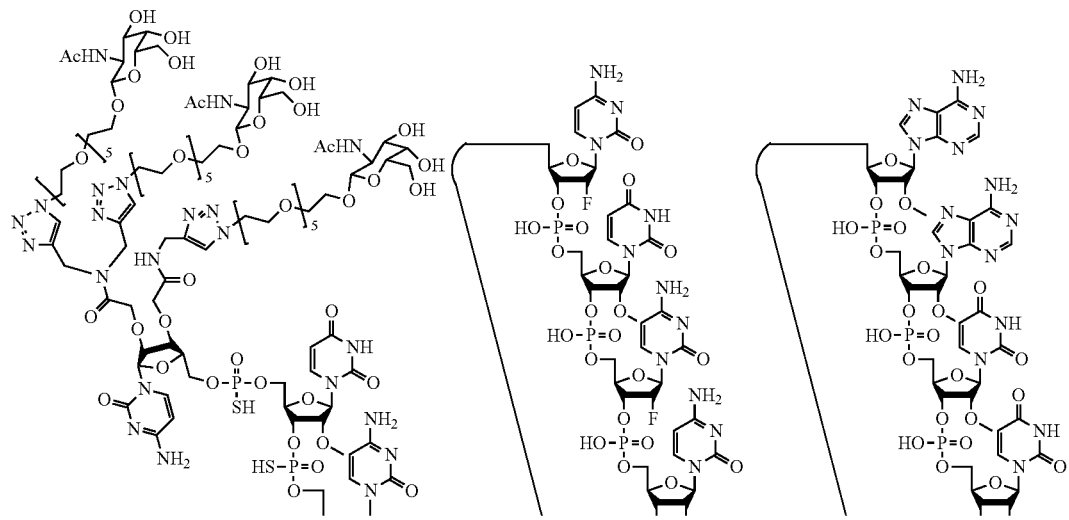
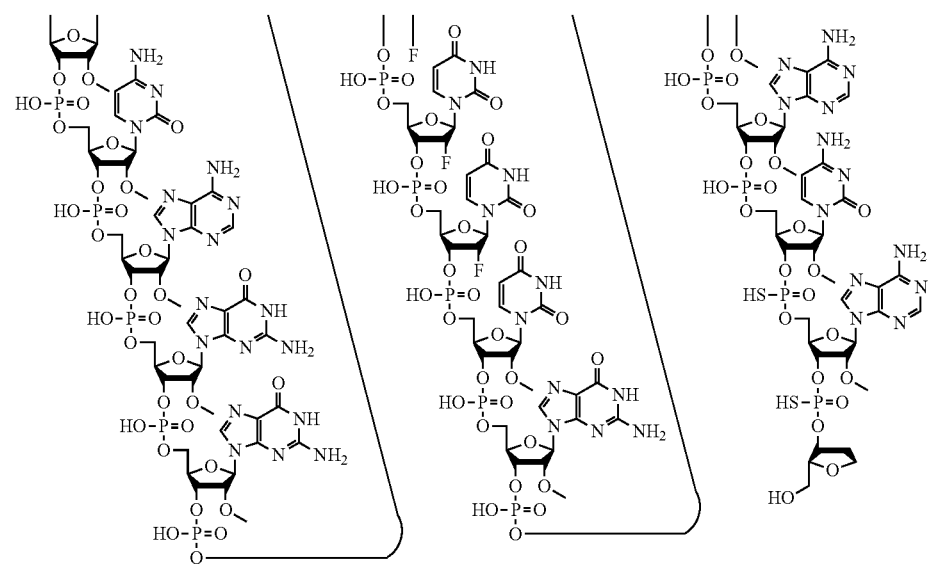

or a pharmaceutically acceptable salt or stereoisomer thereof. In certain embodiments, Ref ID NO: IS1058 is a modified oligonucleotide, or a pharmaceutically acceptable salt or stereoisomer thereof, according to the preceding chemical structure.
In an aspect provided herein, is a modified oligonucleotide according to the following chemical structure:
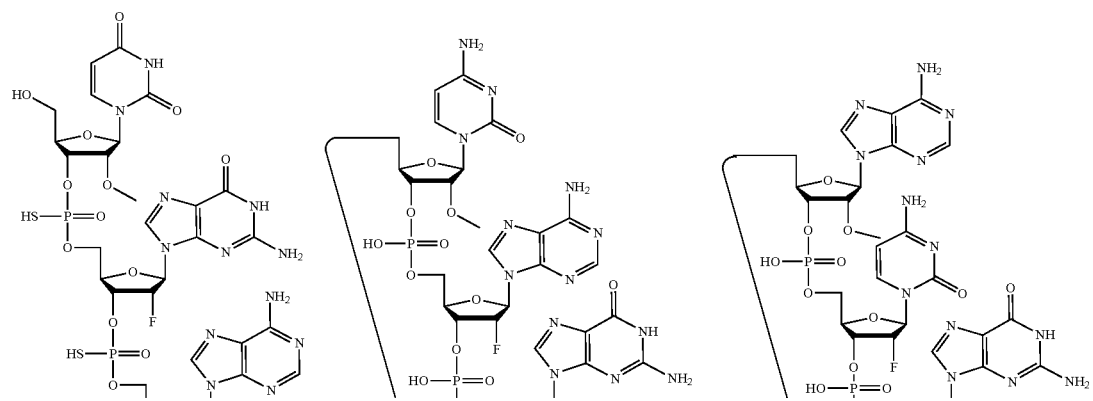
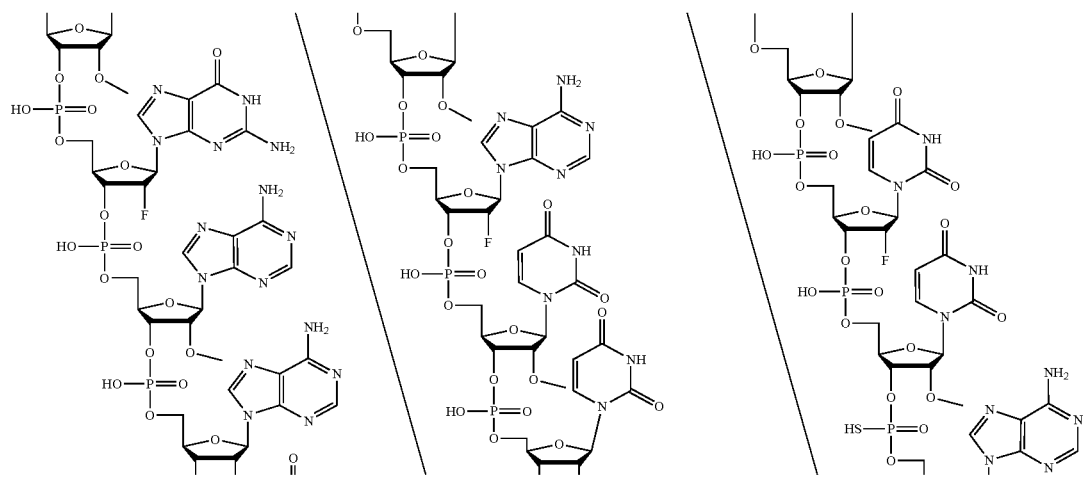
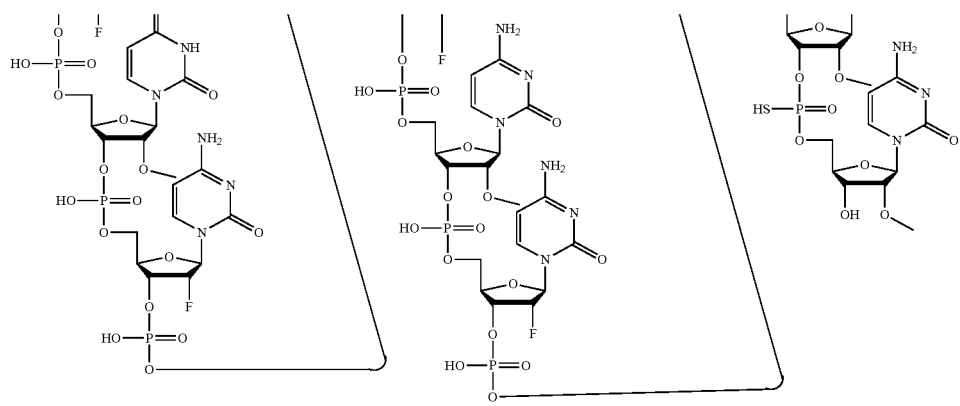

or a pharmaceutically acceptable salt or stereoisomer thereof. In certain embodiments, Ref ID NO: IA0864 is a modified oligonucleotide, or a pharmaceutically acceptable salt or stereoisomer thereof, according to the preceding chemical structure.
In an aspect provided herein, is a modified oligonucleotide according to the following chemical structure:
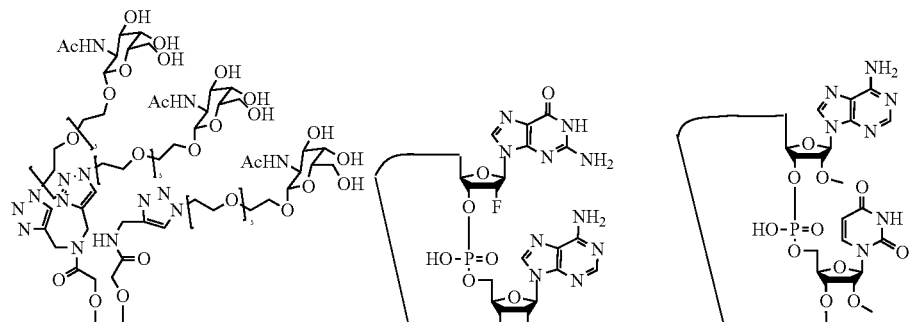
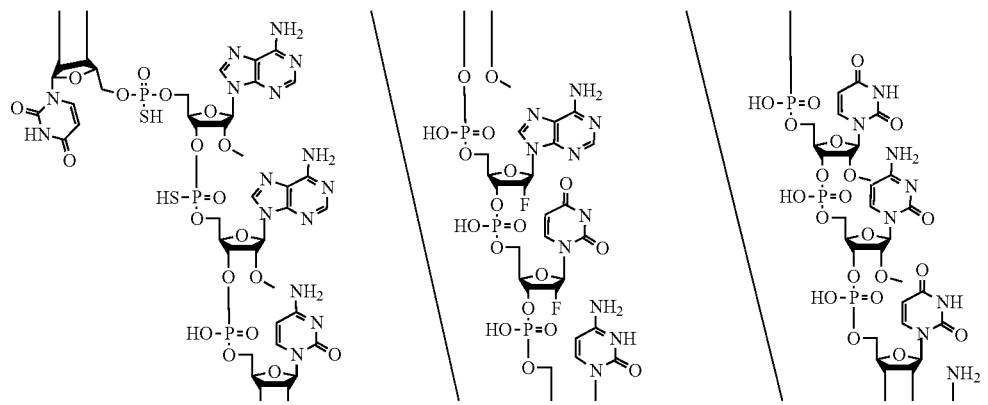
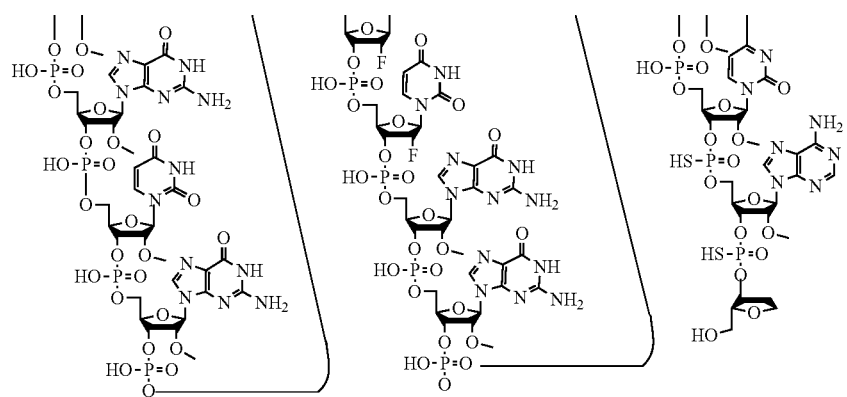

or a pharmaceutically acceptable salt or stereoisomer thereof. In certain embodiments, Ref ID NO: IS1059 is a modified oligonucleotide, or a pharmaceutically acceptable salt or stereoisomer thereof, according to the preceding chemical structure.

In certain embodiments, the pharmaceutically acceptable salt of the modified oligonucleotides provided herein is a sodium salt or a potassium salt.

In an aspect provided herein, is a sodium salt of a modified oligonucleotide according to the following chemical structure:

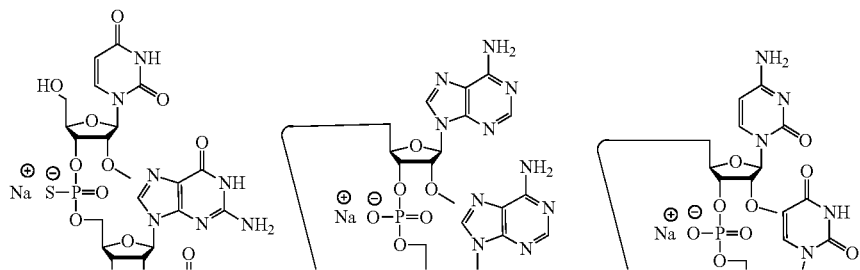

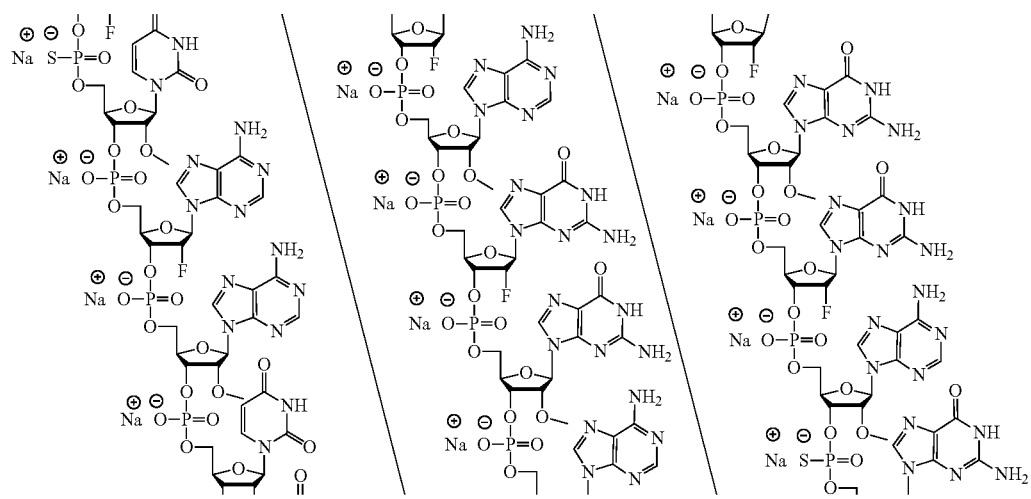

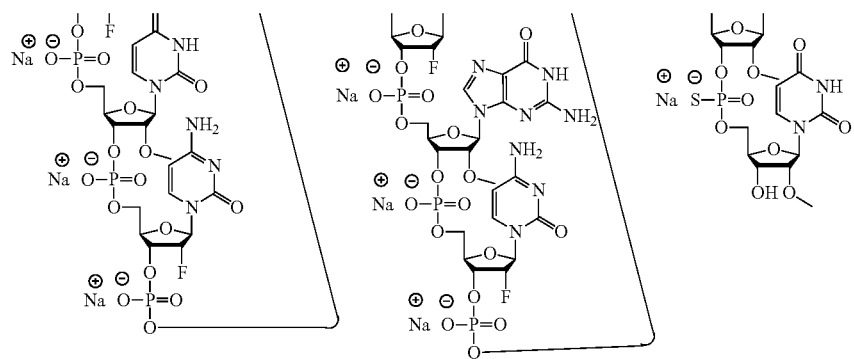

or a stereoisomer thereof. In certain embodiments, Ref ID NO: IA0818 is a modified oligonucleotide or a stereoisomer thereof, according to the preceding chemical structure.
In an aspect provided herein, is a sodium salt of a modified oligonucleotide according to the following chemical structure:
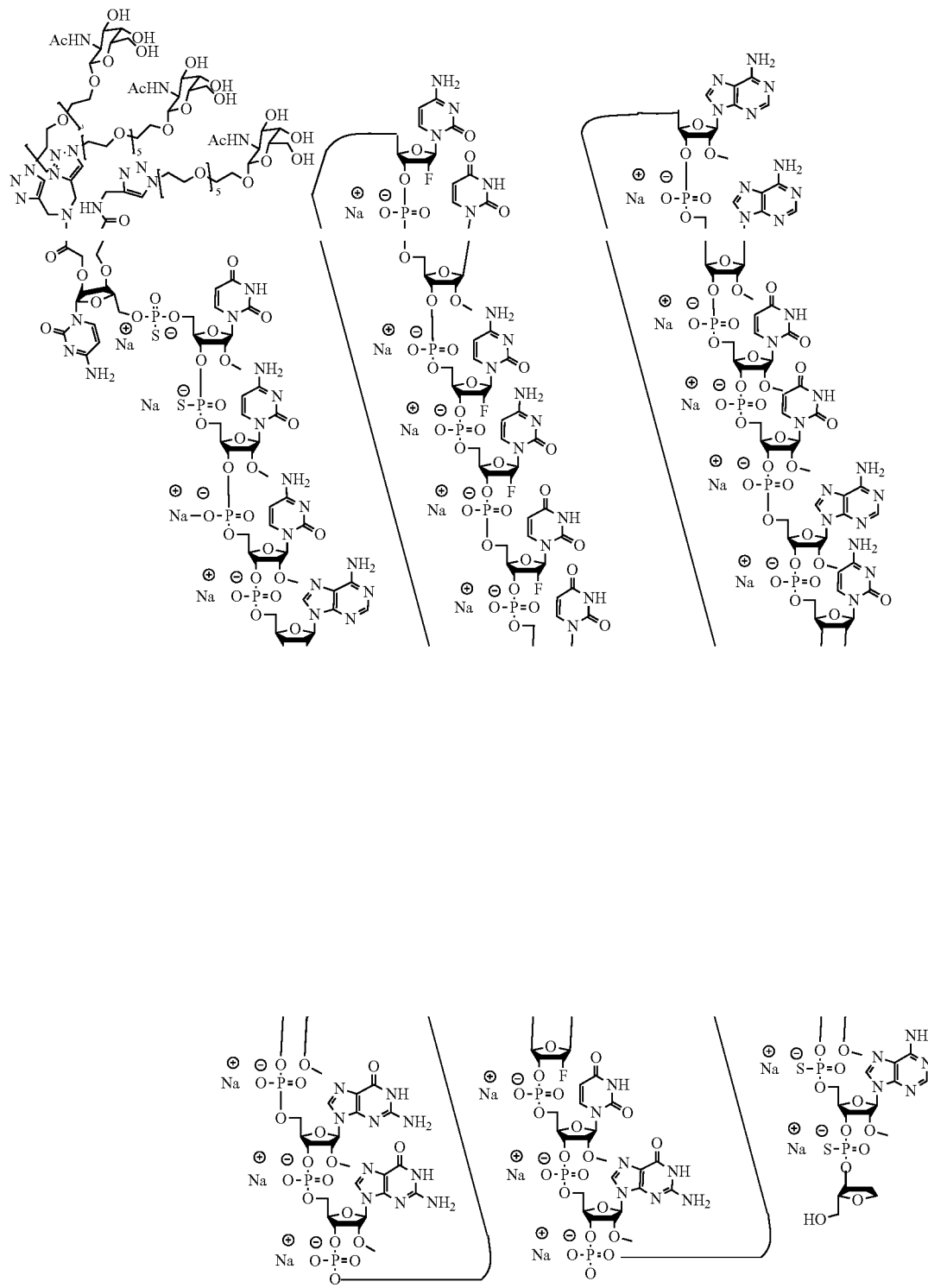

or a stereoisomer thereof. In certain embodiments, Ref ID NO: IS1058 is a modified oligonucleotide or a stereoisomer thereof, according to the preceding chemical structure.
In an aspect provided herein, is a sodium salt of a modified oligonucleotide according to the following chemical structure:
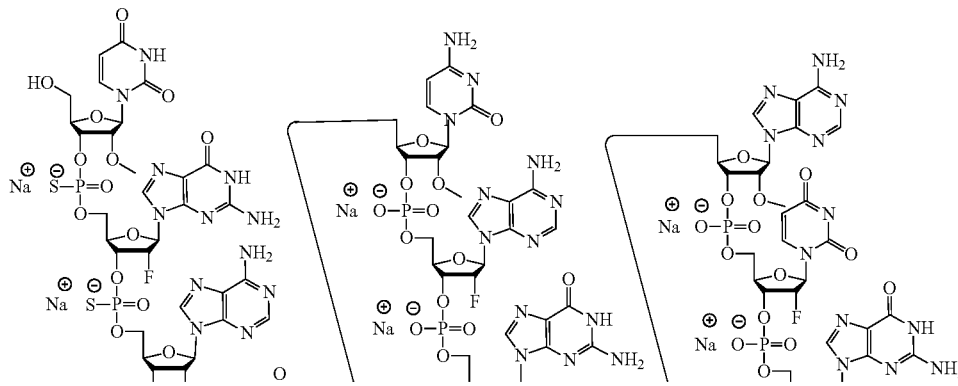
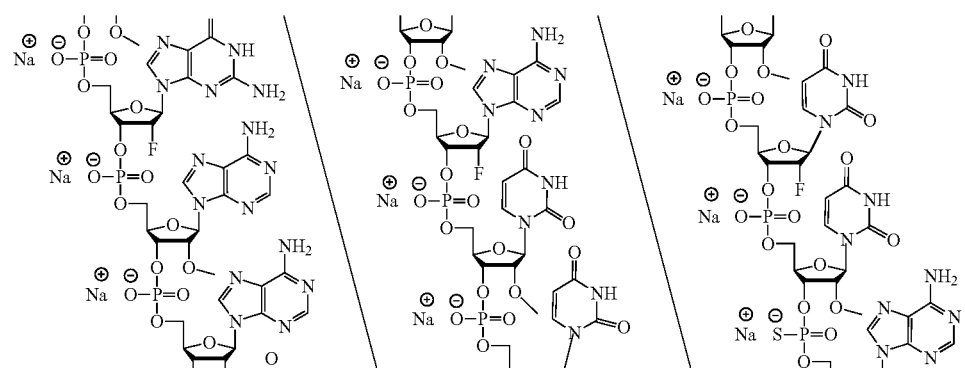
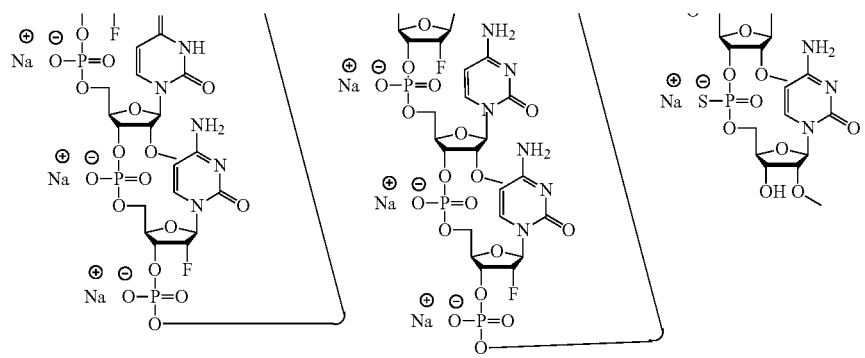

or a stereoisomer thereof. In certain embodiments, Ref ID NO: IA0864 is a modified oligonucleotide or a stereoisomer thereof, according to the preceding chemical structure.
In an aspect provided herein, is a sodium salt of a modified oligonucleotide according to the following chemical structure:
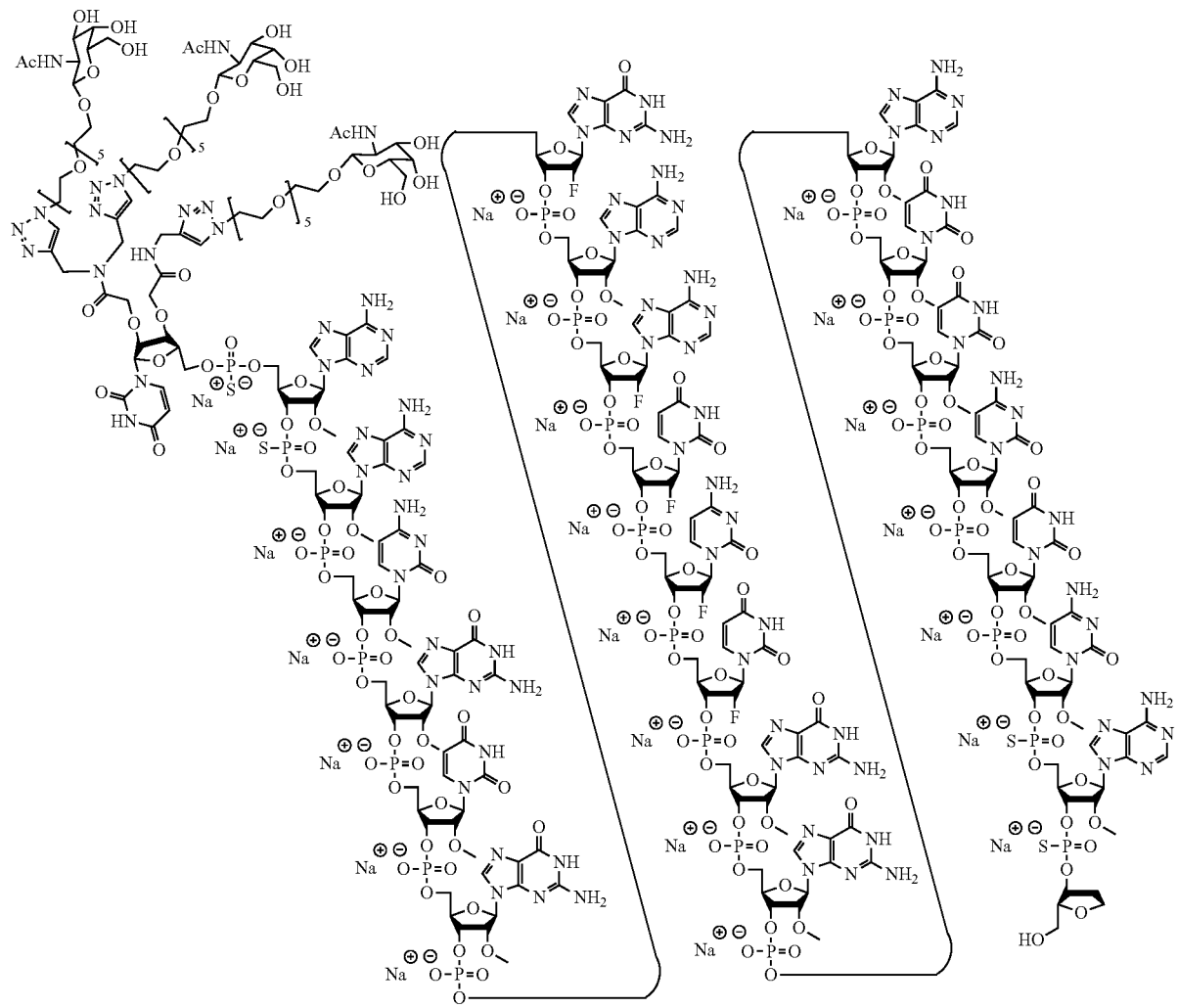

or a stereoisomer thereof. In certain embodiments, Ref ID NO: IS1059 is a modified oligonucleotide or a stereoisomer thereof, according to the preceding chemical structure.
In an aspect provided herein, is a compound according to the following chemical structure:
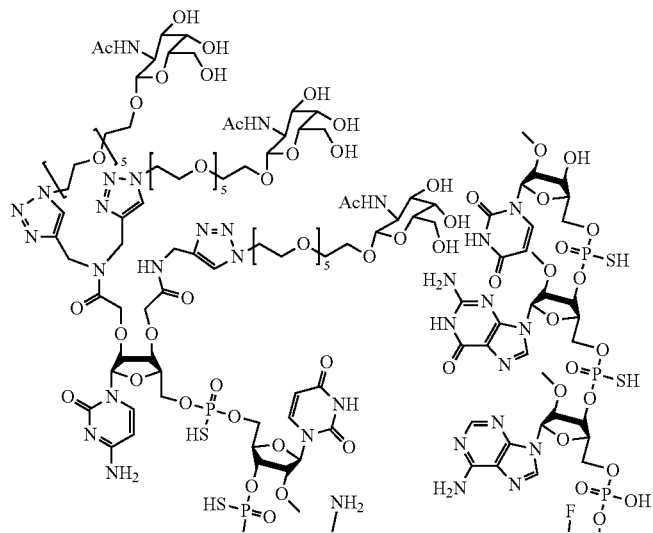
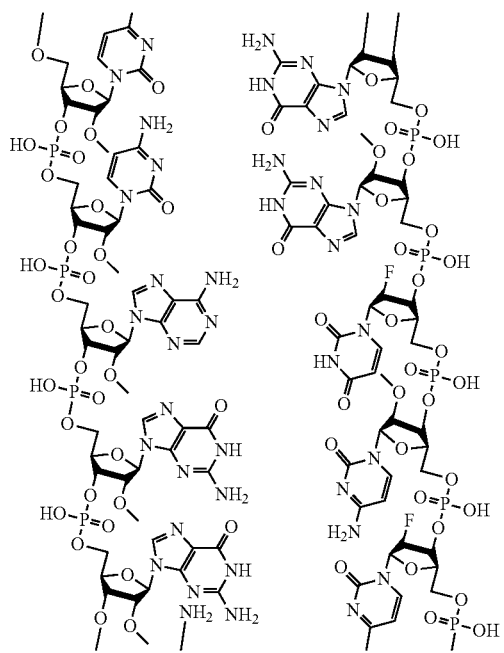

-continued
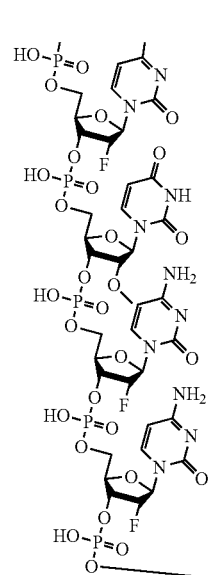
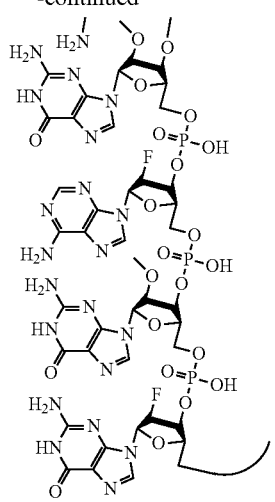
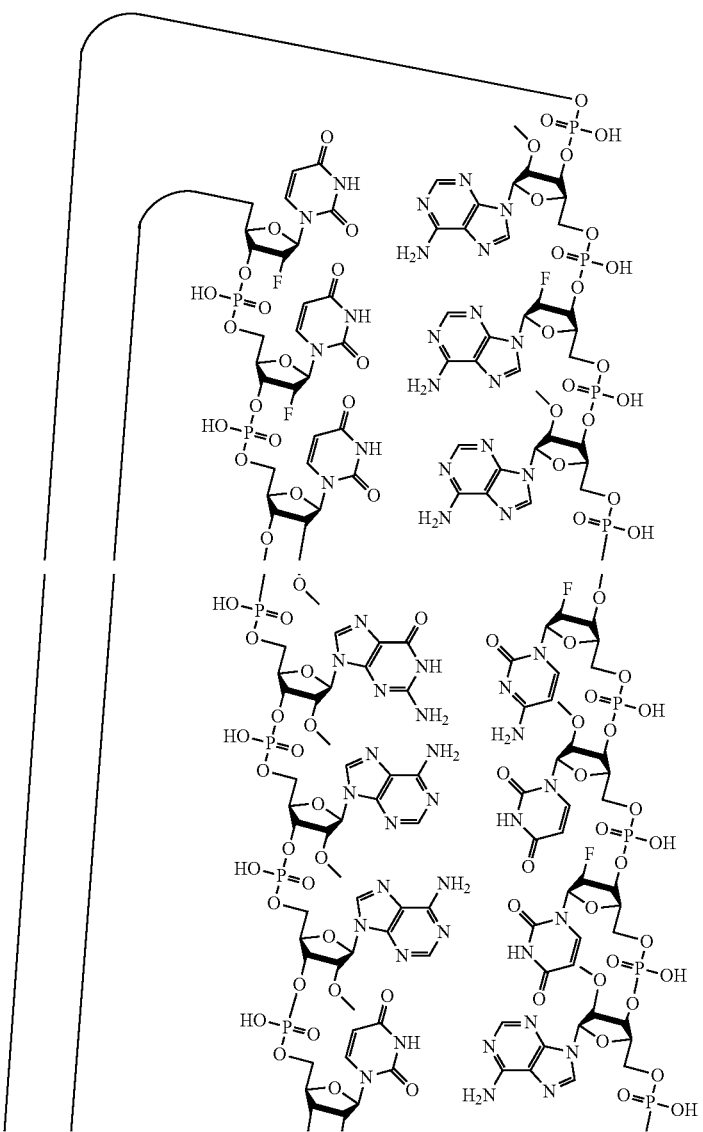

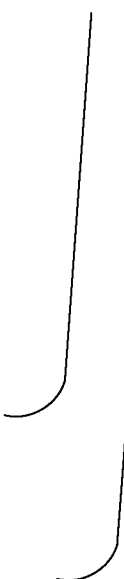
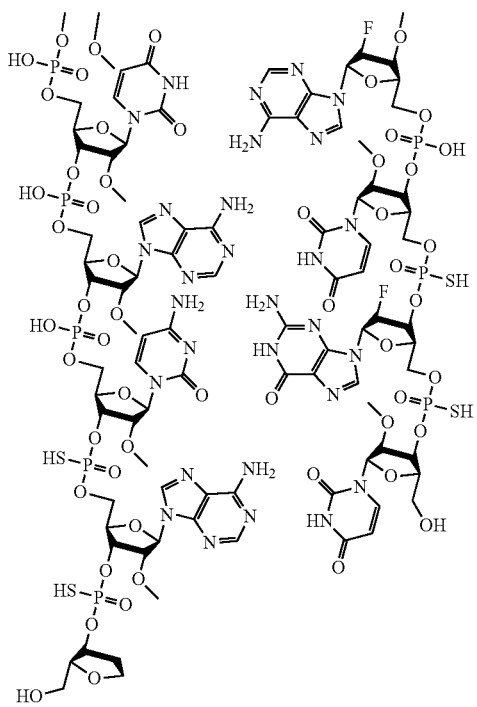
or a pharmaceutically acceptable salt or stereoisomer thereof. In certain embodiments, Compound Number RD2423 is a compound, or a pharmaceutically acceptable salt or stereoisomer thereof, according to the preceding chemical structure.
In an aspect provided herein, is a compound according to the following chemical structure:
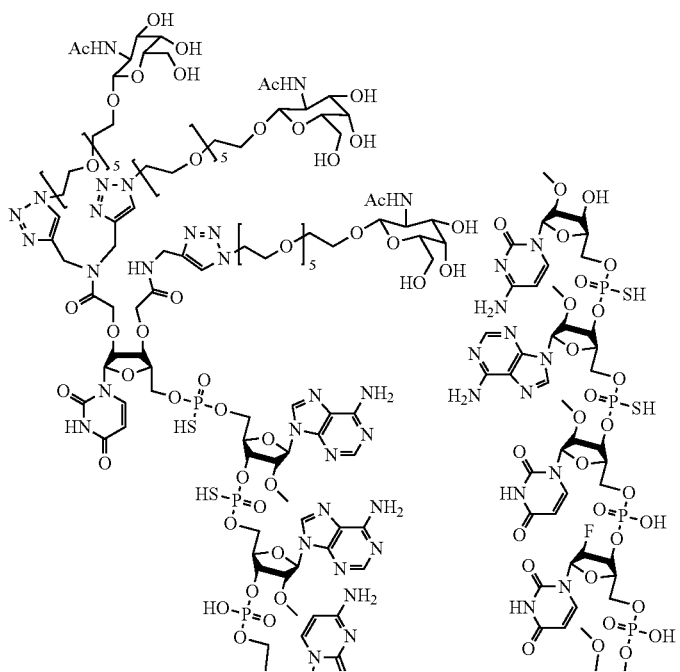

-continued
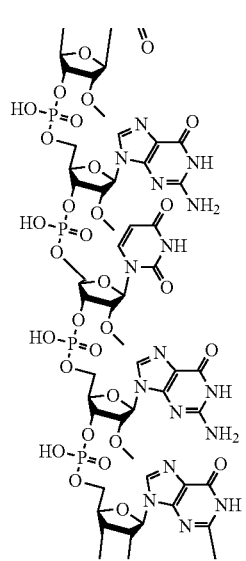
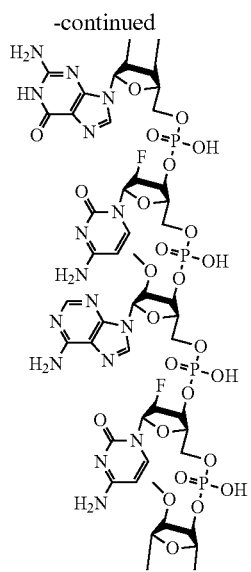
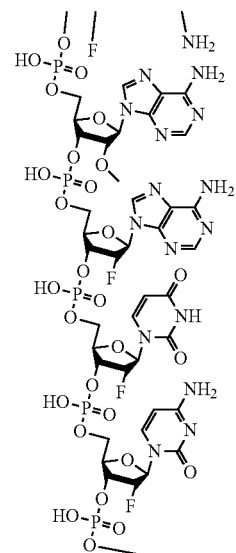
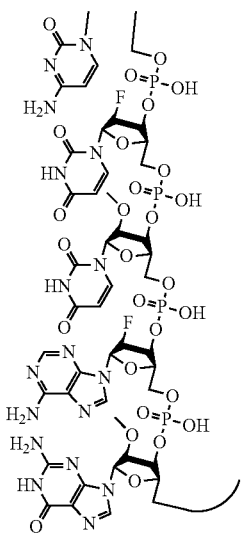
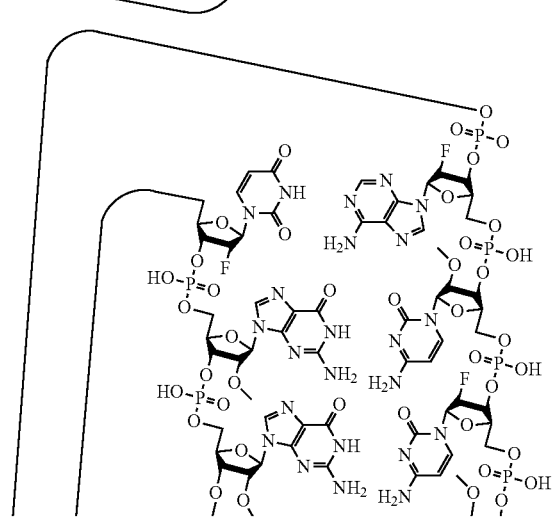

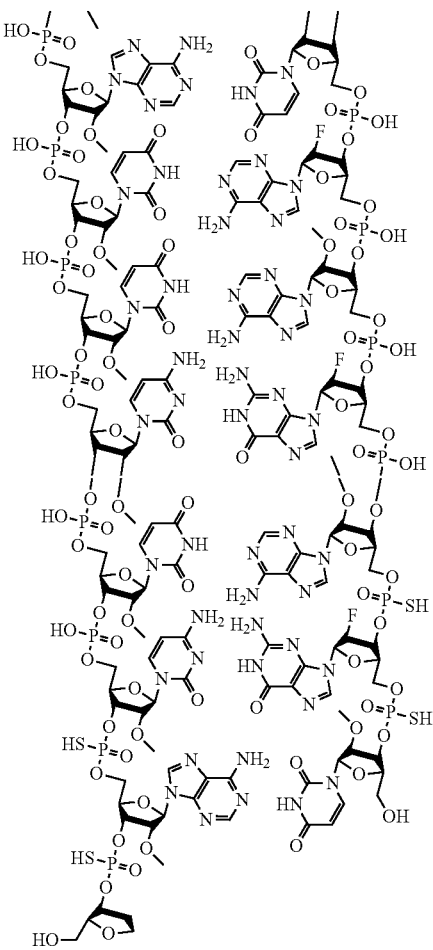

or a pharmaceutically acceptable salt or stereoisomer thereof. In certain embodiments, Compound Number RD2424 is a compound, or a pharmaceutically acceptable salt or stereoisomer thereof, according to the preceding chemical structure.

In certain embodiments, the pharmaceutically acceptable salt of the compounds provided herein is a sodium salt or a potassium salt.

In an aspect provided herein, is a sodium salt of a compound according to the following chemical structure:

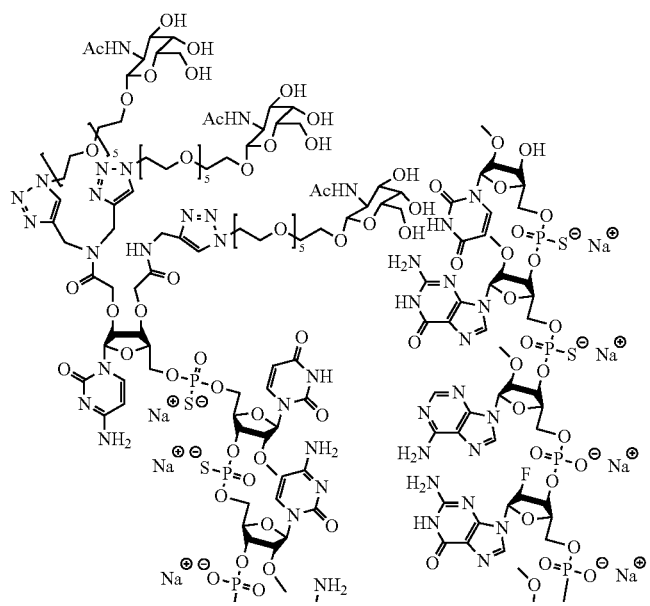

-continued
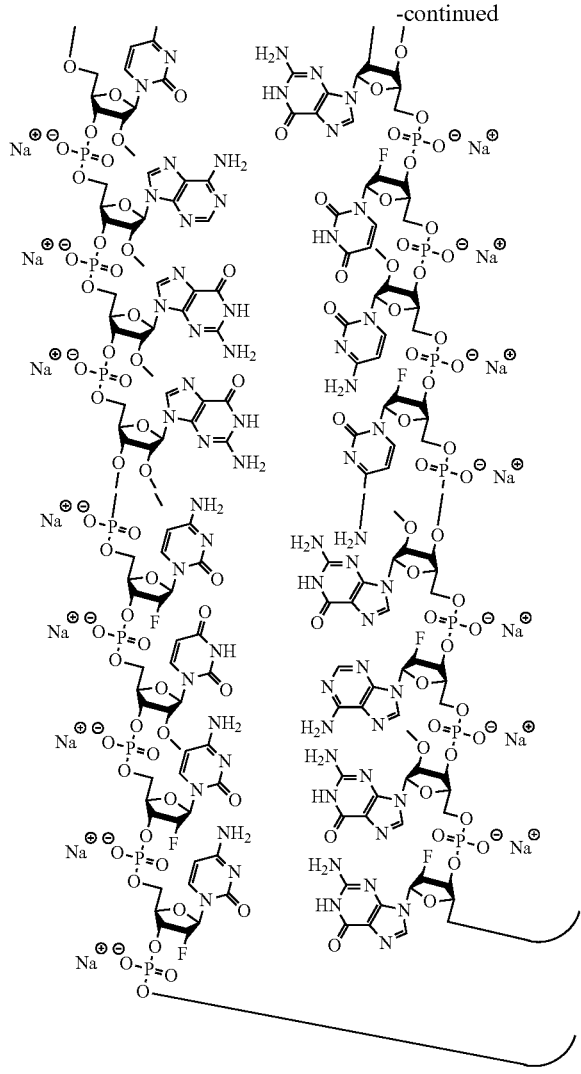
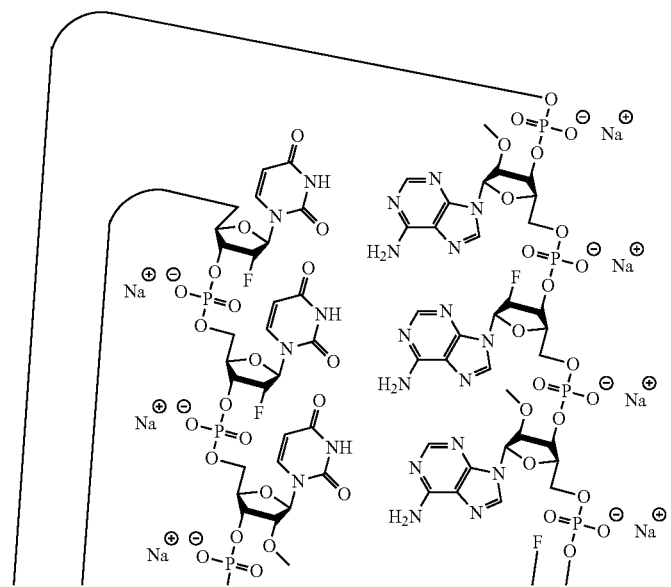

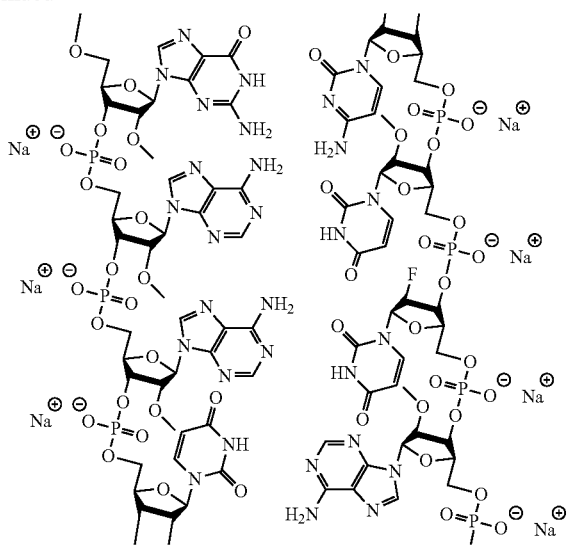
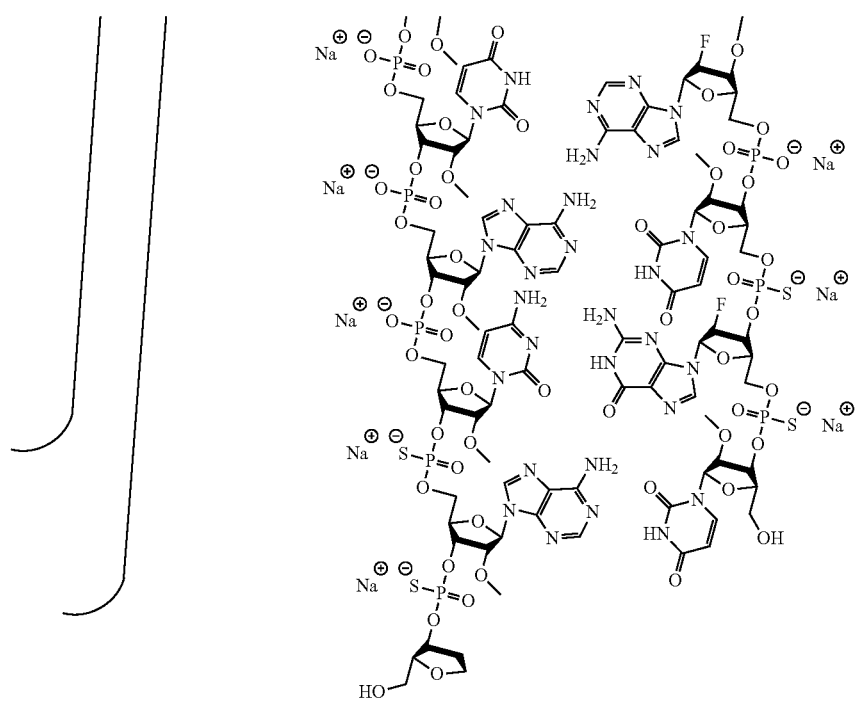

or a stereoisomer thereof. In certain embodiments, Compound Number RD2423 is a compound, or a stereoisomer thereof, according to the preceding chemical structure.
In an aspect provided herein, is a sodium salt of a compound according to the following chemical structure:
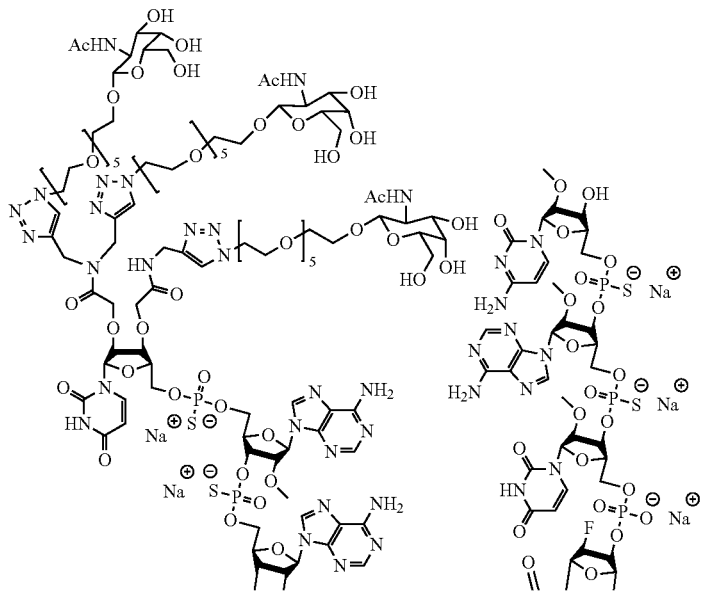
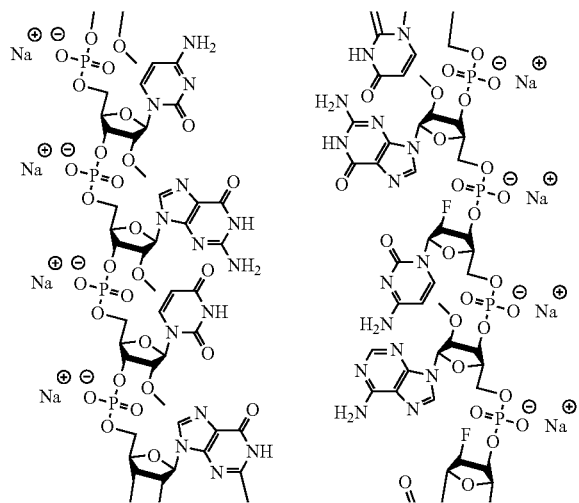

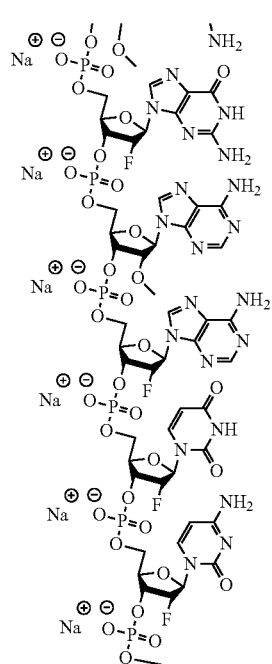
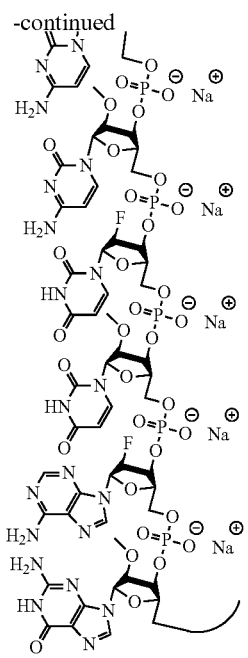
-continued
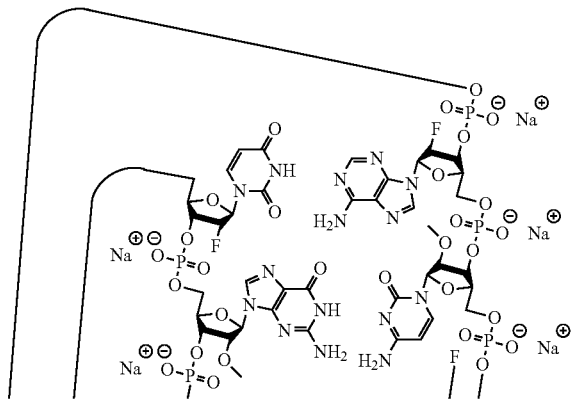
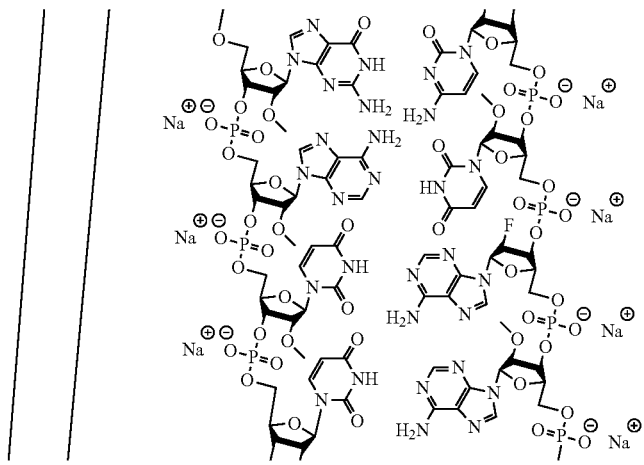

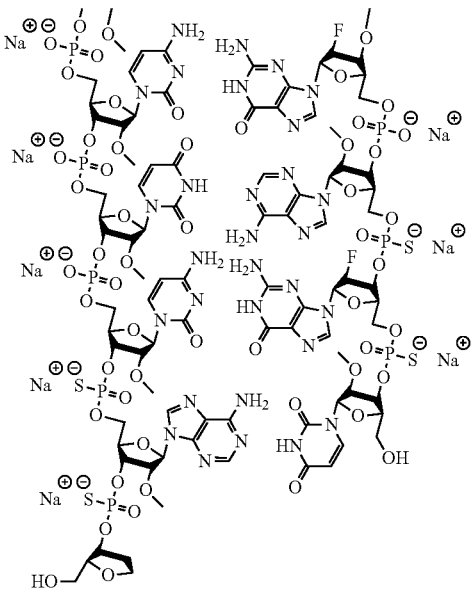

or a stereoisomer thereof. In certain embodiments, Compound Number RD2424 is a compound, or a stereoisomer thereof, according to the preceding chemical structure.

In certain embodiments, provided herein is a population of modified oligonucleotides, wherein all of the phosphorothioate internucleoside linkages of the modified oligonucleotide are stereorandom. In certain embodiments, provided herein is a population of compounds, wherein all of the phosphorothioate internucleoside linkages of the modified oligonucleotide are stereorandom.

Certain embodiments provide a composition comprising the compound of any one of the foregoing embodiments and a pharmaceutically acceptable carrier.

Certain embodiments provide a composition comprising a compound of any preceding embodiment, for use in therapy.

Certain embodiments provide a method of treating, preventing, or ameliorating a disease, disorder or condition associated with PKK and/or a dysregulated kallikrein pathway in an individual comprising administering to the individual a compound targeted to PKK, thereby treating, preventing, or ameliorating the disease, disorder or condition. In certain embodiments, the compound or composition of any foregoing embodiment is administered to an individual. In certain embodiments, the disease, disorder, or condition is an inflammatory or thrombotic disease, disorder or condition or a symptom thereof. In certain embodiments, the disease, disorder, or condition is hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct. In certain embodiments, administering the compound inhibits or reduces or improves an inflammatory or thrombotic disease, disorder or condition or a symptom thereof. In certain embodiments, administering the compound inhibits or reduces or improves hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct, or a symptom thereof.

In certain embodiments, a compound or composition comprising a compound of any preceding embodiment is administered to an individual in a therapeutically effective amount. In certain embodiments, a composition comprising a compound of any preceding embodiment is administered to an individual at a dosage level sufficient to deliver about 1 to 100 mg/kg of body weight of the individual. In certain embodiments, a compound or composition comprising a compound of any preceding embodiment is administered to an individual at a fixed dose of about 25 mg to about 1,000 mg. In certain embodiments, the compound or composition is administered to the individual one or more times in a day up to the dosage level or fixed dose.

In certain embodiments, a composition comprising a compound of any preceding embodiment is administered to an individual daily, weekly, monthly, quarterly or yearly. In certain embodiments, a compound or composition comprising a compound of any preceding embodiment is administered to an individual about once per quarter (i.e., once every three months) to about once per year. In certain embodiments, a compound or composition comprising a compound of any preceding embodiment is administered to an individual about once per quarter, about once every six months or about once per year.

Certain embodiments provide a method of inhibiting expression of PKK in a cell comprising contacting the cell with a compound targeted to PKK, thereby inhibiting expression of PKK in the cell. In certain embodiments, the cell is in the liver of an individual. In certain embodiments, the individual has, or is at risk of having, an inflammatory or thrombotic disease, disorder or condition or a symptom thereof. In certain embodiments, the individual has, or is at risk of having, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct.

Certain embodiments provide a method of reducing or inhibiting an inflammatory or thrombotic disease, disorder or condition or a symptom thereof in an individual, comprising administering a compound targeted to PKK to the individual, thereby reducing or inhibiting an inflammatory or thrombotic disease, disorder or condition or a symptom thereof in the individual. In certain embodiments, the individual has, or is at risk of having, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct. In certain embodiments, the compound is a compound targeted to PKK. In certain embodiments, the compound is any of the foregoing compounds. In certain embodiments, the compound or composition is administered parenterally.

Certain embodiments provide use of a compound targeted to PKK for treating, preventing, or ameliorating a disease, disorder or condition associated with PKK. In certain embodiments, the disease, disorder or condition is an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct. In certain embodiments, the compound is a compound targeted to PKK. In certain embodiments, the compound is any of the foregoing compounds.

Certain embodiments provide use of a compound targeted to PKK in the manufacture of a medicament for treating, preventing, or ameliorating a disease, disorder or condition associated with PKK. In certain embodiments, the disease, disorder or condition is an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct. In certain embodiments, the compound is a compound targeted to PKK. In certain embodiments, the compound is any of the foregoing compounds.

Certain Indications

In certain aspects, the disclosure relates to methods of inhibiting PKK expression, which can be useful for treating, preventing, or ameliorating a disease, disorder or condition associated with PKK in an individual, by administration of a compound that targets PKK. In certain embodiments, the compound can be a PKK specific inhibitor. In certain embodiments, the compound can be an antisense oligonucleotide, an oligomeric compound, or an oligonucleotide targeted to PKK.

In certain aspects, the disclosure relates to treating, preventing, or ameliorating a disease, disorder or condition associated with PKK. In certain embodiments, diseases, disorders or conditions associated with PKK treatable, preventable, and/or ameliorable with the methods provided herein include an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct. Certain compounds provided herein are directed to compounds and compositions that reduce an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct in an animal.

In certain embodiments, a method of treating, preventing, or ameliorating a disease, disorder or condition associated with PKK in an individual comprises administering to the individual a compound comprising a PKK specific inhibitor, thereby treating, preventing, or ameliorating the disease, disorder or condition. In certain embodiments, the individual is identified as having, or at risk of having, a disease, disorder or condition associated with PKK. In certain embodiments, the disease, disorder or condition is a an inflammatory disease or a thrombotic disease. In certain embodiments, the compound comprises an antisense oligonucleotide targeted to PKK. In certain embodiments, the compound comprises an oligonucleotide targeted to PKK. In certain embodiments, a compound comprises a modified oligonucleotide (e.g., of 14 to 30, for example, 14 to 23, linked nucleosides) in length having a nucleobase sequence comprising at least 14, at least 15, at least 16, at least 17, at least 18, at least 19, at least 20, at least 21, at least 22, at least 23 contiguous nucleobases of any of the nucleobase sequences of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 10-313, 626, 627, and 628. In certain embodiments, a compound comprises a modified oligonucleotide having a nucleobase sequence selected from the nucleobase sequence of any one of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising any one of SEQ ID NOs: 307, 312 and 626. In certain embodiments, a compound comprises a modified oligonucleotide having a nucleobase sequence consisting of any one of SEQ ID NOs: 307, 312 and 626.

In any of the foregoing embodiments, the compound can be single-stranded or double-stranded. In certain embodiments, a single-stranded compound can be 14 to 30, 14 to 23, 14 to 20, 16 to 20, or 14 to 16, linked nucleosides in length. In certain embodiments, a single-stranded compound can be 14, 15, 16, 17, 18, 19, 20, 21, 22, 23, 24, 25, 26, 27, 28, 29, or 30, linked nucleosides in length. In certain embodiments, a double-stranded compound can comprise two oligonucleotides of the same or different lengths, as described elsewhere herein. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 307, 312 or 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 468, 611, 616, 619 or 629. In certain embodiments, a compound comprises a modified oligonucleotide having a nucleobase sequence selected from the nucleobase sequence of SEQ ID NO: 307, SEQ ID NO: 312 and SEQ ID NO: 626. In certain embodiments, a compound comprises a modified oligonucleotide having a nucleobase sequence selected from the nucleobase sequence of SEQ ID NO: 468, SEQ ID NO: 611, SEQ ID NO: 616, SEQ ID NO: 619 and SEQ ID NO: 629. In certain embodiments, the compound comprises a first modified oligonucleotide having a nucleobase sequence of SEQ ID NO: 312 and a second modified oligonucleotide having a nucleobase sequence of SEQ ID NO: 619. In certain embodiments, the compound comprises a first modified oligonucleotide having a nucleobase sequence of SEQ ID NO: 626 and a second modified oligonucleotide having a nucleobase sequence of SEQ ID NO: 629.

In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequence of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 10-313, 626, 627, and 628, and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from any one of SEQ ID NOs: 10-631 and a second modified oligonucleotide 19 to 23 linked nucleosides in length having a region of complementarity to the first modified oligonucleotide. In certain embodiments, the compound is administered to the individual parenterally. In certain embodiments, administering the compound improves, preserves, or prevents an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct in an animal.

In certain embodiments, a method of treating, preventing, or ameliorating an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct in an animal comprises administering to the individual a compound comprising a PKK specific inhibitor, thereby treating, preventing, or ameliorating an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct. In certain embodiments, the compound comprises an antisense oligonucleotide targeted to PKK. In certain embodiments, the compound comprises an oligonucleotide targeted to PKK. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequences of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 10-313, 626, 627, and 628. In certain embodiments, a compound comprises a modified oligonucleotide having a nucleobase sequence selected from the nucleobase sequence of any one of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising any one of SEQ ID NOs: 307, 312 and 626. In certain embodiments, a compound comprises a modified oligonucleotide having a nucleobase sequence selected from any one of SEQ ID NOs: 307, 312 and 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 307, 312 or 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 468, 611, 616, 619 or 629. In certain embodiments, a compound comprises a modified oligonucleotide having a nucleobase sequence selected from the nucleobase sequence of SEQ ID NO: 307, SEQ ID NO: 312 and SEQ ID NO: 626. In certain embodiments, a compound comprises a modified oligonucleotide having a nucleobase sequence selected from the nucleobase sequence of SEQ ID NO: 468, SEQ ID NO: 611, SEQ ID NO: 616, SEQ ID NO: 619 and SEQ ID NO: 629. In certain embodiments, the compound comprises a first modified oligonucleotide having a nucleobase sequence of SEQ ID NO: 312 and a second modified oligonucleotide having a nucleobase sequence of SEQ ID NO: 619. In certain embodiments, the compound comprises a first modified oligonucleotide having a nucleobase sequence of SEQ ID NO: 626 and a second modified oligonucleotide having a nucleobase sequence of SEQ ID NO: 629. In any of the foregoing embodiments, the compound can be single-stranded or double-stranded. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequence of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from any one of SEQ ID NOs: 10-631 and a second modified oligonucleotide 19 to 23 linked nucleosides in length having a region of complementarity to the first modified oligonucleotide. In certain embodiments, administering the compound improves, preserves, or prevents an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct in an animal. In certain embodiments, the individual is identified as having, or at risk of having, a disease associated with PKK.

In certain embodiments, a method of inhibiting expression of PKK in an individual having, or at risk of having, a disease, disorder or condition associated with PKK comprises administering to the individual a compound comprising a PKK specific inhibitor, thereby inhibiting expression of PKK in the individual. In certain embodiments, administering the compound inhibits expression of PKK in the liver. In certain embodiments, the disease, disorder or condition is an inflammatory disease or a thrombotic disease. In certain embodiments, the individual has, or is at risk of having, an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct. In certain embodiments, the compound comprises an antisense oligonucleotide targeted to PKK. In certain embodiments, the compound comprises an oligonucleotide targeted to PKK. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequences of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 10-313, 626, 627, and 628. In certain embodiments, a compound comprises a modified oligonucleotide having a nucleobase sequence selected from the nucleobase sequence of any one of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence selected from any one of SEQ ID NOs: 307, 312 and 626. In certain embodiments, a compound comprises a modified oligonucleotide having a nucleobase sequence selected from any one of SEQ ID NOs: 307, 312 and 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 307, 312 or 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 468, 611, 616, 619 or 629. In certain embodiments, a compound comprises a modified oligonucleotide having a nucleobase sequence selected from the nucleobase sequences of SEQ ID NO: 307, SEQ ID NO: 312 and SEQ ID NO: 626. In certain embodiments, a compound comprises a modified oligonucleotide having a nucleobase sequence selected from the nucleobase sequences of SEQ ID NO: 468, SEQ ID NO: 611, SEQ ID NO: 616, SEQ ID NO: 619 and SEQ ID NO: 629. In certain embodiments, the compound comprises a first modified oligonucleotide having a nucleobase sequence of SEQ ID NO: 312 and a second modified oligonucleotide having a nucleobase sequence of SEQ ID NO: 619. In certain embodiments, the compound comprises a first modified oligonucleotide having a nucleobase sequence of SEQ ID NO: 626 and a second modified oligonucleotide having a nucleobase sequence of SEQ ID NO: 629. In any of the foregoing embodiments, the compound can be single-stranded or double-stranded. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequence of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from any one of SEQ ID NOs: 10-631 and a second modified oligonucleotide 19 to 23 linked nucleosides in length having a region of complementarity to the first modified oligonucleotide. In certain embodiments, the compound is administered to the individual parenterally. In certain embodiments, administering the compound improves, preserves, or prevents an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct.

In certain embodiments, a method of inhibiting expression of PKK in a cell comprises contacting the cell with a compound comprising a PKK specific inhibitor, thereby inhibiting expression of PKK in the cell. In certain embodiments, the cell is a hepatocyte. In certain embodiments, the cell is in the liver. In certain embodiments, the cell is in the liver of an individual who has, or is at risk of having, an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct. In certain embodiments, the compound comprises an antisense oligonucleotide targeted to PKK. In certain embodiments, the compound comprises an oligonucleotide targeted to PKK. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequences of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 10-313, 626, 627, and 628. In certain embodiments, a compound comprises a modified oligonucleotide having a nucleobase sequence selected from the nucleobase sequence of any one of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising any one of SEQ ID NOs: 307, 312 and 626. In certain embodiments, a compound comprises a modified oligonucleotide having a nucleobase sequence selected from any one of SEQ ID NOs: 307, 312 and 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 307, 312 or 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 468, 611, 616, 619 or 629. In certain embodiments, a compound comprises a modified oligonucleotide having a nucleobase sequence selected from the nucleobase sequences of SEQ ID NO: 307, SEQ ID NO: 312 and SEQ ID NO: 626. In certain embodiments, a compound comprises a modified oligonucleotide having a nucleobase sequence selected from the nucleobase sequences of SEQ ID NO: 468, SEQ ID NO: 611, SEQ ID NO: 616, SEQ ID NO: 619 and SEQ ID NO: 629. In certain embodiments, the compound comprises a first modified oligonucleotide having a nucleobase sequence of SEQ ID NO: 312 and a second modified oligonucleotide having a nucleobase sequence of SEQ ID NO: 619. In certain embodiments, the compound comprises a first modified oligonucleotide having a nucleobase sequence of SEQ ID NO: 626 and a second modified oligonucleotide having a nucleobase sequence of SEQ ID NO: 629.

In any of the foregoing embodiments, the compound can be single-stranded or double-stranded. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequence of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from any one of SEQ ID NOs: 10-631 and a second modified oligonucleotide 19 to 23 linked nucleosides in length having a region of complementarity to the first modified oligonucleotide.

In certain embodiments, a method of reducing or inhibiting an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct in an individual having, or at risk of having, a disease associated with PKK comprises administering to the individual a compound comprising a PKK specific inhibitor, thereby reducing or inhibiting an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct in the individual. In certain embodiments, the individual has, or is at risk of having, an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct. In certain embodiments, the compound comprises an antisense oligonucleotide targeted to PKK. In certain embodiments, the compound comprises an oligonucleotide targeted to PKK. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequences of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 10-313, 626, 627, and 628. In certain embodiments, a compound comprises a modified oligonucleotide selected from the nucleobase sequence of any one of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising any one of SEQ ID NOs: 307, 312 and 626. In certain embodiments, a compound comprises a modified oligonucleotide having a nucleobase sequence selected from any one of SEQ ID NOs: 307, 312 and 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 307, 312 or 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 468, 611, 616, 619 or 629. In certain embodiments, a compound comprises a modified oligonucleotide having a nucleobase sequence selected from the nucleobase sequences of SEQ ID NO: 307, SEQ ID NO: 312 and SEQ ID NO: 626. In certain embodiments, a compound comprises a modified oligonucleotide having a nucleobase sequence selected from the nucleobase sequences of SEQ ID NO: 468, SEQ ID NO: 611, SEQ ID NO: 616, SEQ ID NO: 619 and SEQ ID NO: 629. In certain embodiments, the compound comprises a first modified oligonucleotide having a nucleobase sequence of SEQ ID NO: 312 and a second modified oligonucleotide having a nucleobase sequence of SEQ ID NO: 619. In certain embodiments, the compound comprises a first modified oligonucleotide having a nucleobase sequence of SEQ ID NO: 626 and a second modified oligonucleotide having a nucleobase sequence of SEQ ID NO: 629. In any of the foregoing embodiments, the compound can be single-stranded or double-stranded. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequence of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from any one of SEQ ID NOs: 10-631 and a second modified oligonucleotide 19 to 23 linked nucleosides in length having a region of complementarity to the first modified oligonucleotide. In certain embodiments, the compound is administered to the individual parenterally. In certain embodiments, the individual is identified as having, or at risk of having, a disease, disorder or condition associated with PKK.

Certain embodiments are drawn to a compound comprising a PKK specific inhibitor for use in treating a disease, disorder or condition associated with PKK. In certain embodiments, the disease, disorder or condition is an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct. In certain embodiments, the compound comprises an antisense oligonucleotide targeted to PKK. In certain embodiments, the compound comprises an oligonucleotide targeted to PKK. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequences of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 10-313, 626, 627, and 628. In certain embodiments, a compound comprises a modified oligonucleotide selected from the nucleobase sequence of any one of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising any one of SEQ ID NOs: 307, 312 and 626. In certain embodiments, a compound comprises a modified oligonucleotide having a nucleobase sequence selected from any one of SEQ ID NOs: 307, 312 and 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 307, 312 or 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 468, 611, 616, 619 or 629. In certain embodiments, a compound comprises a modified oligonucleotide having a nucleobase sequence selected from the nucleobase sequences of SEQ ID NO: 307, SEQ ID NO: 312 and SEQ ID NO: 626. In certain embodiments, a compound comprises a modified oligonucleotide having a nucleobase sequence selected from the nucleobase sequences of SEQ ID NO: 468, SEQ ID NO: 611, SEQ ID NO: 616, SEQ ID NO: 619 and SEQ ID NO: 629. In certain embodiments, the compound comprises a first modified oligonucleotide having a nucleobase sequence of SEQ ID NO: 312 and a second modified oligonucleotide having a nucleobase sequence of SEQ ID NO: 619. In certain embodiments, the compound comprises a first modified oligonucleotide having a nucleobase sequence of SEQ ID NO: 626 and a second modified oligonucleotide having a nucleobase sequence of SEQ ID NO: 629. In any of the foregoing embodiments, the compound can be single-stranded or double-stranded. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequence of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from any one of SEQ ID NOs: 10-631 and a second modified oligonucleotide 19 to 23 linked nucleosides in length having a region of complementarity to the first modified oligonucleotide. In certain embodiments, the compound is administered to the individual parenterally.

Certain embodiments are drawn to a compound comprising a PKK specific inhibitor for use in reducing or inhibiting an inflammatory disease, a thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct. In certain embodiments, the compound comprises an antisense oligonucleotide targeted to PKK. In certain embodiments, the compound comprises an oligonucleotide targeted to PKK. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequences of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 10-313, 626, 627, and 628. In certain embodiments, a compound comprises a modified oligonucleotide selected from the nucleobase sequence of any one of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising any one of SEQ ID NOs: 307, 312 and 626. In certain embodiments, a compound comprises a modified oligonucleotide having a nucleobase sequence selected from any one of SEQ ID NOs: 307, 312 and 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 307, 312 or 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 468, 611, 616, 619 or 629. In certain embodiments, a compound comprises a modified oligonucleotide having a nucleobase sequence selected from the nucleobase sequences of SEQ ID NO: 307, SEQ ID NO: 312 and SEQ ID NO: 626. In certain embodiments, a compound comprises a modified oligonucleotide having a nucleobase sequence selected from the nucleobase sequences of SEQ ID NO: 468, SEQ ID NO: 611, SEQ ID NO: 616, SEQ ID NO: 619 and SEQ ID NO: 629. In certain embodiments, the compound comprises a first modified oligonucleotide having a nucleobase sequence of SEQ ID NO: 312 and a second modified oligonucleotide having a nucleobase sequence of SEQ ID NO: 619. In certain embodiments, the compound comprises a first modified oligonucleotide having a nucleobase sequence of SEQ ID NO: 626 and a second modified oligonucleotide having a nucleobase sequence of SEQ ID NO: 629. In any of the foregoing embodiments, the compound can be single-stranded or double-stranded. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequence of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from any one of SEQ ID NOs: 10-631 and a second modified oligonucleotide 19 to 23 linked nucleosides in length having a region of complementarity to the first modified oligonucleotide.

Certain embodiments are drawn to the use of a compound comprising a PKK specific inhibitor for the manufacture or preparation of a medicament for treating a disease, disorder or condition associated with PKK. Certain embodiments are drawn to the use of a compound comprising a PKK specific inhibitor for the preparation of a medicament for treating a disease, disorder or condition associated with PKK. In certain embodiments, the disease is an inflammatory or thrombotic disease. In certain embodiments, the disease is hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct. In certain embodiments, the compound comprises an antisense oligonucleotide targeted to PKK. In certain embodiments, the compound comprises an oligonucleotide targeted to PKK. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequences of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 10-313, 626, 627, and 628. In certain embodiments, a compound comprises a modified oligonucleotide having a nucleobase sequence selected from the nucleobase sequence of any one of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising any one of SEQ ID NOs: 307, 312 and 626. In certain embodiments, a compound comprises a modified oligonucleotide having a nucleobase sequence selected from any one of SEQ ID NOs: 307, 312 and 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 307, 312 or 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 468, 611, 616, 619 or 629. In certain embodiments, a compound comprises a modified oligonucleotide having a nucleobase sequence selected from the nucleobase sequences of SEQ ID NO: 307, SEQ ID NO: 312 and SEQ ID NO: 626. In certain embodiments, a compound comprises a modified oligonucleotide having a nucleobase sequence selected from the nucleobase sequences of SEQ ID NO: 468, SEQ ID NO: 611, SEQ ID NO: 616, SEQ ID NO: 619 and SEQ ID NO: 629. In certain embodiments, the compound comprises a first modified oligonucleotide having a nucleobase sequence of SEQ ID NO: 312 and a second modified oligonucleotide having a nucleobase sequence of SEQ ID NO: 619. In certain embodiments, the compound comprises a first modified oligonucleotide having a nucleobase sequence of SEQ ID NO: 626 and a second modified oligonucleotide having a nucleobase sequence of SEQ ID NO: 629. In any of the foregoing embodiments, the compound can be single-stranded or double-stranded. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequence of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from any one of SEQ ID NOs: 10-631 and a second modified oligonucleotide 19 to 23 linked nucleosides in length having a region of complementarity to the first modified oligonucleotide.

Certain embodiments are drawn to the use of a compound comprising a PKK specific inhibitor for the manufacture or preparation of a medicament for reducing or inhibiting an inflammatory disease, a thrombotic disease in an individual having, or at risk of having, an inflammatory disease or a thrombotic disease associated with PKK. In certain embodiments, the inflammatory disease or thrombotic disease is hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct. Certain embodiments are drawn to use of a compound comprising a PKK specific inhibitor for the preparation of a medicament for treating a disease associated with PKK. In certain embodiments, the disease is an inflammatory disease, thrombotic disease, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct. In certain embodiments, the compound comprises an antisense oligonucleotide targeted to PKK. In certain embodiments, the compound comprises an oligonucleotide targeted to PKK. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequences of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 10-313, 626, 627, and 628. In certain embodiments, a compound comprises a modified oligonucleotide selected from the nucleobase sequence of any one of SEQ ID NOs: 10-313, 626, 627, and 628. In certain embodiments, a compound comprises a modified oligonucleotide (e.g., of 14 to 30, for example, 14 to 23, linked nucleosides in length) having a nucleobase sequence comprising any one of SEQ ID NOs: 307, 312 and 626. In certain embodiments, a compound comprises a modified oligonucleotide having a nucleobase sequence selected from any one of SEQ ID NOs: 307, 312 and 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 307, 312 or 626. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of the nucleobase sequence of SEQ ID NO: 468, 611, 616, 619 or 629. In certain embodiments, a compound comprises a modified oligonucleotide having a nucleobase sequence selected from the nucleobase sequences of SEQ ID NO: 307, SEQ ID NO: 312 and SEQ ID NO: 626. In certain embodiments, a compound comprises a modified oligonucleotide having a nucleobase sequence selected from the nucleobase sequences of SEQ ID NO: 468, SEQ ID NO: 611, SEQ ID NO: 616, SEQ ID NO: 619 and SEQ ID NO: 629. In certain embodiments, the compound comprises a first modified oligonucleotide having a nucleobase sequence of SEQ ID NO: 312 and a second modified oligonucleotide having a nucleobase sequence of SEQ ID NO: 619. In certain embodiments, the compound comprises a first modified oligonucleotide having a nucleobase sequence of SEQ ID NO: 626 and a second modified oligonucleotide having a nucleobase sequence of SEQ ID NO: 629. In any of the foregoing embodiments, the compound can be single-stranded or double-stranded. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, at least 23 contiguous nucleobases of any of the nucleobase sequence of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 10-631 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from any one of SEQ ID NOs: 10-631 and a second modified oligonucleotide 19 to 23 linked nucleosides in length having a region of complementarity to the first modified oligonucleotide.

In any of the foregoing methods or uses, the compound can be an oligomeric compound. In any of the foregoing methods or uses, the compound can be single-stranded or double-stranded. In any of the foregoing methods or uses, the compound can be targeted to PKK. In certain embodiments, the compound comprises or consists of a modified oligonucleotide. In certain embodiments, the compound comprises one or more modified oligonucleotides. In certain embodiments, the compound comprises a first modified oligonucleotide and a second modified oligonucleotide. In certain embodiments, a modified oligonucleotide is 8 to 80 linked nucleosides in length, 10 to 30 linked nucleosides in length, 14 to 30 linked nucleosides in length, 14 to 23 linked nucleosides in length, or 19 to 23 linked nucleosides in length. In certain embodiments, a modified oligonucleotide is at least 80%, at least 85%, at least 90%, at least 95% or 100% complementary to any of the nucleobase sequences recited in SEQ ID NOs: 1, 3, 5 or 6 over its length. In certain embodiments, a modified oligonucleotide comprises at least one modified internucleoside linkage, at least one modified sugar and/or at least one modified nucleobase. In certain embodiments, the modified internucleoside linkage is a phosphorothioate internucleoside linkage. In certain embodiments, the modified sugar is a bicyclic sugar, 2'-MOE, 2'-F, or 2'-OMe. In certain embodiments, the modified nucleobase is a 5-methylcytosine. In any of the foregoing embodiments, each modified oligonucleotide is independently 12 to 30, 14 to 30, 14 to 25, 14 to 24, 14 to 23, 16 to 23, 17 to 23, 18 to 23, 19 to 23, 19 to 22, or 19 to 20 linked nucleosides in length. In certain embodiments, a modified oligonucleotide has at least 1, at least 2, at least 3 mismatches to a region of SEQ ID NOs: 1, 3, 5 or 6.

In any of the forgoing methods or uses, the compound comprises a first and second modified oligonucleotide, wherein there is a region of complementarity between a first modified oligonucleotide and a second modified oligonucleotide. In certain embodiments, the region of complementarity between the first oligonucleotide and the second oligonucleotide is 14 to 23, 19 to 23, or 21 to 23 linked nucleosides in length. In certain embodiments, the first modified oligonucleotide is fully complementary to the second modified oligonucleotide. In certain embodiments, the first modified oligonucleotide comprises at least one modification selected from a modified internucleoside linkage, a modified sugar, and a modified nucleobase. In certain embodiments, the second modified oligonucleotide comprises at least one modification selected from the group consisting of a modified internucleoside linkage, a modified sugar, and a modified nucleobase. In certain embodiments, the modified internucleoside linkage is a phosphorothioate internucleoside linkage or a methylphosphonate internucleoside linkage. In certain embodiments, the modified internucleoside linkage is at the 3' terminus of the first or second modified oligonucleotide or at the 5' terminus of the first or second modified oligonucleotide. In certain embodiments, the first or second modified oligonucleotide comprises one or more modified sugars. In certain embodiments, each nucleoside of the first or second modified oligonucleotide comprises a modified sugar. In certain embodiments, the modified sugar comprises a modification selected from the group consisting of a halogen, an alkoxy group and a bicyclic sugar. In certain embodiments, the modified sugar comprises a modification selected from group consisting of 2'-MOE, 2'-F, and 2'-OMe or a combination thereof. In certain embodiments, the first or second modified oligonucleotide comprises no more than ten 2'-F sugar modifications. In certain embodiments, the first or second modified oligonucleotide comprises no more than five 2'-F sugar modifications.

In any of the forgoing methods or uses, a compound comprises a conjugate group. In certain embodiments, the conjugate group is attached to the 5' end of a modified oligonucleotide. In certain embodiments, the conjugate group is a targeting moiety. In certain embodiments, the targeting moiety comprises one or more GalNAc. In certain embodiments, the one or more GalNAc is attached to the 2' or 3' position of the ribosyl ring. In certain embodiments, the one or more GalNAc is attached to the 5' nucleoside of the modified oligonucleotide. In certain embodiments, the 5' nucleoside of a modified oligonucleotide is selected from Formulae I-VIII, or a salt, solvate, or hydrate thereof, wherein R is the modified oligonucleotide other than the 5' nucleoside. In certain embodiments, the 5' nucleoside of the modified oligonucleotide is Formula I and R' is O. In certain embodiments, the 5' nucleoside of the modified oligonucleotide is Formula I and R' is S. In certain embodiments, the 5' nucleoside of the modified oligonucleotide is Formula II and R' is O. In certain embodiments, the 5' nucleoside of the modified oligonucleotide is Formula II and R' is S. In certain embodiments, the 5' nucleoside of the modified oligonucleotide is Formula III and R' is O. In certain embodiments, the 5' nucleoside of the modified oligonucleotide is Formula III and R' is S. In certain embodiments, the 5' nucleoside of the modified oligonucleotide is Formula IV and R' is O. In certain embodiments, the 5' nucleoside of the modified oligonucleotide is Formula IV and R' is S. In certain embodiments, the 5' nucleoside of the modified oligonucleotide is Formula V and R' is O. In certain embodiments, the 5' nucleoside of the modified oligonucleotide is Formula V and R' is S. In certain embodiments, the 5' nucleoside of the modified oligonucleotide is Formula VI and R' is O. In certain embodiments, the 5' nucleoside of the modified oligonucleotide is Formula VI and R' is S. In certain embodiments, the 5' nucleoside of the modified oligonucleotide is Formula VII and R' is O. In certain embodiments, the 5' nucleoside of the modified oligonucleotide is Formula VII and R' is S. In certain embodiments, the 5' nucleoside of the modified oligonucleotide is Formula VIII and R' is O. In certain embodiments, the 5' nucleoside of the modified oligonucleotide is Formula VIII and R' is S.

In any of the foregoing methods or uses, the compound comprises a first modified oligonucleotide selected from any one of Ref ID NOs: IA0812-821 and a second modified oligonucleotide 14 to 21 linked nucleosides in length fully complementary to the first modified oligonucleotide. In certain embodiments, the compound comprises a first modified oligonucleotide consisting of IA0813 and a second modified oligonucleotide consisting of IS1002. In certain embodiments, the compound comprises a first modified oligonucleotide consisting of IA0818 and a second modified oligonucleotide consisting of IS1007. In certain embodiments, the compound comprises a first modified oligonucleotide consisting of IA0818 and a second modified oligonucleotide consisting of IS1068.

In any of the foregoing methods or uses, the compound comprises a first modified oligonucleotide selected from any one of Ref ID NOs: IA0864-866 and a second modified oligonucleotide 14 to 21 linked nucleosides in length fully complementary to the first modified oligonucleotide. In certain embodiments, the compound comprises a first modified oligonucleotide consisting of IA0864 and a second modified oligonucleotide consisting of IS1059. Certain embodiments provide a compound comprising a first modified oligonucleotide selected from Ref ID NOs: IA0818 and IA0864 and a second modified oligonucleotide selected from Ref ID NOs: IS1058 and IS1059. Certain embodiments provide a compound comprising a first modified oligonucleotide consisting of IA0864 and a second modified oligonucleotide consisting of IS1059. Certain embodiments provide a compound comprising a first modified oligonucleotide consisting of IA0818 and a second modified oligonucleotide consisting of IS1058.

In certain embodiments, the compound comprises a first modified oligonucleotide selected from Ref ID NOs: IA0818 and IA0864 and a second modified oligonucleotide selected from Ref ID NOs: IS1058 and IS1059. In certain embodiments, the compound comprises a first modified oligonucleotide consisting of IA0864 and a second modified oligonucleotide consisting of IS1059. In certain embodiments, the compound comprises a first modified oligonucleotide consisting of IA0818 and a second modified oligonucleotide consisting of IS1058.

In certain embodiments, the compound is in a pharmaceutically acceptable salt form. In certain embodiments, the pharmaceutically acceptable salt is a sodium salt. In certain embodiments, the pharmaceutically acceptable salt is a potassium salt. In certain embodiments, a composition comprises the compound of any one of the foregoing embodiments and a pharmaceutically acceptable carrier.

In any of the foregoing methods or uses, a compound or composition comprising a compound of any preceding embodiment is administered to an individual in a therapeutically effective amount. In certain embodiments, a compound or composition comprising a compound of any preceding embodiment is administered to an individual at a dosage level sufficient to deliver about 1 to 100 mg/kg of body weight of the individual. In certain embodiments, a compound or composition comprising a compound of any preceding embodiment is administered to an individual at a fixed dose of about 25 mg to about 1,000 mg. In certain embodiments, the composition is administered to the individual one or more times in a day up to the dosage level or fixed dose.

In any of the foregoing methods or uses, a compound or composition comprising a compound of any preceding embodiment is administered to an individual daily, weekly, monthly, quarterly or yearly. In certain embodiments, a compound or composition comprising a compound of any preceding embodiment is administered to an individual about once per quarter (i.e., once every three months) to about once per year. In certain embodiments, a compound or composition comprising a compound of any preceding embodiment is administered to an individual about once per quarter, about once every six months or about once per year.

Certain Compounds

In certain aspects, the disclosure relates to a compound that comprises or consists of an oligomeric compound. In certain embodiments, the oligomeric compound comprises a nucleobase sequence complementary to that of a target nucleic acid.

In certain aspects, the disclosure relates to a compound that comprises or consists of a modified oligonucleotide. In certain embodiments, the modified oligonucleotide has a nucleobase sequence complementary to that of a target nucleic acid.

In certain aspects, the disclosure relates to a compound that comprises or consists of an antisense oligonucleotide. In certain embodiments, the antisense oligonucleotide has a nucleobase sequence complementary to that of a target nucleic acid.

In certain aspects, the disclosure relates to a compound that is a single-stranded compound. In certain embodiments, the single-stranded compound comprises or consists of an oligomeric compound. In certain embodiments, such an oligomeric compound comprises or consists of an oligonucleotide and optionally a conjugate group. In certain embodiments, the oligonucleotide is a modified oligonucleotide. In certain embodiments, the oligonucleotide is an antisense oligonucleotide. In certain embodiments, the oligonucleotide or modified oligonucleotide of a single-stranded compound comprises a self-complementary nucleobase sequence.

In certain aspects, the disclosure relates to a compound that is a double-stranded compound. In certain embodiments, the double-stranded compound comprises or consists of an oligomeric compound. In certain embodiments, the double-stranded compound comprises a first oligonucleotide and a second oligonucleotide. In certain embodiments, the first oligonucleotide has a region complementarity to a target nucleic acid and the second oligonucleotide has a region complementarity to the first modified oligonucleotide. In certain embodiments, the double-stranded compound comprises a modified oligonucleotide. In certain embodiments, the modified oligonucleotide has a region complementarity to a target nucleic acid. In certain embodiments, the double-stranded compound comprises a first modified oligonucleotide and a second modified oligonucleotide. In certain embodiments, the first modified oligonucleotide has a region complementarity to a target nucleic acid and the second modified oligonucleotide has a region complementarity to the first modified oligonucleotide. In certain embodiments, an oligonucleotide or modified oligonucleotide of a double-stranded compound is an RNA oligonucleotide. In such embodiments, the thymine nucleobase in the modified oligonucleotide is replaced by a uracil nucleobase.

In certain embodiments, a compound described herein comprises a conjugate group. In certain embodiments, the first oligonucleotide or first modified oligonucleotide of a double-stranded compound comprises a conjugate group. In certain embodiments, the second oligonucleotide or second modified oligonucleotide of a double-stranded compound comprises a conjugate group. In certain embodiments, a first oligonucleotide or first modified oligonucleotide and a second oligonucleotide or second modified oligonucleotide of a double-stranded compound each comprises a conjugate group.

In certain embodiments, a compound is 14-30 linked nucleosides in length. In certain embodiments, the first oligonucleotide or first modified oligonucleotide of a double-stranded compound is 14-30 linked nucleosides in length. In certain embodiments, the second oligonucleotide or second modified oligonucleotide is 14-30 linked nucleosides in length. In certain embodiments, the oligonucleotides or modified oligonucleotides of a double-stranded compound are blunt ended at one or both ends of the compound. In certain embodiments, the oligonucleotides or modified oligonucleotides of a double-stranded compound include non-complementary overhanging nucleosides at one or both ends of the compound.

In certain embodiments, a compound has a nucleobase sequence comprising at least 14 contiguous nucleobases of any of SEQ ID NOs: 10-313, 626, 627, and 628. In certain embodiments, one of the oligonucleotides or modified oligonucleotides of a double-stranded compound has a nucleobase sequence comprising at least 14 contiguous nucleobases of any of SEQ ID NOs: 10-313, 626, 627, and 628.

Examples of single-stranded and double-stranded compounds include, but are not limited to, oligonucleotides, antisense oligonucleotides, siRNAs, microRNA targeting oligonucleotides, occupancy-based compounds (e.g., mRNA processing or translation blocking compounds and splicing compounds), and single-stranded RNAi compounds (e.g. small hairpin RNAs (shRNAs), single stranded siRNAs (ssRNAs) and microRNA mimics).

In certain embodiments, a compound described herein has a nucleobase sequence that, when written in the 5' to 3' direction, comprises the reverse complement of the target region of a target nucleic acid to which it is targeted.

In certain embodiments, a compound described herein comprises an oligonucleotide 12 to 30 linked subunits in length. In certain embodiments, a compound described herein comprises an oligonucleotide 12 to 23 linked subunits in length. In certain embodiments, compound described herein comprises an oligonucleotide 14 to 30 linked subunits in length. In certain embodiments, compound described herein comprises an oligonucleotide 14 to 23 linked subunits in length. In certain embodiments, a compound described herein comprises an oligonucleotide 15 to 30 linked subunits in length. In certain embodiments, a compound described herein comprises an oligonucleotide 15 to 23 linked subunits in length. In certain embodiments, a compound described herein comprises an oligonucleotide 16 to 30 linked subunits in length. In certain embodiments, a compound described herein comprises an oligonucleotide 16 to 23 linked subunits in length. In certain embodiments, a compound described herein comprises an oligonucleotide 17 to 30 linked subunits in length. In certain embodiments, a compound described herein comprises an oligonucleotide 17 to 23 linked subunits in length. In certain embodiments, a compound described herein comprises an oligonucleotide 18 to 30 linked subunits in length. In certain embodiments, a compound described herein comprises an oligonucleotide 18 to 23 linked subunits in length. In certain embodiments, a compound described herein comprises an oligonucleotide 19 to 30 linked subunits in length. In certain embodiments, a compound described herein comprises an oligonucleotide 19 to 23 linked subunits in length. In other words, such oligonucleotides are 12 to 30 linked subunits, 12 to 23 linked subunits, 14 to 30 linked subunits, 14 to 23 linked subunits, 15 to 30 linked subunits, 15 to 23 linked subunits, 16 to 30 linked subunits, 16 to 23 linked subunits, 17 to 30 linked subunits, 17 to 23 linked subunits, 18 to 30 linked subunits, 18 to 23 linked subunits, 19 to 30 linked subunits or 19 to 23 linked subunits, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In certain embodiments, a compound described herein comprises an oligonucleotide 21 linked subunits in length. In certain embodiments, a compound described herein comprises an oligonucleotide 22 linked subunits in length. In certain embodiments, a compound described herein comprises an oligonucleotide 23 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 23, 18 to 24, 18 to 25, 18 to 50, 19 to 23, 19 to 30, 19 to 50, 20 to 23 or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, or 30 linked subunits in length, or a range defined by any two of the above values.

In certain embodiments, the compound may further comprise an additional moiety, such as a conjugate group or delivery moiety. In certain embodiments, such compounds are oligomeric compounds, and the additional moiety is attached to an oligonucleotide. In certain embodiments, a conjugate group is attached to a nucleoside of an oligonucleotide.

In certain embodiments, compounds may be shortened or truncated. For example, one or more subunits may be deleted from the 5' end (5' truncation), or alternatively from the 3' end (3' truncation) of an oligonucleotide.

In certain embodiments, compounds may be lengthened. For example, one or more subunits may be attached to the 3' end or 5' end of an oligonucleotide. In certain embodiments, at least one subunit (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more subunits) is attached to the 5' end of an oligonucleotide. In certain embodiments, at least one subunit (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more subunits) is attached to the 3' end of an oligonucleotide. In certain embodiments, at least one or more subunits may be attached to the 3' end or 5' end of an oligonucleotide of a double-stranded compound creating a 3' and/or 5' end overhang. In certain embodiments, at least one subunit (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more subunits) is attached to the 5' end of both oligonucleotides of a double-stranded compound. In certain embodiments, at least one subunit (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more subunit) is attached to the 3' end of both oligonucleotides of a double-stranded compound. In certain embodiments, subunits are attached to both oligonucleotides of a double-stranded compound at the same end (e.g., that subunits are attached to the 3' end of one of the oligonucleotides and subunits are attached to the 5' end of the other oligonucleotide). In certain embodiments, when subunits are attached to both oligonucleotides of a double-stranded compound at the same end, the number of subunits attached to each oligonucleotide may be the same or may be different. In certain embodiments, when subunits are attached to both oligonucleotides of a double-stranded compound at the same end, the number of subunits attached to each oligonucleotide is the same. In certain embodiments, when subunits are attached to both oligonucleotides of a double-stranded compound at the same end, the number of subunits attached to each oligonucleotide is different. This scenario, where subunits are attached to both oligonucleotides of a double-stranded compound at the same end, may occur at one or both ends of a double-stranded compound. In certain embodiments, the subunits attached to the 3' and/or 5' end are modified.

In certain embodiments, compounds described herein are oligonucleotides. In certain embodiments, compounds described herein are modified oligonucleotides. In certain embodiments, compounds described herein are antisense oligonucleotides. In certain embodiments, compounds described herein are oligomeric compounds. In certain embodiments, compounds described herein are RNAi compounds. In certain embodiments, compounds described herein are siRNA compounds.

In certain embodiments, a compound described herein can comprise any of the oligonucleotide sequences targeted to PKK described herein. In certain embodiments, the compound can be double-stranded.

In certain embodiments, the compound comprises an oligonucleotide comprising at least an 8, 9, 10, 11, 12, 13, 14, 15, 16, 17, 18, 19, 20, 21, 22 or 23 contiguous nucleobase portion of any one of SEQ ID NOs: 10-313, 626, 627, and 628. In certain embodiments, the compound comprises an oligonucleotide comprising at least an 8, 9, 10, 11, 12, 13, 14, 15, 16, 17, 18, 19, 20, 21, 22 or 23 contiguous nucleobase portion of SEQ ID NO: 307, 312 or 626. In certain embodiments, the compound comprises a second oligonucleotide. In certain embodiments, the compound comprises an oligonucleotide comprising at least an 8, 9, 10, 11, 12, 13, 14, 15, 16, 17, 18, 19, 20, 21, 22 or 23 contiguous nucleobase portion of SEQ ID NO: 468, 611, 616, 619 or 629. In certain embodiments, the compound comprises a first oligonucleotide comprising at least an 8, 9, 10, 11, 12, 13, 14, 15, 16, 17, 18, 19, 20, 21, 22 or 23 contiguous nucleobase portion of SEQ ID NO: 312 and a second oligonucleotide comprising at least an 8, 9, 10, 11, 12, 13, 14, 15, 16, 17, 18, 19, 20, 21, 22 or 23 contiguous nucleobase portion of SEQ ID NO: 619. In certain embodiments, the compound comprises a first oligonucleotide comprising at least an 8, 9, 10, 11, 12, 13, 14, 15, 16, 17, 18, 19, 20, 21, 22 or 23 contiguous nucleobase portion of SEQ ID NO: 626 and a second oligonucleotide comprising at least an 8, 9, 10, 11, 12, 13, 14, 15, 16, 17, 18, 19, 20, 21, 22 or 23 contiguous nucleobase portion of SEQ ID NO: 629.

In certain embodiments, the compound comprises ribonucleotides in which the oligonucleotide has uracil (U) in place of thymine (T) for any of the sequences provided here.

In certain embodiments, the compound comprises deoxyribonucleotides in which the oligonucleotide has thymine (T) in place of uracil (U) for any of the sequences provided here.

Certain Mechanisms

In certain embodiments, compounds described herein comprise or consist of modified oligonucleotides. In certain embodiments, compounds described herein comprise or consist of antisense oligonucleotides. In certain embodiments, compounds comprise or consist of oligomeric compounds. In certain embodiments, compounds described herein are capable of hybridizing to a target nucleic acid. In certain embodiments, compounds described herein selectively affect one or more target nucleic acid. Such compounds comprise a nucleobase sequence that hybridizes to one or more target nucleic acid, resulting in one or more desired activity and does not hybridize to one or more non-target nucleic acid or does not hybridize to one or more non-target nucleic acid in such a way that results in a significant undesired activity.

In certain embodiments, hybridization of a compound described herein to a target nucleic acid results in recruitment of one or more proteins that cause the cleavage of the target nucleic acid. For example, certain compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain embodiments, hybridization of compounds described herein to a target nucleic acid does not result in recruitment of a protein that cleaves that target nucleic acid. In certain such embodiments, hybridization of the compound to the target nucleic acid results in the alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to the target nucleic acid results in the alteration of RNA processing. In certain such embodiments, hybridization of the compound to a target nucleic acid results in alteration of translation of the target nucleic acid.

Activities resulting from the hybridization of a compound to a target nucleic acid may be observed directly or indirectly. In certain embodiments, observation or detection of an activity involves observation or detection of a change in an amount of a target nucleic acid or protein encoded by such target nucleic acid, a change in the ratio of splice variants of a nucleic acid or protein, and/or a phenotypic change in a cell or animal.

Certain Modifications

In certain aspects, the disclosure relates to compounds that comprise or consist of oligonucleotides. Oligonucleotides consist of linked nucleosides. In certain embodiments, oligonucleotides may be unmodified RNA or DNA or may be modified. In certain embodiments, the oligonucleotides are modified oligonucleotides. In certain embodiments, the modified oligonucleotides comprise at least one modified sugar, modified nucleobase or modified internucleoside linkage relative to an unmodified RNA or DNA. In certain embodiments, an oligonucleotide has a modified nucleoside. A modified nucleoside may comprise a modified sugar, a modified nucleobase or both a modified sugar and a modified nucleobase. Modified oligonucleotides may also include end modifications, e.g., 5'-end modifications and 3'-end modifications.

Sugar Modifications and Motifs

In certain embodiments, a modified sugar is a substituted furanosyl sugar or non-bicyclic modified sugar. In certain embodiments, a modified sugar is a bicyclic or tricyclic modified sugar. In certain embodiments, a modified sugar is a sugar surrogate. A sugar surrogate may comprise one or more substitutions described herein.

In certain embodiments, a modified sugar is a substituted furanosyl or non-bicyclic modified sugar. In certain embodiments, the furanosyl sugar is a ribosyl sugar. In certain embodiments, the furanosyl sugar comprises one or more substituent groups, including, but not limited to, substituent groups at the 2', 3', 4', and 5' positions.

In certain embodiments, substituents at the 2' position include, but are not limited to, F and $OCH_3$ ("OMe", "O-methyl" or "methoxy"). In certain embodiments, substituent groups at the 2' position suitable for non-bicyclic modified sugars include, but are not limited to, halo, allyl, amino, azido, SH, CN, OCN, $CF_3$, $OCF_3$, F, Cl, Br, $SCH_3$, $SOCH_3$, $SO_2CH_3$, $ONO_2$, $NO_2$, $N_3$, and $NH_2$. In certain embodiments, substituent groups at the 2' position include, but are not limited to, O—($C_1$-$C_{10}$) alkoxy, alkoxyalkyl, O-alkyl, S-alkyl, N-alkyl, O-alkenyl, S-alkenyl, N-alkenyl, O-alkynyl, S-alkynyl, N-alkynyl, O-alkyl-O-alkyl, alkynyl, wherein the alkyl, alkenyl and alkynyl can be substituted or unsubstituted $C_1$ to $C_{10}$ alkyl or $C_2$ to $C_{10}$ alkenyl and alkynyl. In certain embodiments, substituent groups at the 2' position include, but are not limited to, alkaryl, aralkyl, O-alkaryl, and O-aralkyl. In certain embodiments, these 2' substituent groups can be further substituted with one or more substituent groups independently selected from hydroxyl, alkoxy, carboxy, benzyl, phenyl, nitro ($NO_2$), thiol, thioalkoxy, thioalkyl, halogen, alkyl, aryl, alkenyl, and alkynyl. In certain embodiments, substituent groups at the 2' position include, but are not limited to, $O[(CH_2)_nO]_mCH_3$, $O(CH_2)_nOCH_3$, $O(CH_2)_nCH_3$, $O(CH_2)_nONH_2$, $O(CH_2)_nNH_2$, $O(CH_2)_nSCH_3$, and $O(CH_2)_nON[(CH_2)_nCH_3)]_2$, where n and m are independently from 1 to about 10. In certain embodiments, substituent groups at the 2' position include, but are not limited to, $OCH_2CH_2OCH_3$ ("MOE"), $O(CH_2)_2ON(CH_3)_2$ ("DMAOE"), $O(CH_2)_2O(CH_2)_2N(CH_3)_2$ ("DMAEOE"), and $OCH_2C(=O)$—$N(H)CH_3$ ("NMA").

In certain embodiments, substituent groups at the 4' position suitable for non-bicyclic modified sugars include, but are not limited to, alkoxy (e.g., methoxy), alkyl, and those described in Manoharan et al., WO 2015/106128. In certain embodiments, substituent groups at the 5' position suitable for non-bicyclic modified sugars include, but are not limited to, methyl ("Me") (R or S), vinyl, and methoxy. In certain embodiments, substituents described herein for the 2', 4' and 5' position can be added to other specific positions on the sugar. In certain embodiments, such substituents may be added to the 3' position of the sugar on the 3' terminal nucleoside or the 5' position of the 5' terminal nucleoside. In certain embodiments, a non-bicyclic modified sugar may comprise more than one non-bridging sugar substituent. In certain such embodiments, non-bicyclic modified sugars substituents include, but are not limited to, 5'-Me-2'-F, 5'-Me-2'-OMe (including both R and S isomers). In certain embodiments, modified sugar substituents include those described in Migawa et al., WO 2008/101157 and Rajeev et al., US2013/0203836.

In certain embodiments, a modified sugar is a bicyclic sugar. A bicyclic sugar is a modified sugar comprising two rings, wherein the second ring is formed via a bridge connecting two of the atoms in the first ring thereby forming a bicyclic structure. In certain embodiments, a bicyclic sugar comprises a bridging substituent that bridges two atoms of the furanosyl ring to form a second ring. In certain embodiments, a bicyclic sugar does not comprise a furanosyl moiety. A "bicyclic nucleoside" ("BNA") is a nucleoside having a bicyclic sugar. In certain embodiments, the bicyclic sugar comprises a bridge between the 4' and 2' furanose ring atoms. In certain embodiments, the bicyclic sugar comprises a bridge between the 5' and 3' furanose ring atoms. In certain such embodiments, the furanose ring is a ribose ring. In certain embodiments, 4' to 2' bridging substituents include, but are not limited to, 4'-$CH_2$-2', 4'—$(CH_2)_2$-2', 4'—$(CH_2)_3$-2', 4'-$CH_2$—O-2' ("LNA"), 4'-$CH_2$—S-2', 4'—$(CH_2)_2$—O-2' ("ENA"), 4'-$CH(CH_3)$—O-2' ("constrained ethyl" or "cEt" when in the S configuration), 4'-$CH_2$—O—$CH_2$-2', 4'-$CH_2$—N(R)-2', 4'-$CH(CH_2OCH_3)$—O-2' ("constrained MOE" or "cMOE") and analogs thereof (e.g., U.S. Pat. No. 7,399,845), 4'-$C(CH_3)(CH_3)$—O-2' and analogs thereof (e.g., U.S. Pat. No. 8,278,283), 4'-$CH_2$—$N(OCH_3)$-2' and analogs thereof (e.g., U.S. Pat. No. 8,278,425), 4'-$CH_2$—O—$N(CH_3)$-2' (e.g., U.S. Patent Publication No. 2004/0171570), 4'-$CH_2$—N(R)—O-2', wherein R is H, $C_1$-$C_{12}$ alkyl, or a protecting group (e.g., U.S. Pat. No. 7,427,672), 4'-$CH_2$—C(H)($CH_3$)-2' (e.g., Chattopadhyaya el al., J. Org. Chem., 2009, 74, 118-134), and 4'-$CH_2$—C(=$CH_2$)-2' and analogs thereof (e.g., U.S. Pat. No. 8,278,426). The entire contents of each of the foregoing are hereby incorporated herein by reference. Additional representative U.S. patents and U.S. Patent Publications that teach the preparation of bicyclic nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, US 2013/0190383; and WO 2013/036868, the entire contents of each of which are hereby incorporated herein by reference. Any of the foregoing bicyclic nucleosides can be prepared having one or more stereochemical sugar configurations including for example α-L-ribofuranose and β-D-ribofuranose (see e.g., WO 99/14226). Specified bicyclic nucleosides herein are in the β-D configuration, unless otherwise specified.

In certain embodiments, a modified sugar is a sugar surrogate. In certain embodiments, a sugar surrogate has the oxygen atom replaced, e.g., with a sulfur, carbon or nitrogen atom. In certain such embodiments, the sugar surrogate may also comprise bridging and/or non-bridging substituents as described herein. In certain embodiments, sugar surrogates comprise rings having other than 5 atoms. In certain such embodiments, the sugar surrogate comprises a cyclobutyl moiety in place of the pentofuranosyl sugar. In certain embodiments, the sugar surrogate comprises a six membered ring in place of the pentofuranosyl sugar. In certain embodiments, the sugar surrogate comprises a tetrahydropyran ("THP") in place of the pentofuranosyl sugar. In certain embodiments, the sugar surrogate comprises a morpholino in place of the pentofuranosyl sugar. Representative US patents that teach the preparation of such modified sugar structures include, but are not limited to, U.S. Pat. Nos. 4,981,957; 5,118,800; 5,166,315; 5,185,444; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,700,920; 7,875,733; 7,939,677, 8,088,904; 8,440,803; and 9,005,906, the entire contents of each of the foregoing are hereby incorporated herein by reference.

In some embodiments, sugar surrogates comprise acyclic moieties. In certain embodiments, the sugar surrogate is an unlocked nucleic acid ("UNA"). A UNA is unlocked acyclic nucleic acid, wherein any of the bonds of the sugar has been removed, forming an unlocked "sugar" residue. In one example, UNA also encompasses a monomer where the bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed.

Representative U.S. publications that teach the preparation of UNA include, but are not limited to, U.S. Pat. No. 8,314,227; and U.S. Patent Publication Nos. 2013/0096289; 2013/0011922; and 2011/0313020, the entire contents of each of which are hereby incorporated herein by reference. In certain embodiments, sugar surrogates comprise peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., US2013/130378, the entire contents of which is hereby incorporated herein by reference. Many other bicyclic and tricyclic sugar and sugar surrogate ring systems are known in the art that can be used in modified nucleosides.

In certain aspects, the disclosure relates to compounds comprising at least one oligonucleotide wherein the nucleosides of such oligonucleotide comprise one or more types of modified sugars and/or unmodified sugars arranged along the oligonucleotide or region thereof in a defined pattern or "sugar motif". In certain instances, such sugar motifs include, but are not limited to, any of the patterns of sugar modifications described herein.

In certain embodiments, an oligonucleotide comprises a gapmer sugar motif. A gapmer oligonucleotide comprises or consists of a region having two external "wing" regions and a central or internal "gap" region. The gap and wing regions form a contiguous sequence of nucleosides, wherein the majority of nucleoside sugars of each of the wings differ from the majority of nucleoside sugars of the gap. In certain embodiments, the wing regions comprise a majority of modified sugars and the gap comprises a majority of unmodified sugars. In certain embodiments, the nucleosides of the gap are deoxynucleosides. Compounds with a gapmer sugar motif are described in, for example U.S. Pat. No. 8,790,919, the entire contents of which is hereby incorporated herein by reference.

In certain embodiments, one or both oligonucleotides of a double-stranded compound comprise a triplet sugar motif. An oligonucleotide with a triplet sugar motif comprises three identical sugar modifications on three consecutive nucleosides. In certain embodiments, the triplet is at or near the cleavage site of the oligonucleotide. In certain embodiments, an oligonucleotide of a double-stranded compound may contain more than one triplet sugar motif. In certain embodiments, the identical sugar modification of the triplet sugar motif is a 2'-F modification. Compounds with a triplet sugar motif are disclosed, for example, in U.S. Pat. No. 10,668,170, the entire contents of which is incorporated herein by reference.

In certain embodiments, one or both oligonucleotides of a double-stranded compound comprise a quadruplet sugar motif. An oligonucleotide with a quadruplet sugar motif comprises four identical sugar modifications on four consecutive nucleosides. In certain embodiments, the quadruplet is at or near the cleavage site. In certain embodiments, an oligonucleotide of a double-stranded compound may contain more than one quadruplet sugar motif. In certain embodiments, the identical sugar modification of the quadruplet sugar motif is a 2'-F modification. For a double-stranded compound having a duplex region of 19-23 nucleotides in length, the cleavage site of the antisense oligonucleotide is typically around the 10, 11, and 12 positions from the 5'-end. In certain embodiments, the quadruplet sugar motif is at the 8, 9, 10, 11 positions; the 9, 10, 11, 12 positions; the 10, 11, 12, 13 positions; the 11, 12, 13, 14 positions; or the 12, 13, 14, 15 positions of the sense oligonucleotide, counting from the first nucleoside of the 5'-end of the sense oligonucleotide, or, the count starting from the first paired nucleotide within the duplex region from the 5'-end of the sense oligonucleotide. In certain embodiments, the quadruplet sugar motif is at the 8, 9, 10, 11 positions; the 9, 10, 11, 12 positions; the 10, 11, 12, 13 positions; the 11, 12, 13, 14 positions; or the 12, 13, 14, 15 positions of the antisense oligonucleotide, counting from the first nucleoside of the 5'-end of the antisense oligonucleotide, or, the count starting from the first paired nucleotide within the duplex region from the 5'-end of the antisense oligonucleotide. The cleavage site may change according to the length of the duplex region of the double-stranded compound and may change the position of the quadruplet accordingly.

In certain embodiments, an oligonucleotide comprises an alternating sugar motif. In certain embodiments, one or both oligonucleotides of a double-stranded compound comprise an alternating sugar motif. An oligonucleotide with an alternating sugar motif comprises at least two different sugar modifications wherein one or more consecutive nucleosides comprising a first sugar modification alternates with one or more consecutive nucleosides comprising a second sugar modification and one or more consecutive nucleosides comprising a third sugar modification, etc. For example, if A, B and C each represent one type of modification to the nucleoside, the alternating motif can be "ABABABABABAB . . . ," "AABBAABBAABB . . . ," "AABAABAABAAB . . . ," "AAABAAABAAAB . . . ," "AAABBBAAABBB . . . ," or "ABCABCABCABC . . . " etc. In certain embodiments, the alternating sugar motif is repeated for at least 2, 3, 4, 5, 6, 7, 8, 9, 10, 11, 12, 13, 14, 15, 16, 17, 18, 19, 20, 21, 22, or 23 contiguous nucleobases along an oligonucleotide. In certain embodiments, the alternating sugar motif is comprised of two different sugar modifications. In certain embodiments, the alternating sugar motif comprises 2'-OMe and 2'-F sugar modifications.

In certain embodiments, each nucleoside of an oligonucleotide is independently modified with one or more sugar modifications provided herein. In certain embodiments, each oligonucleotide of a double-stranded compound independently has one or more sugar motifs provided herein. In certain embodiments, an oligonucleotide containing a sugar motif, is fully modified in that each nucleoside other than the nucleosides comprising the sugar motif comprises a sugar modification.

Nucleobase Modifications and Motifs

In certain embodiments, compounds described herein comprise modified oligonucleotides. In certain embodiments, modified oligonucleotides comprise one or more nucleosides comprising a modified nucleobase. In certain embodiments, modified oligonucleotides comprise one or more nucleosides that do not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (C≡C—CH₃) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly, 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size expanded bases, and fluorinated bases. Further modified nucleobases include tricyclic pyrimidines, such as 1,3-diazaphenoxazine-2-one, 1,3-diazaphenothiazine-2-one, and 9-(2-aminoethoxy)-1,3-diazaphenoxazine-2-one (G-clamp). Modified nucleobases may also include those in which the purine or pyrimidine base is replaced with other heterocycles, for example, 7-deaza-adenine, 7-deazaguanosine, 2-aminopyridine and 2-pyridone.

Further nucleobases include those disclosed in U.S. Pat. No. 3,687,808; Modified Nucleosides in Biochemistry, Biotechnology and Medicine, Herdewijn, P. ed. Wiley-VCH, 2008; The Concise Encyclopedia Of Polymer Science And Engineering, pages 858-859; Kroschwitz, J. L., Ed., John Wiley & Sons, 1990, 858-859; Englisch et al., Angewandte Chemie, International Edition, 1991, 30, 613; Sanghvi, Y. S., Chapter 15, dsRNA Research and Applications, pages 289-302; Antisense Research and Applications, Crooke, S. T. and Lebleu, B., Eds., CRC Press, 1993, 273-288; Antisense Drug Technology, Crooke S. T., Ed., CRC Press, 2008, 163-166 and 442-443 (Chapters 6 and 15), each of which are hereby incorporated herein by reference.

Publications that teach the preparation of certain of the above noted modified nucleobases, as well as other modified nucleobases include without limitation, US Applications 2003/0158403 and 2003/0175906; U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,681,941; 5,811,534; 5,750,692; 5,948,903; 5,587,470; 5,457,191; 5,763,588; 5,830,653; 5,808,027; 6,005,096; 6,015,886; 6,147,200; 6,166,197; 6,166,199; 6,222,025; 6,235,887; 6,380,368; 6,528,640; 6,639,062; 6,617,438; 7,045,610; 7,427,672; and 7,495,088, the entire contents of each of which are hereby incorporated herein by reference.

In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments, the block is within 3 nucleosides of the 3'-end of the oligonucleotide. In certain embodiments, the block is at the 5'-end of the oligonucleotide. In certain embodiments, the block is within 3 nucleosides of the 5'-end of the oligonucleotide.

Internucleoside Linkage Modifications and Motifs

A 3' to 5' phosphodiester linkage is the naturally occurring internucleoside linkage of RNA and DNA. In certain embodiments, compounds described herein have one or more modified, i.e., non-naturally occurring, internucleoside linkages. Certain non-naturally occurring internucleoside linkages may impart desirable properties such as, for example, enhanced cellular uptake, enhanced affinity for target nucleic acids, and increased stability in the presence of nucleases. Representative phosphorus-containing modified internucleoside linkages include, but are not limited to, phosphotriesters, alkylphosphonates (e.g. methylphosphonates), phosphoramidates, and phosphorothioates ("P=S"), and phosphorodithioates ("HS-P=S"). Representative non-phosphorus containing internucleoside linking groups include, but are not limited to, methylenemethylimino (—CH₂—N(CH₃)—O—CH₂), thiodiester, thionocarbamate (—O—C(=O)(NH)—S—); siloxane (—O—SiH₂—O—); and N,N'-dimethylhydrazine (—CH₂—N((CH₃)—N((CH₃)—). Methods of preparation of phosphorous-containing and non-phosphorous-containing internucleoside linkages are well known to those skilled in the art. Neutral internucleoside linkages include, without limitation, phosphotriesters, methylphosphonates, MMI (3'-CH₂—N(CH₃)—O-5'), amide-3 (3'-CH₂—C(=O)—N(H)-5'), amide-4 (3'-CH₂—N(H)—C(=O)-5'), formacetal (3'-O—CH₂—O-5'), methoxypropyl, and thioformacetal (3'-S—CH₂—O-5'). Further neutral internucleoside linkages include nonionic linkages comprising siloxane (dialkylsiloxane), carboxylate ester, carboxamide, sulfide, sulfonate ester and amides (See, for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH₂ component parts.

In certain embodiments, compounds provided herein comprise at least one modified internucleoside linkage. A modified internucleoside linkage may be placed at any position of an oligonucleotide. For double-stranded compounds, a modified internucleoside linkage may be placed within the sense oligonucleotide, antisense oligonucleotide, or both oligonucleotides of the double-stranded compound.

In certain embodiments, the internucleoside linkage modification may occur on every nucleoside of an oligonucleotide. In certain embodiments, internucleoside linkage modifications may occur in an alternating pattern along an oligonucleotide. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the pattern of the internucleoside linkage modification on each oligonucleotide of a double-stranded compound is the same. In certain embodiments, the pattern of the internucleoside linkage modification on each oligonucleotide of a double-stranded compound is different. In certain embodiments, a double-stranded compound comprises 6-8 modified internucleoside linkages. In certain embodiments, the 6-8 modified internucleoside linkages are phosphorothioate internucleoside linkages or alkylphosphonate internucleoside linkages. In certain embodiments, the sense oligonucleotide comprises at least two modified internucleoside linkages at either or both the 5'-end and the 3'-end. In certain such embodiments, the modified internucleoside linkages are phosphorothioate internucleoside linkages or alkylphosphonate internucleoside linkages. In certain embodiments, the antisense oligonucleotide comprises at least two modified internucleoside linkages at either or both the 5'-end and the 3'-end. In certain such embodiments, the modified internucleoside linkages are phosphorothioate internucleoside linkages or alkylphosphonate internucleoside linkages.

In certain embodiments, a double-stranded compound comprises an overhang region. In certain embodiments, a double-stranded compound comprises a phosphorothioate or alkylphosphonate internucleoside linkage modification in the overhang region. In certain embodiments, a double-stranded compound comprises a phosphorothioate or alkylphosphonate internucleotide linkage linking the overhang nucleotide with a paired nucleotide that is next to the overhang nucleotide. For instance, there may be at least two phosphorothioate internucleoside linkages between the terminal three nucleosides, in which two of the three nucleosides are overhang nucleosides, and the third is a paired nucleoside next to the overhang nucleoside. These terminal three nucleosides may be at the 3'-end of the antisense oligonucleotide, the 3'-end of the sense oligonucleotide, the 5'-end of the antisense oligonucleotide, or the 5'end of the antisense oligonucleotide.

In certain embodiments, modified oligonucleotides comprise one or more internucleoside linkages having chiral centers. Representative chiral internucleoside linkages include, but are not limited to, alkylphosphonates and phosphorothioates. Modified oligonucleotides comprising internucleoside linkages having chiral centers can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. As is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such enriched populations of modified oligonucleotides can be generated using synthetic methods known in the art, e.g., methods described in Oka et al., JACS 125, 8307 (2003), Wan et al. Nuc. Acid. Res. 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration.

Conjugate Groups

In certain embodiments, the compounds described herein comprise or consist of one or more oligonucleotides and, optionally, one or more conjugate groups. Conjugate groups may be attached to either or both ends of an oligonucleotide and/or at any internal position. In certain embodiments, a conjugate group is attached at the 3' end of an oligonucleotide. In certain embodiments, a conjugate group is attached at the 5' end of an oligonucleotide. In certain embodiments, oligonucleotides are covalently attached to one or more conjugate groups.

In certain embodiments, conjugate groups are terminal groups attached to either or both ends of an oligonucleotide. In certain such embodiments, terminal groups are attached at the 3' end of an oligonucleotide. In certain such embodiments, terminal groups are attached at the 5' end of an oligonucleotide. In certain embodiments, terminal groups include, but are not limited to, capping groups, phosphate moieties, protecting groups, modified or unmodified nucleosides, and two or more nucleosides that are independently modified or unmodified, such as an overhang.

In certain embodiments, conjugate groups modify one or more properties of the attached oligonucleotide, including, but not limited to, pharmacodynamics, pharmacokinetics, stability, activity, half-life, binding, absorption, tissue distribution, cellular distribution, cellular uptake, charge and clearance. In certain embodiments, conjugate groups enhance the affinity of a compound for a selected target, e.g., molecule, cell or cell type, compartment, e.g., a cellular or organ compartment, tissue, organ or region of the body, as, e.g., compared to a compound absent such a conjugate group. In certain embodiments, conjugate groups impart a new property on the attached oligonucleotide, e.g., fluorophores or reporter groups that enable detection of the oligonucleotide.

In certain embodiments, conjugate groups include, but are not limited to, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, conjugate groups include an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial, or an antibiotic.

In certain embodiments, conjugate groups are targeting moieties. In certain embodiments, a targeting moiety includes, but is not limited to, a lectin, glycoprotein, lipid, protein, peptide, peptide mimetic, receptor ligand, antibody, thyrotropin, melanotropin, surfactant protein A, carbohydrate, carbohydrate derivative, modified carbohydrate, carbohydrate cluster, polysaccharide, modified polysaccharide, or polysaccharide derivative, mucin carbohydrate, multivalent lactose, multivalent galactose, N-acetyl-galactosamine (GalNAc), N-acetylglucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

In certain embodiments, conjugate groups may include, but are not limited to, the conjugate groups described in the following references such as cholesterol (e.g., Letsinger et al., Proc. Natl. Acid. Sci. USA, 1989, 86: 6553-6556), cholic acid (e.g., Manoharan et al., Biorg. Med. Chem. Let., 1994, 4:1053-1060), thioether, e.g., hexyl-S-tritylthiol (e.g., Manoharan et al., Ann. NY. Acad. Sci., 1992, 660:306-309; Manoharan et al., Biorg. Med. Chem. Let., 1993, 3:2765-2770), thiocholesterol (e.g., Oberhauser et al., Nucl. Acids Res., 1992, 20:533-538), aliphatic chains, e.g., do-decandiol or undecyl residues (e.g., Saison-Behmoaras et al., EMBO J, 1991, 10:1111-1118; Kabanov et al., FEBS Lett., 1990, 259:327-330; Svinarchuk et al., Biochimie, 1993, 75:49-54), phospholipids, e.g., di-hexadecyl-rac-glycerol or triethyl-ammonium 1,2-di-O-hexadecyl-rac-glycero-3-H-phosphonate (e.g, Manoharan et al., Tetrahedron Lett., 1995, 36:3651-3654; Shea et al., Nucl. Acids Res., 1990, 18:3777-3783), polyamines or a polyethylene glycol chains (e.g., Manoharan et al., Nucleosides & Nucleotides, 1995, 14:969-973), adamantane acetic acid (e.g., Manoharan et al., Tetrahedron Lett., 1995, 36:3651-3654), palmityl (e.g., Mishra et al., Biochim. Biophys. Acta, 1995, 1264:229-237), octadecylamine or hexylamino-carbonyloxychole sterol moiety (e.g., Crooke et al. J. Pharmacol. Exp. Ther., 1996, 277:923-937), tocopherol (e.g., Nishina et al., Molecular Therapy Nucleic Acids, 2015, 4, e220 and Nishina et al., Molecular Therapy, 2008, 16:734-740), GalNAc and other carbohydrates (e.g., Maier et al., Bioconjugate Chemistry, 2003, 14, 18-29; Rensen et al., J. Med. Chem. 2004, 47, 5798-5808; WO2009/073809 and U.S. Pat. Nos. 8,106,022; 8,450,467 and 8,828,957; and WO2014/179445; WO2014/179620 and U.S. Pat. Nos. 9,127,276; 9,181,549 and 10,844,379) each of which is incorporated herein by reference in its entirety.

Conjugate groups may be attached to oligonucleotides through conjugate linkers. In certain embodiments, a conjugate linker comprises a chain structure, such as a hydrocarbyl chain, or an oligomer of repeating units or combination of such repeating units. In certain embodiments, a conjugate linker comprises one or more groups selected from alkyl, amino, oxo, amide, disulfide, polyethylene glycol, ether, thioether, and hydroxylamino. In certain embodiments, a conjugate linker comprises at least one phosphorus group. In certain embodiments, a conjugate linker comprises at least one phosphate group. In certain embodiments, a conjugate linker includes at least one neutral linking group. In certain embodiments, conjugate linkers include, but are not limited to, pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include, but are not limited to, substituted or unsubstituted $C_1$-$C_{10}$ alkyl, substituted or unsubstituted $C_2$-$C_{10}$ alkenyl, or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl, and alkynyl. In certain embodiments, conjugate linkers comprise 1-10 linker-nucleosides. In certain embodiments, such linker-nucleosides may be modified or unmodified nucleosides. It is typically desirable for linker-nucleosides to be cleaved from the compound after it reaches a target tissue. Accordingly, linker-nucleosides herein can be linked to one another and to the remainder of the compound through cleavable bonds. Herein, linker-nucleosides are not considered to be part of the oligonucleotide. Accordingly, in embodiments in which a compound comprises an oligonucleotide consisting of a specified number or range of linked nucleosides and/or a specified percent complementarity to a reference nucleic acid and the compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid.

In certain embodiments, conjugate groups and conjugate linkers as well as other modifications include, without limitation, those described in the following references: U.S. Pat. Nos. 5,994,517; 6,300,319; 6,660,720; 6,906,182; 7,262,177; 7,491,805; 8,106,022; 7,723,509; 9,127,276; US 2006/0148740; US 2011/0123520; WO2013/033230; WO2012/037254, Biessen et al., J. Med. Chem. 1995, 38, 1846-1852; Lee et al., Bioorganic & Medicinal Chemistry 2011, 19, 2494-2500; Rensen et al., J. Biol. Chem. 2001, 276, 37577-37584; Rensen et al., J. Med. Chem. 2004, 47, 5798-5808; Sliedregt et al., J. Med. Chem. 1999, 42, 609-618; Valentijn et al., Tetrahedron, 1997, 53, 759-770; Lee, Carhohydr Res, 1978, 67, 509-514; Connolly et al., J Biol Chem, 1982, 257, 939-945; *Pavia* et al., Int J Pep Protein Res, 1983, 22, 539-548; Lee et al., Biochem, 1984, 23, 4255-4261; Lee et al., Glycoconjugate J, 1987, 4, 317-328; Toyokuni et al., Tetrahedron Lett, 1990, 31, 2673-2676; Biessen et al., J Med Chem, 1995, 38, 1538-1546; Valentijn et al., Tetrahedron, 1997, 53, 759-770; Kim et al., Tetrahedron Lett, 1997, 38, 3487-3490; Lee et al., Bioconjug Chem, 1997, 8, 762-765; Kato et al., Glycohiol, 2001, 11, 821-829; Rensen et al., J Biol Chem, 2001, 276, 37577-37584; Lee et al., Methods Enzymol, 2003, 362, 38-43; Westerlind et al., Glycoconj J, 2004, 21, 227-241; Lee et al., Bioorg Med Chem Lett, 2006, 16(19), 5132-5135; Maierhofer et al., Bioorg Med Chem, 2007, 15, 7661-7676; Khorev et al., Bioorg Med Chem, 2008, 16, 5216-5231; Lee et al., Bioorg Med Chem, 2011, 19, 2494-2500; Kornilova et al., Analyt Biochem, 2012, 425, 43-46; Pujol et al., Angew Chemie Int Ed Engl, 2012, 51, 7445-7448; Biessen et al., J Med Chem, 1995, 38, 1846-1852; Sliedregt et al., J Med Chem, 1999, 42, 609-618; Rensen et al., J Med Chem, 2004, 47, 5798-5808; Rensen et al., Arterioscler Thromh Vase Biol, 2006, 26, 169-175; van Rossenberg et al., Gene Ther, 2004, 11, 457-464; Sato et al., J Am Chem Soc, 2004, 126, 14013-14022; Lee et al., J Org Chem, 2012, 77, 7564-7571; Biessen et al., FASEB J, 2000, 14, 1784-1792; Rajur et al., Bioconjug Chem, 1997, 8, 935-940; Duff et al., Methods Enzymol, 2000, 313, 297-321; Maier et al., Bioconjug Chem, 2003, 14, 18-29; Jayaprakash et al., Org Lett, 2010, 12, 5410-5413; Manoharan, Antisense Nucleic Acid Drug Dev, 2002, 12, 103-128; Merwin et al., Bioconjug Chem, 1994, 5, 612-620; Tomiya et al., Bioorg Med Chem, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/

166121; WO2013/165816; U.S. Pat. Nos. 4,751,219; 7,582,744; 8,552,163; 8,137,695; 6,908,903; 6,383,812; 7,262,177; 6,525,031; 5,994,517; 6,660,720; 6,300,319; 7,723,509; 8,106,022; 7,491,805; 7,491,805; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2003/0119724; US2011/0207799; US2012/0035115; US2012/0230938; US2005/0164235; US2006/0183886; US2012/0136042; US2012/0095075; US2013/0109817; US2006/0148740; US2008/0206869; US2012/0165393; US2012/0101148; US2013/0121954; US2011/0123520; US2003/0077829; US2008/0108801; and US2009/0203132; each of which is incorporated herein by reference in its entirety.

Certain Targeting Moieties

In certain embodiments, a compound provided herein comprises a conjugate group. In certain embodiments, an oligonucleotide provided herein comprises a conjugate group. In certain embodiments, the conjugate group is a targeting moiety. In certain embodiments, the targeting moiety comprises one or more GalNAc. In certain embodiments, the one or more GalNAc are attached to one or more positions on a furanose ring. In certain embodiments, the one or more GalNAc are attached to the 2' or 3' position on a furanose ring. In certain embodiments, the furanose ring is a subunit of the oligonucleotide. In certain embodiments, the furanose ring is the 5' nucleoside sugar of an oligonucleotide. In certain embodiments, the furanose ring is the 5' nucleoside sugar of a sense oligonucleotide. In certain embodiments, a compound or oligonucleotide comprises one or more subunits with the following formula or a salt, solvate, or hydrate thereof:

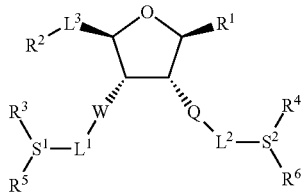

Formula IX wherein:
R$^1$ is H, adenine, guanine, thymine, cytosine, uracil, carbocyclyl, heterocyclyl, aryl, heteroaryl, or a nucleobase isostere;
R$^2$ is the oligonucleotide sequence;
L$^1$ is alkyl, or alkyl-C(=O)—NH-alkyl;
L$^2$ is alkyl, or alkyl-C(=O)—NH-alkyl;
L$^3$ is a bond, a phosphodiester bond, a phosphorothioate bond, a triazole, a tetrazole, an amide, a reverse-amide, a carbamate, a carbonate, urea, O, S, S(=O), S(=O)$_2$, NH, substituted N group, alkyl, alkenyl, dienyl, alkynyl, heteroalkyl, phosphate;
R$^3$ is H, —C(=O)—NH—(CH$_2$CH$_2$O)$_j$-GalNAc, or —C(=O)—NH-alkyl-NH—C(=O)-alkyl-O-GalNAc;
R$^4$ is H, —C(=O)—NH—(CH$_2$CH$_2$O)$_k$-GalNAc, or —C(=O)—NH-alkyl-NH—C(=O)-alkyl-O-GalNAc;
R$^5$ is —C(=O)—NH—(CH$_2$CH$_2$O)$_m$-GalNAc, or —C(=O)—NH-alkyl-NH—C(=O)-alkyl-O-GalNAc;
R$^6$ is —C(=O)—NH—(CH$_2$CH$_2$O)$_n$-GalNAc, or —C(=O)—NH-alkyl-NH—C(=O)-alkyl-O-GalNAc;
W and Q are each independently O, NH, CH$_2$, or CH$_2$O;
S$^1$ and S$^2$ are each independently C(R$^7$) or N, wherein each instance of R$^7$ is independently H, alkyl, heteroalkyl, or halogen;
j is an integer 1-10, inclusive;
k is an integer 1-10, inclusive;
m is an integer 1-10, inclusive; and
n is an integer 1-10, inclusive.

In certain embodiments, R$^3$, R$^4$, R$^5$, and R$^6$ are the same. In certain embodiments, R$^3$, R$^5$, and R$^6$ are the same. In certain embodiments, R$^3$ or R$^4$ is H.

In certain embodiments, L$^1$ and L$^2$ are the same.

In certain embodiments, L$^1$ and L$^2$ are each independently alkyl; R$^3$ is H, —C(=O)—NH—(CH$_2$CH$_2$O)$_j$-GalNAc, or —C(=O)—NH-alkyl-NH—C(=O)-alkyl-O-GalNAc; R$^4$ is H, —C(=O)—NH—(CH$_2$CH$_2$O)$_k$-GalNAc, or —C(=O)—NH-alkyl-NH—C(=O)-alkyl-O-GalNAc; R$^5$ is —C(=O)—NH—(CH$_2$CH$_2$O)$_m$-GalNAc, or —C(=O)—NH-alkyl-NH—C(=O)-alkyl-O-GalNAc; and R$^6$ is —C(=O)—NH—(CH$_2$CH$_2$O)$_n$-GalNAc, or —C(=O)—NH-alkyl-NH—C(=O)-alkyl-O-GalNAc.

In certain embodiments, L$^1$ and L$^2$ are each independently alkyl-C(=O)—NH-alkyl; R$^3$ is H, —C(=O)—NH—(CH$_2$CH$_2$O)$_j$-GalNAc, or —C(=O)—NH-alkyl-NH—C(=O)-alkyl-O-GalNAc; R$^4$ is H, —C(=O)—NH—(CH$_2$CH$_2$O)$_k$-GalNAc, or —C(=O)—NH-alkyl-NH—C(=O)-alkyl-O-GalNAc; R$^5$ is —C(=O)—NH—(CH$_2$CH$_2$O)$_m$-GalNAc, or —C(=O)—NH-alkyl-NH—C(=O)-alkyl-O-GalNAc; and R$^6$ is —C(=O)—NH—(CH$_2$CH$_2$O)$_n$-GalNAc, or —C(=O)—NH-alkyl-NH—C(=O)-alkyl-O-GalNAc.

In certain embodiments, R$^4$ is H.

In certain embodiments, L$^1$ and L$^2$ are each independently alkyl; R$^3$ is —C(=O)—NH—(CH$_2$CH$_2$O)$_j$-GalNAc, or —C(=O)—NH-alkyl-NH—C(=O)-alkyl-O-GalNAc; R$^4$ is H; R$^5$ is —C(=O)—NH—(CH$_2$CH$_2$O)$_m$-GalNAc, or —C(=O)—NH-alkyl-NH—C(=O)-alkyl-O-GalNAc; and R$^6$ is —C(=O)—NH—(CH$_2$CH$_2$O)$_n$-GalNAc, or —C(=O)—NH-alkyl-NH—C(=O)-alkyl-O-GalNAc.

In certain embodiments, L$^1$ and L$^2$ are each independently alkyl-C(=O)—NH-alkyl; R$^3$ is —C(=O)—NH—(CH$_2$CH$_2$O)$_j$-GalNAc, or —C(=O)—NH-alkyl-NH—C(=O)-alkyl-O-GalNAc; R$^4$ is H; R$^5$ is —C(=O)—NH—(CH$_2$CH$_2$O)$_m$-GalNAc, or —C(=O)—NH-alkyl-NH—C(=O)-alkyl-O-GalNAc; and R$^6$ is —C(=O)—NH—(CH$_2$CH$_2$O)$_n$-GalNAc, or —C(=O)—NH-alkyl-NH—C(=O)-alkyl-O-GalNAc.

In certain embodiments, R$^3$ is —C(=O)—NH—(CH$_2$CH$_2$O)$_j$-GalNAc; R$^4$ is H; R$^5$ is —C(=O)—NH—(CH$_2$CH$_2$O)$_m$-GalNAc; and R$^6$ is —C(=O)—NH—(CH$_2$CH$_2$O)$_n$-GalNAc.

In certain embodiments, R$^3$ is —C(=O)—NH-alkyl-NH—C(=O)-alkyl-O-GalNAc; R$^4$ is H; R$^5$ is —C(=O)—NH-alkyl-NH—C(=O)-alkyl-O-GalNAc; and R$^6$ is —C(=O)—NH-alkyl-NH—C(=O)-alkyl-O-GalNAc.

In certain embodiments, a compound or oligonucleotide comprises one or more subunits with the following formula or a salt, solvate, or hydrate thereof:

Formula X

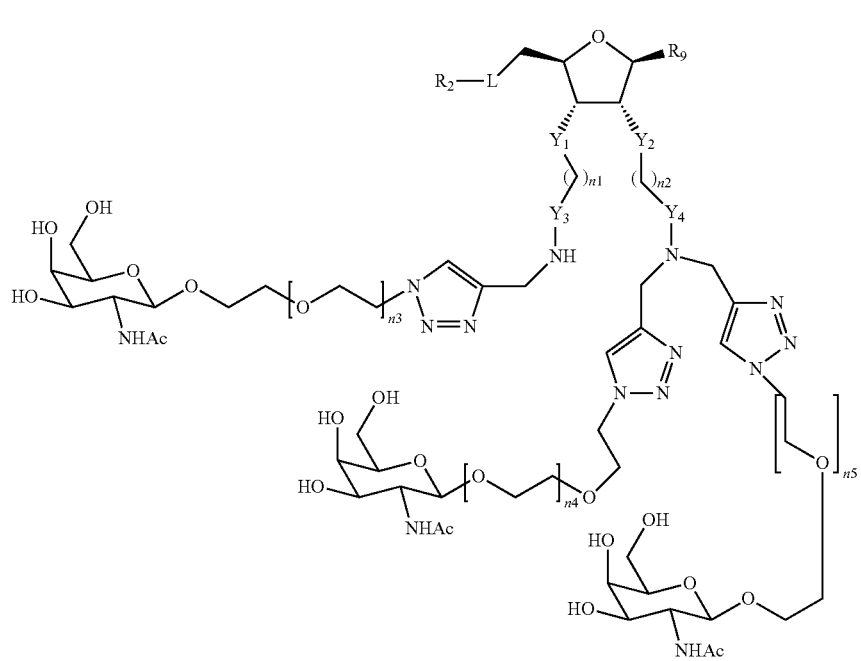

wherein:
R⁹ is H, adenine, guanine, thymine, cytosine, or uracil, or adenine, guanine, thymine, cytosine, or uracil, each comprising a Protecting Group (PG), a modified nucleobase, optionally substituted alkyl, optionally substituted aryl, optionally substituted heteroaryl, optionally substituted carbocyclyl, optionally substituted heterocyclyl, or a nucleobase isostere;

L is a bond, a phosphodiester bond, a phosphorothioate bond, a triazole, a tetrazole, an amide, a reverse-amide, a carbamate, a carbonate, urea, alkyl, or heteroalkyl;

R² is the oligonucleotide sequence;

Y₁ is O, CH₂, CH₂O, or optionally substituted NH;

Y₂ is O, CH₂, CH₂O, or optionally substituted NH;

Y₃ is CO, SO₂, P(O)O, CH₂—O—C(O), CH₂—NH—C(O), CH₂—NH—SO₂, or CH₂;

Y₄ is CO, SO₂, P(O)O, CH₂—O—C(O), CH₂—NH—C(O), CH₂—NH—SO₂, or CH₂;

n₂ is 0, 1, 2, 3, 4, 5, or 6; and each n₁, n₃, n₄ and n₅ is independently 0, 1, 2, 3, 4, 5, 6, 7, 8, 9, or 10.

In certain embodiments, a compound or oligonucleotide comprises one or more subunits with the following formula or a salt, solvate, or hydrate thereof:

Formula XI

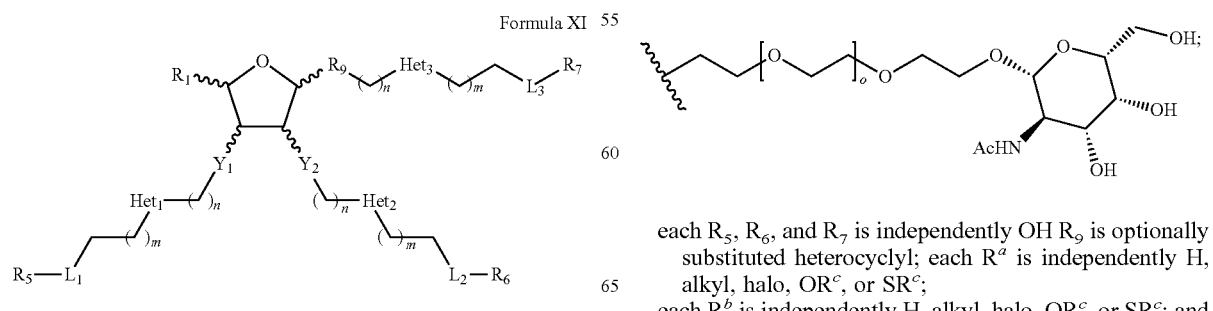

wherein:
each n is independently 1, 2, 3, 4, or 5;
each m is independently 0, 1, 2, 3, 4, 5, or 6;
each o is independently 0, 1, 2, 3, 4, 5, or 6;
each of L₁, L₂, and L₃ is independently absent, C(=O), or C(=O)NH;
each Y₁ is independently O, CH(Rᵃ), S, S(=O), S(=O)₂, NH, substituted N group, NHC(=O), C(=O)NH, P(=O)₂—O—, P(=O)(=S)—O, P(=S)₂—O, —O—P(=O)₂—O—, —O—P(=O)(=S)—O—, —O—P(=S)₂—O—, —O—P(=O)₂—, —O—P(=O)(=S)—, —O—P(=S)₂—;
each Y₂ is independently O, CH(Rᵇ), S, S(=O), S(=O)₂, NH, substituted N group, NHC(=O), C(=O)NH, P(=O)₂—O—, P(=O)(=S)-0, P(=S)₂—O, —O—P(=O)₂—O—, —O—P(=O)(=S)—O—, —O—P(=S)₂—O—, —O—P(=O)₂—, —O—P(=O)(=S)—, —O—P(=S)₂—;
each of Het₁, Het₂, and Het₃ is independently optionally substituted heteroaryl or optionally substituted heterocyclyl;
R¹ is the oligonucleotide sequence linked by a bond, a phosphodiester bond, a phosphorothioate bond, a triazole, a tetrazole, an amide, a reverse-amide, a carbamate, a carbonate, urea, alkyl, or heteroalkyl;

each R₅, R₆, and R₇ is independently OH R₉ is optionally substituted heterocyclyl; each Rᵃ is independently H, alkyl, halo, ORᶜ, or SRᶜ;
each Rᵇ is independently H, alkyl, halo, ORᶜ, or SRᶜ; and
each R' is independently H or alkyl.

In certain embodiments, the subunit is selected from Formulae I through VIII or a salt, solvate, or hydrate thereof, wherein R is the modified oligonucleotide other than the 5' nucleoside. In certain embodiments, the 5' nucleoside of the modified oligonucleotide is Formula I and R' is O. In certain embodiments, the 5' nucleoside of the modified oligonucleotide is Formula I and R' is S. In certain embodiments, the 5' nucleoside of the modified oligonucleotide is Formula II and R' is O. In certain embodiments, the 5' nucleoside of the modified oligonucleotide is Formula II and R' is S. In certain embodiments, the 5' nucleoside of the modified oligonucleotide is Formula III and R' is O. In certain embodiments, the 5' nucleoside of the modified oligonucleotide is Formula III and R' is S. In certain embodiments, the 5' nucleoside of the modified oligonucleotide is Formula IV and R' is O. In certain embodiments, the 5' nucleoside of the modified oligonucleotide is Formula IV and R' is S. In certain embodiments, the 5' nucleoside of the modified oligonucleotide is Formula V and R' is O. In certain embodiments, the 5' nucleoside of the modified oligonucleotide is Formula V and R' is S. In certain embodiments, the 5' nucleoside of the modified oligonucleotide is Formula VI and R' is O. In certain embodiments, the 5' nucleoside of the modified oligonucleotide is Formula VI and R' is S. In certain embodiments, the 5' nucleoside of the modified oligonucleotide is Formula VII and R' is O. In certain embodiments, the 5' nucleoside of the modified oligonucleotide is Formula VII and R' is S. In certain embodiments, the 5' nucleoside of the modified oligonucleotide is Formula VIII and R' is O. In certain embodiments, the 5' nucleoside of the modified oligonucleotide is Formula VIII and R' is S.

Target Nucleic Acids and Target Regions

In certain embodiments, compounds described herein comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain embodiments, the target nucleic acid is non-coding. In certain such embodiments, the target nucleic acid is selected from an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an exon. In certain such embodiments, the target region is entirely within an intron. In certain embodiments, the target region spans an intron/exon junction. In certain embodiments, the target region is at least 50% within an intron.

In certain embodiments, compounds disclosed herein hybridize with a PKK nucleic acid. The most common mechanism of hybridization involves hydrogen bonding between complementary nucleobases of the nucleic acid molecules. Hybridization can occur under varying conditions. Hybridization conditions are sequence-dependent and are determined by the nature and composition of the nucleic acid molecules to be hybridized. Methods of determining whether a sequence hybridizes specifically to a target nucleic acid are well known in the art. In certain embodiments, the compounds provided herein specifically hybridize with a PKK nucleic acid.

Nucleotide sequences that encode PKK include, without limitation, the following: GENBANK Accession Nos. NM_000892.5 (incorporated herein as SEQ ID NO: 1), NG_012095.2 truncated from 23529 . . . 54493 (incorporated herein as SEQ ID NO: 2), XM_017008181.1 (incorporated herein as SEQ ID NO: 3), NC_000004.12 truncated from 186215714 to 186258477 (incorporated herein as SEQ ID NO: 4), NM_001318394.2 (incorporated herein as SEQ ID NO: 5) and NM_001318396.2 (incorporated herein as SEQ ID NO: 6).

Complementarity

Oligonucleotides provided herein may have a defined percent complementarity to a particular nucleic acid, target region, oligonucleotide, or portion thereof. Non-complementary nucleobases may be tolerated provided that the oligonucleotide remains able to specifically hybridize to the nucleic acid, oligonucleotide, or portion thereof. In certain embodiments, the oligonucleotides provided herein, or a specified portion thereof are at least, or are up to 70%, 80%, 85%, 86%, 87%, 88%, 89%, 90%, 91%, 92%, 93%, 94%, 95%, 96%, 97%, 98%, 99%, or 100% complementary to a target nucleic acid, a target region, an oligonucleotide or specified portion thereof. In certain embodiments, the oligonucleotides provided herein, or a specified portion thereof, are 70% to 75%, 75% to 80%, 80% to 85%, 85% to 90%, 90% to 95%, 95% to 100%, or any number in between these ranges, complementary to a target nucleic acid, a target region, an oligonucleotide or specified portion thereof. Percent complementarity of an oligonucleotide with a target nucleic acid, a target region, an oligonucleotide or specified portion thereof can be determined using routine methods. For example, an oligonucleotide in which 18 of 20 nucleobases of the oligonucleotide are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, an oligonucleotide which is 18 nucleobases in length having four non-complementary nucleobases which are flanked by two regions of complete complementarity with the target nucleic acid would have 77.8% overall complementarity with the target nucleic acid. Percent complementarity of an oligonucleotide with a region of a target nucleic acid, a target region, an oligonucleotide or specified portion thereof can be determined routinely using BLAST programs (basic local alignment search tools) known in the art. In certain embodiments, oligonucleotides described herein, or specified portions thereof, are fully complementary (i.e. 100% complementary) to a target nucleic acid, a target region, an oligonucleotide or specified portion thereof. For example, an oligonucleotide may be fully complementary to a target nucleic acid, a target region, an oligonucleotide, or specified portion thereof. As used herein, "fully complementary" means each nucleobase of an oligonucleotide is complementary to the corresponding nucleobase of a target nucleic acid, a target region, an oligonucleotide, or a specified portion thereof. For example, a 20 nucleobase oligonucleotide is fully complementary to a target sequence that is 400 nucleobases long, so long as there is a corresponding 20 nucleobase portion of the target nucleic acid that is fully complementary to the compound. "Fully complementary" can also be used in reference to a specified portion of the first and/or the second nucleic acid. For example, a 20 nucleobase portion of a 30 nucleobase oligonucleotide can be "fully complementary" to a 20 nucleobase region of a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, oligonucleotides described herein comprise one or more mismatched nucleobases relative to a target nucleic acid, a target region, an oligonucleotide or a specified portion thereof. In certain embodiments, oligonucleotides described herein that are, or are up to 12, 13, 14, 15, 16, 17, 18, 19, 20, 21, 22, or 23 nucleobases in length comprise no more than 4, no more than 3, no more than 2, or no more than 1 non-complementary nucleobase(s) relative to a target nucleic acid, or specified portion thereof. In certain embodiments, oligonucleotides described herein that are, or are up to 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, a target region, an oligonucleotide, or specified portion thereof. In certain embodiments, the mismatch is at position 1, 2, 3, 4, 5, 6, 7, 8, 9, 10, 11, 12, 13 or 14 from the 5'-end of the oligonucleotide. In certain embodiments, the mismatch is at position 1, 2, 3, 4, 5, 6, 7, 8, 9, 10, 11, or 12, 13 or 14 from the 3'-end of the oligonucleotide. In certain embodiments, the mismatch forms a wobble base pair with a corresponding nucleobase on the target nucleic acid. For example, in certain embodiments, the mismatch forms a wobble base pair selected from hypoxanthine (nucleobase of inosine) and uracil (I:U base pair); guanine and uracil (G:U base pair); hypoxanthine and adenine (I:A base pair); and hypoxanthine and cytosine (I:C base pair). Accordingly, in certain embodiments, a mismatched nucleobase on an oligonucleotide comprises hypoxanthine, guanine, or uracil.

In certain embodiments, oligonucleotides described herein may be complementary to a portion of a nucleic acid. As used herein, "portion" refers to a defined number of contiguous nucleobases within a region of a nucleic acid. A "portion" can also refer to a defined number of contiguous nucleobases of an oligonucleotide. In certain embodiments, the oligonucleotides are complementary to at least an 8 nucleobase portion of a nucleic acid. In certain embodiments, the oligonucleotides are complementary to at least a 9 nucleobase portion of a nucleic acid. In certain embodiments, the oligonucleotides are complementary to at least a 10 nucleobase portion of a nucleic acid. In certain embodiments, the oligonucleotides are complementary to at least an 11 nucleobase portion of a nucleic acid. In certain embodiments, the oligonucleotides are complementary to at least a 12 nucleobase portion of a nucleic acid. In certain embodiments, the oligonucleotides are complementary to at least a 13 nucleobase portion of a nucleic acid. In certain embodiments, the oligonucleotides are complementary to at least a 14 nucleobase portion of a nucleic acid. In certain embodiments, the oligonucleotides are complementary to at least a 15 nucleobase portion of a nucleic acid. In certain embodiments, the oligonucleotides are complementary to at least a 16 nucleobase portion of a nucleic acid. Also contemplated are oligonucleotides that are complementary to at least a 9, 10, 17, 18, 19, 20, 21, 22, 23 or more nucleobase portion of a nucleic acid, or a range defined by any two of these values. In certain embodiments, the oligonucleotide is an antisense oligonucleotide. In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid. In certain embodiments, the oligonucleotide is a sense oligonucleotide. In certain embodiments, a portion of the sense oligonucleotide is compared to an equal length portion of an antisense oligonucleotide. In certain embodiments, an 8, 9, 10, 11, 12, 13, 14, 15, 16, 17, 18, 19, 20, 21, 22, 23, 24, or 25 nucleobase portion of a sense oligonucleotide is compared to an equal length portion of an antisense oligonucleotide.

Identity

The oligonucleotides provided herein may also have a defined percent identity to a particular nucleic acid, target region, oligonucleotide, or specified portion thereof. As used herein, an oligonucleotide is identical to a sequence disclosed herein if it has the same nucleobase pairing ability. For example, a DNA which contains thymidine in place of uracil in a disclosed RNA sequence would be considered identical to the RNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of an oligonucleotide is calculated according to the number of bases that have identical base pairing relative to the sequence to which it is being compared. In certain embodiments, oligonucleotides described herein, or portions thereof, are, or are at least, 70%, 75%, 80%, 85%, 90%, 91%, 92%, 93%, 94%, 95%, 96%, 97%, 98%, 99% or 100% identical to one or more of the nucleic acids, oligonucleotides, or a portion thereof, disclosed herein. In certain embodiments, oligonucleotides described herein are about 70%, 75%, 80%, 85%, 90%, 91%, 92%, 93%, 94%, 95%, 96%, 97%, 98%, or 99% identical, or any percentage between such values, to a particular nucleic acid or oligonucleotide, or portion thereof.

In certain embodiments, an oligonucleotide may have one or more mismatched nucleobases. In certain such embodiments, the mismatch is at position 1, 2, 3, 4, 5, 6, 7, 8, 9, 10, 11, 12, 13 or 14 from the 5'-end of the oligonucleotide. In certain such embodiments, the mismatch is at position 1, 2, 3, 4, 5, 6, 7, 8, 9, 10, 11, or 12, 13 or 14 from the 3'-end of the oligonucleotide. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid. In certain embodiments, the oligonucleotide is a sense oligonucleotides. In certain embodiments, a portion of the sense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Pharmaceutical Compositions and Formulations

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered. Certain embodiments provide pharmaceutical compositions comprising one or more compounds or a salt thereof. In certain embodiments, the compounds are antisense oligonucleotides. In certain embodiments, the compounds are oligomeric compounds. In certain embodiments, the compounds comprise or consist of one or more modified oligonucleotides. In certain such embodiments, the pharmaceutical composition comprises one or more compound and a suitable pharmaceutically acceptable diluent or carrier. In certain embodiments, a pharmaceutical composition comprises one or more compound and a sterile saline solution. In certain embodiments, such pharmaceutical composition consists of one compound and a sterile saline solution. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compounds and phosphate-buffered saline (PBS). In certain embodiments, a pharmaceutical composition consists of one compound and sterile PBS. In certain embodiments, the sterile PBS is pharmaceutical grade PBS.

A compound described herein targeted to PKK can be utilized in pharmaceutical compositions by combining the compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising a compound targeted to PKK and a pharmaceutically acceptable diluent. In certain embodiments, the pharmaceutically acceptable diluent is water. In certain embodiments, the compound comprises or consists of one or more modified oligonucleotide provided herein.

Pharmaceutical compositions comprising compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the compounds are antisense oligonucleotides. In certain embodiments, the compounds are oligomeric compounds. In certain embodiments, the compound comprises or consists of one or more modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts. A prodrug can include the incorporation of additional nucleosides at one or both ends of a compound which are cleaved by endogenous nucleases within the body, to form the active compound. In certain embodiments, the compounds or compositions further comprise a pharmaceutically acceptable carrier or diluent.

EXAMPLES

The following examples describe the process to identify lead compounds targeted to PKK. Certain compounds are distinguished as having high potency and tolerability.

The following examples serve only to illustrate the compounds described herein and are not intended to limit the same. The following examples and related sequence listing accompanying this filing may identify sequence as either "RNA" or "DNA"; however, as disclosed herein, those sequences may be modified with any combination of chemical modifications. One of skill in the art will readily appreciate that the designation of a sequence as "RNA" or "DNA" is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (methylated uracil for natural uracil of RNA). Accordingly, nucleic acid sequences provided herein, including, but not limited to, those in the sequence listing, are intended to encompass nucleic acids containing any combination of natural or modified RNA and/or DNA, including, but not limited to, such nucleic acids having modified nucleobases.

Each of the references recited in the present application is incorporated herein by reference in its entirety.

Unless otherwise indicated in a separate compound chemistry table below, compounds are unmodified. Abbreviations for chemical modifications are provided in Table 1 below. IA and IS in a Ref ID NO:, identifies an antisense strand and sense strand of a compound, respectively.

TABLE 1

Chemical Nomenclature

| Abbreviation | Structure |
|---|---|
| 'm' | 2'-O-methyl sugar modification (e.g., mA, mG, mC, mU) |
| 'f' | 2'-F sugar modification (e.g., fA, fG, fC, fU) |
| '*' | Phosphorothioate internucleoside linkage |
| '.' | Phosphate internucleoside linkage |
| 'dQ' | Inverted abasic deoxyribose |
| 'H1' | Formula I |
| 'H2' | Formula II |
| 'H4" | Formula III |
| 'H6" | Formula IV |
| 'H7' | Formula V |
| 'H9' | Formula VI |
| 'Hd' | Formula VII |
| Hl | Formula VIII |

Example 1—Inhibition of PKK in HEK-293T Cells

HEK-293T cells were seeded in antibiotic-free media at 20,000 cells/well in white-walled 96-well plates. The following day, the cells were co-transfected with 50 ng of PKK-siCHECK-2 and 10 nM PKK compound using Lipofectamine 2000 (each transfection was performed in triplicate). The cells were then incubated at 37° C./5% $CO_2$ for 48 hours.

Dual-Luciferase Reporter 1000 Assay (Promega Cat #E1980) was used to evaluate expression of firefly and *renilla* luciferase according to kit instructions. Firefly and *renilla* luciferase expression were measured using a luminimeter. *Renilla* luciferase was the readout for PKK gene expression while firefly served as the internal control. All *renillla* readings from each well were normalized to its corresponding firefly reading to obtain a *renilla*:firefly ratio. The ratios obtained for each well of transfected compound were then further normalized to the ratios obtained for cells that were not transfected with compound. These untransfected cells served as the 100% control. PKK inhibition was determined by comparing PKK expression to the untransfected cells and reported as % PKK inhibition (Tables 2-4).

TABLE 2

Inhibition of PKK mRNA by double-stranded compounds targeting SEQ ID NO: 1

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: | PKK % inhibition |
|---|---|---|---|---|---|---|---|
| RD1839 | 171 | 191 | UUACAUCCCCACCUCUGAAGA | 10 | UCUUCAGAGGUGGGGAUGUAA | 314 | 70 |
| RD1840 | 172 | 192 | UCUACAUCCCCACCUCUGAAG | 11 | CUUCAGAGGUGGGGAUGUAGA | 315 | 56 |
| RD1841 | 173 | 193 | AGCUACAUCCCCACCUCUGAA | 12 | UUCAGAGGUGGGGAUGUAGCU | 316 | 34 |
| RD1842 | 174 | 194 | AAGCUACAUCCCCACCUCUGA | 13 | UCAGAGGUGGGGAUGUAGCUU | 317 | 53 |
| RD1843 | 175 | 195 | UAAGCUACAUCCCCACCUCUG | 14 | CAGAGGUGGGGAUGUAGCUUA | 318 | 64 |
| RD1844 | 176 | 196 | UGAAGCUACAUCCCCACCUCU | 15 | AGAGGUGGGGAUGUAGCUUCA | 319 | 71 |
| RD1845 | 177 | 197 | UGGAAGCUACAUCCCCACCUC | 16 | GAGGUGGGGAUGUAGCUUCCA | 320 | 70 |
| RD1846 | 178 | 198 | AUGGAAGCUACAUCCCCACCU | 17 | AGGUGGGGAUGUAGCUUCCAU | 321 | 81 |
| RD1847 | 179 | 199 | UAUGGAAGCUACAUCCCCACC | 18 | GGUGGGGAUGUAGCUUCCAUA | 322 | 74 |
| RD1848 | 180 | 200 | ACAUGGAAGCUACAUCCCCAC | 19 | GUGGGGAUGUAGCUUCCAUGU | 323 | 64 |
| RD1849 | 181 | 201 | UACAUGGAAGCUACAUCCCCA | 20 | UGGGGAUGUAGCUUCCAUGUA | 324 | 74 |
| RD1850 | 182 | 202 | UUACAUGGAAGCUACAUCCCC | 21 | GGGGAUGUAGCUUCCAUGUAA | 325 | 70 |
| RD1851 | 232 | 252 | UACCUUGGGUGGAAUGUGCAC | 22 | GUGCACAUUCCACCCAAGGUA | 326 | 77 |
| RD1852 | 233 | 253 | ACACCUUGGGUGGAAUGUGCA | 23 | UGCACAUUCCACCCAAGGUGU | 327 | 62 |
| RD1853 | 234 | 254 | AACACCUUGGGUGGAAUGUGC | 24 | GCACAUUCCACCCAAGGUGUU | 328 | 72 |
| RD1854 | 237 | 257 | UCAAACACCUUGGGUGGAAUG | 25 | CAUUCCACCCAAGGUGUUUGA | 329 | 61 |
| RD1855 | 238 | 258 | AGCAAACACCUUGGGUGGAAU | 26 | AUUCCACCCAAGGUGUUUGCU | 330 | 51 |
| RD1856 | 241 | 261 | AAUAGCAAACACCUUGGGUGG | 27 | CCACCCAAGGUGUUUGCUAUU | 331 | 82 |
| RD1857 | 242 | 262 | UAAUAGCAAACACCUUGGGUG | 28 | CACCCAAGGUGUUUGCUAUUA | 332 | 62 |
| RD1858 | 243 | 263 | UGAAUAGCAAACACCUUGGGU | 29 | ACCCAAGGUGUUUGCUAUUCA | 333 | 91 |
| RD1859 | 245 | 265 | ACUGAAUAGCAAACACCUUGG | 30 | CCAAGGUGUUUGCUAUUCAGU | 334 | 91 |
| RD1860 | 246 | 266 | AACUGAAUAGCAAACACCUUG | 31 | CAAGGUGUUUGCUAUUCAGUU | 335 | 94 |
| RD1861 | 247 | 267 | AAACUGAAUAGCAAACACCUU | 32 | AAGGUGUUUGCUAUUCAGUUU | 336 | 90 |
| RD1862 | 248 | 268 | AAAACUGAAUAGCAAACACCU | 33 | AGGUGUUUGCUAUUCAGUUUU | 337 | 91 |
| RD1863 | 249 | 269 | UAAAACUGAAUAGCAAACACC | 34 | GGUGUUUGCUAUUCAGUUUUA | 338 | 92 |
| RD1864 | 250 | 270 | AGAAAACUGAAUAGCAAACAC | 35 | GUGUUUGCUAUUCAGUUUUCU | 339 | 90 |
| RD1865 | 254 | 274 | UGGAAGAAAACUGAAUAGCAA | 36 | UUGCUAUUCAGUUUUCUUCCA | 340 | 91 |
| RD1866 | 262 | 282 | UAACUUGCUGGAAGAAAACUG | 37 | CAGUUUUCUUCCAGCAAGUUA | 341 | 89 |
| RD1867 | 284 | 304 | UCUUUUCUCCAUGUCAUUGAU | 38 | AUCAAUGACAUGGAGAAAAGA | 342 | 93 |

TABLE 3

Inhibition of PKK mRNA by double-stranded compounds targeting SEQ ID NO: 1

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: | PKK % inhibition |
|---|---|---|---|---|---|---|---|
| RD1868 | 287 | 307 | AAACCUUUCUCCAUGUCAUU | 39 | AAUGACAUGGAGAAAAGGUUU | 343 | 65 |
| RD1869 | 288 | 308 | UAAACCUUUUCUCCAUGUCAU | 40 | AUGACAUGGAGAAAAGGUUUA | 344 | 44 |
| RD1870 | 484 | 504 | UACCUUUUUUGGCAUUCUUCA | 41 | UGAAGAAUGCCAAAAAGGUA | 345 | 66 |
| RD1871 | 489 | 509 | UGGUGCACCUUUUUUGGCAUU | 42 | AAUGCCAAAAAGGUGCACCA | 346 | 45 |
| RD1872 | 662 | 682 | ACCAAUUUCUGAAAGGGCACA | 43 | UGUGCCCUUUCAGAAAUUGGU | 347 | 66 |
| RD1873 | 663 | 683 | AACCAAUUUCUGAAAGGGCAC | 44 | GUGCCCUUUCAGAAAUUGGUU | 348 | 50 |
| RD1874 | 691 | 711 | UCAAGAUGCUGGAAGAUGUUC | 45 | GAACAUCUUCCAGCAUCUUGA | 349 | 49 |
| RD1875 | 867 | 887 | AGGAACUUGGUGUGCCACUUU | 46 | AAAGUGGCACACCAAGUUCCU | 350 | 17 |
| RD1876 | 868 | 888 | UAGGAACUUGGUGUGCCACUU | 47 | AAGUGGCACACCAAGUUCCUA | 351 | 52 |
| RD1877 | 869 | 889 | AGAGGAACUUGGUGUGCCACU | 48 | AGUGGCACACCAAGUUCCUCU | 352 | 70 |
| RD1878 | 870 | 890 | UAGAGGAACUUGGUGUGCCAC | 49 | GUGGCACACCAAGUUCCUCUA | 353 | 68 |
| RD1879 | 871 | 891 | UUAGAGGAACUUGGUGUGCCA | 50 | UGGCACACCAAGUUCCUCUAA | 354 | 38 |
| RD1880 | 876 | 896 | UAGGAGUAGAGGAACUUGGUG | 51 | CACCAAGUUCCUCUACUCCUA | 355 | 75 |
| RD1881 | 877 | 897 | UGAGGAGUAGAGGAACUUGGU | 52 | ACCAAGUUCCUCUACUCCUCA | 356 | 69 |
| RD1882 | 878 | 898 | UUGAGGAGUAGAGGAACUUGG | 53 | CCAAGUUCCUCUACUCCUCAA | 357 | 85 |
| RD1883 | 879 | 899 | UUUGAGGAGUAGAGGAACUUG | 54 | CAAGUUCCUCUACUCCUCAAA | 358 | 82 |
| RD1884 | 880 | 900 | UCUUGAGGAGUAGAGGAACUU | 55 | AAGUUCCUCUACUCCUCAAGA | 359 | 69 |
| RD1885 | 881 | 901 | UUCUUGAGGAGUAGAGGAACU | 56 | AGUUCCUCUACUCCUCAAGAA | 360 | 68 |
| RD1886 | 882 | 902 | UUUCUUGAGGAGUAGAGGAAC | 57 | GUUCCUCUACUCCUCAAGAAA | 361 | 63 |
| RD1887 | 883 | 903 | UUUUCUUGAGGAGUAGAGGAA | 58 | UUCCUCUACUCCUCAAGAAAA | 362 | 71 |
| RD1888 | 886 | 906 | UUGUUUUCUUGAGGAGUAGAG | 59 | CUCUACUCCUCAAGAAAACAA | 363 | 64 |
| RD1889 | 887 | 907 | UGUGUUUUCUUGAGGAGUAGA | 60 | UCUACUCCUCAAGAAAACACA | 364 | 75 |
| RD1890 | 888 | 908 | UGGUGUUUUCUUGAGGAGUAG | 61 | CUACUCCUCAAGAAAACACCA | 365 | 88 |
| RD1891 | 920 | 940 | UCUUUUGCAGGUUAAAAGGCU | 62 | AGCCUUUUAACCUGCAAAAGA | 366 | 88 |
| RD1892 | 936 | 956 | AGGGUUCAGGUAAAGUUCUUU | 63 | AAAGAACUUUACCUGAACCCU | 367 | 58 |
| RD1893 | 937 | 957 | UAGGGUUCAGGUAAAGUUCUU | 64 | AAGAACUUUACCUGAACCCUA | 368 | 83 |
| RD1894 | 938 | 958 | UCAGGGUUCAGGUAAAGUUCU | 65 | AGAACUUUACCUGAACCCUGA | 369 | 78 |
| RD1895 | 939 | 959 | UGCAGGGUUCAGGUAAAGUUC | 66 | GAACUUUACCUGAACCCUGCA | 370 | 76 |
| RD1924 | 1060 | 1080 | UAAGUGAAAAACUGACAGCGA | 95 | UCGCUGUCAGUUUUUCACUUA | 399 | 77 |
| RD1925 | 1061 | 1081 | AUAAGUGAAAAACUGACAGCG | 96 | CGCUGUCAGUUUUUCACUUAU | 400 | 73 |
| RD1926 | 1062 | 1082 | AAUAAGUGAAAAACUGACAGC | 97 | GCUGUCAGUUUUUCACUUAUU | 401 | 81 |
| RD1927 | 1065 | 1085 | AAGAAUAAGUGAAAAACUGAC | 98 | GUCAGUUUUUCACUUAUUCUU | 402 | 58 |
| RD1928 | 1066 | 1086 | AAAGAAUAAGUGAAAAACUGA | 99 | UCAGUUUUUCACUUAUUCUUU | 403 | 43 |
| RD1929 | 1070 | 1090 | UAGUAAAGAAUAAGUGAAAAA | 100 | UUUUUCACUUAUUCUUUACUA | 404 | 0 |
| RD1930 | 1071 | 1091 | UGAGUAAAGAAUAAGUGAAAA | 101 | UUUUCACUUAUUCUUUACUCA | 405 | 4 |
| RD1931 | 1072 | 1092 | UGGAGUAAAGAAUAAGUGAAA | 102 | UUUCACUUAUUCUUUACUCCA | 406 | 8 |

TABLE 3-continued

Inhibition of PKK mRNA by double-stranded compounds targeting SEQ ID NO: 1

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: | PKK % inhibition |
|---|---|---|---|---|---|---|---|
| RD1932 | 1073 | 1093 | UGGGAGUAAAGAAUAAGUGAA | 103 | UUCACUUAUUCUUUACUCCCA | 407 | 65 |
| RD1933 | 1074 | 1094 | UUGGGAGUAAAGAAUAAGUGA | 104 | UCACUUAUUCUUUACUCCCAA | 408 | 75 |
| RD1934 | 1075 | 1095 | UCUGGGAGUAAAGAAUAAGUG | 105 | CACUUAUUCUUUACUCCCAGA | 409 | 85 |
| RD1935 | 1076 | 1096 | UUCUGGGAGUAAAGAAUAAGU | 106 | ACUUAUUCUUUACUCCCAGAA | 410 | 69 |
| RD1936 | 1077 | 1097 | UUUCUGGGAGUAAAGAAUAAG | 107 | CUUAUUCUUUACUCCCAGAAA | 411 | 75 |
| RD1937 | 1078 | 1098 | UCUUCUGGGAGUAAAGAAUAA | 108 | UUAUUCUUUACUCCCAGAAGA | 412 | 55 |
| RD1938 | 1080 | 1100 | AGUCUUCUGGGAGUAAAGAAU | 109 | AUUCUUUACUCCCAGAAGACU | 413 | 53 |
| RD1939 | 1081 | 1101 | UAGUCUUCUGGGAGUAAAGAA | 110 | UUCUUUACUCCCAGAAGACUA | 414 | 58 |
| RD1940 | 1085 | 1105 | UUUACAGUCUUCUGGGAGUAA | 111 | UUACUCCCAGAAGACUGUAAA | 415 | 75 |
| RD1941 | 1086 | 1106 | UCUUACAGUCUUCUGGGAGUA | 112 | UACUCCCAGAAGACUGUAAGA | 416 | 80 |
| RD1942 | 1087 | 1107 | UCCUUACAGUCUUCUGGGAGU | 113 | ACUCCCAGAAGACUGUAAGGA | 417 | 53 |
| RD1943 | 1109 | 1129 | UAAGAAACACUUACACUUCUC | 114 | GAGAAGUGUAAGUGUUUCUUA | 418 | 85 |
| RD1944 | 1110 | 1130 | UUAAGAAACACUUACACUUCU | 115 | AGAAGUGUAAGUGUUUCUUAA | 419 | 87 |
| RD1945 | 1111 | 1131 | UUUAAGAAACACUUACACUUC | 116 | GAAGUGUAAGUGUUUCUUAAA | 420 | 77 |
| RD1946 | 1117 | 1137 | UAUAAUCUUAAGAAACACUUA | 117 | UAAGUGUUUCUUAAGAUUAUA | 421 | 84 |
| RD1947 | 1141 | 1161 | AUCCUAGUUGGAGAACCAUCC | 118 | GGAUGGUUCUCCAACUAGGAU | 422 | 77 |
| RD1948 | 1142 | 1162 | AAUCCUAGUUGGAGAACCAUC | 119 | GAUGGUUCUCCAACUAGGAUU | 423 | 82 |
| RD1949 | 1167 | 1187 | UAGAGCUCCCUUGUGUCCAU | 120 | AUGGGACACAAGGGAGCUCUA | 424 | 86 |
| RD1950 | 1168 | 1188 | UCAGAGCUCCCUUGUGUCCCA | 121 | UGGGACACAAGGGAGCUCUGA | 425 | 73 |
| RD1951 | 1170 | 1190 | AACCAGAGCUCCCUUGUGUCC | 122 | GGACACAAGGGAGCUCUGGUU | 426 | 74 |
| RD1952 | 1171 | 1191 | UAACCAGAGCUCCCUUGUGUC | 123 | GACACAAGGGAGCUCUGGUUA | 427 | 32 |
| RD1953 | 1172 | 1192 | UUAACCAGAGCUCCCUUGUGU | 124 | ACACAAGGGAGCUCUGGUUAA | 428 | 64 |
| RD1954 | 1174 | 1194 | UAGUAACCAGAGCUCCCUUGU | 125 | ACAAGGGAGCUCUGGUUACUA | 429 | 78 |
| RD1955 | 1175 | 1195 | AGAGUAACCAGAGCUCCCUUG | 126 | CAAGGGAGCUCUGGUUACUCU | 430 | 81 |
| RD1956 | 1179 | 1199 | UCAAAGAGUAACCAGAGCUCC | 127 | GGAGCUCUGGUUACUCUUUGA | 431 | 61 |
| RD1957 | 1196 | 1216 | UCCAGUGUUACACAAUCUCAA | 128 | UUGAGAUUGUGUAACACUGGA | 432 | 85 |
| RD1958 | 1197 | 1217 | UCCCAGUGUUACACAAUCUCA | 129 | UGAGAUUGUGUAACACUGGGA | 433 | 71 |
| RD1959 | 1200 | 1220 | UGUCCCCAGUGUUACACAAUC | 130 | GAUUGUGUAACACUGGGGACA | 434 | 70 |
| RD1960 | 1261 | 1281 | UCCCAAGAAGAGUUUGUUCCU | 131 | AGGAACAAACUCUUCUUGGGA | 435 | 37 |
| RD1961 | 1262 | 1282 | UCCCCAAGAAGAGUUUGUUCC | 132 | GGAACAAACUCUUCUUGGGGA | 436 | 40 |
| RD1962 | 1263 | 1283 | UUCCCCAAGAAGAGUUUGUUC | 133 | GAACAAACUCUUCUUGGGGAA | 437 | 25 |
| RD1963 | 1264 | 1284 | UCUCCCCAAGAAGAGUUUGUU | 134 | AACAAACUCUUCUUGGGGAGA | 438 | 2 |
| RD1964 | 1265 | 1285 | UUCUCCCCAAGAAGAGUUUGU | 135 | ACAAACUCUUCUUGGGGAGAA | 439 | 0 |
| RD1965 | 1266 | 1286 | ACUCUCCCCAAGAAGAGUUUG | 136 | CAAACUCUUCUUGGGGAGAGU | 440 | 0 |
| RD1966 | 1268 | 1288 | UCACUCUCCCCAAGAAGAGUU | 137 | AACUCUUCUUGGGGAGAGUGA | 441 | 12 |
| RD1967 | 1269 | 1289 | UCCACUCUCCCCAAGAAGAGU | 138 | ACUCUUCUUGGGGAGAGUGGA | 442 | 8 |

TABLE 3-continued

Inhibition of PKK mRNA by double-stranded compounds targeting SEQ ID NO: 1

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: | PKK % inhibition |
|---|---|---|---|---|---|---|---|
| RD1968 | 1272 | 1292 | AGGGCCACUCUCCCCAAGAAG | 139 | CUUCUUGGGGAGAGUGGCCCU | 443 | 0 |
| RD1969 | 1273 | 1293 | UAGGGCCACUCUCCCCAAGAA | 140 | UUCUUGGGGAGAGUGGCCCUA | 444 | 11 |
| RD1970 | 1274 | 1294 | UCAGGGCCACUCUCCCCAAGA | 141 | UCUUGGGGAGAGUGGCCCUGA | 445 | 42 |
| RD1971 | 1343 | 1363 | UUGGUGUCCUAUGAGUGACCC | 142 | GGGUCACUCAUAGGACACCAA | 446 | 60 |
| RD1972 | 1344 | 1364 | ACUGGUGUCCUAUGAGUGACC | 143 | GGUCACUCAUAGGACACCAGU | 447 | 37 |
| RD1973 | 1347 | 1367 | UCCACUGGUGUCCUAUGAGUG | 144 | CACUCAUAGGACACCAGUGGA | 448 | 43 |
| RD1974 | 1348 | 1368 | ACCCACUGGUGUCCUAUGAGU | 145 | ACUCAUAGGACACCAGUGGGU | 449 | 8 |
| RD1975 | 1349 | 1369 | UACCCACUGGUGUCCUAUGAG | 146 | CUCAUAGGACACCAGUGGGUA | 450 | 59 |
| RD1976 | 1381 | 1401 | UGAAGCCCAUCAAAGCAGUGG | 147 | CCACUGCUUUGAUGGGCUUCA | 451 | 77 |
| RD1977 | 1425 | 1445 | ACAGAUUUAAAAUGCCACUAU | 148 | AUAGUGGCAUUUUAAAUCUGU | 452 | 78 |
| RD1978 | 1426 | 1446 | UACAGAUUUAAAAUGCCACUA | 149 | UAGUGGCAUUUUAAAUCUGUA | 453 | 91 |
| RD1979 | 1427 | 1447 | UGACAGAUUUAAAAUGCCACU | 150 | AGUGGCAUUUUAAAUCUGUCA | 454 | 90 |
| RD1980 | 1428 | 1448 | UUGACAGAUUUAAAAUGCCAC | 151 | GUGGCAUUUUAAAUCUGUCAA | 455 | 83 |
| RD1981 | 1429 | 1449 | UCUGACAGAUUUAAAAUGCCA | 152 | UGGCAUUUUAAAUCUGUCAGA | 456 | 90 |
| RD1982 | 1430 | 1450 | UUCUGACAGAUUUAAAAUGCC | 153 | GGCAUUUUAAAUCUGUCAGAA | 457 | 68 |
| RD1983 | 1431 | 1451 | UGUCUGACAGAUUUAAAAUGC | 154 | GCAUUUUAAAUCUGUCAGACA | 458 | 72 |
| RD1984 | 1436 | 1456 | UGUAAUGUCUGACAGAUUUAA | 155 | UUAAAUCUGUCAGACAUUACA | 459 | 92 |
| RD1985 | 1441 | 1461 | UCUUUUGUAAUGUCUGACAGA | 156 | UCUGUCAGACAUUACAAAAGA | 460 | 92 |
| RD1986 | 1513 | 1533 | AUAUCAUGAUUCCCUUCUGAG | 157 | CUCAGAAGGGAAUCAUGAUAU | 461 | 63 |
| RD1987 | 1516 | 1536 | UCGAUAUCAUGAUUCCCUUCU | 158 | AGAAGGGAAUCAUGAUAUCGA | 462 | 71 |
| RD1988 | 1517 | 1537 | UGCGAUAUCAUGAUUCCCUUC | 159 | GAAGGGAAUCAUGAUAUCGCA | 463 | 80 |
| RD1989 | 1518 | 1538 | AGGCGAUAUCAUGAUUCCCUU | 160 | AAGGGAAUCAUGAUAUCGCCU | 464 | 77 |
| RD1990 | 1545 | 1565 | AAUUCAAAGGAGCCUGGAGUU | 161 | AACUCCAGGCUCCUUUGAAUU | 465 | 61 |
| RD1991 | 1546 | 1566 | UAAUUCAAAGGAGCCUGGAGU | 162 | ACUCCAGGCUCCUUUGAAUUA | 466 | 55 |
| RD1992 | 1547 | 1567 | UUAAUUCAAAGGAGCCUGGAG | 163 | CUCCAGGCUCCUUUGAAUUAA | 467 | 65 |
| RD1993 | 1548 | 1568 | UGUAAUUCAAAGGAGCCUGGA | 164 | UCCAGGCUCCUUUGAAUUACA | 468 | 51 |
| RD1994 | 1549 | 1569 | UUGUAAUUCAAAGGAGCCUGG | 165 | CCAGGCUCCUUUGAAUUACAA | 469 | 82 |
| RD1995 | 1550 | 1570 | AGUGUAAUUCAAAGGAGCCUG | 166 | CAGGCUCCUUUGAAUUACACU | 470 | 74 |
| RD1996 | 1551 | 1571 | UAGUGUAAUUCAAAGGAGCCU | 167 | AGGCUCCUUUGAAUUACACUA | 471 | 80 |
| RD1997 | 1552 | 1572 | UCAGUGUAAUUCAAAGGAGCC | 168 | GGCUCCUUUGAAUUACACUGA | 472 | 71 |
| RD1998 | 1557 | 1577 | UGAAUUCAGUGUAAUUCAAAG | 169 | CUUUGAAUUACACUGAAUUCA | 473 | 0 |
| RD1999 | 1567 | 1587 | AUUGGUUUUGGAAUUCAGUG | 170 | CACUGAAUUCCAAAACCAAU | 474 | 88 |
| RD2000 | 1568 | 1588 | UAUGGUUUUGGAAUUCAGU | 171 | ACUGAAUUCCAAAACCAUA | 475 | 91 |
| RD2001 | 1570 | 1590 | UAUAUGGUUUUGGAAUUCA | 172 | UGAAUUCCAAAACCAUAUA | 476 | 77 |
| RD2002 | 1571 | 1591 | UCAUAUGGUUUUGGAAUUC | 173 | GAAUUCCAAAACCAUAUGA | 477 | 83 |
| RD2003 | 1575 | 1595 | UUAGGCAUAUUGGUUUUGGA | 174 | UCCAAAACCAUAUGCCUAA | 478 | 70 |

TABLE 3-continued

Inhibition of PKK mRNA by double-stranded compounds targeting SEQ ID NO: 1

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: | PKK % inhibition |
|---|---|---|---|---|---|---|---|
| RD2004 | 1576 | 1596 | UGUAGGCAUAUUGGUUUUGG | 175 | CCAAAAACCAAUAUGCCUACA | 479 | 63 |
| RD2005 | 1577 | 1597 | AGGUAGGCAUAUUGGUUUUG | 176 | CAAAAACCAAUAUGCCUACCU | 480 | 52 |
| RD2006 | 1578 | 1598 | AAGGUAGGCAUAUUGGUUUU | 177 | AAAAACCAAUAUGCCUACCUU | 481 | 71 |
| RD2007 | 1579 | 1599 | UAAGGUAGGCAUAUUGGUUU | 178 | AAAACCAAUAUGCCUACCUUA | 482 | 77 |
| RD2008 | 1580 | 1600 | UGAAGGUAGGCAUAUUGGUU | 179 | AAACCAAUAUGCCUACCUUCA | 483 | 0 |
| RD2009 | 1581 | 1601 | UGGAAGGUAGGCAUAUUGGUU | 180 | AACCAAUAUGCCUACCUUCCA | 484 | 66 |
| RD2010 | 1588 | 1608 | UCACCUUUGGAAGGUAGGCAU | 181 | AUGCCUACCUUCCAAAGGUGA | 485 | 65 |
| RD2011 | 1591 | 1611 | UUGUCACCUUUGGAAGGUAGG | 182 | CCUACCUUCCAAAGGUGACAA | 486 | 37 |
| RD2012 | 1592 | 1612 | UGUGUCACCUUUGGAAGGUAG | 183 | CUACCUUCCAAAGGUGACACA | 487 | 57 |
| RD2013 | 1593 | 1613 | UUGUGUCACCUUUGGAAGGUA | 184 | UACCUUCCAAAGGUGACACAA | 488 | 22 |
| RD2014 | 1849 | 1869 | UUGAUGCCCACCAAACGCCAC | 185 | GUGGCGUUUGGUGGGCAUCAA | 489 | 18 |
| RD2015 | 1880 | 1900 | UUCCCUGCGGGCACAGCCUUC | 186 | GAAGGCUGUGCCCGCAGGGAA | 490 | 36 |
| RD2016 | 1889 | 1909 | ACCAGGUUGCUCCCUGCGGGC | 187 | GCCCGCAGGGAGCAACCUGGU | 491 | −6 |
| RD2017 | 1890 | 1910 | UACCAGGUUGCUCCCUGCGGG | 188 | CCCGCAGGGAGCAACCUGGUA | 492 | 45 |
| RD2018 | 1891 | 1911 | ACACCAGGUUGCUCCCUGCGG | 189 | CCGCAGGGAGCAACCUGGUGU | 493 | 51 |
| RD2019 | 1892 | 1912 | UACACCAGGUUGCUCCCUGCG | 190 | CGCAGGGAGCAACCUGGUGUA | 494 | 51 |
| RD2020 | 1893 | 1913 | AGACACCAGGUUGCUCCCUGC | 191 | GCAGGGAGCAACCUGGUGUCU | 495 | 2 |
| RD2021 | 1894 | 1914 | UAGACACCAGGUUGCUCCCUG | 192 | CAGGGAGCAACCUGGUGUCUA | 496 | 67 |
| RD2022 | 1895 | 1915 | UUAGACACCAGGUUGCUCCCU | 193 | AGGGAGCAACCUGGUGUCUAA | 497 | 85 |
| RD2023 | 1896 | 1916 | UGUAGACACCAGGUUGCUCCC | 194 | GGGAGCAACCUGGUGUCUACA | 498 | 75 |
| RD2024 | 1897 | 1917 | UUGUAGACACCAGGUUGCUCC | 195 | GGAGCAACCUGGUGUCUACAA | 499 | 55 |
| RD2025 | 1907 | 1927 | AGCGACUUUGGUGUAGACACC | 196 | GGUGUCUACACCAAAGUCGCU | 500 | 66 |
| RD2026 | 1922 | 1942 | UCAGUCCAUGUACUCAGCGAC | 197 | GUCGCUGAGUACAUGGACUGA | 501 | 69 |
| RD2027 | 1923 | 1943 | UCCAGUCCAUGUACUCAGCGA | 198 | UCGCUGAGUACAUGGACUGGA | 502 | 71 |
| RD2028 | 1924 | 1944 | AUCCAGUCCAUGUACUCAGCG | 199 | CGCUGAGUACAUGGACUGGAU | 503 | 75 |
| RD2029 | 1941 | 1961 | UCUGUGUUUUCUCUAAAUCC | 200 | GGAUUUAGAGAAAACACAGA | 504 | 73 |
| RD2030 | 1942 | 1962 | UUCUGUGUUUUCUCUAAAUC | 201 | GAUUUAGAGAAAACACAGAA | 505 | 67 |
| RD2031 | 1943 | 1963 | UCUCUGUGUUUUCUCUAAAU | 202 | AUUUAGAGAAAACACAGAGA | 506 | 68 |
| RD2032 | 1944 | 1964 | UGCUCUGUGUUUUCUCUAAAA | 203 | UUUUAGAGAAAACACAGAGCA | 507 | 71 |
| RD2033 | 1945 | 1965 | UUGCUCUGUGUUUUCUCUAAA | 204 | UUUAGAGAAAACACAGAGCAA | 508 | 82 |
| RD2034 | 1950 | 1970 | UAUCACUGCUCUGUGUUUUCU | 205 | AGAAAACACAGAGCAGUGAUA | 509 | 72 |
| RD2035 | 1953 | 1973 | UUCCAUCACUGCUCUGUGUUU | 206 | AAACACAGAGCAGUGAUGGAA | 510 | 81 |

TABLE 4

Inhibition of PKK mRNA by double-stranded compounds targeting SEQ ID NO: 1

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: | PKK % inhibition |
|---|---|---|---|---|---|---|---|
| RD1896 | 940 | 960 | UGGCAGGGUUCAGGUAAAGUU | 67 | AACUUUACCUGAACCCUGCCA | 371 | 44 |
| RD1897 | 941 | 961 | AUGGCAGGGUUCAGGUAAAGU | 68 | ACUUUACCUGAACCCUGCCAU | 372 | 41 |
| RD1898 | 943 | 963 | UAAUGGCAGGGUUCAGGUAAA | 69 | UUUACCUGAACCCUGCCAUUA | 373 | 75 |
| RD1899 | 944 | 964 | AGAAUGGCAGGGUUCAGGUAA | 70 | UUACCUGAACCCUGCCAUUCU | 374 | 67 |
| RD1900 | 945 | 965 | UAGAAUGGCAGGGUUCAGGUA | 71 | UACCUGAACCCUGCCAUUCUA | 375 | 73 |
| RD1901 | 946 | 966 | UUAGAAUGGCAGGGUUCAGGU | 72 | ACCUGAACCCUGCCAUUCUAA | 376 | 72 |
| RD1902 | 947 | 967 | UUUAGAAUGGCAGGGUUCAGG | 73 | CCUGAACCCUGCCAUUCUAAA | 377 | 79 |
| RD1903 | 948 | 968 | UUUUAGAAUGGCAGGGUUCAG | 74 | CUGAACCCUGCCAUUCUAAAA | 378 | 80 |
| RD1904 | 949 | 969 | AUUUUAGAAUGGCAGGGUUCA | 75 | UGAACCCUGCCAUUCUAAAAU | 379 | 79 |
| RD1905 | 950 | 970 | AAUUUUAGAAUGGCAGGGUUC | 76 | GAACCCUGCCAUUCUAAAAUU | 380 | 67 |
| RD1906 | 951 | 971 | AAAUUUUAGAAUGGCAGGGUU | 77 | AACCCUGCCAUUCUAAAAUUU | 381 | 57 |
| RD1907 | 952 | 972 | UAAAUUUUAGAAUGGCAGGGU | 78 | ACCCUGCCAUUCUAAAAUUUA | 382 | 74 |
| RD1908 | 953 | 973 | UUAAAUUUUAGAAUGGCAGGG | 79 | CCCUGCCAUUCUAAAAUUUAA | 383 | 84 |
| RD1909 | 954 | 974 | UGUAAAUUUUAGAAUGGCAGG | 80 | CCUGCCAUUCUAAAAUUUACA | 384 | 83 |
| RD1910 | 957 | 977 | UCGGGUAAAUUUUAGAAUGGC | 81 | GCCAUUCUAAAAUUUACCCGA | 385 | 81 |
| RD1911 | 958 | 978 | UCCGGGUAAAUUUUAGAAUGG | 82 | CCAUUCUAAAAUUUACCCGGA | 386 | 78 |
| RD1912 | 989 | 1009 | UACAUUCAAUUCUUCUCCUCC | 83 | GGAGGAGAAGAAUUGAAUGUA | 387 | 73 |
| RD1913 | 990 | 1010 | UCACAUUCAAUUCUUCUCCUC | 84 | GAGGAGAAGAAUUGAAUGUGA | 388 | 91 |
| RD1914 | 992 | 1012 | AGUCACAUUCAAUUCUUCUCC | 85 | GGAGAAGAAUUGAAUGUGACU | 389 | 77 |
| RD1915 | 1017 | 1037 | UGCAAACAUUCACUCCUUUAA | 86 | UUAAAGGAGUGAAUGUUUGCA | 390 | 85 |
| RD1916 | 1050 | 1070 | ACUGACAGCGAAUCAUCUUUG | 87 | CAAAGAUGAUUCGCUGUCAGU | 391 | 93 |
| RD1917 | 1051 | 1071 | AACUGACAGCGAAUCAUCUUU | 88 | AAAGAUGAUUCGCUGUCAGUU | 392 | 92 |
| RD1918 | 1052 | 1072 | AAACUGACAGCGAAUCAUCUU | 89 | AAGAUGAUUCGCUGUCAGUUU | 393 | 91 |
| RD1919 | 1053 | 1073 | AAAACUGACAGCGAAUCAUCU | 90 | AGAUGAUUCGCUGUCAGUUUU | 394 | 81 |
| RD1920 | 1054 | 1074 | AAAAACUGACAGCGAAUCAUC | 91 | GAUGAUUCGCUGUCAGUUUUU | 395 | 93 |
| RD1921 | 1057 | 1077 | UUGAAAAACUGACAGCGAAUC | 92 | GAUUCGCUGUCAGUUUUUCAA | 396 | 91 |
| RD1922 | 1058 | 1078 | AGUGAAAAACUGACAGCGAAU | 93 | AUUCGCUGUCAGUUUUUCACU | 397 | 85 |
| RD1923 | 1059 | 1079 | AAGUGAAAAACUGACAGCGAA | 94 | UUCGCUGUCAGUUUUUCACUU | 398 | 93 |
| RD2036 | 1954 | 1974 | UUUCCAUCACUGCUCUGUGUU | 207 | AACACAGAGCAGUGAUGGAAA | 511 | 69 |
| RD2037 | 2037 | 2057 | UGCUCAGAAUUUGACUUGAAC | 208 | GUUCAAGUCAAAUUCUGAGCA | 512 | 0 |
| RD2038 | 2038 | 2058 | AGGCUCAGAAUUUGACUUGAA | 209 | UUCAAGUCAAAUUCUGAGCCU | 513 | 0 |
| RD2039 | 2039 | 2059 | UAGGCUCAGAAUUUGACUUGA | 210 | UCAAGUCAAAUUCUGAGCCUA | 514 | 0 |
| RD2040 | 2040 | 2060 | UCAGGCUCAGAAUUUGACUUG | 211 | CAAGUCAAAUUCUGAGCCUGA | 515 | 0 |
| RD2041 | 2041 | 2061 | UCCAGGCUCAGAAUUUGACUU | 212 | AAGUCAAAUUCUGAGCCUGGA | 516 | 0 |
| RD2042 | 2043 | 2063 | UCCCCAGGCUCAGAAUUUGAC | 213 | GUCAAAUUCUGAGCCUGGGGA | 517 | 0 |
| RD2043 | 2067 | 2087 | UCUCCAUGCUUUGCAGAUGAG | 214 | CUCAUCUGCAAAGCAUGGAGA | 518 | 0 |

TABLE 4-continued

Inhibition of PKK mRNA by double-stranded compounds targeting SEQ ID NO: 1

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: | PKK % inhibition |
|---|---|---|---|---|---|---|---|
| RD2044 | 2070 | 2090 | UACUCUCCAUGCUUUGCAGAU | 215 | AUCUGCAAAGCAUGGAGAGUA | 519 | 0 |
| RD2045 | 2071 | 2091 | UCACUCUCCAUGCUUUGCAGA | 216 | UCUGCAAAGCAUGGAGAGUGA | 520 | 11 |
| RD2046 | 2072 | 2092 | UCCACUCUCCAUGCUUUGCAG | 217 | CUGCAAAGCAUGGAGAGUGGA | 521 | 16 |
| RD2047 | 2073 | 2093 | UGCCACUCUCCAUGCUUUGCA | 218 | UGCAAAGCAUGGAGAGUGGCA | 522 | 28 |
| RD2048 | 2074 | 2094 | AUGCCACUCUCCAUGCUUUGC | 219 | GCAAAGCAUGGAGAGUGGCAU | 523 | 28 |
| RD2049 | 2075 | 2095 | UAUGCCACUCUCCAUGCUUUG | 220 | CAAAGCAUGGAGAGUGGCAUA | 524 | 35 |
| RD2050 | 2076 | 2096 | AGAUGCCACUCUCCAUGCUUU | 221 | AAAGCAUGGAGAGUGGCAUCU | 525 | 0 |
| RD2051 | 2131 | 2151 | UAUUGUCCUCAGCAGCUCUGA | 222 | UCAGAGCUGCUGAGGACAAUA | 526 | 0 |
| RD2064 | 172 | 192 | UCUACAUCCCCACUUCUGAAG | 223 | CUUCAGAAGUGGGGAUGUAGA | 527 | 48 |
| RD2065 | 173 | 193 | AGCUACAUCCCCAUCUCUGAA | 224 | UUCAGAGAUGGGGAUGUAGCU | 528 | 45 |
| RD2066 | 175 | 195 | UAAGCUACAUCCCUACCUCUG | 225 | CAGAGGUAGGGAUGUAGCUUA | 529 | 47 |
| RD2067 | 176 | 196 | UGAAGCUACAUCCUCACCUCU | 226 | AGAGGUGAGGAUGUAGCUUCA | 530 | 65 |
| RD2068 | 177 | 197 | UGGAAGCUACAUCUCCACCUC | 227 | GAGGUGGAGAUGUAGCUUCCA | 531 | 66 |
| RD2069 | 178 | 198 | AUGGAAGCUACAUUCCCACCU | 228 | AGGUGGGAAUGUAGCUUCCAU | 532 | 83 |
| RD2070 | 181 | 201 | UACAUGGAAGCUAUAUCCCCA | 229 | UGGGGAUAUAGCUUCCAUGUA | 533 | 79 |
| RD2071 | 242 | 262 | UAAUAGCAAACACUUUGGGUG | 230 | CACCCAAAGUGUUUGCUAUUA | 534 | 10 |
| RD2072 | 243 | 263 | UGAAUAGCAAACAUCUUGGGU | 231 | ACCCAAGAUGUUUGCUAUUCA | 535 | 90 |
| RD2073 | 245 | 265 | ACUGAAUAGCAAAUACCUUGG | 232 | CCAAGGUAUUUGCUAUUCAGU | 536 | 82 |
| RD2074 | 249 | 269 | UAAAACUGAAUAGUAAACACC | 233 | GGUGUUUACUAUUCAGUUUUA | 537 | 74 |
| RD2075 | 288 | 308 | UAAACCUUUUCUCUAUGUCAU | 234 | AUGACAUAGAGAAAAGGUUUA | 538 | 48 |
| RD2076 | 312 | 332 | UAACACUAUCUUUUAAGAAGC | 235 | GCUUCUUAAAAGAUAGUGUUA | 539 | 0 |
| RD2077 | 316 | 336 | UCUGUAACACUAUUUUUCAAG | 236 | CUUGAAAAAUAGUGUUACAGA | 540 | 0 |
| RD2078 | 438 | 458 | AAUUGACUCCUCUUAUAUCAA | 237 | UUGAUAUAAGAGGAGUCAAUU | 541 | 85 |
| RD2079 | 440 | 460 | AAAAUUGACUCCUUUCAUAUC | 238 | GAUAUGAAAGGAGUCAAUUUU | 542 | 76 |
| RD2080 | 442 | 462 | UUAAAAUUGACUCUUCUCAUA | 239 | UAUGAGAAGAGUCAAUUUUAA | 543 | 63 |
| RD2081 | 443 | 463 | AUUAAAAUUGACUUCUCUCAU | 240 | AUGAGAGAAGUCAAUUUUAAU | 544 | 29 |
| RD2082 | 445 | 465 | ACAUUAAAAUUGAUUCCUCUC | 241 | GAGAGGAAUCAAUUUUAAUGU | 545 | 28 |
| RD2083 | 473 | 493 | UCAUUCUUCAACAUUGCUAAC | 242 | GUUAGCAAUGUUGAAGAAUGA | 546 | 82 |
| RD2084 | 475 | 495 | UGGCAUUCUUCAAUACUGCUA | 243 | UAGCAGUAUUGAAGAAUGCCA | 547 | 71 |
| RD2085 | 478 | 498 | UUUUGGCAUUCUUUAACACUG | 244 | CAGUGUUAAAGAAUGCCAAAA | 548 | 86 |
| RD2086 | 631 | 651 | UAGAAUCCAGAUUUCACGUUA | 245 | UAACGUGAAAUCUGGAUUCUA | 549 | 52 |
| RD2087 | 637 | 657 | UUCAGUGAGAAUCUAGAUUCC | 246 | GGAAUCUAGAUUCUCACUGAA | 550 | 65 |
| RD2088 | 926 | 946 | UAAAGUUCUUUUGUAGGUUAA | 247 | UUAACCUACAAAAGAACUUUA | 551 | 0 |
| RD2089 | 932 | 952 | UUCAGGUAAAGUUUUUUUGCA | 248 | UGCAAAAAAACUUUACCUGAA | 552 | 8 |
| RD2090 | 943 | 963 | UAAUGGCAGGGUUUAGGUAAA | 249 | UUUACCUAAACCCUGCCAUUA | 553 | 82 |
| RD2091 | 950 | 970 | AAUUUUAGAAUGGUAGGGUUC | 250 | GAACCCUACCAUUCUAAAAUU | 554 | 81 |

TABLE 4-continued

Inhibition of PKK mRNA by double-stranded compounds targeting SEQ ID NO: 1

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: | PKK % inhibition |
| --- | --- | --- | --- | --- | --- | --- | --- |
| RD2092 | 969 | 989 | UAAAGUCAACUCCUGGGUAAA | 251 | UUUACCCAGGAGUUGACUUUA | 555 | 50 |
| RD2093 | 970 | 990 | UCAAAGUCAACUCUCGGGUAA | 252 | UUACCCGAGAGUUGACUUUGA | 556 | 65 |
| RD2094 | 971 | 991 | UCCAAAGUCAACUUCCGGGUA | 253 | UACCCGGAAGUUGACUUUGGA | 557 | 84 |
| RD2095 | 985 | 1005 | UUCAAUUCUUCUCUUCCAAAG | 254 | CUUUGGAAGAGAAGAAUUGAA | 558 | 91 |
| RD2096 | 986 | 1006 | AUUCAAUUCUUCUUCUCCAAA | 255 | UUUGGAGAAGAAGAAUUGAAU | 559 | 80 |
| RD2097 | 1020 | 1040 | UUUGGCAAACAUUUACUCCUU | 256 | AAGGAGUAAAUGUUUGCCAAA | 560 | 92 |
| RD2098 | 1050 | 1070 | ACUGACAGCGAAUUAUCUUUG | 257 | CAAAGAUAAUUCGCUGUCAGU | 561 | 92 |
| RD2099 | 1058 | 1078 | AGUGAAAAACUGAUAGCGAAU | 258 | AUUCGCUAUCAGUUUUUCACU | 562 | 74 |
| RD2100 | 1062 | 1082 | AAUAAGUGAAAAAUUGACAGC | 259 | GCUGUCAAUUUUUCACUUAUU | 563 | 78 |
| RD2101 | 1087 | 1107 | UCCUUACAGUCUUUUGGGAGU | 260 | ACUCCCAAAAGACUGUAAGGA | 564 | 36 |
| RD2103 | 1171 | 1191 | UAACCAGAGCUCCUUUGUGUC | 261 | GACACAAAGGAGCUCUGGUUA | 565 | 67 |
| RD2104 | 1172 | 1192 | UUAACCAGAGCUCUCUUGUGU | 262 | ACACAAGAGAGCUCUGGUUAA | 566 | 89 |
| RD2105 | 1175 | 1195 | AGAGUAACCAGAGUUCCCUUG | 263 | CAAGGGAACUCUGGUUACUCU | 567 | 93 |
| RD2106 | 1181 | 1201 | UCUCAAAGAGUAAUCAGAGCU | 264 | AGCUCUGAUUACUCUUUGAGA | 568 | 77 |
| RD2107 | 1197 | 1217 | UCCCAGUGUUACAUAAUCUCA | 265 | UGAGAUUAUGUAACACUGGGA | 569 | 44 |
| RD2108 | 1249 | 1269 | UUUGUUCCUCCAAUAAUGCGU | 266 | ACGCAUUAUUGGAGGAACAAA | 570 | 70 |
| RD2109 | 1252 | 1272 | UAGUUUGUUCCUCUAACAAUG | 267 | CAUUGUUAGAGGAACAAACUA | 571 | 49 |
| RD2110 | 1253 | 1273 | AGAGUUUGUUCCUUCAACAAU | 268 | AUUGUUGAAGGAACAAACUCU | 572 | 69 |
| RD2111 | 1255 | 1275 | UAAGAGUUUGUUCUUCCAACA | 269 | UGUUGGAAGAACAAACUCUUA | 573 | 48 |
| RD2112 | 1256 | 1276 | AGAAGAGUUUGUUUCUCCAAC | 270 | GUUGGAGAAACAAACUCUUCU | 574 | 78 |
| RD2113 | 1272 | 1292 | AGGGCCACUCUCCUCAAGAAG | 271 | CUUCUUGAGGAGAGUGGCCCU | 575 | 33 |
| RD2114 | 1273 | 1293 | UAGGGCCACUCUCUCCAAGAA | 272 | UUCUUGGAGAGAGUGGCCCUA | 576 | 59 |
| RD2115 | 1274 | 1294 | UCAGGGCCACUCUUCCCAAGA | 273 | UCUUGGGAAGAGUGGCCCUGA | 577 | 61 |
| RD2116 | 1331 | 1351 | UAGUGACCCUCCAUACAGGUG | 274 | CACCUGUAUGGAGGGUCACUA | 578 | 58 |
| RD2117 | 1334 | 1354 | UAUGAGUGACCCUUCACACAG | 275 | CUGUGUGAAGGGUCACUCAUA | 579 | 90 |
| RD2118 | 1336 | 1356 | UCUAUGAGUGACCUUCCACAC | 276 | GUGUGGAAGGUCACUCAUAGA | 580 | 76 |
| RD2119 | 1337 | 1357 | UCCUAUGAGUGACUCUCCACA | 277 | UGUGGAGAGUCACUCAUAGGA | 581 | 76 |
| RD2120 | 1338 | 1358 | UUCCUAUGAGUGAUCCUCCAC | 278 | GUGGAGGAUCACUCAUAGGAA | 582 | 81 |
| RD2121 | 1348 | 1368 | ACCCACUGGUGUCUUAUGAGU | 279 | ACUCAUAAGACACCAGUGGGU | 583 | 42 |
| RD2122 | 1349 | 1369 | UACCCACUGGUGUUCUAUGAG | 280 | CUCAUAGAACACCAGUGGGUA | 584 | 54 |
| RD2123 | 1441 | 1461 | UCUUUUGUAAUGUUUGACAGA | 281 | UCUGUCAAACAUUACAAAAGA | 585 | 90 |
| RD2124 | 1513 | 1533 | AUAUCAUGAUUCCUUUCUGAG | 282 | CUCAGAAAGGAAUCAUGAUAU | 586 | 59 |
| RD2125 | 1545 | 1565 | AAUUCAAAGGAGCUGGAGUU | 283 | AACUCCAAGCUCCUUUGAAUU | 587 | 78 |
| RD2126 | 1546 | 1566 | UAAUUCAAAGGAGUCUGGAGU | 284 | ACUCCAGACUCCUUUGAAUUA | 588 | 78 |
| RD2127 | 1844 | 1864 | UCCCACCAAACGCUACAUUCC | 285 | GGAAUGUAGCGUUUGGUGGGA | 589 | 40 |
| RD2128 | 1845 | 1865 | UGCCCACCAAACGUCACAUUC | 286 | GAAUGUGACGUUUGGUGGGCA | 590 | 64 |

TABLE 4-continued

Inhibition of PKK mRNA by double-stranded compounds targeting SEQ ID NO: 1

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: | PKK % inhibition |
|---|---|---|---|---|---|---|---|
| RD2129 | 1847 | 1867 | UAUGCCCACCAAAUGCCACAU | 287 | AUGUGGCAUUUGGUGGGCAUA | 591 | 76 |
| RD2130 | 1880 | 1900 | UUCCCUGCGGGCAUAGCCUUC | 288 | GAAGGCUAUGCCCGCAGGGAA | 592 | 71 |
| RD2131 | 1889 | 1909 | ACCAGGUUGCUCCUUGCGGGC | 289 | GCCCGCAAGGAGCAACCUGGU | 593 | 36 |
| RD2132 | 1890 | 1910 | UACCAGGUUGCUCUCUGCGGG | 290 | CCCGCAGAGAGCAACCUGGUA | 594 | 63 |
| RD2133 | 1891 | 1911 | ACACCAGGUUGCUUCCUGCGG | 291 | CCGCAGGAAGCAACCUGGUGU | 595 | 52 |
| RD2134 | 1893 | 1913 | AGACACCAGGUUGUUCCCUGC | 292 | GCAGGGAACAACCUGGUGUCU | 596 | 6 |
| RD2135 | 1915 | 1935 | AUGUACUCAGCGAUUUUGGUG | 293 | CACCAAAAUCGCUGAGUACAU | 597 | 82 |
| RD2136 | 1918 | 1938 | UCCAUGUACUCAGUGACUUUG | 294 | CAAAGUCACUGAGUACAUGGA | 598 | 83 |
| RD2137 | 1921 | 1941 | UAGUCCAUGUACUUAGCGACU | 295 | AGUCGCUAAGUACAUGGACUA | 599 | 71 |
| RD2138 | 1923 | 1943 | UCCAGUCCAUGUAUUCAGCGA | 296 | UCGCUGAAUACAUGGACUGGA | 600 | 68 |
| RD2139 | 1929 | 1949 | UUAAAAUCCAGUCUAUGUACU | 297 | AGUACAUAGACUGGAUUUUAA | 601 | 57 |
| RD2140 | 1930 | 1950 | UCUAAAAUCCAGUUCAUGUAC | 298 | GUACAUGAACUGGAUUUUAGA | 602 | 68 |
| RD2141 | 1942 | 1962 | UUCUGUGUUUUCUUUAAAAUC | 299 | GAUUUUAAAGAAAACACAGAA | 603 | 26 |
| RD2142 | 1944 | 1964 | UGCUCUGUGUUUUUUCUAAAA | 300 | UUUUAGAAAAAACACAGAGCA | 604 | 68 |
| RD2143 | 1953 | 1973 | UUCCAUCACUGCUUUGUGUUU | 301 | AAACACAAAGCAGUGAUGGAA | 605 | 85 |
| RD2144 | 2067 | 2087 | UCUCCAUGCUUUGUAGAUGAG | 302 | CUCAUCUACAAAGCAUGGAGA | 606 | 39 |
| RD2145 | 2072 | 2092 | UCCACUCUCCAUGUUUUGCAG | 303 | CUGCAAAACAUGGAGAGUGGA | 607 | 28 |
| RD2146 | 2076 | 2096 | AGAUGCCACUCUCUAUGCUUU | 304 | AAAGCAUAGAGAGUGGCAUCU | 608 | 0 |

Example 2—Dose-Dependent Inhibition of Human PKK in HEK-293T Cells

Compounds from the studies described above exhibiting significant in vitro inhibition of PKK mRNA were selected and tested at various doses in HEK-293T Cells as described above. Compounds were tested at concentrations of 0.01, 0.1, 1 and 10 nM and IC50 values were calculated (Table 5).

TABLE 5

| Compound Number | IC50 (nM) |
|---|---|
| RD1872 | 0.33 |
| RD1874 | 0.41 |
| RD1913 | 0.033 |
| RD1923 | 0.044 |
| RD1948 | 0.16 |
| RD1956 | 0.11 |
| RD1978 | 0.14 |
| RD1993 | 0.038 |
| RD1996 | 0.086 |
| RD2022 | 0.16 |
| RD2028 | 0.10 |

Example 3: Effect of Compounds Targeting Human PKK in Cynomolgus Monkeys

Compounds of interest, identified from in vitro gene expression screening, were evaluated in cynomolgus monkeys (Table 7). Prior to the study the monkeys were kept in quarantine during which the animals were observed daily for general health. Ten groups of 1 cynomolgus monkey each were injected with a single 6 mg/kg subcutaneous dose of oligonucleotide on Day 1 of the study. During the study period, the monkeys were observed daily for signs of illness or distress. Animals were bled on day −6 and on days 1 (prior to dosing), 4, 8, 15, 22, 29, 36, 43, 50, 57 and 64 for serum collection and analysis. The protocols described were approved by the Institutional Animal Care and Use Committee (IACUC). Circulating PKK levels were quantified using an ELISA specific for human angiotensinogen (and cross-reactive with cynomolgus), according to manufacturer's protocol (IBL America #27412). PKK inhibition data were expressed as percent of baseline value (Day 1 prior to dosing) (Table 8).

TABLE 6

Compound Sequence

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: |
|---|---|---|---|---|---|---|
| RD2305 | 660 | 682 | ACCAAUUUCUGAAAGGGCACAGG | 306 | UCCUGUGCCCUUUCAGAAAUUGGU | 610 |
| RD2306 | 988 | 1010 | UCACAUUCAAUUCUUCUCCUCCA | 307 | CGGAGGAGAAGAAUUGAAUGUGA | 611 |
| RD2307 | 1057 | 1079 | AAGUGAAAAACUGACAGCGAACC | 308 | UGGUUCGCUGUCAGUUUUUCACUU | 612 |
| RD2308 | 1140 | 1162 | AAUCCAGUUGGAGAACCAUCCG | 309 | CGGAUGGUUCUCCAACUAGGAUU | 613 |
| RD2309 | 1177 | 1199 | UCAAAGAGUAACCAGAGCUCCCU | 310 | UGGAGCUCUGGUUACUCUUUGA | 614 |
| RD2310 | 1424 | 1446 | UACAGAUUUAAAAUGCCACUGCG | 311 | UCGCAGUGGCAUUUUAAAUCUGUA | 615 |
| RD2311 | 1546 | 1568 | UGUAAUUCAAAGGAGCCUGGAGU | 312 | UCUCCAGGCUCCUUUGAAUUACA | 616 |
| RD2312 | 1895 | 1915 | UUAGACACCAGGUUGCUCCCU | 193 | UAGGGAGCAACCUGGUGUCUAA | 617 |
| RD2313 | 1924 | 1944 | AUCCAGUCCAUGUACUCAGCG | 199 | UCGCUGAGUACAUGGACUGGAU | 618 |
| RD2192 | 1549 | 1571 | UAGUGUAAUUCAAAGGAGCCUGG | 305 | CCAGGCUCCUUUGAAUUACACUA | 609 |

TABLE 7

Compound Chemistry

| Compound | Modified Strands (5'-3') | Ref ID NO: | SEQ ID NO: |
|---|---|---|---|
| RD2305 | mA*fC*mC.fA.mA.fU.mU.fU.mC.fU.mA.fA.mG.fG.mG.fC.mA.fC.mA*mG*mG | IA0812 | 306 |
|  | H1.mC*mC*mU*mG*mU.mG.mC.mC.fC.mU.fU.fU.fC.fA.mG.mA.mA.mA.mU.mU.mG.mG*mU*dQ | IS1001 | 610 |
| RD2306 | mU*fC*mA.fC.fU.mU.fC.mA.fA.fU.mC.fU.mU.fC.mU.fC.mC.fU.mC* mC*mA | IA0813 | 307 |
|  | H7.mG*mG*mA.mG.mG.mA.mG.fA.mA.fG.fA.fA.fU.mU.mG.mA.mA.mU.mG.mU.mG*mA*dQ | IS1002 | 611 |
| RD2307 | mA*fA*mG.fU.mG.fA.mA.fA.mA.fA.mC.fU.mG.fA.mC.fA.fG.fC.mG.fA.mA*mC*mC | IA0814 | 308 |
|  | H1.mG*mG*mU.mU.mC.mG.mC.mU.fG.mU.fC.fA.fG.fU.mU.mU.mU.mU.mC.mA.mC.mU*mU*dO | IS1003 | 612 |
| RD2309 | mU*fC*mA.fA.mA.fG.mA.fG.mU.fA.mA.fC.mC.fA.mG.fA.mG.fC.mU.fC.mC*mC*mU | IA0816 | 310 |
|  | H1.mG*mG*mA.mG.mC.mU.fC.mU.fG.fG.fU.fU.mA.mC.mU.mC.mU.mU.mU.mG* mA*dQ | IS1005 | 614 |
| RD2308 | mA*fA*mU.fC.mC.fU.mA.fG.mU.fU.mG.fG.mA.fG.mA.fA.mC.fC.mA.fU.mC* mC*mG | IA0815 | 309 |
|  | H7.mG.mG*mA*mU.mG.mG.mU.fU.mC.fU.fC.fC.fA.mA.mC.mU.mA.mG.mG.mA.mU*mU*dQ | IS1004 | 613 |
| RD2310 | mU*fA*mC.fA.mG.fA.mU.fU.mU.fA.mA.fA.mA.fU.mG.mG.fC.mC.fA.mC.fU.mG* mC*mG | IA0817 | 311 |
|  | H1.mC*mG*mC.mA.mG.mU.mG.mG.fC.mA.fU.fU.fU.fU.mA.mA.mA.mU.mC.mU. mG.mU*mA*dQ | IS1006 | 615 |
| RD2311 | mu*fG*mU.fA.mA.fU.mU.fC.mA.fA.mA.fG.mG.fA.mG.fC.mC.fU.mG.fG.mA*mG*mU | IA0818 | 312 |
|  | H1.mC*mU*mC.mC.mA.mG.mG.fC.mU.fC.fC.fU.fU.mU.mG.mA.mA.mU.mU.mA.mC*mA*dQ | IS1007 | 616 |
| RD2192 | mU*fA*mG.fU.mG.fU.mA.fA.mU.fU.mC.fA.mA.fA.mG.fG.mA.fG.mC.fC.mU*mG*mG | IA0819 | 305 |
|  | H6.mC*mA*mG.mG.mC.mU.mC.fC.mU.fU.fU.fG.fA.mA.mU.mU.mA.mC.mA.mC.mU*mA*dO | IS0925 | 609 |
| RD2312 | mU*fU*mA.fG.mA.fC.mA.fC.mC.fA.mG.fG.mU.fU.mG.fC.mU.fC.mC* fC*mU | IA0820 | 193 |

TABLE 7-continued

Compound Chemistry

| Compound | Modified Strands (5'-3') | Ref ID NO: | SEQ ID NO: |
|---|---|---|---|
| | H1.mA*mG*mG.mG.mA.mG. fC.mA.fA.fC.fC.fU.mG. mG.mU.mG.mU.mC.mU.mA* mA*dQ | IS1008 | 617 |
| RD2313 | mA*fU*mC.fC.mA.fG.mU. fC.mC.fA.mU.fG.mU.fA. mC.fU.mC.fA.mG*fC*mG | IA0821 | 199 |
| | H1.mC*mG*mC.mU.mG.mA. fG.mU.fA.fC.fA.fU.mG. mG.mA.mC.mU.mG.mG.mA* mU*dQ | IS1009 | 618 |

TABLE 8

Average PKK Inhibition

| Compound | Days | | | | | | | | | |
|---|---|---|---|---|---|---|---|---|---|---|
| | 4 | 8 | 15 | 22 | 29 | 36 | 43 | 50 | 57 | 64 |
| RD2305 | 1 | 0 | 2 | 37 | 11 | 5 | 0 | 0 | 0 | 0 |
| RD2306 | 43 | 60 | 74 | 88 | 89 | 84 | 72 | 70 | 72 | 63 |
| RD2307 | 35 | 54 | 60 | 69 | 70 | 79 | 55 | 54 | 55 | 50 |
| RD2309 | 18 | 58 | 47 | 69 | 58 | 71 | 44 | 54 | 49 | 45 |
| RD2308 | 47 | 32 | 33 | 42 | 44 | 45 | 28 | 24 | 20 | 18 |
| RD2310 | 4 | 37 | 46 | 64 | 69 | 72 | 59 | 62 | 58 | 53 |
| RD2311 | 29 | 55 | 74 | 85 | 92 | 92 | 80 | 75 | 71 | 63 |
| RD2192 | 20 | -6 | -46 | 26 | 2 | 18 | -4 | 5 | -6 | 0 |
| RD2312 | 34 | 42 | 74 | 78 | 75 | 72 | 59 | 51 | 57 | 54 |
| RD2313 | 33 | 50 | 75 | 90 | 84 | 93 | 82 | 82 | 83 | 84 |

Example 4: Effect of Compounds Targeting Human PKK in Cynomolgus Monkeys

Compounds of interest, identified from in vitro gene expression screening, were evaluated in cynomolgus monkeys (Table 10). Prior to the study the monkeys were kept in quarantine during which the animals were observed daily for general health. Eight groups of 2 cynomolgus monkey each were injected with a single 4 mg/kg subcutaneous dose of oligonucleotide on Day 1 of the study. During the study period, the monkeys were observed daily for signs of illness or distress. Animals were bled on day −6 and on days 1 (prior to dosing), 4, 8, and 15 for serum collection and analysis. Future collections will be on days 22, 29, 36, 43, 50, 57, 64, 71, 78 and 85. In a second set of experiments, animals were bled on day −6 and days 1 (prior to dosing), 4, 8, 15 and 22 for serum collection and analysis. Future collections for the second set of experiments will be on days 29, 36, 43, 50, 57, 64, 71, 78 and 85. In a third set of experiments, animals were bled on day −6 and days 1 (prior to dosing), 4, 8, 15, 22, 29 and 36 for serum collection and analysis. Future collections for the third set of experiments will be on days 43, 50, 57, 64, 71, 78 and 85. In a fourth set of experiments, animals were bled on day −6 and days 1 (prior to dosing), 4, 8, 15, 22, 29, 36, 43, 50, 57, 64, 71, 78 and 85 for serum collection and analysis. The protocols described were approved by the Institutional Animal Care and Use Committee (IACUC). Circulating PKK levels were quantified using an ELISA specific for human angiotensinogen (and cross-reactive with cynomolgus), according to manufacturer's protocol (IBL America #27412). PKK inhibition data were expressed as percent of baseline value (Day 1 prior to dosing) and as an average of the group for each compound. Results from the four sets of experiments are shown in Tables 11, 12, 13 and 14. Clinical chemistry was performed on Day −1 or Day −6 and Day 63 or 64 and Day 92. There were no test article-related effects on body weight (Table 15) and all serum chemistry values were within reference ranges (Table 16 and 17).

TABLE 9

Compound Sequence

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: |
|---|---|---|---|---|---|---|
| RD2423 | 1546 | 1568 | UGUAAUU CAAAGGA GCCUGGA GU | 312 | CUCCAGG CUCCUUU GAAUUAC A | 619 |
| RD2436 | 1546 | 1568 | UGUAAUU CAAAGGA GCCUGGA GU | 312 | UCUCCAG GCUCCUU UGAAUUA CA | 616 |
| RD2437 | 1546 | 1568 | UGUAAUU CAAAGGA GCCUGGA GU | 312 | UCUCCAG GCUCCUU UGAAUUA CAU | 620 |
| RD2438 | 1546 | 1568 | UGUAAUU CAAAGGA GCCUGGA GU | 312 | UCCAGGC UCCUUUG AAUUACA | 468 |
| RD2439 | 988 | 1010 | UCACAUU CAAUUCU UCUCCUC CA | 307 | UGGAGGA GAAGAAU UGAAUGU GA | 622 |
| RD2440 | 988 | 1010 | UCACAUU CAAUUCU UCUCCUC CA | 307 | UGGAGGA GAAGAAU UGAAUGU GAU | 623 |
| RD2442 | 1569 | 1591 | UCAUAUU GGUUUUU GGAAUUC AG | 313 | CUGAAUU CCAAAAA CCAAUAU GA | 624 |
| RD2492 | 1548 | 1568 | UGUAAUU CAAAGGA GCCUGGA | 164 | UUCCUUU GAAUUAC A | 625 |

TABLE 10

Compound Chemistry

| Compound | Modified Strands (5'-3') | Ref ID NO: | SEQ ID NO: |
|---|---|---|---|
| RD2423 | mu*fG*mU.fA.mA.fU. mU.fC.mA.fA.mA.fG. mG.fA.mG.fC.mC.fU. mG.fG.mA*mG*mU | IA0818 | 312 |
| | H9*mU*mC.mC.mA.mG. mG.fC.mU.fC.fC.fU. fU.mU.mG.mA.mA.mU. mU.mA.mC*mA*dQ | IS1058 | 619 |

TABLE 10-continued

Compound Chemistry

| Compound | Modified Strands (5'-3') | Ref ID NO: | SEQ ID NO: |
|---|---|---|---|
| RD2436 | mu*fG*mU.fA.mA.fU.mU.fC.mA.fA.mA.fG.mG.fA.mG.fC.mC.fU.mG.fG.mA*mG*mU | IA0818 | 312 |
|  | H2*mC*mU.mC.mC.mA.mG.mG.fC.mU.fC.fC.fU.fU.mU.mG.mA.mA.mU.mU.mA.mC*mA*dQ | IS1066 | 616 |
| RD2437 | mu*fG*mU.fA.mA.fU.mU.fC.mA.fA.mA.fG.mG.fA.mG.fC.mC.fU.mG.fG.mA*mG*mU | IA0818 | 312 |
|  | H2*mC*mU.mC.mC.mA.mG.mG.fC.mU.fC.fC.fU.fU.mU.mG.mA.mA.mU.mU.mA.mC.mA*mU*dQ | IS1067 | 620 |
| RD2438 | mu*fG*mU.fA.mA.fU.mU.fC.mA.fA.mA.fG.mG.fA.mG.fC.mC.fU.mG.fG.mA*mG*mU | IA0818 | 312 |
|  | H2*mC*mC.mA.mG.mG.fC.mU.fC.fC.fU.fU.mU.mG.mA.mA.mU.mU.mA.mC*mA*dQ | IS1068 | 468 |
| RD2439 | mU*fC*mA.fC.mA.fU.mU.fC.mA.fA.mU.fU.mC.fU.mU.fC.mU.fC.mC.fU.mC*mC*mA | IA0813 | 307 |
|  | H2*mG*mG.mA.mG.mG.mA.mG.fA.mA.fG.fA.fA.fU.mU.mG.mA.mA.mU.mG.mU.mG*mA*dQ | IS1069 | 622 |
| RD2440 | mU*fC*mA.fC.mA.fU.mU.fC.mA.fA.mU.fU.mC.fU.mU.fC.mU.fC.mC.fU.mC*mC*mA | IA0813 | 307 |
|  | H2*mG*mG.mA.mG.mG.mA.mG.fA.mA.fG.fA.fA.fU.mU.mG.mA.mA.mU.mG.mU.mG.mA*mU*dQ | IS1070 | 623 |
| RD2442 | mU*fC*mA.fU.mA.fU.mU.fG.mG.fU.mU.fU.mU.fU.mG.fG.mA.fA.mU.fU.mC*mA*mG | IA0828 | 313 |
|  | H9*mU*mG.mA.mA.mU.mU.mC.fC.mA.fA.fA.fA.fA.mC.mC.mA.mA.mU.mA.mU.mG*mA*dQ | IS1072 | 624 |
| RD2492 | mU*fG*mU.fA.mA.fU.mU.fC.mA.fA.mA.fG.mG.fA*mG*fC*mC*fU*mG*fG*mA | IA0867 | 164 |

TABLE 10-continued

Compound Chemistry

| Compound | Modified Strands (5'-3') | Ref ID NO: | SEQ ID NO: |
|---|---|---|---|
|  | H2*mU.fC.fC.fU.fU.mU.mG.mA.mA.mU.mU.mA.mC.mA*dQ | IS1074 | 625 |

TABLE 11

Average PKK Inhibition

| Compound | Days | | |
|---|---|---|---|
|  | 4 | 8 | 15 |
| RD2423 | 28 | 52 | 66 |
| RD2436 | 22 | 43 | 67 |
| RD2437 | 62 | 45 | 66 |
| RD2438 | 21 | 50 | 77 |
| RD2439 | 26 | 43 | 55 |
| RD2440 | 21 | 31 | 46 |
| RD2442 | 20 | 41 | 71 |
| RD2492 | 23 | 37 | 55 |

TABLE 12

Average PKK Inhibition

| Compound | Days | | | |
|---|---|---|---|---|
|  | 4 | 8 | 15 | 22 |
| RD2423 | 26 | 51 | 79 | 85 |
| RD2436 | 20 | 40 | 69 | 76 |
| RD2437 | 5 | 33 | 64 | 75 |
| RD2438 | 30 | 49 | 74 | 81 |
| RD2439 | 4 | 36 | 58 | 64 |
| RD2440 | 4 | 27 | 46 | 39 |
| RD2442 | 9 | 39 | 63 | 70 |
| RD2492 | 17 | 33 | 52 | 54 |

TABLE 13

Average PKK Inhibition

| Compound | Days | | | | | |
|---|---|---|---|---|---|---|
|  | 4 | 8 | 15 | 22 | 29 | 36 |
| RD2423 | 26 | 51 | 79 | 85 | 85 | 84 |
| RD2436 | 20 | 40 | 69 | 76 | 77 | 79 |
| RD2437 | 5 | 33 | 64 | 75 | 77 | 79 |
| RD2438 | 30 | 49 | 74 | 81 | 76 | 76 |
| RD2439 | 4 | 36 | 58 | 64 | 63 | — |
| RD2440 | 4 | 27 | 46 | 39 | 47 | — |
| RD2442 | 9 | 39 | 63 | 70 | 67 | — |
| RD2492 | 17 | 33 | 52 | 54 | 52 | — |

TABLE 14

Average PKK Inhibition

| Compound | Day 4 | Day 8 | Day 15 | Day 22 | Day 29 | Day 36 | Day 43 | Day 50 | Day 57 | Day 64 | Day 71 | Day 78 | Day 85 |
|---|---|---|---|---|---|---|---|---|---|---|---|---|---|
| RD2423 | 14 | 41 | 74 | 88 | 91 | 90 | 88 | 92 | 81 | 85 | 87 | 80 | 68 |
| RD2436 | 20 | 40 | 69 | 76 | 77 | 79 | 73 | 77 | 76 | 69 | 61 | 64 | 37 |
| RD2437 | 5 | 33 | 64 | 75 | 77 | 79 | 70 | 80 | 79 | 71 | 70 | 68 | 54 |
| RD2438 | 30 | 49 | 74 | 81 | 76 | 76 | 68 | 71 | 60 | 52 | 42 | 36 | |
| RD2439 | 4 | 36 | 58 | 64 | 63 | 58 | 65 | 66 | | | | | |
| RD2440 | 4 | 27 | 46 | 39 | 47 | | | | | | | | |
| RD2442 | 9 | 39 | 63 | 70 | 67 | 73 | 72 | 72 | 71 | 59 | 60 | 62 | 56 |
| RD2492 | 17 | 33 | 52 | 54 | 52 | | | | | | | | |

TABLE 15

Body Weight (kg)

| Compound | Day −1 | Day 63 | Day 91 |
|---|---|---|---|
| RD2423 Cyno#1 | 2.4 | 2.4 | 2.4 |
| RD2423 Cyno#2 | 2.6 | 2.6 | 2.7 |
| RD2436 Cyno#1 | 2.9 | 3.1 | 3.2 |
| RD2436 Cyno#2 | 2.5 | 2.6 | 2.7 |
| RD2437 Cyno#1 | 3.1 | 3.2 | 3.2 |
| RD2437 Cyno#2 | 2.6 | 2.7 | 2.9 |
| RD2438 Cyno#1 | 3.2 | 3.2 | 3.4 |
| RD2438 Cyno#2 | 2.5 | 2.6 | 2.6 |
| RD2439 Cyno#1 | 3.6 | 4.1 | N/A |
| RD2439 Cyno#2 | 2.7 | 2.8 | N/A |
| RD2440 Cyno#1 | 3.9 | 4.3 | N/A |
| RD2440 Cyno#2 | 2.3 | 2.4 | N/A |
| RD2442 Cyno#1 | 4.4 | 4.5 | 4.6 |
| RD2442 Cyno#2 | 2.3 | 2.4 | 2.5 |
| RD2492 Cyno#1 | 4 | 4 | N/A |
| RD2492 Cyno#2 | 2.3 | 2.3 | N/A |

TABLE 16

Liver Function Markers

| | ALT (U/L) | | | AST (U/L) | | | Bilirubin (mg/dL) | | | Albumin (g/dL) | | |
|---|---|---|---|---|---|---|---|---|---|---|---|---|
| Compound | Day −6 | Day 64 | Day 92 | Day −6 | Day 64 | Day 92 | Day −6 | Day 64 | Day 92 | Day −6 | Day 64 | Day 92 |
| RD2423 Cyno#1 | 47 | 47 | 51 | 53 | 46 | 46 | 0.25 | 0.26 | 0.28 | 4.3 | 4.5 | 4.5 |
| RD2423 Cyno#2 | 76 | 75 | 58 | 69 | 65 | 46 | 0.15 | 0.36 | 0.27 | 4.0 | 4.3 | 3.9 |
| RD2436 Cyno#1 | 25 | 22 | 25 | 45 | 48 | 39 | 0.24 | 0.34 | 0.32 | 4.5 | 4.3 | 4.1 |
| RD2436 Cyno#2 | 65 | 73 | 78 | 64 | 41 | 42 | 0.19 | 0.23 | 0.25 | 4.4 | 4.5 | 4.5 |
| RD2437 Cyno#1 | 41 | 40 | 51 | 39 | 43 | 43 | 0.24 | 0.28 | 0.27 | 4.3 | 4.5 | 4.4 |
| RD2437 Cyno#2 | 55 | 51 | 50 | 55 | 57 | 48 | 0.14 | 0.24 | 0.26 | 4.5 | 4.6 | 4.4 |
| RD2438 Cyno#1 | 66 | 64 | 64 | 101 | 62 | 50 | 0.18 | 0.17 | 0.17 | 4.2 | 4.5 | 4.2 |
| RD2438 Cyno#2 | 25 | 21 | 25 | 38 | 33 | 33 | 0.33 | 0.44 | 0.53 | 4.8 | 4.6 | 4.5 |
| RD2439 Cyno#1 | 80 | 64 | N/A | 87 | 48 | N/A | 0.16 | 0.16 | N/A | 4.4 | 4.6 | N/A |
| RD2439 Cyno#2 | 105 | 88 | N/A | 49 | 54 | N/A | 0.15 | 0.23 | N/A | 4.5 | 4.4 | N/A |
| RD2440 Cyno#1 | 66 | 48 | N/A | 115 | 52 | N/A | 0.32 | 0.30 | N/A | 4.4 | 4.6 | N/A |
| RD2440 Cyno#2 | 50 | 58 | N/A | 45 | 48 | N/A | 0.25 | 0.39 | N/A | 4.8 | 5.0 | N/A |
| RD2442 Cyno#1 | 66 | 61 | 69 | 54 | 38 | 55 | 0.17 | 0.17 | 0.30 | 4.1 | 4.2 | 4.1 |
| RD2442 Cyno#2 | 63 | 70 | 70 | 51 | 54 | 56 | 0.21 | 0.23 | 0.17 | 4.3 | 4.4 | 4.3 |
| RD2492 Cyno#1 | 57 | 39 | N/A | 84 | 38 | N/A | 0.12 | 0.17 | N/A | 4.2 | 4.2 | N/A |
| RD2492 Cyno#2 | 92 | 78 | N/A | 72 | 85 | N/A | 0.18 | 0.27 | N/A | 4.7 | 4.5 | N/A |

TABLE 17

Kidney Function Markers

| Compound | BUN (mg/dL) | | | Creatinine (mg/dL) | | |
|---|---|---|---|---|---|---|
| | Day −6 | Day 64 | Day 92 | Day −6 | Day 64 | Day 92 |
| RD2423 Cyno#1 | 24 | 20 | 18 | 0.51 | 0.62 | 0.58 |
| RD2423 Cyno#2 | 34 | 30 | 28 | 0.51 | 0.61 | 0.55 |
| RD2436 Cyno#1 | 27 | 26 | 23 | 0.48 | 0.49 | 0.47 |
| RD2436 Cyno#2 | 22 | 19 | 19 | 0.46 | 0.51 | 0.56 |
| RD2437 Cyno#1 | 31 | 24 | 21 | 0.61 | 0.71 | 0.75 |
| RD2437 Cyno#2 | 25 | 21 | 23 | 0.48 | 0.48 | 0.43 |
| RD2438 Cyno#1 | 23 | 27 | 20 | 0.46 | 0.64 | 0.61 |
| RD2438 Cyno#2 | 21 | 18 | 22 | 0.50 | 0.47 | 0.46 |
| RD2439 Cyno#1 | 21 | 21 | N/A | 0.53 | 0.63 | N/A |
| RD2439 Cyno#2 | 28 | 27 | N/A | 0.39 | 0.36 | N/A |
| RD2440 Cyno#1 | 23 | 24 | N/A | 0.53 | 0.74 | N/A |
| RD2440 Cyno#2 | 24 | 19 | N/A | 0.32 | 0.44 | N/A |
| RD2442 Cyno#1 | 30 | 26 | 25 | 0.57 | 0.75 | 0.62 |
| RD2442 Cyno#2 | 28 | 30 | 27 | 0.50 | 0.61 | 0.59 |
| RD2492 Cyno#1 | 23 | 22 | N/A | 0.52 | 0.59 | N/A |
| RD2492 Cyno#2 | 33 | 26 | N/A | 0.66 | 0.44 | N/A |

Example 5: Effect of Compounds Targeting Human PKK in Cynomolgus Monkeys

Compounds of interest were evaluated in cynomolgus monkeys (Table 19). Prior to the study the monkeys were kept in quarantine during which the animals were observed daily for general health. Eight groups of 2 cynomolgus monkey each were injected with a single 4 mg/kg subcutaneous dose of oligonucleotide on Day 1 of the study. During the study period, the monkeys were observed daily for signs of illness or distress. Animals were bled on day −6 and on days 1 (prior to dosing), 8, 15 and 22 for serum collection and analysis. Future collections will be on days 29, 36, 43, 50, 57, 64 and 71. In a second set of experiments, animals were bled on day −6 and days 1 (prior to dosing), 8, 15, 22, 29, 36, 43, 50, 57, 64 and 71. The protocols described were approved by the Institutional Animal Care and Use Committee (IACUC). Circulating PKK levels were quantified using an ELISA specific for human angiotensinogen (and cross-reactive with cynomolgus), according to manufacturer's protocol (IBL America #27412). PKK inhibition data were expressed as percent of baseline value (Day 1 prior to dosing) and as an average of the group for each compound. Results from the two sets of experiments are shown in Tables 20 and 21. Clinical chemistry was performed on Day −1 or Day −6 and Day 64 and Day 92. There were no test article-related effects on body weight (Table 22) and all serum chemistry values were within reference ranges (Tables 23 and 24).

TABLE 18

Compound Sequence

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: |
|---|---|---|---|---|---|---|
| RD2424 | 630 | 652 | UGAGAA UCCAGA UUCCAC GUUAC | 626 | UAACGU GGAAUC UGGAUU CUCA | 629 |
| RD2425 | 689 | 711 | UCAAGA UGCUGG AAGAUG UUCAU | 627 | UGAACA CUCUUC AGCAUC UUGA | 630 |
| RD2426 | 1183 | 1205 | ACAAUC UCAAAG AGUAAC CAGAG | 628 | CUCUGG UUACUC UUUGAG AUUGU | 631 |

TABLE 19

Compound Chemistry

| Compound | Modified Strands (5'-3') | Ref ID NO: | SEQ ID NO: |
|---|---|---|---|
| RD2424 | mu*fG*mA.fG.mA.fA. mU.fC.mC.fA.mG.fA. mU.fU.mC.fC.mA.fC. mG.fU.mU*mA*mC | IA0864 | 626 |
| | H4*mA*mA.mC.mG.mU. mG.fG.mA.fA.fU.fC. fU.mG.mG.mA.mU.mU. mC.mU.mC*mA*dQ | IS1059 | 629 |
| RD2425 | mU*fC*mA.fA.mG.fA. mU.fG.mC.fU.mG.fG. mA.fA.mG.fA.mU.fG. mU.fU.mC*mA*mU | IA0865 | 627 |
| | H4*mG*mA.mA.mC.mA. mU.fC.mU.fU.fC.fC. fA.mG.mC.mA.mU.mC. mU.mU.mG*mA*dO | IS1060 | 630 |
| RD2426 | mA*fC*mA.fA.mU.fC. mU.fC.mA.fA.mA.fG. mA.fG.mU.fA.mA.fC. mC.fA.mG*mA*mG | IA0866 | 628 |
| | H9*mU*mC.mU.mG.mG. mU.mU.fA.mC.fU.fC. fU.fU.mU.mG.mA.mG. mA.mU.mU.mG*mU*dQ | IS1061 | 631 |

TABLE 20

Average PKK Inhibition

| Compound | Days | | |
|---|---|---|---|
| | 8 | 15 | 22 |
| RD2424 | 53 | 80 | 87 |
| RD2425 | 31 | 60 | 69 |
| RD2426 | 30 | 54 | 58 |

TABLE 22

| Body Weight (kg) | | | |
|---|---|---|---|
| Compound | Day −1 | Day 64 | Day 92 |
| RD2424 Cyno#1 | 3.1 | 3.1 | 3.1 |
| RD2424 Cyno#2 | 3.2 | 3.6 | 3.7 |
| RD2425 Cyno#1 | 2.9 | 3.3 | N/A |
| RD2425 Cyno#2 | 3.1 | 3.5 | N/A |
| RD2426 Cyno#1 | 3.5 | 3.9 | N/A |
| RD2426 Cyno#2 | 2.8 | 3.2 | N/A |

TABLE 21

| Average PKK Inhibition | | | | | | | | | | |
|---|---|---|---|---|---|---|---|---|---|---|
| Compound | Day 8 | Day 15 | Day 22 | Day 29 | Day 36 | Day 43 | Day 50 | Day 57 | Day 64 | Day 71 |
| RD2424 | 71 | 87 | 94 | 91 | 91 | 84 | 88 | 80 | 79 | 74 |
| RD2425 | 42 | 60 | 76 | 73 | 80 | 75 | 72 | 72 | 68 | |
| RD2426 | 30 | 54 | 58 | 57 | | 57 | 65 | 58 | 58 | |

TABLE 23

| | Liver Function Markers | | | | | | | | | | | |
|---|---|---|---|---|---|---|---|---|---|---|---|---|
| | ALT (U/L) | | | AST (U/L) | | | Bilirubin (mg/dL) | | | Albumin (g/dL) | | |
| Compound | Day −6 | Day 64 | Day 92 | Day −6 | Day 64 | Day 92 | Day −6 | Day 64 | Day 92 | Day −6 | Day 64 | Day 92 |
| RD2424 Cyno#1 | 58 | N/A | 65 | 50 | N/A | 45 | <0.2 | N/A | <0.2 | 4.3 | N/A | 4.4 |
| RD2424 Cyno#2 | 50 | N/A | 42 | 34 | N/A | 32 | 0.3 | N/A | 0.2 | 4.5 | N/A | 4.5 |
| RD2425 Cyno#1 | 57 | 49 | N/A | 49 | 38 | N/A | 0.2 | <0.2 | N/A | 4.2 | 4.2 | N/A |
| RD2425 Cyno#2 | 37 | 42 | N/A | 39 | 39 | N/A | 0.4 | 0.2 | N/A | 4.5 | 4.5 | N/A |
| RD2426 Cyno#1 | 46 | 40 | N/A | 46 | 40 | N/A | 0.2 | 0.3 | N/A | 4.2 | 4.6 | N/A |
| RD2426 Cyno#2 | 68 | 52 | N/A | 68 | 52 | N/A | 0.3 | <0.2 | N/A | 4.4 | 4.4 | N/A |

TABLE 24

| | Kidney Function Markers | | | | | |
|---|---|---|---|---|---|---|
| | BUN (mg/dL) | | | Creatinine (mg/dL) | | |
| Compound | Day −6 | Day 64 | Day 92 | Day −6 | Day 64 | Day 92 |
| RD2424 Cyno#1 | 22 | N/A | 14 | 0.5 | N/A | 0.5 |
| RD2424 Cyno#2 | 22 | N/A | 18 | 0.8 | N/A | 0.8 |
| RD2425 Cyno#1 | 21 | 15 | N/A | 0.4 | 0.4 | N/A |
| RD2425 Cyno#2 | 28 | 22 | N/A | 0.6 | 0.5 | N/A |
| RD2426 Cyno#1 | 23 | 20 | N/A | 0.6 | 0.6 | N/A |
| RD2426 Cyno#2 | 31 | 26 | N/A | 0.7 | 0.5 | N/A |

Example 6: Effect of Compounds Targeting Human PKK in Lewis Rats

Female Lewis rats (5 females/group, 8 weeks of age) were given single subcutaneous SC injections of 0 (Vehicle Control (phosphate buffered saline (PBS)), 200 mg/kg RD2423 or 200 mg/kg RD2438 at a dose volume of mL/kg to groups 1-3, respectively, on Day 1. Observations included viability, clinical signs and body weight (Days 1 and 10). Blood samples were collected for clinical chemistry (Day 0 (pre-dose), 3 and 10), hematology (Day 10) and coagulation (Day 10). On Day 10, heart, liver, and both kidneys were harvested from each rat and fixed in 10% neutral buffered formalin after weighing.

Results: There were no drug-related effects on viability, clinical observations, body weight or organ weight (heart, liver, and kidneys), clinical chemistry, hematology or coagulation (prothrombin clotting time) parameters. A single subcutaneous administration of 200 mg/kg of compounds RD2423 or RD2438 to female Lewis rats was well tolerated.

SEQ ID NO: 1

AGTGCCACATTAGAACAGCTTGAAGACCGTTCATTT

TTAAGTGACAAGAGACTCACCTCCAAGAAGCAATT

GTGTTTTCAGAATGATTTTATTCAAGCAAGCAACT

TATTTCATTTCCTTGTTTGCTACAGTTTCCTGTGG

ATGTCTGACTCAACTCTATGAAAACGCCTTCTTCA

GAGGTGGGATGTAGCTTCCATGTACACCCCAAAT

GCCCAATACTGCCAGATGAGGTGCACATTCCACCC

AAGGTGTTTGCTATTCAGTTTTCTTCCAGCAAGTT

CAATCAATGACATGGAGAAAAGGTTTGGTTGCTTC

TTGAAAGATAGTGTTACAGGAACCCTGCCAAAAGT

ACATCGAACAGGTGCAGTTTCTGGACATTCCTTGA

AGCAATGTGGTCATCAAATAAGTGCTTGCCATCGA

```
GACATTTATAAAGGAGTTGATATGAGAGGAGTCAA

TTTTAATGTGTCTAAGGTTAGCAGTGTTGAAGAAT

GCCAAAAAGGTGCACCAGTAACATTCGCTGCCAG

ITTTTTTCATATGCCACGCAAACATTTCACAAGGC

AGAGTACCGGAACAATTGCCTATTAAAGTACAGTC

CCGGAGGAACACCTACCGCTATAAAGGTGCTGAGT

AACGTGGAATCTGGATTCTCACTGAAGCCCTGTGC

CCTTTCAGAAATTGGTTGCCACATGAACATCTTCC

AGCATCTTGCGTTCTCAGATGTGGATGTTGCCAGG

GTTCTCACTCCAGATGCTTTTGTGTGTCGGACCAT

CTGCACCTATCACCCCAACTGCCTCTTCTTTACAT

TCTATACAAATGTATGGAAAATCGAGTCACAAAGA

AATGTTTGTCTTCTTAAAACATCTGAAAGTGGCAC

ACCAAGTTCCTCTACTCCTCAAGAAAACACCATAT

CTGGATATAGCCTTTTAACCTGCAAAAGAACTTTA

CCTGAACCCTGCCATTCTAAAATTTACCCGGGAGT

TGACTTTGGAGGAGAAGAATTGAATGTGACTTTTG

TTAAAGGAGTGAATGTTTGCCAAGAGACTTGCACA

AAGATGATTCGCTGTCAGTTTTTCACTTATTCTTT

ACTCCCAGAAGACTGTAAGGAAGAGAAGTGTAAGT

GTTTCTTAAGATTATCTATGGATGGTTCTCCAACT

AGGATTGCGTATGGGACACAAGGGAGCTCTGGTTA

CTCTTTGAGATTGTGTAACACTGGGGACAACTCTG

TCTGCACAACAAAAACAAGCACACGCATTGTTGGA

GGAACAAACTCTTCTTGGGGAGAGTGGCCCTGGCA

GGTGAGCCTGCAGGTGAAGCTGACAGCTCAGAGGC
```

```
ACCTGTGTGGAGGGTCACTCATAGGACACCAGTGG

GTCCTCACTGCTGCCCACTGCTTTGATGGGCTTCC

CCTGCAGGATGTTTGGCGCATCTATAGTGGCATTT

TAAATCTGTCAGACATTACAAAAGATACACCTTTC

TCACAAATAAAAGAGATTATTATTCACCAAAACTA

TAAAGTCTCAGAAGGGAATCATGATATCGCCTTGA

TAAAACTCCAGGCTCCTTTGAATTACACTGAATTC

CAAAAACCAATATGCCTACCTTCCAAAGGTGACAC

AAGCACAATTTATACCAACTGTTGGGTAACCGGAT

GGGGCTTCTCGAAGGAGAAAGGTGAAATCCAAAAT

ATTCTACAAAAGGTAAATATTCCTTTGGTAACAAA

TGAAGAATGCCAGAAAAGATATCAAGATTATAAAA

TAACCCAACGGATGGTCTGTGCTGGCTATAAAGAA

GGGGGAAAAGATGCTTGTAAGGGAGATTCAGGTGG

TCCCTTAGTTTGCAAACACAATGGAATGTGGCGTT

TGGTGGGCATCACCAGCTGGGGTGAAGGCTGTGCC

CGCAGGGAGCAACCTGGTGTCTACACCAAAGTCGC

TGAGTACATGGACTGGATTTTAGAGAAAACACAGA

GCAGTGATGGAAAAGCTCAGATGCAGTCACCAGCA

TGAGAAGCAGTCCAGAGTCTAGGCAATTTTTACAA

CCTGAGTTCAAGTCAAATTCTGAGCCTGGGGGGTC

CTCATCTGCAAAGCATGGAGAGTGGCATCTTCTTT

GCATCCTAAGGACGAAAAACACAGTGCACTCAGAG

CTGCTGAGGACAATGTCTGGCTGAAGCCCGCTTTC

AGCACGCCGTAACCAGGGGCTGACAATGCGAGGTC

GCAACTGAGATCTCCATGACTGTGTGTTGTGAAAT

AAAATGGTGAAAGATCA
```

---

What is claimed is:

1. A compound comprising a first modified oligonucleotide 14 to 23 linked nucleosides in length having a nucleobase sequence comprising at least 14 contiguous nucleobases of the nucleobase sequence of SEQ ID NO: 619 and a second modified oligonucleotide having a region of complementarity to the first modified oligonucleotide, wherein one or more GalNAc are attached to the 2' or 3' position of the ribosyl ring of the 5' nucleoside of the first modified oligonucleotide, wherein the second modified oligonucleotide consists of the formula:

mU*fG*mU.fA.mA.fU.mU.fC.mA.fA.mA.
   fG.mG.fA.mG.fC.mC.fU.
      mG.fG.mA*mG*mU   (SEQ ID NO: 312), wherein:
'A' is a nucleoside having an adenine nucleobase, 'G' is a nucleoside having a guanine nucleobase, 'C' is a nucleoside having a cytosine nucleobase, and '11' is a nucleoside having a uracil nucleobase;
'm' is a 2'-O-methyl sugar modification;
'f' is a 2'-F sugar modification;
'*' is a phosphorothioate internucleoside linkage; and
'.' is a phosphate internucleoside linkage.

2. The compound of claim 1, wherein the first modified oligonucleotide is 22 to 23 linked nucleosides in length having a nucleobase sequence comprising the nucleobase sequence of SEQ ID NO: 619.

3. The compound of claim 2, wherein the region of complementarity between the first modified oligonucleotide and the second modified oligonucleotide is 19 to 23 linked nucleosides in length.

4. The compound of claim 1, wherein at least one internucleoside linkage of the first modified oligonucleotide is a phosphorothioate internucleoside linkage or a methylphosphonate internucleoside linkage.

5. The compound of claim 4, wherein the phosphorothioate internucleoside linkage or methylphosphonate internucleoside linkage is at the 3' terminus of the first modified oligonucleotide or at the 5' terminus of the first modified oligonucleotide.

6. The compound of claim 1, wherein the first modified oligonucleotide comprises a modification selected from group consisting of LNA, cEt, 2'-MOE, 2'-F, 2'-OMe, and 2'-deoxy, or a combination thereof.

7. The compound of claim 1, wherein the first modified oligonucleotide comprises no more than five 2'-F sugar modifications.

8. The compound of claim 1, wherein the 5' nucleoside of the first modified oligonucleotide is of the following formula:

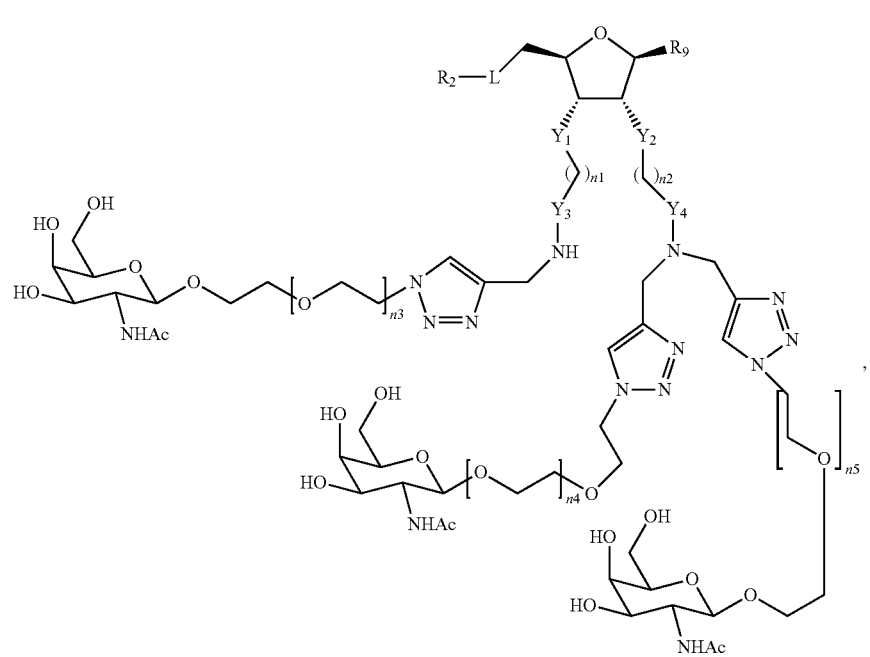

Formula X wherein:
R⁹ is H, adenine, guanine, thymine, cytosine, or uracil, or adenine, guanine, thymine, cytosine, or uracil, each comprising a Protecting Group (PG), a modified nucleobase, optionally substituted alkyl, optionally substituted aryl, optionally substituted heteroaryl, optionally substituted carbocyclyl, optionally substituted heterocyclyl, or a nucleobase isostere;
L is a bond, a phosphodiester bond, a phosphorothioate bond, a triazole, a tetrazole, an amide, a reverse-amide, a carbamate, a carbonate, urea, alkyl, or heteroalkyl;
$R^2$ is the oligonucleotide sequence;
$Y^1$ is O, $CH_2$, $CH_2O$, or optionally substituted NH;
$Y_2$ is O, $CH_2$, $CH_2O$, or optionally substituted NH;
$Y_3$ is CO, $SO_2$, P(O)O, $CH_2$—O—C(O), $CH_2$—NH—C(O), $CH_2$—NH—$SO_2$, or $CH_2$;
$Y_4$ is CO, $SO_2$, P(O)O, $CH_2$—O—C(O), $CH_2$—NH—C(O), $CH_2$—NH—$SO_2$, or $CH_2$;
$n_2$ is 0, 1, 2, 3, 4, 5, or 6; and
each $n_1$, $n_3$, $n_4$ and $n_5$ is independently 0, 1, 2, 3, 4, 5, 6, 7, 8, 9, or 10.

9. The compound of claim 1, wherein the first modified oligonucleotide is 19 to 23 linked nucleosides in length having a nucleobase sequence comprising at least 19 contiguous nucleobases of the nucleobase sequence of SEQ ID NO: 619.

10. The compound of claim 1, wherein the first modified oligonucleotide has a nucleobase sequence consisting of the nucleobase sequence of SEQ ID NO: 619.

11. The compound of claim 1, wherein the compound is of the following chemical structure:

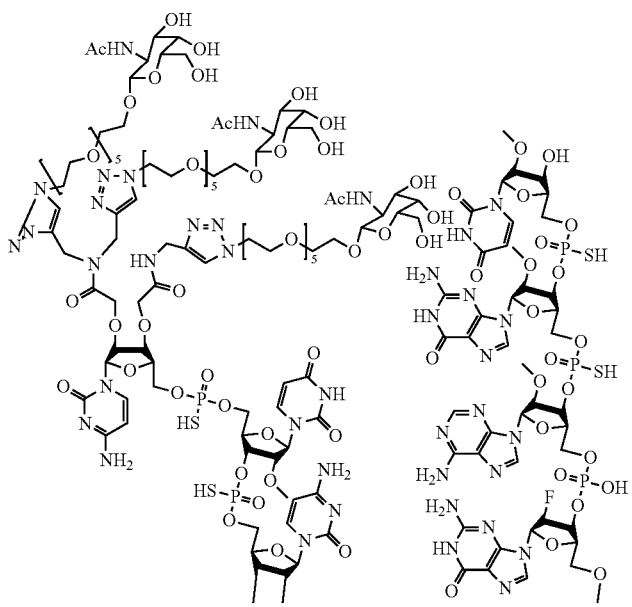

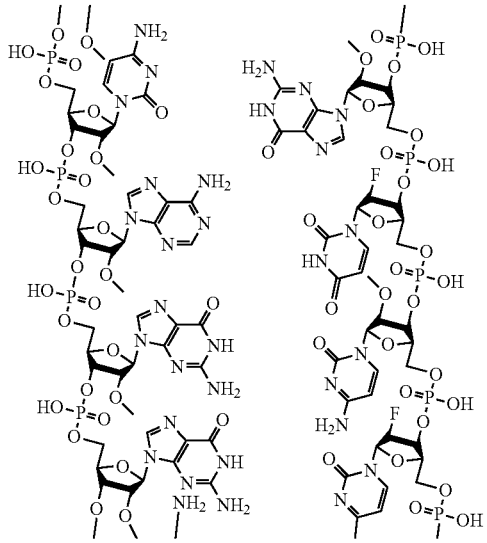

301
302
-continued
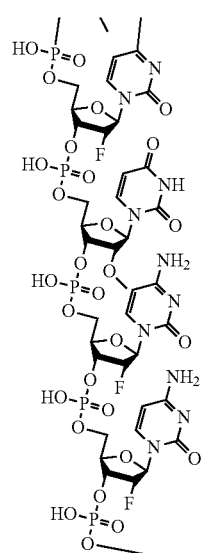
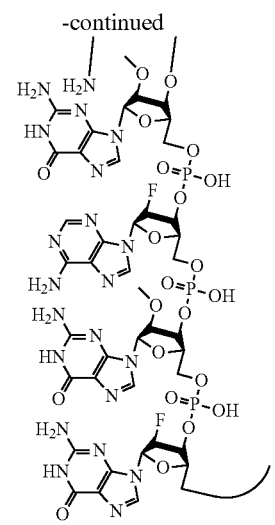
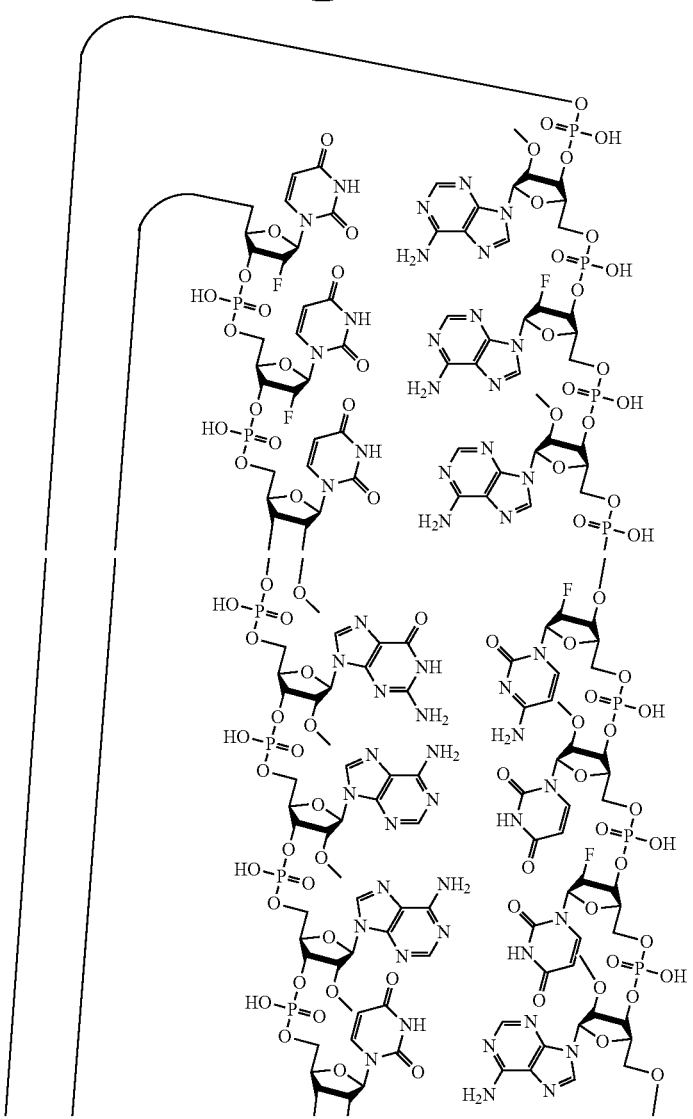

-continued
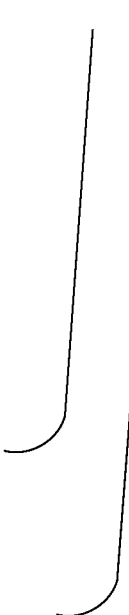
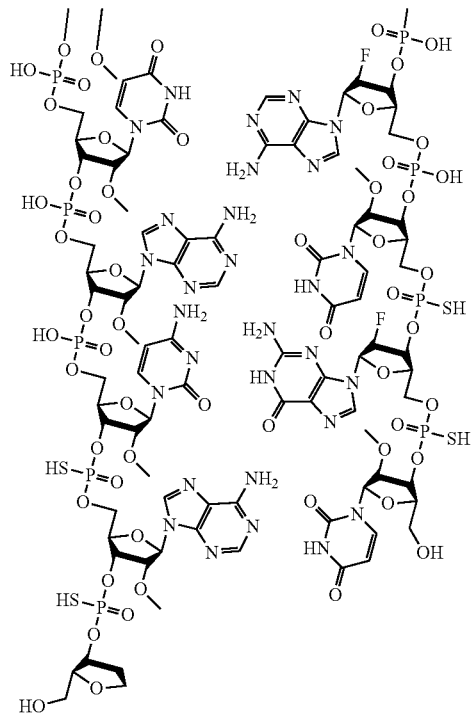
or a pharmaceutically acceptable salt or stereoisomer thereof.
12. The compound of claim 11, wherein the pharmaceutically acceptable salt is a sodium salt or a potassium salt.
13. The compound of claim 12, which is a sodium salt according to the following chemical structure:
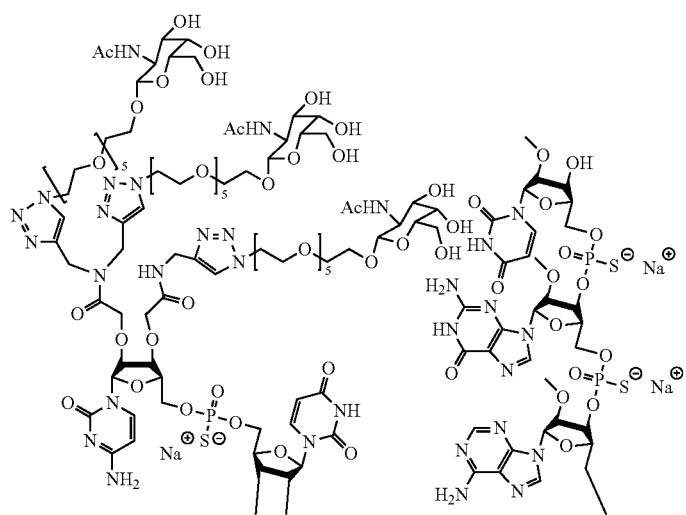

-continued
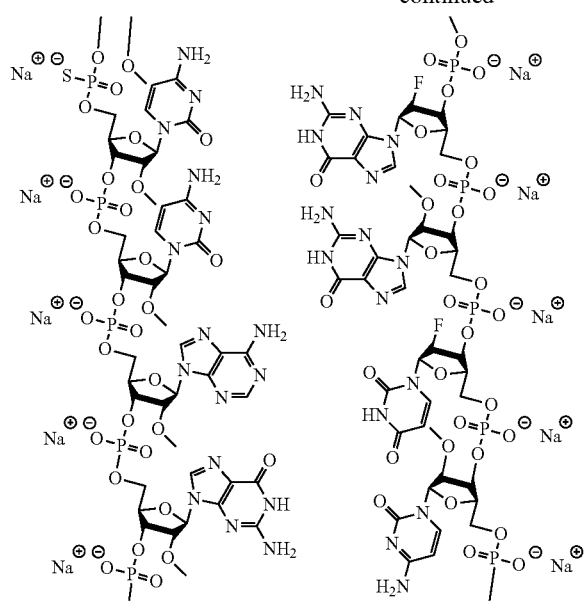
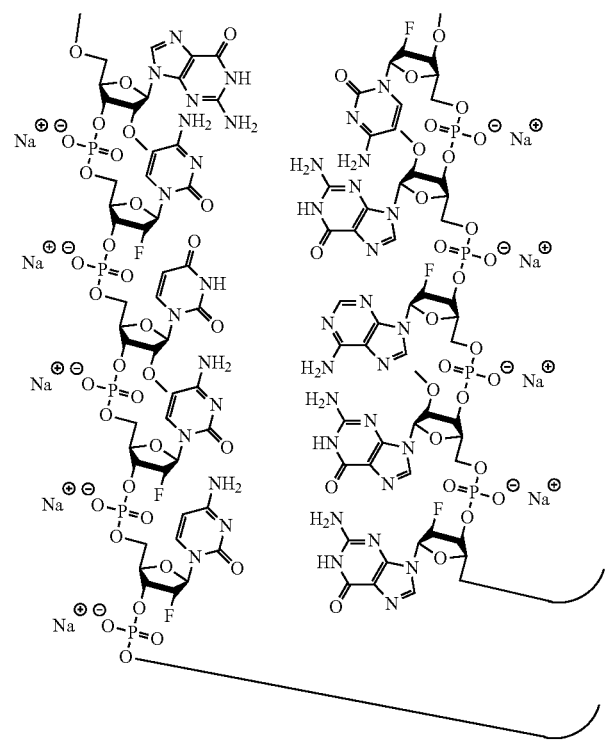

-continued
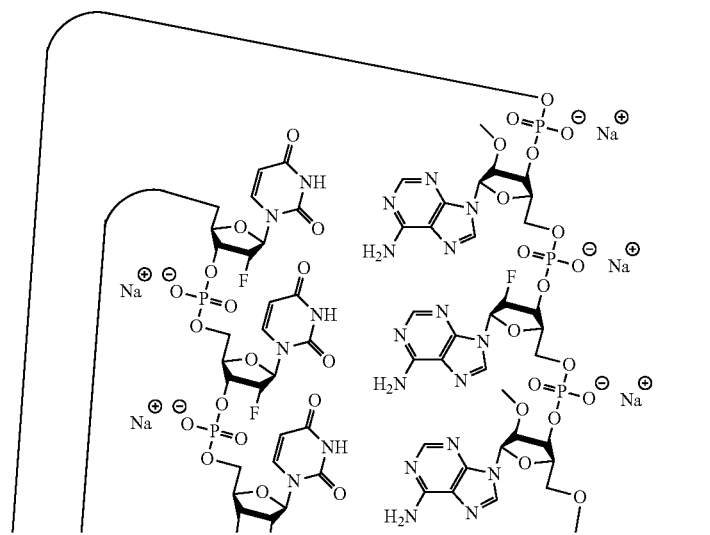
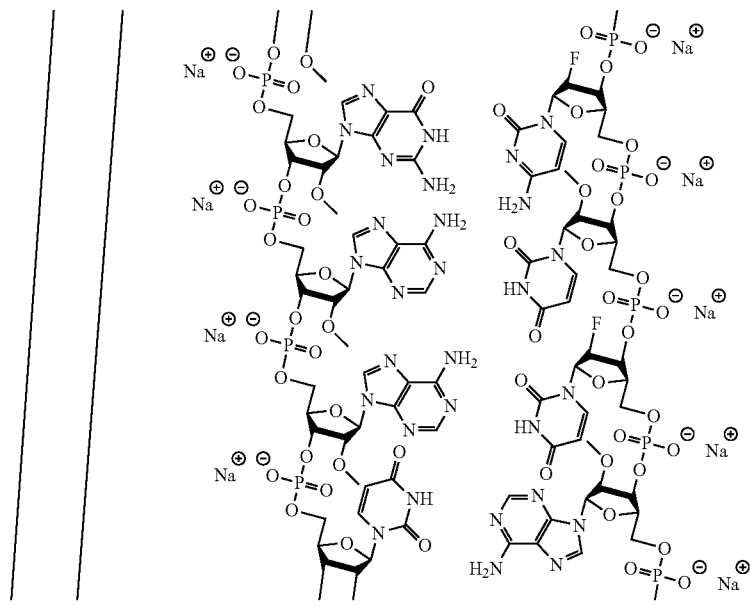

-continued

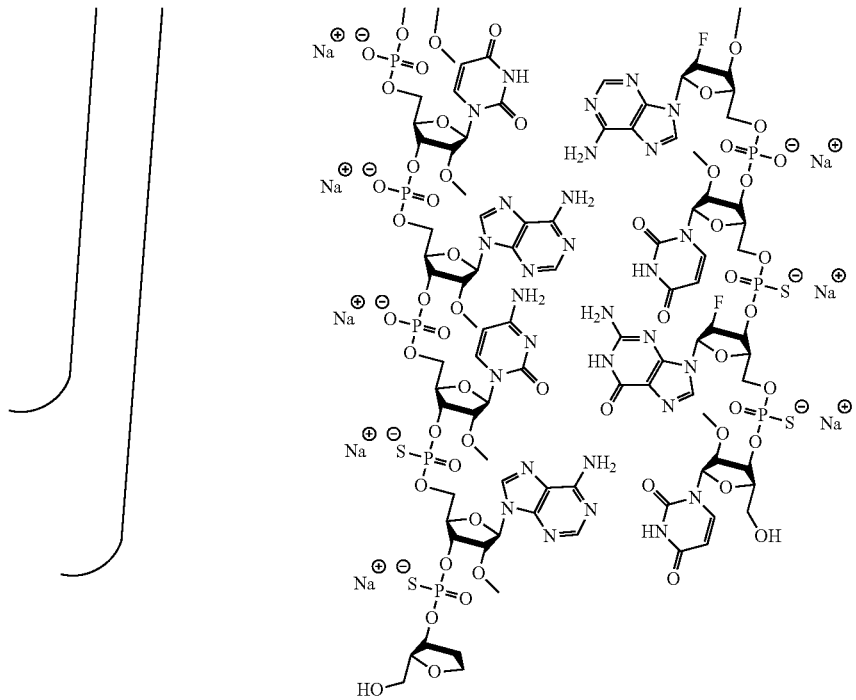

or a stereoisomer thereof.

14. A composition comprising the compound of claim 11 or a salt thereof and a pharmaceutically acceptable carrier.

15. A composition comprising the compound of claim 1 and a pharmaceutically acceptable carrier.

16. A method comprising administering the compound of claim 1 to an individual.

17. The method of claim 16, wherein administering the compound inhibits or reduces or improves an inflammatory or thrombotic disease, disorder or condition or a symptom thereof, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct.

18. A method of inhibiting expression of PKK in a cell comprising contacting the cell with the compound of claim 7, thereby inhibiting expression of PKK in the cell.

19. The method of claim 18, wherein the cell is in the liver of an individual.

20. A method comprising administering the composition of claim 15 to an individual.

21. A compound comprising a first modified oligonucleotide and a second modified oligonucleotide 14 to 23 linked nucleosides in length having a region of complementarity to the first modified oligonucleotide, wherein the first modified oligonucleotide consists of the formula:

H9*mU*mC.mC.mA.mG.mG.fC.
  mU.fC.fC.fU.fU.mU.
  mG.mA.mA.mU.mU.mA.mC*mA*dQ   (SEQ ID NO: 619), wherein:

'A' is a nucleoside having an adenine nucleobase, 'G' is a nucleoside having a guanine nucleobase, 'C' is a nucleoside having a cytosine nucleobase, and '11' is a nucleoside having a uracil nucleobase;

'm' is a 2'-O-methyl sugar modification;

'f' is a 2'-F sugar modification;

'*' is a phosphorothioate internucleoside linkage;

'.' is a phosphate internucleoside linkage;

'dQ' is an inverted abasic deoxyribose; and

'H9' is of the formula:

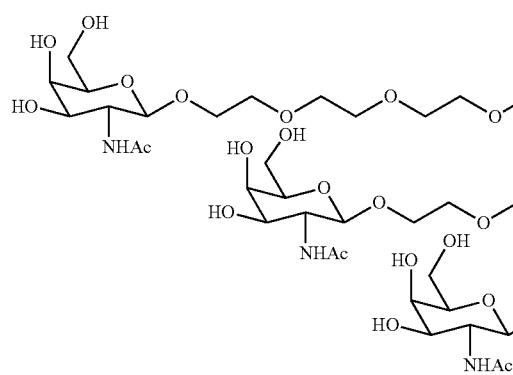
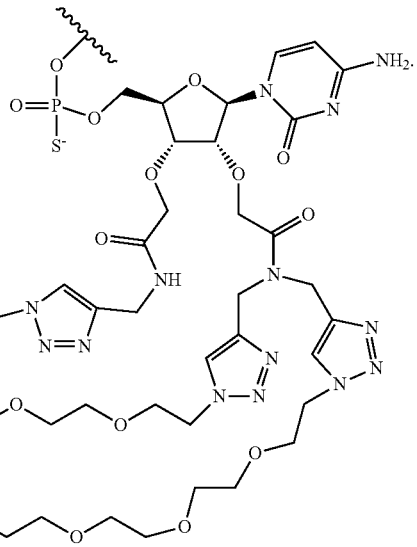

22. The compound of claim 21, wherein the region of complementarity between the first modified oligonucleotide and the second modified oligonucleotide is 19 to 23 linked nucleosides in length.

23. The compound of claim 21, wherein at least one internucleoside linkage of the second modified oligonucleotide is a phosphorothioate internucleoside linkage or a methylphosphonate internucleoside linkage.

24. The compound of claim 23, wherein the phosphorothioate internucleoside linkage or methylphosphonate internucleoside linkage is at the 3' terminus of the second modified oligonucleotide or at the 5' terminus of the second modified oligonucleotide.

25. The compound of claim 21, wherein the second modified oligonucleotide comprises a modification selected from group consisting of LNA, cEt, 2'-MOE, 2'-F, 2'-OMe, and 2'-deoxy, or a combination thereof.

26. The compound of claim 21, wherein the second modified oligonucleotide comprises no more than ten 2'-F sugar modifications.

27. The compound of claim 21, wherein the second modified oligonucleotide is 14 to 23 linked nucleosides in length having a nucleobase sequence comprising at least 14 contiguous nucleobases of the nucleobase sequence of SEQ ID NO: 312.

28. The compound of claim 21, wherein the second modified oligonucleotide is 19 to 23 linked nucleosides in length having a nucleobase sequence comprising at least 19 contiguous nucleobases of the nucleobase sequence of SEQ ID NO: 312.

29. The compound of claim 21, wherein the second modified oligonucleotide is 22 to 23 linked nucleosides in length having a nucleobase sequence comprising at least 22 contiguous nucleobases of the nucleobase sequence of SEQ ID NO: 312.

30. The compound of claim 21, wherein the second modified oligonucleotide has a nucleobase sequence consisting of the nucleobase sequence of SEQ ID NO: 312.

31. A composition comprising the compound of claim 21 or a salt thereof and a pharmaceutically acceptable carrier.

32. A method comprising administering the compound of claim 21 to an individual.

33. The method of claim 32, wherein administering the compound inhibits or reduces or improves an inflammatory or thrombotic disease, disorder or condition or a symptom thereof, hereditary angioedema (HAE), edema, angioedema, swelling, angioedema of the lids, ocular edema, macular edema, cerebral edema, thrombosis, embolism, thromboembolism, deep vein thrombosis, pulmonary embolism, myocardial infarction, stroke, or infarct.

34. A method of inhibiting expression of PKK in a cell comprising contacting the cell with the compound of claim 21, thereby inhibiting expression of PKK in the cell.

35. The method of claim 34, wherein the cell is in the liver of an individual.

36. A method comprising administering the composition of claim 31 to an individual.

* * * * *

UNITED STATES PATENT AND TRADEMARK OFFICE
CERTIFICATE OF CORRECTION

Page 1 of 2

PATENT NO.        : 12,042,509 B2
APPLICATION NO.   : 17/937344
DATED             : July 23, 2024
INVENTOR(S)       : Zhen Li et al.

It is certified that error appears in the above-identified patent and that said Letters Patent is hereby corrected as shown below:

In the Claims

In Claim 1, Column 297, Line 18, the text:
"nucleoside having a cytosine nucleobase, and '11' is"
Should read:
--nucleoside having a cytosine nucleobase, and 'U' is--

In Claim 11, Column 299, Line 17, that portion of the chemical formula shown as:

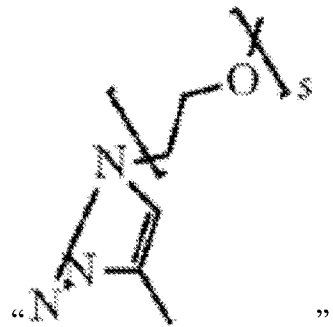

Should be replaced with:

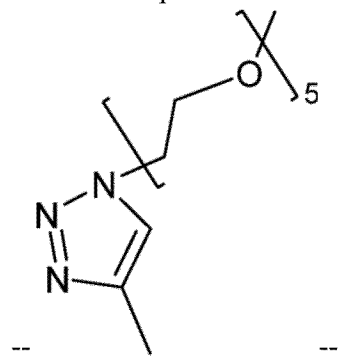

In Claim 18, Column 309, Lines 62-63, the text:

Signed and Sealed this
Twenty-fifth Day of February, 2025

Coke Morgan Stewart
*Acting Director of the United States Patent and Trademark Office*

"comprising contacting the cell with the compound of claim 7, thereby inhibiting expression of PKK in the cell"
Should read:
--comprising contacting the cell with the compound of claim 1, thereby inhibiting expression of PKK in the cell--

In Claim 21, Column 310, Line 59, the text:
"nucleoside having a cytosine nucleobase, and '11' is"
Should read:
--nucleoside having a cytosine nucleobase, and 'U' is--